United States Patent
Dehring et al.

(10) Patent No.: US 8,163,516 B2
(45) Date of Patent: Apr. 24, 2012

(54) SELECTION OF ADH IN GENETICALLY MODIFIED CYANOBACTERIA FOR THE PRODUCTION OF ETHANOL

(75) Inventors: Ulf Dehring, Fredersdorf (DE); Dan Kramer, Berlin (DE); Karl Ziegler, Zeuthen (DE)

(73) Assignee: Algenol Biofuels Inc., Bonita Springs, FL (US)

( * ) Notice: Subject to any disclaimer, the term of this patent is extended or adjusted under 35 U.S.C. 154(b) by 0 days.

(21) Appl. No.: 12/368,160

(22) Filed: Feb. 9, 2009

(65) Prior Publication Data

US 2010/0003739 A1    Jan. 7, 2010

Related U.S. Application Data

(60) Provisional application No. 61/065,292, filed on Feb. 8, 2008.

(51) Int. Cl.
*C12P 1/00* (2006.01)
(52) U.S. Cl. ......... 435/41
(58) Field of Classification Search ......... 435/41
See application file for complete search history.

(56) References Cited

U.S. PATENT DOCUMENTS

| | | | |
|---|---|---|---|
| 5,270,175 | A | 12/1993 | Moll |
| 6,306,639 | B1 | 10/2001 | Woods et al. |
| 6,699,696 | B2 | 3/2004 | Woods et al. |
| 7,314,974 | B2 | 1/2008 | Cao et al. |
| 2002/0042111 | A1 * | 4/2002 | Woods et al. ......... 435/161 |
| 2009/0155871 | A1 | 6/2009 | Fu et al. |

FOREIGN PATENT DOCUMENTS

WO    WO/2009/078712    6/2009

OTHER PUBLICATIONS

Bowie et al (Science, 1990, 247:1306-1310).*
Deng et al Applied and Environmental Microbiology vol. 65 No. 2 Feb. (1999) pp. 523-528.*
Kaneko et al DNA Research vol. 3 (1996) pp. 109-136.*
Deng, M-D. And Coleman, J.R. Appl. Environ. Microbiol., vol. 65, p. 523-528 (1999).
International Search Report WO 2009/098089 A3.

* cited by examiner

*Primary Examiner* — Gary Nickol
*Assistant Examiner* — Nina Archie
(74) *Attorney, Agent, or Firm* — Lawrence B. Ebert; Robert McIsaac

(57) ABSTRACT

The present invention discloses genetically-modified cyanobacteria with ethanol-production capabilities enhanced over the currently-reported art, and methods of making such cyanobacteria. The invention provides a genetically modified photoautotrophic, ethanol producing host cell comprising an overexpressed pyruvate decarboxylase enzyme converting pyruvate to acetaldehyde and an overexpressed Zn2+ dependent alcohol dehydrogenase enzyme converting acetaldehyde to ethanol.

8 Claims, 140 Drawing Sheets

```
GAGCTCTATATCAACAAAAGGTAGTCACCATGTCAGCCGCAGATTTGTCGACTGACCTCTAT

CTCTCCGAGATATATCAACAAAAGGTAGTCACCATGAAAGCAGCCGTCATAACTAAAGATCA

TACGATCGAAGTGAAAGACACCAAATTACGCCCTCTGAAATACGGGGAAGCGCTTTTGGAAA

TGGAATATTGCGGGGTATGTCATACCGATCTCCACGTGAAAAACGGGGATTTTGGCGATGAA

ACCGGCAGAATTACCGGCCATGAAGGCATCGGTATCGTCAAGCAGGTCGGGGAAGGGGTTAC

TTCTCTGAAAGTCGGTGACCGTGCCAGTGTTGCATGGTTCTTCAAAGGCTGCGGCCATTGCG

AATATTGTGTCAGTGGAAATGAAACGCTTTGCCGCAACGTTGAAAATGCCGGTTATACGGTT

GACGGCGCTATGGCAGAAGAATGCATCGTCGTTGCCGATTACTCGGTCAAAGTGCCAGATGG

TCTTGATCCTGCGGTTGCCAGCAGCATCACTTGCGCGGGTGTAACCACCTATAAAGCAGTCA

AGTTTCTCAGATACAGCCGGGACAATGGCTGGCTATCTATGGCTTGGGCGGTTTAGGCAAT

CTAGCCCTTCAATATGCCAAGAATGTTTTCAACGCCAAAGTGATCGCGATCGATGTCAATGA

TGAACAGCTCGCTTTTGCCAAAGAGCTGGGCGCAGATATGGTCATCAATCCGAAAAACGAAG

ATGCTGCCAAAATCATTCAGGAAAAGTCGGCGGCGCACATGCGACGGTGGTGACAGCTGTT

GCCAAATCCGCCTTTAACTCGGCTGTTGAGGCTATCCGCGCGGGTGGCCGTGTTGTCGCCGT

TGGTCTGCCTCCTGAAAAAATGGATTTGAGCATTCCTCGCTTGGTGCTTGACGGTATCGAAG

TCTTAGGTTCTTTGGTCGGAACGCGGGAAGATTTGAAAGAAGCCTTCCAGTTTGCAGCCGAA

GGTAAGGTCAAACCGAAAGTCACCAAGCGTAAAGTCGAAGAAATCAACCAAATCTTTGACGA

AATGGAACATGGTAAATTCACAGGCCGTATGGTTGTTGATTTTACCCATCACTAGGTTTCCG

TGAAGGCGGAAGCATAAACGGAAAAAGCCTTTCTCTTACCAGAAAGGCTTTTTCTTTGTCGT

CTGATAAAAATTTTCATACAGAATTTAATACACTGCAG (SEQ ID NO:1)
```

Figure 1A

```
MKAAVITKDHTIEVKDTKLRPLKYGEALLEMEYCGVCHTDLHVKNGDFGDETGRITGHEGIG
IVKQVGEGVTSLKVGDRASVAWFFKGCGHCEYCVSGNETLCRNVENAGYTVDGAMAEECIVV
ADYSVKVPDGLDPAVASSITCAGVTTYKAVKVSQIQPGQWLAIYGLGGLGNLALQYAKNVFN
AKVIAIDVNDEQLAFAKELGADMVINPKNEDAAKIIQEKVGGAHATVVTAVAKSAFNSAVEA
IRAGGRVVAVGLPPEKMDLSIPRLVLDGIEVLGSLVGTREDLKEAFQFAAEGKVKPKVTKRK
VEEINQIFDEMEHGKFTGRMVVDFTHH (SEQ ID NO:2)
```

Figure 1B

```
GAGCTCTCTGGATAAAACTAATAAACTCTATTACCCATGATTAAAGCCTACGCTGCCCTGGA
AGCCAACGGAAAACTCCAACCCTTTGAATACGACCCCGGTGCCCTGGGTGCTAATGAGGTGG
AGATTGAGGTGCAGTATTGTGGGGTGTGCCACAGTGATTTGTCCATGATTAATAACGAATGG
GGCATTTCCAATTACCCCCTAGTGCCGGGTCATGAGGTGGTGGGTACTGTGGCCGCCATGGG
CGAAGGGGTGAACCATGTTGAGGTGGGGATTTAGTGGGGCTGGGTTGGCATTCGGGCTACT
GCATGACCTGCCATAGTTGTTTATCTGGCTACCACAACCTTTGTGCCACGGCGGAATCGACC
ATTGTGGGCCACTACGGTGGCTTTGGCGATCGGGTTCGGGCCAAGGGAGTCAGCGTGGTGAA
ATTACCTAAAGGCATTGACCTAGCCAGTGCCGGGCCCCTTTTCTGTGGAGGAATTACCGTTT
TCAGTCCTATGGTGGAACTGAGTTTAAAGCCCACTGCAAAAGTGGCAGTGATCGGCATTGGG
GGCTTGGGCCATTTAGCGGTGCAATTTCTCCGGGCCTGGGGCTGTGAAGTGACTGCCTTTAC
CTCCAGTGCCAGGAAGCAAACGGAAGTGTTGGAATTGGGCGCTCACCACATACTAGATTCCA
CCAATCCAGAGGCGATCGCCAGTGCGGAAGGCAAATTTGACTATATTATCTCCACTGTGAAC
CTGAAGCTTGACTGGAACTTATACATCAGCACCCTGGCGCCCCAGGGACATTTCCACTTTGT
TGGGGTGGTGTTGGAGCCTTTGGATCTAAATCTTTTTCCCCTTTTGATGGGACAACGCTCCG
TTTCTGCCTCCCCAGTGGGTAGTCCCGCCACCATTGCCACCATGTTGGACTTTGCTGTGCGC
CATGACATTAAACCCGTGGTGGAACAATTTAGCTTTGATCAGATCAACGAGGCGATCGCCCA
TCTAGAAAGCGGCAAAGCCCATTATCGGGTAGTGCTCAGCCATAGTAAAAATTAGCTCTGCA
AAGGTTGCTTCTGGGTCCGTGGAATGGTCAAACGGAGTCGATCTCAGTTTTGATACGCTCTA
TCTGGAAAGCTTGACATTCGATCTGCAG (SEQ ID NO:3)
```

Figure 2A

MIKAYAALEANGKLQPFEYDPGALGANEVEIEVQYCGVCHSDLSMINNEWGISNYPLVPGHE
VVGTVAAMGEGVNHVEVGDLVGLGWHSGYCMTCHSCLSGYHNLCATAESTIVGHYGGFGDRV
RAKGVSVVKLPKGIDLASAGPLFCGGITVFSPMVELSLKPTAKVAVIGIGGLGHLAVQFLRA
WGCEVTAFTSSARKQTEVLELGAHHILDSTNPEAIASAEGKFDYIISTVNLKLDWNLYISTL
APQGHFHFVGVVLEPLDLNLFPLLMGQRSVSASPVGSPATIATMLDFAVRHD
IKPVVEQFSFDQINEAIAHLESGKAHYRVVLSHSKN (SEQ ID NO:4)

Figure 2B

```
ATGAATTCTGCTGTTACTAATGTCGCTGAACTTAACGCACTCGTAGAGCGTGTAAAAAAGCCCAGCGTGAATAT
GCCAGTTTCACTCAAGAGCAAGTAGACAAAATCTTCCGCGCCGCCGCTCTGGCTGCTGCAGATGCTCGAATCCCA
CTCGCGAAAATGGCCGTTGCCGAATCCGGCATGGGTATCGTCGAAGATAAAGTGATCAAAAACCACTTTGCTTCT
GAATATATCTACAACGCCTATAAAGATGAAAAAACCTGTGGTGTTCTGTCTGAAGACGACACTTTTGGTACCATC
ACTATCGCTGAACCAATCGGTATTATTTGCGGTATCGTTCCGACCACTAACCCGACTTCAACTGCTATCTTCAAA
TCGCTGATCAGTCTGAAGACCCGTAACGCCATTATCTTCTCCCCGCACCCGCGTGCAAAAGATGCCACCAACAAA
GCGGCTGATATCGTTCTGCAGGCTGCTATCGCTGCCGGTGCTCCGAAAGATCTGATCGGCTGGATCGATCAACCT
TCTGTTGAACTGTCTAACGCACTGATGCACCACCCAGACATCAACCTGATCCTCGCGACTGGTGGTCCGGGCATG
GTTAAAGCCGCATACAGCTCCGGTAAACCAGCTATCGGTGTAGGCGCGGGCAACACTCCAGTTGTTATCGATGAA
ACTGCTGATATCAAACGTGCAGTTGCATCTGTACTGATGTCCAAAACCTTCGACAACGGCGTAATCTGTGCTTCT
GAACAGTCTGTTGTTGTTGTTGACTCTGTTTATGACGCTGTACGTGAACGTTTTGCAACCCACGGCGGCTATCTG
TTGCAGGGTAAAGAGCTGAAAGCTGTTCAGGATGTTATCCTGAAAAACGGTGCGCTGAACGCGGCTATCGTTGGT
CAGCCAGCCTATAAAATTGCTGAACTGGCAGGCTTCTCTGTACCAGAAAACACCAAGATTCTGATCGGTGAAGTG
ACCGTTGTTGATGAAAGCGAACCGTTCGCACATGAAAAACTGTCCCGACTCTGGCAATGTACCGCGCTAAAGAT
TTCGAAGACGCGGTAGAAAAAGCAGAGAAACTGGTTGCTATGGGCGGTATCGGTCATACCTCTTGCCTGTACACT
GACCAGGATAACCAACCGGCTCGCGTTTCTTACTTCGGTCAGAAAATGAAAACGGCGCGTATCCTGATTAACACC
CCAGCGTCTCAGGGTGGTATCGGTGACCTGTATAACTTCAAACTCGCACCTTCCCTGACTCTGGGTTGTGGTTCT
TGGGGTGGTAACTCCATCTCTGAAAACGTTGGTCCGAAACACCTGATCAACAAGAAAACCGTTGCTAAGCGAGCT
GAAAACATGTTGTGGCACAAACTTCCGAAATCTATCTACTTCCGCCGTGGCTCCCTGCCAATCGCGCTGGATGAA
GTGATTACTGATGGCCACAAACGTGCGCTCATCGTGACTGACCGCTTCCTGTTCAACAATGGTTATGCTGATCAG
ATCACTTCCGTACTGAAAGCAGCAGGCGTTGAAACTGAAGTCTTCTTCGAAGTAGAAGCGGACCCGACCCTGAGC
ATCGTTCGTAAAGGTGCAGAACTGGCAAACTCCTTCAAACCAGACGTGATTATCGCGCTGGGTGGTGGTTCCCCG
ATGGACGCCGCGAAGATCATGTGGGTTATGTACGAACATCCGGAAACTCACTTCGAAGAGCTGGCGCTGCGCTTT
ATGGATATCCGTAAACGTATCTACAAGTTCCCGAAAATGGGCGTGAAAGCGAAAATGATCGCTGTCACCACCACT
TCTGGTACAGGTTCTGAAGTCACTCCGTTTGCGGTTGTAACTGACGACGCTACTGGTCAGAAATATCCGCTGGCA
GACTATGCGCTGACTCCGGATATGGCGATTGTCGACGCCAACCTGGTTATGGACATGCCGAAGTCCCTGTGTGCT
TTCGGTGGTCTGGACGCAGTAACTCACGCCATGGAAGCTTATGTTTCTGTACTGGCATCTGAGTTCTCTGATGGT
CAGGCTCTGCAGGCACTGAAACTGCTGAAAGAATATATCTGCCAGCGTCCTACCACGAAGGGTCTAAAAATCCGGTA
GCGCGTGAACGTGTTCACAGTGCAGCGACTATCGCGGGTATCGCGTTTGCGAACGCCTTCCTGGGTGTATGTCAC
TCAATGGCGCACAAACTGGGTTCCCAGTTCCATATTCCGCACGGTCTGGCAAACGCCCTGCTGATTTGTAACGTT
ATTCGCTACAATGCGAACGACAACCCGACCAAGCAGACTGCATTCAGCCAGTATGACCGTCCGCAGGCTCGCCGT
CGTTATGCTGAAATTGCCGACCACTTGGGTCTGAGCGCACCGGGCGACCGTACTGCTGCTAAGATCGAGAAACTG
CTGGCATGGCTGGAAACGCTGAAAGCTGAACTGGGTATTCCGAAATCTATCCGTGAAGCTGGCGTTCAGGAAGCA
GACTTCCTGGCGAACGTGGATAAACTGTCTGAAGATGCATTCGATGACCAGTGCACCGGCGCTAACCCGCGTTAC
CCGCTGATCTCCGAGCTGAAACAGATTCTGCTGGATACCTACTACGGTCGTGATTATGTAGAAGGTGAAACTGCA
GCGAAGAAGAAGCTGCTCCGGCTAAAGCTGAGAAAAAAGCGAAAAAATCCGCTTAATCAGTAGCGCTGTCTGGC
AACATAAACGGCCCCTTCTGGGCAATGCCGATCAGTTAAGGATTAGTTGACCGATCCTTAAACTGAGGCACTATA
GGATCC (SEQ ID NO:5)
```

Figure 3A

```
MNSAVTNVAELNALVERVKKAQREYASFTQEQVDKIFRAAALAAADARIPLAKMAVAESGMG
IVEDKVIKNHFASEYIYNAYKDEKTCGVLSEDDTFGTITIAEPIGIICGIVPTTNPTSTAIF
KSLISLKTRNAIIFSPHPRAKDATNKAADIVLQAAIAAGAPKDLIGWIDQPSVELSNALMHH
PDINLILATGGPGMVKAAYSSGKPAIGVGAGNTPVVIDETADIKRAVASVLMSKTFDNGVIC
ASEQSVVVVDSVYDAVRERFATHGGYLLQGKELKAVQDVILKNGALNAAIVGQPAYKIAELA
GFSVPENTKILIGEVTVVDESEPFAHEKLSPTLAMYRAKDFEDAVEKAEKLVAMGGIGHTSC
LYTDQDNQPARVSYFGQKMKTARILINTPASQGGIGDLYNFKLAPSLTLGCGSWGGNSISEN
VGPKHLINKKTVAKRAENMLWHKLPKSIYFRRGSLPIALDEVITDGHKRALIVTDRFLFNNG
YADQITSVLKAAGVETEVFFEVEADPTLSIVRKGAELANSFKPDVIIALGGGSPMDAAKIMW
VMYEHPETHFEELALRFMDIRKRIYKFPKMGVKAKMIAVTTTSGTGSEVTPFAVVTDDATGQ
KYPLADYALTPDMAIVDANLVMDMPKSLCAFGGLDAVTHAMEAYVSVLASEFSDGQALQALK
LLKEYLPASYHEGSKNPVARERVHSAATIAGIAFANAFLGVCHSMAHKLGSQFHIPHGLANA
LLICNVIRYNANDNPTKQTAFSQYDRPQARRRYAEIADHLGLSAPGDRTAAKIEKLLAWLET
LKAELGIPKSIREAGVQEADFLANVDKLSEDAFDDQCTGANPRYPLISELKQILLDTYYGRD
YVEGETAAKKEAAPAKAEKKAKKSA (SEQ ID NO:6)
```

Figure 3B

```
ATGAATTCCCCAACCTTGACCAGTGACCCCCCCGTTCAAAGCCTTGCCGATCTGGAAGGGCT
GATTGAGCGCGTCCAACGGGCGCAGAGTCAGTACGCCCAATTTACCCAAGAGCAAGTGGATC
ACATTTTCCACGAAGCAGCCATGGCGGCCAACCAAGCCCGGATTCCCCTGGCCAAACAAGCC
GTAGCCGAAACGGGCATGGGGGTTGTCGAAGATAAAGTTATTAAAAATCACTTTGCTTCGGA
ATACATCTACAACAAGTACAAAAATGAGAAACCTGCGGCGTCATTGAGGATGACCCCATCT
TTGGTATCCAAAAAATTGCTGAACCGGTGGGGATCATTGCCGGTGTGGTGCCGGTCACGAAC
CCCACTTCAACGACCATCTTTAAGGCACTGATTGCCCTGAAGACTCGCAATGGCATTATCTT
TTCGCCCCACCCCGGGCAAAGGCCTGTACGGTTGCAGCGGCCAAGGTAGTGTTGGATGCAG
CGGTCGCTGCCGGCGCACCCCCCGATATTATTGGCTGGATTGATGAGCCGACGATTGAACTC
TCCCAAGCCCTGATGCAGCACCCGCAGATCAAGCTGATTTTGGCCACGGGGGGACCAGGTAT
GGTCAAGGCAGCCTATTCCTCTGGCCATCCGGCGATCGGGGTCGGGGCCGGGAATACCCCCG
TGCTCATTGATGCCACAGCCGATATTCCCACGGCAGTGAGTTCGATTCTCCTCAGTAAGGCC
TTTGACAATGGCATGATCTGTGCCTCGGAGCAGGCAGTGATTGTTGTGGATGAGATTTATGA
CGCACTTAAAGCTGAGTTTCAACGGCGAGGGGCCTACCTTCTCTCCCCTGAGGAACGGCAGC
AGGTGGCACAACTACTGCTGAAGGATGGTCGCCTCAATGCCGCCATTGTTGGTCAATCGGCC
GCCACCATTGCCGCAATGGCCAATATCCAAGTACCGCCAGAAACCCGGGTACTCATTGGCGA
GGTGAGTGAAGTGGGGCCGCAGGAGCCATTTTCCTATGAGAAACTCTGTCCGGTATTGGCGT
TATATCGGGCACCCCAGTTCCATAAAGGGGTGGAGATTGCGGCCCAGTTGGTGAATTTTGGG
GGCAAGGGGCATACATCTGTGCTCTATACCGATCCCCGCAATCAAGATGATATTGCCTATTT
CAAATACCGCATGCAAACGGCGCGGGTTCTGATTAACACCCCTTCTTCCCAGGGGGCAATTG
GCGATCTCTACAACTTCAAGTTAGATCCGTCGCTAACCCTTGGTTGTGGTACGTGGGCGGC
AACGTCACATCGGAAAATGTTGGTCCCCGTCACTTGCTGAATATTAAAACGGTGAGCGATCG
CCGGGAAAATATGCTTTGGTTTCGGGTGCCGCCCAAGATCTACTTCAAACCCGGCTGTTTGC
CCATTGCCCTGCGGGAGCTGGCGGGGAAAAAACGCGCCTTCCTCGTGACGGATAAACCCCTC
TTTGACTTGGGGATCACTGAACCGATTGTCCATACCCTCGAAGAACTGGGCATCAAGTATGA
CATCTTCCATGAAGTGGAACCAGATCCAACCCTCAGTACCGTTAACCGCGGTCTAGGGTTGC
TGCGGCAATATCAGCCGGATGTGATTGTTGCTGTGGGGGGTGGCTCACCTATGGATGCAGCC
AAGGTGATGTGGCTGTTGTATGAGCATCCGGAGGTGGAGTTTGACGGCCTTGCGATGCGCTT
CATGGATATTCGCAAGCGGGTGTATCAACTGCCTCCCTTGGGTCAAAAGGCAATCCTGGTGG
CTATTCCCACCACCTCGGGGACGGGTTCAGAGGTGACCCCCTTTGCCGTGGTTACCGACGAT
```

Figure 4A(1)

```
CGCGTGGGGATTAAATATCCCTTGGCAGACTATGCCCTTACGCCAACGATGGCGATTGTGGA
TCCCGACTTGGTGCTGCACATGCCCAAGAAACTGACGGCCTACGGTGGCATTGATGCGCTGA
CCCATGCCCTGGAGGCCTATGTGTCGGTGCTCTCGACGGAGTTTACGGAGGGACTGGCTCTA
GAGGCCATTAAACTGCTCTTTACCTACCTACCCCGTGCCTATCGCTTGGGGGCGGCGGATCC
GGAGGCACGGGAGAAGGTCCACTATGCGGCGACGATCGCTGGCATGGCCTTTGCGAATGCCT
TCTTGGGGGTCTGCCACTCGCTGGCCCACAAACTAGGCTCCACCTTCCACGTGCCCCACGGC
TTGGCGAATGCACTCATGATTTCCCATGTGATTCGCTACAATGCCACGGATGCTCCCCTGAA
GCAGGCGATTTTCCCGCAGTACAAGTATCCCCAAGCGAAGGAGCGCTATGCCCAAATTGCCG
ACTTCCTCGAATTGGGGGGCACGACCCCAGAGGAAAAAGTGGAGCGTCTCATTGCGGCAATT
GAGGATTTGAAAGCCCAATTAGAAATTCCCGCCACGATTAAGGAGGCCCTCAACAGTGAGGA
TCAAGCGTTCTATGAGCAGGTGGAGAGCATGGCCGAACTGGCCTTTGACGATCAGTGCACGG
GGGCCAATCCCCGCTATCCGCTGATCCAAGACCTCAAGGAGTTGTATATCCTGGCCTATATG
GGGTGTCGGCGGATGCGGCAGCCTACTATGGGGGGGAGGCAACGGGGAGTTGATGTGGCGT
TATATTCCCCCCTTTGCAGCTCCAGCGAAGGTGCAAATGGCGGTGGATTCCTGGCTCTGGCA
GCGGAGCGATCGCCTGCAG (SEQ ID NO:7)
```

Figure 4A(2)

```
MNSPTLTSDPPVQSLADLEGLIERVQRAQSQYAQFTQEQVDHIFHEAAMAANQARIPLAKQA
VAETGMGVVEDKVIKNHFASEYIYNKYKNEKTCGVIEDDPIFGIQKIAEPVGIIAGVVPVTN
PTSTTIFKALIALKTRNGIIFSPHPRAKACTVAAAKVVLDAAVAAGAPPDIIGWIDEPTIEL
SQALMQHPQIKLILATGGPGMVKAAYSSGHPAIGVGAGNTPVLIDATADIPTAVSSILLSKA
FDNGMICASEQAVIVVDEIYDALKAEFQRRGAYLLSPEERQQVAQLLLKDGRLNAAIVGQSA
ATIAAMANIQVPPETRVLIGEVSEVGPQEPFSYEKLCPVLALYRAPQFHKGVEIAAQLVNFG
GKGHTSVLYTDPRNQDDIAYFKYRMQTARVLINTPSSQGAIGDLYNFKLDPSLTLGCGTWGG
NVTSENVGPRHLLNIKTVSDRRENMLWFRVPPKIYFKPGCLPIALRELAGKKRAFLVTDKPL
FDLGITEPIVHTLEELGIKYDIFHEVEPDPTLSTVNRGLGLLRQYQPDVIVAVGGGSPMDAA
KVMWLLYEHPEVEFDGLAMRFMDIRKRVYQLPPLGQKAILVAIPTTSGTGSEVTPFAVVTDD
RVGIKYPLADYALTPTMAIVDPDLVLHMPKKLTAYGGIDALTHALEAYVSVLSTEFTEGLAL
EAIKLLFTYLPRAYRLGAADPEAREKVHYAATIAGMAFANAFLGVCHSLAHKLGSTFHVPHG
LANALMISHVIRYNATDAPLKQAIFPQYKYPQAKERYAQIADFLELGGTTPEEKVERLIAAI
EDLKAQLEIPATIKEALNSEDQAFYEQVESMAELAFDDQCTGANPRYPLIQDLKELYILAYM
GCRRDAAAYYGGEATGS (SEQ ID NO:8)
```

Figure 4B

```
ATGAATTCCGTTGGTATGTACTTGGCAGAACGCCTAGCCCAGATCGGCCTGAAACAC
CACTTTGCCGTGGCCGGTGACTACAACCTGGTGTTGCTTGATCAGCTCCTGCTGAAC
AAAGACATGGAGCAGGTCTACTGCTGTAACGAACTTAACTGCGGCTTTAGCGCCGAA
GGTTACGCTCGTGCACGTGGTGCCGCCGCTGCCATCGTCACGTTCAGCGTAGGTGCT
ATCTCTGCAATGAACGCCATCGGTGGCGCCTATGCAGAAACCTGCCGGTCATCCTG
ATCTCTGGCTCACCGAACACCAATGACTACGGCACAGGCCACATCCTGCACCACACC
ATTGGTACTACTGACTATAACTATCAGCTGGAAATGGTAAAACACGTTACCTGCGCA
CGTGAAAGCATCGTTTCTGCCGAAGAAGCACCGGCAAAAATCGACCACGTCATCCGT
ACGGCTCTACGTGAACGCAAACCGGCTTATCTGGAAATCGCATGCAACGTCGCTGGC
GCTGAATGTGTTCGTCCGGGCCCGATCAATAGCCTGCTGCGTGAACTCGAAGTTGAC
CAGACCAGTGTCACTGCCGCTGTAGATGCCGCCGTAGAATGGCTGCAGGACCGCCAG
AACGTCGTCATGCTGGTCGGTAGCAAACTGCGTGCCGCTGCCGCTGAAAAACAGGCT
GTTGCCCTAGCGGACCGCCTGGGCTGCGCTGTCACGATCATGGCTGCCGAAAAGGC
TTCTTCCCGGAAGATCATCCGAACTTCCGCGGCCTGTACTGGGGTGAAGTCAGCTCC
GAAGGTGCACAGGAACTGGTTGAAAACGCCGATGCCATCCTGTGTCTGGCACCGGTA
TTCAACGACTATGCTACCGTTGGCTGGAACTCCTGGCCGAAAGGCGACAATGTCATG
GTCATGGACACCGACCGCGTCACTTTCGCAGGACAGTCCTTCGAAGGTCTGTCATTG
AGCACCTTCGCCGCAGCACTGGCTGAGAAAGCACCTTCTCGCCCGGCAACGACTCAA
GGCACTCAAGCACCGGTACTGGGTATTGAGGCCGCAGAGCCCAATGCACCGCTGACC
AATGACGAAATGACGCGTCAGATCCAGTCGCTGATCACTTCCGACACTACTCTGACA
GCAGAAACAGGTGACTCTTGGTTCAACGCTTCTCGCATGCCGATTCCTGGCGGTGCT
CGTGTCGAACTGGAAATGCAATGGGGTCATATCGGTTGGTCCGTACCTTCTGCATTC
GGTAACGCCGTTGGTTCTCCGGAGCGTCGCCACATCATGATGGTCGGTGATGGCTCT
TTCCAGCTGACTGCTCAAGAAGTTGCTCAGATGATCCGCTATGAAATCCCGGTCATC
ATCTTCCTGATCAACAACCGCGGTTACGTCATCGAAATCGCTATCCATGACGGCCCT
TACAACTACATCAAAACTGGAACTACGCTGGCCTGATCGACGTCTTCAATGACGAA
GATGGTCATGGCCTGGGTCTGAAAGCTTCTACTGGTGCAGAACTAGAAGGCGCTATC
AAGAAAGCACTCGACAATCGTCGCGGTCCGACGCTGATCGAATGTAACATCGCTCAG
GACGACTGCACTGAAACCCTGATTGCTTGGGGTAAACGTGTAGCAGCTACCAACTCT
CGCAAACCACAAGCGTAAGTTGAGCTC (SEQ ID NO:9)
```

Figure 5A

MNSVGMYLAERLAQIGLKHHFAVAGDYNLVLLDQLLLNKDMEQVYCCNELNCGFSAEGYARA
RGAAAAIVTFSVGAISAMNAIGGAYAENLPVILISGSPNTNDYGTGHILHHTIGTTDYNYQL
EMVKHVTCARESIVSAEEAPAKIDHVIRTALRERKPAYLEIACNVAGAECVRPGPINSLLRE
LEVDQTSVTAAVDAAVEWLQDRQNVVMLVGSKLRAAAAEKQAVALADRLGCAVTIMAAEKGF
FPEDHPNFRGLYWGEVSSEGAQELVENADAILCLAPVFNDYATVGWNSWPKGDNVMVMDTDR
VTFAGQSFEGLSLSTFAAALAEKAPSRPATTQGTQAPVLGIEAAEPNAPLTNDEMTRQIQSL
ITSDTTLTAETGDSWFNASRMPIPGGARVELEMQWGHIGWSVPSAFGNAVGSPERRHIMMVG
DGSFQLTAQEVAQMIRYEIPVIIFLINNRGYVIEIAIHDGPYNYIKNWNYAGLIDVFNDEDG
HGLGLKASTGAELEGAIKKALDNRRGPTLIECNIAQDDCTETLIAWGKRVAATNSRKPQA
(SEQ ID NO:10)

Figure 5B

```
   1 GTCGACATAT GTTTCTCGGC AAAAATTAAT TATCGATTGG CTGGAACCTG
  51 GTCAAACCAG GGCTTTTCAT CCATTGGAAA AGCGATTTTG ATCATCTAGG
 101 GTCAGGAGCA AAGATCTGAT CAAATATTGA TCATTTATTA GGAAAGCTGA
 151 ACTTTCACCA CTTTATTTTT GGCTTCCTCT ACTTTGGGCA AAGTCAAAGT
 201 TAGGATACCG GCATCGTAAT TAGCTTTAAC TTCTGTGTTT TGGATTGCTC
 251 CAGGTACAGG AATAACCCGG CGGAAACTGC CATAGCGGAA CTCTGTGCGC
 301 CGCACCCCAT CTTTTCGGT GCTATGGGTA TCCTGGCGAT CGCCGCTGAC
 351 GGTCACCGCA TCCCTGGCGG CTTGGATGTC CAAATTATCG GGGTCCATGC
 401 CAGGTAATTC TAGTTTGAGC ACATAGGCTT CTTCAGTTTC AGTTAGTTCT
 451 GCTTTAGGAT TAAACCCTTG GCGATCGCCG TGGCGGTCCG TAGGGACAAA
 501 AACTTCTTCA AACAGTTGGT TCATCTGCTG CTGGAAATTA TCCATTTCCC
 551 GCAGGGGATT GTAAAGAATG AGAGACATAA TGTTAACTCC TGATGTGTGG
 601 AAGGAATTGA TTACCCTTGA ATGGTCTAT CTTAAAATTT CCCCTTCCAG
 651 GTTAGATTCG GTTTTCAGGA AAGAAGGTGG GGGGATTGCC GAAATTACAT
 701 TTCTAGCCGC AATTTTTAGT AAAAAAAGA TGAGTTTTTA CCTCACCTTA
 751 AGTAAATATT TGAGTGGCAA AACAAAATGG TAAAAATAGC TAAGCTTCCA
 801 CCGCCCTATG GATTTTTGGA AGGAAGTCTT AGGTTGTGAA AAACTATAAA
 851 AACCAACCAT AGGAATGGAG ACCTTTACCC AACAAGTTGA CCCCTAGGTA
 901 ACAAATCCAA ACCACCGTAA AACCGCTGGC GGCCAAAATA GCGGGCTTGC
 951 GGCCTTGCCA ACCTTTGGTA ATGCGGGCAT GGAGATAGGC GGCAAATACT
1001 AGCCAGGTGA TTAGGGCCCG GTACCCAGCT TTTGTTCCCT TTAGTGAGGG
1051 TTAATTTCGA GCTTGGCGTA ATCATGGTCA TAGCTGTTTC CTGTGTGAAA
1101 TTGTTATCCG CTCACAATTC CACACAACAT ACGAGCCGGA AGCATAAAGT
1151 GTAAAGCCTG GGGTGCCTAA TGAGTGAGCT AACTCACATT AATTGCGTTG
1201 CGCTCACTGC CCGCTTTCCA GTCGGGAAAC CTGTCGTGCC AGCTGCATTA
1251 ATGAATCGGC CAACGCGCGG GGAGAGGCGG TTTGCGTATT GGGCGCTCTT
1301 CCGCTTCCTC GCTCACTGAC TCGCTGCGCT CGGTCGTTCG GCTGCGGCGA
1351 GCGGTATCAG CTCACTCAAA GGCGGTAATA CGGTTATCCA CAGAATCAGG
1401 GGATAACGCA GGAAAGAACA TGTGAGCAAA AGGCCAGCAA AAGGCCAGGA
1451 ACCGTAAAAA GGCCGCGTTG CTGGCGTTTT TCCATAGGCT CCGCCCCCCT
1501 GACGAGCATC ACAAAATCG ACGCTCAAGT CAGAGGTGGC GAAACCCGAC
1551 AGGACTATAA AGATACCAGG CGTTTCCCCC TGGAAGCTCC CTCGTGCGCT
```

Figure 6A(1)

```
1601 CTCCTGTTCC GACCCTGCCG CTTACCGGAT ACCTGTCCGC CTTTCTCCCT
1651 TCGGGAAGCG TGGCGCTTTC TCATAGCTCA CGCTGTAGGT ATCTCAGTTC
1701 GGTGTAGGTC GTTCGCTCCA AGCTGGGCTG TGTGCACGAA CCCCCCGTTC
1751 AGCCCGACCG CTGCGCCTTA TCCGGTAACT ATCGTCTTGA GTCCAACCCG
1801 GTAAGACACG ACTTATCGCC ACTGGCAGCA GCCACTGGTA ACAGGATTAG
1851 CAGAGCGAGG TATGTAGGCG GTGCTACAGA GTTCTTGAAG TGGTGGCCTA
1901 ACTACGGCTA CACTAGAAGG ACAGTATTTG GTATCTGCGC TCTGCTGAAG
1951 CCAGTTACCT TCGGAAAAAG AGTTGGTAGC TCTTGATCCG GCAAACAAAC
2001 CACCGCTGGT AGCGGTGGTT TTTTGTTTG CAAGCAGCAG ATTACGCGCA
2051 GAAAAAAGG ATCTCAAGAA GATCCTTTGA TCTTTTCTAC GGGGTCTGAC
2101 GCTCAGTGGA ACGAAAACTC ACGTTAAGGG ATTTTGGTCA TGAGATTATC
2151 AAAAGGATC TTCACCTAGA TCCTTTTAAA TTAAAAATGA AGTTTTAAAT
2201 CAATCTAAAG TATATATGAG TAAACTTGGT CTGACAGTTA CCAATGCTTA
2251 ATCAGTGAGG CACCTATCTC AGCGATCTGT CTATTTCGTT CATCCATAGT
2301 TGCCTGACTC CCCGTCGTGT AGATAACTAC GATACGGGAG GGCTTACCAT
2351 CTGGCCCCAG TGCTGCAATG ATACCGCGAG ACCCACGCTC ACCGGCTCCA
2401 GATTTATCAG CAATAAACCA GCCAGCCGGA AGGGCCGAGC GCAGAAGTGG
2451 TCCTGCAACT TTATCCGCCT CCATCCAGTC TATTAATTGT TGCCGGGAAG
2501 CTAGAGTAAG TAGTTCGCCA GTTAATAGTT TGCGCAACGT TGTTGCCATT
2551 GCTACAGGCA TCGTGGTGTC ACGCTCGTCG TTTGGTATGG CTTCATTCAG
2601 CTCCGGTTCC CAACGATCAA GGCGAGTTAC ATGATCCCCC ATGTTGTGCA
2651 AAAAAGCGGT TAGCTCCTTC GGTCCTCCGA TCGTTGTCAG AAGTAAGTTG
2701 GCCGCAGTGT TATCACTCAT GGTTATGGCA GCACTGCATA ATTCTCTTAC
2751 TGTCATGCCA TCCGTAAGAT GCTTTTCTGT GACTGGTGAG TACTCAACCA
2801 AGTCATTCTG AGAATAGTGT ATGCGGCGAC CGAGTTGCTC TTGCCCGGCG
2851 TCAATACGGG ATAATACCGC GCCACATAGC AGAACTTTAA AAGTGCTCAT
2901 CATTGGAAAA CGTTCTTCGG GGCGAAAACT CTCAAGGATC TTACCGCTGT
2951 TGAGATCCAG TTCGATGTAA CCCACTCGTG CACCCAACTG ATCTTCAGCA
3001 TCTTTTACTT TCACCAGCGT TTCTGGGTGA GCAAAAACAG GAAGGCAAAA
3051 TGCCGCAAAA AAGGGAATAA GGGCGACACG GAAATGTTGA ATACTCATAC
3101 TCTTCCTTTT TCAATATTAT TGAAGCATTT ATCAGGGTTA TTGTCTCATG
3151 AGCGGATACA TATTTGAATG TATTTAGAAA AATAAACAAA TAGGGGTTCC
```

Figure 6A(2)

```
3201 GCGCACATTT CCCCGAAAAG TGCCACCTAA ATTGTAAGCG TTAATATTTT
3251 GTTAAAATTC GCGTTAAATT TTTGTTAAAT CAGCTCATTT TTTAACCAAT
3301 AGGCCGAAAT CGGCAAAATC CCTTATAAAT CAAAGAATA GACCGAGATA
3351 GGGTTGAGTG TTGTTCCAGT TTGGAACAAG AGTCCACTAT TAAAGAACGT
3401 GGACTCCAAC GTCAAAGGGC GAAAAACCGT CTATCAGGGC GATGGCCCAC
3451 TACGTGAACC ATCACCCTAA TCAAGTTTTT TGGGGTCGAG GTGCCGTAAA
3501 GCACTAAATC GGAACCCTAA AGGGAGCCCC CGATTTAGAG CTTGACGGGG
3551 AAAGCCGGCG AACGTGGCGA GAAAGGAAGG GAAGAAAGCG AAAGGAGCGG
3601 GCGCTAGGGC GCTGGCAAGT GTAGCGGTCA CGCTGCGCGT AACCACCACA
3651 CCCGCCGCGC TTAATGCGCC GCTACAGGGC GCGTCCCATT CGCCATTCAG
3701 GCTGCGCAAC TGTTGGGAAG GGCGATCGGT GCGGGCCTCT TCGCTATTAC
3751 GCCAGCTGGC GAAAGGGGGA TGTGCTGCAA GGCGATTAAG TTGGGTAACG
3801 CCAGGGTTTT CCCAGTCACG ACGTTGTAAA ACGACGGCCA GTGAATTGTA
3851 ATACGACTCA CTATAGGGCG AATTGGAGGC CAGTGCTGGA GGAATATGAT
3901 TTTGTCATCC TCGACTGTGC CCTGGTTAT AATCTGTTGA CCCGCAGTGG
3951 CATTGCGGCC AGCGACTTTT ATCTGTTGCC GGCTCGTCCT GAACCCTAT
4001 CGGTGGTGGG GATGCAGTTA CTGGAAAGAA GAATTGAGAA ACTGAAGGAA
4051 AGCCATAAGG CCTCCGATGA TCCCCTGAAT ATCAATCTGA TCGGAGTGGT
4101 GTTTATTCTG TCCGGCGGCG GTTTGATGAG TCGCTACTAT AACCAGGTAA
4151 TGCGGCGGGT ACAAACGGAT TTCACCCCGG GACAACTTTT TCAGCAGTCC
4201 ATTCCCATGG ATGTCAATGT GGCTAAGGCA GTGGATAGCT TTATGCCGGT
4251 GGTTACCTCC ATGCCCAATA CGGCGGGTTC AAAAGCTTTT ATTAAATTAA
4301 CCCAGGAATT TTTACAGAAA GTAGAAGCTT TTGGCTAAAG CAAAGCCCCC
4351 ATTGATTAAC AACGGGAGGG GTACCGAGGT GCTGCTGAAG TTGCCCGCAA
4401 CAGAGAGTGG AACCAACCGG TAGTGCATCT AACGCTTGAG TTAAGCCGCG
4451 CCGCGAAGCG GCGTCGGCTT GAACGAATTG TTAGACATTA TTTGCCGACT
4501 ACCTTGGTGA TCTCGCCTTT CACGTAGTGG ACAAATTCTT CCAACTGATC
4551 TGCGCGCGAG GCCAAGCGAT CTTCTTCTTG TCCAAGATAA GCCTGTCTAG
4601 CTTCAAGTAT GACGGGCTGA TACTGGGCCG GCAGGCGCTC CATTGCCCAG
4651 TCGGCAGCGA CATCCTTCGG CGCGATTTTG CCGGTTACTG CGCTGTACCA
4701 AATGCGGGAC AACGTAAGCA CTACATTTCG CTCATCGCCA GCCCAGTCGG
```

Figure 6A(3)

```
4751 GCGGCGAGTT CCATAGCGTT AAGGTTTCAT TTAGCGCCTC AAATAGATCC
4801 TGTTCAGGAA CCGGATCAAA GAGTTCCTCC GCCGCTGGAC CTACCAAGGC
4851 AACGCTATGT TCTCTTGCTT TTGTCAGCAA GATAGCCAGA TCAATGTCGA
4901 TCGTGGCTGG CTCGAAGATA CCTGCAAGAA TGTCATTGCG CTGCCATTCT
4951 CCAAATTGCA GTTCGCGCTT AGCTGGATAA CGCCACGGAA TGATGTCGTC
5001 GTGCACAACA ATGGTGACTT CTACAGCGCG GAGAATCTCG CTCTCTCCAG
5051 GGGAAGCCGA AGTTTCCAAA AGGTCGTTGA TCAAAGCTCG CCGCGTTGTT
5101 TCATCAAGCC TTACGGTCAC CGTAACCAGC AAATCAATAT CACTGTGTGG
5151 CTTCAGGCCG CCATCCACTG CGGAGCCGTA CAAATGTACG GCCAGCAACG
5201 TCGGTTCGAG ATGGCGCTCG ATGACGCCAA CTACCTCTGA TAGTTGAGTC
5251 GATACTTCGG CGATCACCGC TTCCCTCATG ATGTTTAACT TTGTTTTAGG
5301 GCGACTGCCC TGCTGCGTAA CATCGTTGCT GCTCCATAAC ATCAAACATC
5351 GACCCACGGC GTAACGCGCT TGCTGCTTGG ATGCCCGAGG CATAGACTGT
5401 ACCCCAAAAA AACAGTCATA ACAAGCCATG AAAACCGCCA CTGCGCCGTT
5451 ACCACCGCTG CGTTCGGTCA AGGTTCTGGA CCAGTTGCGT GAGCGCATAC
5501 GCTACTTGCA TTACAGCTTA CGAACCGAAC AGGCTTATGT CCACTGGGTT
5551 CGTGCCTTCA TCCGTTTCCA CGGTGTGCGT CACCCGGCAA CCTTGGGCAG
5601 CAGCGAAGTC GAGGCATTTC TGTCCTGGCT GGCGAACGAG CGCAAGGTTT
5651 CGGTCTCCAC GCATCGTCAG GCATTGGCGG CCTTGCTGTT CTTCTAGACA
5701 AGGCTGCAGT T (SEQ ID NO:11)
```

Figure 6A(4)

```
GTCGACTCTAGAAAGATGCCACTAGCACCAGACGACTAGTTAGCGATAGTCTATCCACCATT
GTTCGTTTTGTAGGTTTTGCTTTTATAGCGATCGGTTTTGTATTTTGCGGTAACTTCATCAA
TTTTTAGGGGCTGGTAATTTTTAACATATCTCACGGGGTGCAATCTTCGCGCCCCTACTAG
TCCATCGAATCGTCATTTCCAACTATTAATATTAAAGTTTAGAGAAATTGGATTATATGTAA
CCTGTACTCTGTTAAGATTCACCATTGGGGTATTCGCTATCAGTCTTGGCGCTACTGCCCAT
CCCGCCCCTCAAACCTTTGTCCGTCCGCCTAAGACTGATACCGCTACTGGTGACAGGCCGAT
GTTATATCTGGAGTTCTATGAATTC (SEQ ID NO:12)
```

Figure 6R

GTCGACTTTTTTGCTGAGGTACTGAGTACACAGCTAATAAAATTGGGCAATCTCCGCGCCTC
TATGACTTGAAGGAGAGTGTAGGGGTATAGGGGAAAGATATCTTTTATCTACATCACATAAA
TAAAAAATTTAATTTGTCGCTCTGGCTGCATATATTGATGTATTTTAGCCATAAGTTTTTT
AGTGCCATGTAATTATAGTGATTTTTAGCGATCGCAGAGCATTTTTCCCTGGATTTATCGCG
ATCTCAAAAAAATTTGCCCGAAGTATGACAGATTGTCATATTGGTGTCGATTTTATTTAA
AATGAAATAAGAAAAATAAAACTACAGGTTAGGAGAACGCCATGAATTC (SEQ ID
NO:13)

Figure 6S

```
   1 ATCGATAATT AATTTTTGCC GAGAAACATA TGTCGACTTT TTTGCTGAGG
  51 TACTGAGTAC ACAGCTAATA AAATTGGGCA ATCTCCGCGC TCTATGACT
 101 TGAAGGAGAG TGTAGGGGTA TAGGGGAAAG ATATCTTTTA TCTACATCAC
 151 ATAAATAAAA AATTTAATTT GTCGCTCTGG CTGCATATAT TGATGTATTT
 201 TTAGCCATAA GTTTTTAGT GCCATGTAAT TATAGTGATT TTTAGCGATC
 251 GCAGAGCATT TTTCCCTGGA TTTATCGCGA TCTCAAAAAA AATTTGCCCG
 301 AAGTATGACA GATTGTCATA TTTGGTGTCG ATTTTATTTA AAATGAAATA
 351 AGAAAAATAA AACTACAGGT TAGGAGAACG CCATGAATTC TTATACTGTC
 401 GGTACCTATT TAGCGGAGCG GCTTGTCCAG ATTGGTCTCA AGCATCACTT
 451 CGCAGTCGCG GGCGACTACA ACCTCGTCCT TCTTGACAAC CTGCTTTTGA
 501 ACAAAAACAT GGAGCAGGTT TATTGCTGTA ACGAACTGAA CTGCGGTTTC
 551 AGTGCAGAAG GTTATGCTCG TGCCAAAGGC GCAGCAGCAG CCGTCGTTAC
 601 CTACAGCGTC GGTGCGCTTT CCGCATTTGA TGCTATCGGT GGCGCCTATG
 651 CAGAAAACCT TCCGGTTATC CTGATCTCCG GTGCTCCGAA CAACAATGAT
 701 CACGCTGCTG GTCACGTGTT GCATCACGCT CTTGGCAAAA CCGACTATCA
 751 CTATCAGTTG GAAATGGCCA AGAACATCAC GGCCGCAGCT GAAGCGATTT
 801 ACACCCCAGA AGAAGCTCCG GCTAAAATCG ATCACGTGAT TAAAACTGCT
 851 CTTCGTGAGA AGAAGCCGGT TTATCTCGAA ATCGCTTGCA ACATTGCTTC
 901 CATGCCCTGC GCCGCTCCTG GACCGGCAAG CGCATTGTTC AATGACGAAG
 951 CCAGCGACGA AGCTTCTTTG AATGCAGCGG TTGAAGAAAC CCTGAAATTC
1001 ATCGCCAACC GCGACAAAGT TGCCGTCCTC GTCGGCAGCA AGCTGCGCGC
1051 AGCTGGTGCT GAAGAAGCTG CTGTCAAATT TGCTGATGCT CTCGGTGGCG
1101 CAGTTGCTAC CATGGCTGCT GCAAAAGCT TCTTCCCAGA AGAAAACCCG
1151 CATTACATCG GTACCTCATG GGGTGAAGTC AGCTATCCGG GCGTTGAAAA
1201 GACGATGAAA GAAGCCGATG CGGTTATCGC TCTGGCTCCT GTCTTCAACG
1251 ACTACTCCAC CACTGGTTGG ACGGATATTC TGATCCTAA GAAACTGGTT
1301 CTCGCTGAAC CGCGTTCTGT CGTCGTTAAC GGCGTTCGCT TCCCCAGCGT
1351 TCATCTGAAA GACTATCTGA CCCGTTTGGC TCAGAAAGTT CCAAGAAAA
1401 CCGGTGCTTT GGACTTCTTC AAATCCCTCA ATGCAGGTGA ACTGAAGAAA
1451 GCCGCTCCGG CTGATCCGAG TGCTCCGTTG GTCAACGCAG AAATCGCCCG
1501 TCAGGTCGAA GCTCTTCTGA CCCCGAACAC GACGGTTATT GCTGAAACCG
1551 GTGACTCTTG GTTCAATGCT CAGCGCATGA AGCTCCCGAA CGGTGCTCGC
1601 GTTGAATATG AAATGCAGTG GGGTCACATC GGTTGGTCCG TTCCTGCCGC
```

Figure 6U(1)

```
1651 CTTCGGTTAT GCCGTCGGTG CTCCGGAACG TCGCAACATC CTCATGGTTG
1701 GTGATGGTTC CTTCCAGCTG ACGGCTCAGG AAGTCGCTCA GATGGTTCGC
1751 CTGAAACTGC CGGTTATCAT CTTCTTGATC AATAACTATG GTTACACCAT
1801 CGAAGTTATG ATCCATGATG GTCCGTACAA CAACATCAAG AACTGGGATT
1851 ATGCCGGTCT GATGGAAGTG TTCAACGGTA ACGGTGGTTA TGACAGCGGT
1901 GCTGGTAAAG GCCTGAAGGC TAAAACCGGT GGCGAACTGG CAGAAGCTAT
1951 CAAGGTTGCT CTGGCAAACA CCGACGGCCC AACCCTGATC GAATGCTTCA
2001 TCGGTCGTGA AGACTGCACT GAAGAATTGG TCAAATGGGG TAAGCGCGTT
2051 GCTGCCGCCA ACAGCCGTAA GCCTGTTAAC AAGCTCCTCT AGTTTTGGG
2101 GATCAATTCG AGCTCGGTAC CCAAACTAGT ATGTAGGGTG AGGTTATAGC
2151 TATGGCTTCT TCAACTTTTT ATATTCCTTT CGTCAACGAA ATGGGCGAAG
2201 GTTCGCTTGA AAAAGCAATC AAGGATCTTA ACGGCAGCGG CTTTAAAAAT
2251 GCGCTGATCG TTTCTGATGC TTTCATGAAC AAATCCGGTG TTGTGAAGCA
2301 GGTTGCTGAC CTGTTGAAAG CACAGGGTAT TAATTCTGCT GTTTATGATG
2351 GCGTTATGCC GAACCCGACT GTTACCGCAG TTCTGGAAGG CCTTAAGATC
2401 CTGAAGGATA ACAATTCAGA CTTCGTCATC TCCCTCGGTG GTGGTTCTCC
2451 CCATGACTGC GCCAAAGCCA TCGCTCTGGT CGCAACCAAT GGTGGTGAAG
2501 TCAAAGACTA CGAAGGTATC GACAAATCTA AGAAACCTGC CCTGCCTTTG
2551 ATGTCAATCA ACACGACGGC TGGTACGGCT TCTGAAATGA CGCGTTTCTG
2601 CATCATCACT GATGAAGTCC GTCACGTTAA GATGGCCATT GTTGACCGTC
2651 ACGTTACCCC GATGGTTTCC GTCAACGATC CTCTGTTGAT GGTTGGTATG
2701 CCAAAAGGCC TGACCGCCGC CACCGGTATG GATGCTCTGA CCCACGCATT
2751 TGAAGCTTAT TCTTCAACGG CAGCTACTCC GATCACCGAT GCTTGCGCCT
2801 TGAAGGCTGC GTCCATGATC GCTAAGAATC TGAAGACCGC TTGCGACAAC
2851 GGTAAGGATA TGCCAGCTCG TGAAGCTATG GCTTATGCCC AATTCCTCGC
2901 TGGTATGGCC TTCAACAACG CTTCGCTTGG TTATGTCCAT GCTATGGCTC
2951 ACCAGTTGGG CGGCTACTAC AACCTGCCGC ATGGTGTCTG CAACGCTGTT
3001 CTGCTTCCGC ATGTTCTGGC TTATAACGCC TCTGTCGTTG CTGGTCGTCT
3051 GAAAGACGTT GGTGTTGCTA TGGGTCTCGA TATCGCCAAT CTCGGTGATA
3101 AGAAGGCGC AGAAGCCACC ATTCAGGCTG TTCGCGATCT GGCTGCTTCC
3151 ATTGGTATTC CAGCAAATCT GACCGAGCTG GGTGCTAAGA AAGAAGATGT
```

Figure 6U(2)

```
3201 GCCGCTTCTT GCTGACCACG CTCTGAAAGA TGCTTGTGCT CTGACCAACC
3251 CGCGTCAGGG TGATCAGAAA GAAGTTGAAG AACTCTTCCT GAGCGCTTTC
3301 TAATTTCAAA ACAGGAAAAC GGTTTTCCGT CCTGTCTTGA TTTTCAAGCA
3351 AACAATGCCT CCGATTTCTA ATCGGAGGCA TTTGTTTTTG TTTATTGCAA
3401 AAACAAAAAA TATTGTTACA AATTTTTACA GGCTATTAAG CCTACCGTCA
3451 TAAATAATTT GCCATTTGGG GATCCCGGTA GAGGGAAACC GTTGTGGTCT
3501 CCCTATAGTG AGTCGTATTA ATTTCGCGGG ATCGAGATCC TTTTTGATAA
3551 TCTCATGACC AAAATCCCTT AACGTGAGTT TTCGTTCCAC TGAGCGTCAG
3601 ACCCCGTAGA AAGATCAAA GGATCTTCTT GAGATCCTTT TTTTCTGCGC
3651 GTAATCTGCT GCTTGCAAAC AAAAAAACCA CCGCTACCAG CGGTGGTTTG
3701 TTTGCCGGAT CAAGAGCTAC CAACTCTTTT TCCGAAGGTA ACTGGCTTCA
3751 GCAGAGCGCA GATACCAAAT ACTGTCCTTC TAGTGTAGCC GTAGTTAGGC
3801 CACCACTTCA AGAACTCTGT AGCACCGCCT ACATACCTCG CTCTGCTAAT
3851 CCTGTTACCA GTGGCTGCTG CCAGTGGCGA TAAGTCGTGT CTTACCGGGT
3901 TGGACTCAAG ACGATAGTTA CCGGATAAGG CGCAGCGGTC GGGCTGAACG
3951 GGGGGTTCGT GCACACAGCC CAGCTTGGAG CGAACGACCT ACACCGAACT
4001 GAGATACCTA CAGCGTGAGC ATTGAGAAAG CGCCACGCTT CCCGAAGGGA
4051 GAAAGGCGGA CAGGTATCCG GTAAGCGGCA GGGTCGGAAC AGGAGAGCGC
4101 ACGAGGGAGC TTCCAGGGGG AAACGCCTGG TATCTTTATA GTCCTGTCGG
4151 GTTTCGCCAC CTCTGACTTG AGCGTCGATT TTTGTGATGC TCGTCAGGGG
4201 GGCGGAGCCT ATGGAAAAAC GCCAGCAACG CGGCCTTTTT ACGGTTCCTG
4251 GCCTTTTGCT GGCCTTTTGC TCACATGTTC TTTCCTGCGT TATCCCCTGA
4301 TTCTGTGGAT AACCGTATTA CCGCCTTTGA GTGAGCTGAT ACCGCTCGCC
4351 GCAGCCGAAC GACCGAGCGC AGCGAGTCAG TGAGCGAGGA AGCGGAAGAG
4401 CGCCTGATGC GGTATTTTCT CCTTACGCAT CTGTGCGGTA TTTCACACCG
4451 CATATGGTGC ACTCTCAGTA CAATCTGCTC TGATGCCGCA TAGTTAAGCC
4501 AGTATACACT CCGCTATCGC TACGTGACTG GGTCATGGCT GCGCCCCGAC
4551 ACCCGCCAAC ACCCGCTGAC GCGCCCTGAC GGGCTTGTCT GCTCCCGGCA
4601 TCCGCTTACA GACAAGCTGT GACCGTCTCC GGGAGCTGCA TGTGTCAGAG
4651 GTTTTCACCG TCATCACCGA AACGCGCGAG GCAGCTGCGG TAAAGCTCAT
4701 CAGCGTGGTC GTGAAGCGAT TCACAGATGT CTGCCTGTTC ATCCGCGTCC
4751 AGCTCGTTGA GTTTCTCCAG AAGCGTTAAT GTCTGGCTTC TGATAAAGCG
4801 GGCCTGCCAC CATACCCACG CCGAAACAAG CGCTCATGAG CCCGAAGTGG
```

Figure 6U(3)

```
4851 CGAGCCCGAT CTTCCCCATC GGTGATGTCG GCGATATCCT CGTGATGATC
4901 AGTGATGGAA AAAGCACTGT AATTCCCTTG GTTTTTGGCT GAAAGTTTCG
4951 GACTCAGTAG ACCTAAGTAC AGAGTGATGT CAACGCCTTC AAGCTAGACG
5001 GGAGGCGGCT TTTGCCATGG TTCAGCGATC GCTCCTCATC TTCAATAAGC
5051 AGGGCATGAG CCAGCGTTAA GCAAATCAAA TCAAATCTCG CTTCTGGGCT
5101 TCAATAAATG GTTCCGATTG ATGATAGGTT GATTCATGCA AGCTTGGAGC
5151 ACAGGATGAC GCCTAACAAT TCATTCAAGC CGACACCGCT TCGCGGCGCG
5201 GCTTAATTCA GGAGTTAAAC ATCATGAGGG AAGCGGTGAT CGCCGAAGTA
5251 TCGACTCAAC TATCAGAGGT AGTTGGCGTC ATCGAGCGCC ATCTCGAACC
5301 GACGTTGCTG GCCGTACATT TGTACGGCTC CGCAGTGGAT GGCGGCCTGA
5351 AGCCACACAG TGATATTGAT TTGCTGGTTA CGGTGACCGT AAGGCTTGAT
5401 GAAACAACGC GGCGAGCTTT GATCAACGAC CTTTTGGAAA CTTCGGCTTC
5451 CCCTGGAGAG AGCGAGATTC TCCGCGCTGT AGAAGTCACC ATTGTTGTGC
5501 ACGACGACAT CATTCCGTGG CGTTATCCAG CTAAGCGCGA ACTGCAATTT
5551 GGAGAATGGC AGCGCAATGA CATTCTTGCA GGTATCTTCG AGCCAGCCAC
5601 GATCGACATT GATCTGGCTA TCTTGCTGAC AAAAGCAAGA GAACATAGCG
5651 TTGCCTTGGT AGGTCCAGCG GCGGAGGAAC TCTTTGATCC GGTTCCTGAA
5701 CAGGATCTAT TTGAGGCGCT AAATGAAACC TTAACGCTAT GGAACTCGCC
5751 GCCCGACTGG GCTGGCGATG AGCGAAATGT AGTGCTTACG TTGTCCCGCA
5801 TTTGGTACAG CGCAGTAACC GGCAAAATCG CGCCGAAGGA TGTCGCTGCC
5851 GACTGGGCAA TGGAGCGCCT GCCGGCCCAG TATCAGCCCG TCATACTTGA
5901 AGCTAGGCAG GCTTATCTTG GACAAGAAGA TCGCTTGGCC TCGCGCGCAG
5951 ATCAGTTGGA AGAATTTGTT CACTACGTGA AGGCGAGAT CACCAAGGTA
6001 GTCGGCAAAT AATGTCTAAC AATTCGTTCA AGCCGACGCC GCTTCGCGGC
6051 GCGGCTTAAC TCAAGCGTTA GAGAGCTGGG GAAGACTATG CGCGATCTGT
6101 TGAAGGTGGT TCTAAGCCTC GTACTTGCGA TGGCATCGGG GCAGGCACTT
6151 GCTGACCTGC CAATTGTTTT AGTGGATGAA GCTCGTCTTC CCTATGACTA
6201 CTCCCCATCC AACTACGACA TTTCTCCAAG CAACTACGAC AACTCCATAA
6251 GCAATTACGA CAATAGTCCA TCAAATTACG ACAACTCTGA GAGCAACTAC
6301 GATAATAGTT CATCCAATTA CGACAATAGT CGCAACGGAA ATCGTAGGCT
6351 TATATATAGC GCAAATGGGT CTCGCACTTT CGCCGGCTAC TACGTCATTG
6401 CCAACAATGG GACAACGAAC TTCTTTTCCA CATCTGGCAA AAGGATGTTC
```

```
6451 TACACCCCAA AAGGGGGGCG CGGCGTCTAT GGCGGCAAAG ATGGGAGCTT
6501 CTGCGGGGCA TTGGTCGTCA TAAATGGCCA ATTTTCGCTT GCCCTGACAG
6551 ATAACGGCCT GAAGATCATG TATCTAAGCA ACTAGCCTGC TCTCTAATAA
6601 AATGTTAGGC CTCAACATCT AGTCGCAAGC TGAGGGAAC CACTAGCAGC
6651 ACGCCATAGT GACTGGCGAT GCTGTCGGAA TGGACGATAT CTAGACTTAT
6701 ATAGACACTA ATATAGACAA TAGTTTATAC TGCTATCTAT ACAAGTATAG
6751 ACATTATCTA ATCATGGCAG ACAAAACTCT AGCCACTTTT CGTATTGACT
6801 CCGAAGAATG GGAGTCTTTT AAAAACCTTG CTAGTTCTGA AGTTCCAAC
6851 GCCTCAGCAC TGTTAACAGA ATTTGTTCGT TGGTATTTGG CAGGTAACAG
6901 GTTAATACT CCCACTTCTC ACACTCCCAC CCATCTAGAC ACATCCCTCG
6951 AACAGCGTAT AGACAATATT GAACAACGTC TAGATAAAGT CACAACTAAT
7001 AATCTAGACA ATATAGATGA ATTTATAGAC AAGCGTATAG AAGATAATCT
7051 AGCAACACGT CTAGACAAAC TTCAATCGCA ACTGGAGGAA CTGCGGGGAA
7101 AATCGAAAGC CCGGTAGTTC AGGCAGAAGG ACAAGCTACC GGGCAAGACA
7151 GAAAGAATAT AGACAATAGT ATAGACAATC TAGCAAATT GGAGGCAACC
7201 CGCGATCGCA CCCTCAATAA GCTAAAAATG GGTAGGCAGT CAGCCGCCGG
7251 GAAAGCCATC GACGCGTTTA TCAAAGAGTT GCTTCTTCA GGAGACAACA
7301 TAAGCTGAAG TTATCAAAAT TCTGTCCTTA CGTCGAAAGC CTGATTTTAC
7351 CGTGCAACGA TTGATAAGCT TGGCTAAACT AGCACTGGCT TTCAACAGAA
7401 AGCATACGAA GAATCAATAG ATATAGCCAC CAATTCCACA AAATGCAGAT
7451 AACGTGTAGA GTATTGGAAT GCTTAATCTG TAAGGGTTAT GAAGGTTAAC
7501 GGCAACGGAC GAGCCAAAAT ACTCACCTCC GACGAACTCA GGCGACTGTT
7551 TAGCGACGGA TTCACCACAC CGCGCGATCG CGTTTTGTTT GGCATCTGTC
7601 TATTCACCGG TTGCCGCGTT AGTGAAGCTC TAGCACTCCA ACAACGGAC
7651 ATTAAAGGCG AAACACTAAC CTTTAGGAAG TCTACCACCA AAGGGAAACT
7701 CAAAACCCGC GTGGTTGACA TCCAGCCAGG ACTAGCCGCA CTCATGGCTG
7751 ACTATCACCC CAAACCGGGA ACCCTGTTCC CTGGCATGAG GGGAGTCAGC
7801 GATAGGCTCA CGCGATACGC GGCGGATAAA ATCTTGCGCG ATGCAGCCAA
7851 AAGAATCGGG CTAGAAGGCA TCAGTACCCA CAGTTTCCGC CGTACTGCCC
7901 TCAACCAAAT GTCTAGCGCC GGTATCCCGT TGCGACACAT TCAAGAGATA
7951 TCCGGTCACA ATGACCTTGG CACACTGCAA CGCTATCTTG AAGTTACACC
8001 CGAACAGCGA CGCAAAGCTG TATCCGTGAT TGGCTTCTAA TGTACGCCAA
```

Figure 6U(5)

```
8051 CGCTGTTTAG ACCCCTATGG GTGCTAAAAA AAGACGCAGC CTAAACACAC
8101 GCTCTACACT TGAGGATACT TTTAAAGTAT CCATCGGTTC TAGAACTCTG
8151 CACACGTTCC GGACTTTGGA AACGTTATAC CTTTCCCTGT GTTGCAGAAT
8201 GCTGCAATAT TTCTTCGACA AGTTAACTTG TGACTGGTTT AATATTTTCT
8251 CAAATTGCCC CAAAACAACA CGCCTAAATC CTTAGACGTT TCTGTGGAAA
8301 CCTATTAGGT TTTTATCGCC GTTGTTTTAG TGGTAAACCC AAAGGGTTTG
8351 TATATTCTTG TATGAAGTTC GACTCTGAGG GTTAAGAAGA ATGGCTCGCC
8401 GAATTTTTTA CAAGTGGAAA CCGATTAAAG GTTAAGGGTC AATCGGGACG
8451 ATGAATATTT TCTAATTGTG ACCTTCTCCA TCTAATAAGC TTTCTTTGGG
8501 GTTAAGGTCG AAGAAAGTAC TACGCATGAT CTGCATACGA TCTCTATTGC
8551 CAAAAAGCCG CGACCCTATA GGCTCTCGGT CATGCTGCAC TAGTTCGTGT
8601 CGATCACTAT ACTGGTTGCC GCAGCATTTC ACGCTAAAAA AAAATTCTTA
8651 AAAATGTCCT TCATATCTCG CCAGAGTGGC AACCTATTAC AAAACGGTTG
8701 CCTACCCGAC CGGCTCGATT TTCGCTGAAG TGGCACTGTG ACAGTTTGAA
8751 ATGGTACTTC CGCCGTGCTG CTGACATCGT TGTTAGGGTG AATTGTTCGC
8801 GGTAGATGTT GCACCGATTC ATGAACACCT TGTCACCCAC TTTGAATAAT
8851 CGACCGTCAA ATTCAGTCGC GTCAATTTGG TAAGTGTTGG GCTGTCTCTT
8901 TTTGGCTCCA GGGGCAATGC CATCAGAAAA CACAACCGCG TCACCCATAA
8951 CTTGATAACC GATATCAGTT TTGGTTCCAG TGAAAGCCCA AAATTCAGAC
9001 GCGTCATTAT TCCGAGCGTG CCGGAGTTGA TTGTACTCAA TTTTGGCTTG
9051 GCAAAGTTGA CGGCGATTCA TGCCCAGCTG CTTTTGATGT CGTCGCACTG
9101 TGCGCTTGTG AATACCCAAC TCACAGCTGA CAGCTTTTTG AGATGTACCA
9151 TAGTGGATGA AACTTTTTGA CACGAATATC CGCGACGAAC TAATGTGAAG
9201 TACACAAGGT ACTTCCCCCT CTGGCGATTT AAGAGAGGAT TGCCTTGTGT
9251 CCTTCACTAG CTCGTTCGGG TGTGGCGCTC CAAAAAGTTT TCTGTACTCT
9301 GGTTTAAGTT GTCTGTTGGC CGCATAGCGG CTCTTTTGTT GAAAGCTTTG
9351 TGTGACTATG CCAGTGGTCA GTGAGCGTAA ATCGCTTAAC ACTTGGACTA
9401 AAGGCACTAC TGCAACATCA CCCCATCTTT TTAAATTTAG GTTGTAACAA
9451 ACTTGAAACA TACCGCCCAA GTAGACGGTT ATCATTCCTG CTTTAATTTT
9501 GTAGCGGCGG AATGCTCCTA TTTTTTTTCC ATCCTGTAAC CAACGGTAAA
9551 CAGACTTATC ACTACAATCT AAGAACGTCT GTACTACAGG CAATGGCAAT
9601 GTTAAATGAC CAGACCCATC CTTATCAAGC GCTCGACACA AATACCACAA
```

Figure 6U(6)

```
 9651 CCGCGCACAA GGTTCTCGAC CAATGCGAGT GTGTACCCTG ACCGTGTAAG
 9701 TGCCAAGAAT TATTTCAGTT TGTAGTTCCC TTGTAAGCAG GGTTAGTGAT
 9751 ACATTTGTAT TTAAGCTTTC TGGGCTGATC ATTTGGAAAT GTCTCAGTCC
 9801 AGTACCTATT GAATGTTATT TGCTTAACCT GAAGCTAAAT AAAACTTGTT
 9851 AACTACACCC ATTAATTGAT AAATTCAAAG CACGTTTTTT CTGTTTGGTG
 9901 TTTGGTGTGG TAACAATTCT GTGTATGTGT GTTTATTTA GCTTCGGTTA
 9951 AGTAGCATAA CAACCCCCAA GCACTGAACT TTTTTAATA GGTAATTTAA
10001 ACTTTGCCTA TCGGCAAAAT TTTCAATCAA TTGTACGCCA AGTGTTGCA
10051 TGATCAACGT TTGACTTATT TTTGTATTTA CTAAATACTG AATTTCGCCG
10101 TGACGCTTTT TACAGATGGA AATTCACGGC AAAATGTTTT TTGCTAACTT
10151 TGCTATGTAA AACAAGAAAC TTGGCACTCG GTTATTACTA ATAAACTGG
10201 TAAAAAATAA CCATTAGAAC CAAAAGAAC GAAAACCAGT ACACCCTTGC
10251 CAGTTTTCAA GCTTTTGCTA TGACGACTCT AATAATCGGG TTTAACACCA
10301 TTCCGCTTTG AGAAAATTAT CCTTGTACAG CAAGTAACAG TCAATGCTAA
10351 ACCGCACCGC TACAAATCCT TAAGTTTTTC CAGTAGCGAT TTACCTTCTT
10401 GGTAACGCCC GCCTTGATAG CCCAAAATTT CTTAATCAC CTTACTTTCT
10451 GAAAAACCCG CTTCCAGACA GGCTTTTACC ACTTTTGCTA GGGTTTCATC
10501 TCTTGGTTCT GGGAGGGATG AAACGGGCTG TAATGCTTGT TCTGAGGTCG
10551 GTTGAGCCGT TTGGAGTGGC TGAAAACTGG TTACAGACTG TAACCGGGGC
10601 ATAACCATTT TGTAACTGCT TACATCTGGT AACTGACACG GCATATCATC
10651 CACCATGCAG CGATATTTCC CCGACTTTAA CCACTCCACA AGGGCAAGGT
10701 CTTTTAAGGA CTTGGCGTGG CTAACTGCAA ACTTACCCAG GCGTAACATC
10751 CTAAAACACT TACGGACACC GCCTTCACCC TCGATACCTA AGGTCTTGAC
10801 ATTATCATCT TGAGTCAGCC CAATAACAAA ACGCTTGGGC TTGCGGCCGC
10851 GCCTGGCGTG TTTGATGAGC CATTCGGTTG CTATCTCGAC TTCATCTCTC
10901 AGCAGTGGCA GTTCTTCAGC AATTAAAACG CTTTCTTTTC CTGCTAGTGC
10951 CTTATCCCCA GACTCACCCC GTAGCTCAAT CCGGCGCTGC AATTCCTCCA
11001 GGTCAGCAGC CATGCCCGAC TGTATAGCCT CAAAGTCACC ACGGCGGCCA
11051 ATGACATTTA ACCCCGTCCA CTCGTCCGGT GCAGCGTCAG CGTCATAGAC
11101 TGTCACCTCA CCCCCGACTT GATAAGCAAG CCATTGGGCT ATGGTGCTTT
11151 TGCCAGTTCC CGTATCCCCA ACTATTAAAC AGTGCTTACC AGACAGAGCT
11201 TGCATCAAGT CGGTGATGAT TCCCTCTGGT TCGACCGCAA GGGTGACGGC
```

Figure 6U(7)

```
11251 GGTAGTGTCA ATGATAGCCG CGCCGTAAGT GCCAGCATAG GGCAATTGGT
11301 CGTAAACTTT GACCAAGTTG TATACAGACT GTCTACACCA CTTCACCACT
11351 GTTAACGCTG TTTGCAAAGC GTAAGACGTG GCATCAAATA AAAATATGCT
11401 GGCACTAAAA GTTAATCGCC CCAATCCCCA CAGTAAAAAC CTGCCTAGCT
11451 GTTGACGACT AGGCAAGTGC ATTTCAATCC AGTCATTTGC CATAAATCAC
11501 CCCGTCTTTA AAGCCTTGCA GTTGAGCGCG ACAGGTATTT AACTGTGCTT
11551 GTAACTCTGT TTGCTGGTTT TGATACCACA GACTGACGGC GGCGGCCGCC
11601 AGTCCTAAAA ATAGAAACTG GCGATCGCTC ATTATTGACT TACTCCCTGT
11651 TGATTAGCGT GGTAGTGAGT CATAGCCGCA TTGACCGCTT CTTGGGCTTG
11701 GGGTGTTCTG CCAAGATTGG GTTTTGTAGG GTCATCGTTG GCTACGACTA
11751 AGGACGCTTG TTCGGCTATC GCTTGCGGGA CACCAACTTT AGTTAACTCT
11801 GTCAAGGATA CTTGGTAAAG TCGCTCGTTC ATTAGCCGAT CTCCGGTAC
11851 ATAAAACTGT TGCTGGCAGT CCCTTCATTG GCGACGAGTT CTTCAGCCGG
11901 AGTATCAGCG ATAATGTCAG CCCAGCCGGT GACATTATTA TTAATAATGT
11951 TTTGTTCGGC AATTGCACCC AAGCCAGGAC GCGCCGTTTC AAACTCAGAG
12001 ATGACTTGCT GCTCTTTCTC GGTGAGTGGT CTATCTGTCA TGATAATTAT
12051 GTCCTTCATT ATGTAGGCGA TTCCAGTGGG TGTTTACGAG GCAGTCCACA
12101 GGAATCAGTG CGATTCACCT TTAAGGTGAA TCGTCATCAA AAAATCACTC
12151 GGTAGCAACG ACCCGAACCG ACCAGGATTG ATTTCCCGGT CTCAGTTCG
12201 CAGGCTTTTG AGCGCGTCAC CTTGACCATT GGGTAACTGC CATCAGCCGA
12251 TAAGCTAAAC GGGCTGTATA GCGGTAAAGC ATCCCACACA GTCGGGCTGG
12301 CATCAACTTT GCAGGAATAG CTCACGTCAC TCATCTCACT CGCGCCTGGG
12351 TTGGATGGCA GCGAAGGCAG ATTACGACGC AGTTTTTTAC TGGCACTTTT
12401 ACCCGCATTA AAACGGGTA CAGTGCCATT GTTGACGGTC TGTACTTCGG
12451 TCATATACTC GGTGTACACT TAATACACTC TATACTATTA CTGCCGATTA
12501 GTACATTTGT CAATCACTCT TTGCACAAGG TGTATGATAT GGACTCAGGA
12551 GTACACCAAA CGTCATGCCA ACCAATAAAG GGAGAATAGC AGTCACTCTA
12601 GAAGCTGAAA TTTACCAATG GATTGCTAAC CGAGCGTCTG AGGAAGGAAG
12651 ACCGTTGGCT AATCTTGCCG CTTTCTTACT CACACGAGTT GTTAAAGAAC
12701 AAATGGAACA AGAAGCCAAG GACAACCAAG ACAAGCAGGG GGCAGCATGA
12751 GCGAAGACAG ACTAGCCAGA ATAGAAGCTG CGTTAGACAG CCAAGTTGCA
12801 GTGAATGCCG ACCTCCGCAC ATCGGTTACA GAACTCCGCG CAACCGCAGA
```

Figure 6U(8)

```
12851 AGCATTGTTG CAAACAGTTC AAATCCATCA GCAGAACTTT GAAATTCTTA
12901 CCGCTAGGCA ATTACAAACC GAAGCACGGC TTGATGAGTA CCAACGTACC
12951 ACTAGCGCGG CACTCGACAG AATTGGCGCG GTCTTAGACT ACCTCGTTAG
13001 GCAGCAAAAC GGTTGAGGTG AGGGATGAGC GATGACTATC TAGACGGATA
13051 TCCCGCAAGA GGCCCTTTCG TCTTCAAGAA TTCTCATGTT TGACAGCTTA
13101 TC (SEQ ID NO:14)
```
Figure 6U(9)

```
   1 CTAGCGCTAT ATGCGTTGAT GCAATTTCTA TGCGCACCCG TTCTCGGAGC
  51 ACTGTCCGAC CGCTTTGGCC GCCGCCCAGT CCTGCTCGCT TCGCTACTTG
 101 GAGCCACTAT CGACTACGCG ATCATGGCGA CCACACCCGT CCTGTGGATC
 151 ACTACCGGGC GTATTTTTG AGTTATCGAG ATTTTCAGGA GCTAAGGAAG
 201 CTAAAATGGA GAAAAAATC ACTGGATATA CCACCGTTGA TATATCCCAA
 251 TGGCATCGTA AGAACATTT TGAGGCATTT CAGTCAGTTG CTCAATGTAC
 301 CTATAACCAG ACCGTTCAGC TGGATATTAC GGCCTTTTTA AAGACCGTAA
 351 AGAAAAATAA GCACAAGTTT TATCCGGCCT TTATTCACAT TCTTGCCCGC
 401 CTGATGAATG CTCATCCGGA ATTCCGTATG GCAATGAAAG ACGGTGAGCT
 451 GGTGATATGG GATAGTGTTC ACCCTTGTTA CACCGTTTTC CATGAGCAAA
 501 CTGAAACGTT TTCATCGCTC TGGAGTGAAT ACCACGACGA TTTCCGGCAG
 551 TTTCTACACA TATATTCGCA AGATGTGGCG TGTTACGGTG AAAACCTGGC
 601 CTATTTCCCT AAAGGGTTTA TTGAGAATAT GTTTTCGTC TCAGCCAATC
 651 CCTGGGTGAG TTTCACCAGT TTTGATTTAA ACGTGGCCAA TATGGACAAC
 701 TTCTTCGCCC CCGTTTTCAC CATGGGCAAA TATTATACGC AAGGCGACAA
 751 GGTGCTGATG CCGCTGGCGA TTCAGGTTCA TCATGCCGTT TGTGATGGCT
 801 TCCATGTCGG CAGAATGCTT AATGAATTAC AACAGTACTG CGATGAGTGG
 851 CAGGGCGGGG CGTAATTTTT TTAAGGCAGT TATTGGTGCC CTTAAACGCC
 901 TGGTGCTACG CCTGAATAAG TGATAATAAG CGGATGAATG CAGAAATTC
 951 GAAAGCAAAT TCGACCCGGT CGTCGGTTCA GGGCAGGGTC GTTAAATAGC
1001 CGCTTATGTC TATTGCTGGT TTACCGGTTT ATTGACTACC GGAAGCAGTG
1051 TGACCGTGTG CTTCTCAAAT GCCTGAGGCC AGTTTGCTCA GGCTCTCCCC
1101 GTGGAGGTAA TAATTGACGA TATGATCCTC TACGCCGGAC GCATCGTGGC
1151 CGGCATCACC GGCGATAAGC TTCACGCTGC CGCAAGCACT CAGGGCGCAA
1201 GGGCTGCTAA AGGAAGCGGA ACACGTAGAA AGCCAGTCCG CAGAAACGGT
1251 GCTGACCCCG GATGAATGTC AGCTACTGGG CTATCTGGAC AAGGGAAAAC
1301 GCAAGCGCAA AGAGAAAGCA GGTAGCTTGC AGTGGGCTTA CATGGCGATA
1351 GCTAGACTGG GCGGTTTTAT GGACAGCAAG CGAACCGGAA TTGCCAGCTG
1401 GGGCGCCCTC TGGTAAGGTT GGGAAGCCCT GCAAAGTAAA CTGGATGGCT
1451 TTCTTGCCGC CAAGGATCTG ATGGCGCAGG GGATCAAGAT CTGATCAAGA
1501 GACAGGATGA GGATCGTTTC GCATGATTGA ACAAGATGGA TTGCACGCAG
1551 GTTCTCCGGC CGCTTGGGTG GAGAGGCTAT TCGGCTATGA CTGGGCACAA
1601 CAGACAATCG GCTGCTCTGA TGCCGCCGTG TTCCGGCTGT CAGCGCAGGG
```

Figure 6W(1)

```
1651 GCGCCCGGTT CTTTTTGTCA AGACCGACCT GTCCGGTGCC CTGAATGAAC
1701 TGCAGGACGA GGCAGCGCGG CTATCGTGGC TGGCCACGAC GGGCGTTCCT
1751 TGCGCAGCTG TGCTCGACGT TGTCACTGAA GCGGGAAGGG ACTGGCTGCT
1801 ATTGGGCGAA GTGCCGGGGC AGGATCTCCT GTCATCTCAC CTTGCTCCTG
1851 CCGAGAAAGT ATCCATCATG GCTGATGCAA TGCGGCGGCT GCATACGCTT
1901 GATCCGGCTA CCTGCCCATT CGACCACCAA GCGAAACATC GCATCGAGCG
1951 AGCACGTACT CGGATGGAAG CCGGTCTTGT CGATCAGGAT GATCTGGACG
2001 AAGAGCATCA GGGGCTCGCG CCAGCCGAAC TGTTCGCCAG GCTCAAGGCG
2051 CGCATGCCCG ACGGCGAGGA TCTCGTCGTG ACCCATGGCG ATGCCTGCTT
2101 GCCGAATATC ATGGTGGAAA ATGGCCGCTT TTCTGGATTC ATCGACTGTG
2151 GCCGGCTGGG TGTGGCGGAC CGCTATCAGG ACATAGCGTT GGCTACCCGT
2201 GATATTGCTG AAGAGCTTGG CGGCGAATGG GCTGACCGCT TCCTCGTGCT
2251 TTACGGTATC GCCGCTCCCG ATTCGCAGCG CATCGCCTTC TATCGCCTTC
2301 TTGACGAGTT CTTCTGAGCG GGACTCTGGG GTTCGAAATG ACCGACCAAG
2351 CGACGCCCAA CCTGCCATCA CGAGATTTCG ATTCCACCGC CGCCTTCTAT
2401 GAAAGGTTGG GCTTCGGAAT CGTTTTCCGG GACGCCGGCT GGATGATCCT
2451 CCAGCGCGGG GATCTCATGC TGGAGTTCTT CGCCCACCCC AACGATCTGA
2501 TAGAGAAGGG TTTGCTCGGG TCGGTGGCTC TGGTAACGAC CAGTATCCCG
2551 ATCCCGGCTG GCCGTCCTGG CCGCCACATG AGGCATGTTC CGCGTCCTTG
2601 CAATACTGTG TTTACATACA GTCTATCGCT TAGCGGAAAG TTCTTTTACC
2651 CTCAGCCGAA ATGCCTGCCG TTGCTAGACA TTGCCAGCCA GTGCCCGTCA
2701 CTCCCGTACT AACTGTCACG AACCCCTGCA ATAACTGTCA CGCCCCCCTG
2751 CAATAACTGT CACGAACCCC TGCAATAACT GTCACGCCCC CAAACCTGCA
2801 AACCCAGCAG GGGCGGGGGC TGGCGGGGTG TTGGAAAAAT CCATCCATGA
2851 TTATCTAAGA ATAATCCACT AGGCGCGGTT ATCAGCGCCC TTGTGGGGCG
2901 CTGCTGCCCT TGCCCAATAT GCCCGGCCAG AGGCCGGATA GCTGGTCTAT
2951 TCGCTGCGCT AGGCTACACA CCGCCCCACC GCTGCGCGGC AGGGGGAAAG
3001 GCGGGCAAAG CCCGCTAAAC CCCACACCAA ACCCCGCAGA AATACGCTGG
3051 AGCGCTTTTA GCCGCTTTAG CGGCCTTTCC CCTACCCGA AGGGTGGGGG
3101 CGCGTGTGCA GCCCCGCAGG GCCTGTCTCG GTCGATCATT CAGCCCGGCT
3151 CATCCTTCTG GCGTGGCGGC AGACCGAACA AGGCGCGGTC GTGGTCGCGT
3201 TCAAGGTACG CATCCATTGC CGCCATGAGC CGATCCTCCG GCCACTCGCT
3251 GCTGTTCACC TTGGCCAAAA TCATGGCCCC CACCAGCACC TTGCGCCTTG
```

```
3301 TTTCGTTCTT GCGCTCTTGC TGCTGTTCCC TTGCCCGCTC CCGCTGAATT
3351 TCGGCATTGA TTCGCGCTCG TTGTTCTTCG AGCTTGGCCA GCCGATCCGC
3401 CGCCTTGTTG CTCCCCTTAA CCATCTTGAC ACCCCATTGT TAATGTGCTG
3451 TCTCGTAGGC TATCATGGAG GCACAGCGGC GGCAATCCCG ACCCTACTTT
3501 GTAGGGGAGG GCGCACTTAC CGGTTTCTCT TCGAGAAACT GGCCCTAACG
3551 GCCACCCTTC GGGCGGTGCG CTCTCGAGG GCCATTGCAT GGAGCCGAAA
3601 AGCAAAAGCA ACAGCGAGGC AGCATGGCGA TTTATCACCT TACGGCGAAA
3651 ACCGGCAGCA GGTCGGGCGG CCAATCGGCC AGGGCCAAGG CCGACTACAT
3701 CCAGCGCGAA GGCAAGTATG CCCGCGACAT GGATGAAGTC TTGCACGCCG
3751 AATCCGGGCA CATGCCGGAG TTCGTCGAGC GGCCCGCCGA CTACTGGGAT
3801 GCTGCCGACC TGTATGAACG CGCCAATGGG CGGCTGTTCA GGAGGTCGA
3851 ATTTGCCCTG CCGGTCGAGC TGACCCTCGA CCAGCAGAAG GCGCTGGCGT
3901 CCGAGTTCGC CCAGCACCTG ACCGGTGCCG AGCGCCTGCC GTATACGCTG
3951 GCCATCCATG CCGGTGGCGG CGAGAACCCG CACTGCCACC TGATGATCTC
4001 CGAGCGGATC AATGACGGCA TCGAGCGGCC CGCCGCTCAG TGGTTCAAGC
4051 GGTACAACGG CAAGACCCCG GAGAAGGGCG GGGCACAGAA GACCGAAGCG
4101 CTGAAGCCCA AGGCATGGCT TGAGCAGACC CGCGAGGCAT GGGCCGACCA
4151 TGCCAACCGG GCATTAGAGC GGGCTGGCCA CGACGCCCGC ATTGACCACA
4201 GAACACTTGA GGCGCAGGGC ATCGAGCGCC TGCCCGGTGT TCACCTGGGG
4251 CCGAACGTGG TGGAGATGGA AGGCCGGGGC ATCCGCACCG ACCGGGCAGA
4301 CGTGGCCCTG AACATCGACA CCGCCAACGC CCAGATCATC GACTTACAGG
4351 AATACCGGGA GGCAATAGAC CATGAACGCA ATCGACAGAG TGAAGAAATC
4401 CAGAGGCATC AACGAGTTAG CGGAGCAGAT CGAACCGCTG GCCCAGAGCA
4451 TGGCGACACT GGCCGACGAA GCCCGGCAGG TCATGAGCCA GACCAAGCAG
4501 GCCAGCGAGG CGCAGGCGGC GGAGTGGCTG AAAGCCCAGC GCCAGACAGG
4551 GGCGGCATGG GTGGAGCTGG CCAAAGAGTT GCGGGAGGTA GCCGCCGAGG
4601 TGAGCAGCGC CGCGCAGAGC GCCCGGAGCG CGTCGCGGGG GTGGCACTGG
4651 AAGCTATGGC TAACCGTGAT GCTGGCTTCC ATGATGCCTA CGGTGGTGCT
4701 GCTGATCGCA TCGTTGCTCT TGCTCGACCT GACGCCACTG ACAACCGAGG
4751 ACGGCTCGAT CTGGCTGCGC TTGGTGGCCC GATGAAGAAC GACAGGACTT
4801 TGCAGGCCAT AGGCCGACAG CTCAAGGCCA TGGGCTGTGA GCGCTTCGAT
4851 ATCGGCGTCA GGGACGCACC CACCGGCCAG ATGATGAACC GGGAATGGTC
```

Figure 6W(3)

```
4901 AGCCGCCGAA GTGCTCCAGA ACACGCCATG GCTCAAGCGG ATGAATGCCC
4951 AGGGCAATGA CGTGTATATC AGGCCCGCCG AGCAGGAGCG GCATGGTCTG
5001 GTGCTGGTGG ACGACCTCAG CGAGTTTGAC CTGGATGACA TGAAAGCCGA
5051 GGGCCGGGAG CCTGCCCTGG TAGTGGAAAC CAGCCCGAAG AACTATCAGG
5101 CATGGGTCAA GGTGGCCGAC GCCGCAGGCG GTGAACTTCG GGGGCAGATT
5151 GCCCGGACGC TGGCCAGCGA GTACGACGCC GACCCGGCCA GCGCCGACAG
5201 CCGCCACTAT GGCCGCTTGG CGGGCTTCAC CAACCGCAAG GACAAGCACA
5251 CCACCCGCGC CGGTTATCAG CCGTGGGTGC TGCTGCGTGA ATCCAAGGGC
5301 AAGACCGCCA CCGCTGGCCC GGCGCTGGTG CAGCAGGCTG GCCAGCAGAT
5351 CGAGCAGGCC CAGCGGCAGC AGGAGAAGGC CCGCAGGCTG GCCAGCCTCG
5401 AACTGCCCGA GCGGCAGCTT AGCCGCCACC GGCGCACGGC GCTGGACGAG
5451 TACCGCAGCG AGATGGCCGG GCTGGTCAAG CGCTTCGGTC ATGACCTCAG
5501 CAAGTGCGAC TTTATCGCCG CGCAGAAGCT GGCCAGCCGG GGCCGCAGTG
5551 CCGAGGAAAT CGGCAAGGCC ATGGCCGAGG CCAGCCCAGC GCTGGCAGAG
5601 CGCAAGCCCG GCCACGAAGC GGATTACATC GAGCGCACCG TCAGCAAGGT
5651 CATGGGTCTG CCCAGCGTCC AGCTTGCGCG GGCCGAGCTG GCACGGGCAC
5701 CGGCACCCCG CCAGCGAGGC ATGGACAGGG GCGGGCCAGA TTTCAGCATG
5751 TAGTGCTTGC GTTGGTACTC ACGCCTGTTA TACTATGAGT ACTCACGCAC
5801 AGAAGGGGGT TTTATGGAAT ACGAAAAAAG CGCTTCAGGG TCGGTCTACC
5851 TGATCAAAAG TGACAAGGGC TATTGGTTGC CCGGTGGCTT TGGTTATACG
5901 TCAAACAAGG CCGAGGCTGG CCGCTTTTCA GTCGCTGATA TGGCCAGCCT
5951 TAACCTTGAC GGCTGCACCT TGTCCTTGTT CCGCGAAGAC AAGCCTTTCG
6001 GCCCCGGCAA GTTTCTCGGT GACTGATATG AAAGACCAAA AGGACAAGCA
6051 GACCGGCGAC CTGCTGGCCA GCCCTGACGC TGTACGCCAA GCGCGATATG
6101 CCGAGCGCAT GAAGGCCAAA GGGATGCGTC AGCGCAAGTT CTGGCTGACC
6151 GACGACGAAT ACGAGGCGCT GCGCGAGTGC CTGGAAGAAC TCAGAGCGGC
6201 GCAGGGCGGG GGTAGTGACC CCGCCAGCGC CTAACCACCA ACTGCCTGCA
6251 AAGGAGGCAA TCAATGGCTA CCCATAAGCC TATCAATATT CTGGAGGCGT
6301 TCGCAGCAGC GCCGCCACCG CTGGACTACG TTTTGCCCAA CATGGTGGCC
6351 GGTACGGTCG GGGCGCTGGT GTCGCCCGGT GGTGCCGGTA ATCCATGCT
6401 GGCCCTGCAA CTGGCCGCAC AGATTGCAGG CGGGCCGGAT CTGCTGGAGG
6451 TGGGCGAACT GCCCACCGGC CCGGTGATCT ACCTGCCCGC CGAAGACCCG
```

Figure 6W(4)

```
6501 CCCACCGCCA TTCATCACCG CCTGCACGCC CTTGGGGCGC ACCTCAGCGC
6551 CGAGGAACGG CAAGCCGTGG CTGACGGCCT GCTGATCCAG CCGCTGATCG
6601 GCAGCCTGCC CAACATCATG GCCCCGGAGT GGTTCGACGG CCTCAAGCGC
6651 GCCGCCGAGG GCCGCCGCCT GATGGTGCTG GACACGCTGC GCCGGTTCCA
6701 CATCGAGGAA GAAAACGCCA GCGGCCCCAT GGCCCAGGTC ATCGGTCGCA
6751 TGGAGGCCAT CGCCGCCGAT ACCGGGTGCT CTATCGTGTT CCTGCACCAT
6801 GCCAGCAAGG GCGCGGCCAT GATGGGCGCA GGCGACCAGC AGCAGGCCAG
6851 CCGGGGCAGC TCGGTACTGG TCGATAACAT CCGCTGGCAG TCCTACCTGT
6901 CGAGCATGAC CAGCGCCGAG GCCGAGGAAT GGGGTGTGGA CGACGACCAG
6951 CGCCGGTTCT TCGTCCGCTT CGGTGTGAGC AAGGCCAACT ATGGCGCACC
7001 GTTCGCTGAT CGGTGGTTCA GGCGGCATGA CGGCGGGGTG CTCAAGCCCG
7051 CCGTGCTGGA GAGGCAGCGC AAGAGCAAGG GGGTGCCCCG TGGTGAAGCC
7101 TAAGAACAAG CACAGCCTCA GCCACGTCCG GCACGACCCG GCGCACTGTC
7151 TGGCCCCCGG CCTGTTCCGT GCCCTCAAGC GGGGCGAGCG CAAGCGCAGC
7201 AAGCTGGACG TGACGTATGA CTACGGCGAC GGCAAGCGGA TCGAGTTCAG
7251 CGGCCCGGAG CCGCTGGGCG CTGATGATCT GCGCATCCTG CAAGGGCTGG
7301 TGGCCATGGC TGGGCCTAAT GGCCTAGTGC TTGGCCCGGA ACCCAAGACC
7351 GAAGGCGGAC GGCAGCTCCG GCTGTTCCTG GAACCCAAGT GGGAGGCCGT
7401 CACCGCTGAA TGCCATGTGG TCAAAGGTAG CTATCGGGCG CTGGCAAAGG
7451 AAATCGGGGC AGAGGTCGAT AGTGGTGGGG CGCTCAAGCA CATACAGGAC
7501 TGCATCGAGC GCCTTTGGAA GGTATCCATC ATCGCCCAGA ATGGCCGCAA
7551 GCGGCAGGGG TTTCGGCTGC TGTCGGAGTA CGCCAGCGAC GAGGCGGACG
7601 GGCGCCTGTA CGTGGCCCTG AACCCCTTGA TCGCGCAGGC CGTCATGGGT
7651 GGCGGCCAGC ATGTGCGCAT CAGCATGGAC GAGGTAGCGG CGCTGGACA
7701 GCGAAACCGC CCGCCTGCTG CACCAGCGGC TGTGTGGCTG GATCGACCCC
7751 GGCAAAACCG GCAAGGCTTC CATAGATACC TTGTGCGGCT ATGTCTGGCC
7801 GTCAGAGGCC AGTGGTTCGA CCATGCGCAA GCGCCGCAAG CGGGTGCGCG
7851 AGCGTTGCCG GAGCTGGTCG CGCTGGGCTG ACGGTAACC GAGTTCGCGG
7901 CGGGCAAGTA CGACATCACC CGGCCCAAGG CGGCAGGCTG ACCCCCCCCA
7951 CTCTATTGTA AACAACACAT TTTTATCTTT TATATTCAAT GGCTTATTTT
8001 CCTGCTAATT GGTAATACCA TGAAAAATAC CATGCTCAGA AAAGGCTTAA
8051 CAATATTTTG AAAAATTGCC TACTGAGCGC TGCCGCACAG CTCCATAGGC
```

Figure 6W(5)

```
8101 CGCTTTCCAG GCTTTGCTTC CAGATGTATG CTCTTCTGCT CCTGCAGTTC
8151 ATTCAGGGCA CCGGACAGGT CGGTCTTGAC AAAAAGAACC GGGCGCCCCT
8201 GCGCTGACAG CCGGAACACG GCGGCATCAG AGCAGCCGAT TGTCTGTTGT
8251 GCCCAGTCAT AGCCGAATAG CCTCTCCACC CAAGCGGCCG GAGAACCTGC
8301 GTGCAATCCA TCTTGTTCAA TCATGCGAAA CGATCCTCAT CCTGTCTCTT
8351 GATCATTGAT CCCCTGCGCC ATCAGATCCT TGGCGGCAAG AAAGCCATCC
8401 AGTTTACTTT GCAGGGCTTC CCAACCTTAC CAGAGGGCGC CCCAGCTGGC
8451 AATTCCGGTT CGCTTGCTGT CCATAAAACC GCCCAGTCTA GCTATCGCCA
8501 TGTAAGCCCA CTGCAAGCTA CCTGCTTTCT CTTTGCGCTT GCGTTTTCCC
8551 TTGTCCAGAT AGCCCAGTAG CTGACATTCA TCCGGGGTCA GCACCGTTTC
8601 TGCGGACTGG CTTTCTACGT GTTCCGCTTC CTTTAGCAGC CCTTGCGCCC
8651 TGAGTGCTTG CGGCAGCGTG AAGCTTATCG ATTCACAAAA ATAGGCACA
8701 CGAAAAACAA GTTAAGGGAT GCAGTTTATG CACTAGCCTA GGCTCGAGAA
8751 GCTTGTCGAC CTTCCAGCAC CACGTCAACT TTGTTAACT GCTCCCGGAG
8801 TTGTCTTTCC GCTTTGGCAA TGTGCCCGGG ATACCATTGG ATTAAAGCCA
8851 TGAGTTGTTC ACTTTTTTAC TGACGAGGGC TTCCGGAGGC CACGCTCCCA
8901 CCCATAACAG CTTGCCACAT CCCCGTCGGA AGTTACGTTA CCCTTGGGCG
8951 ATCGCCAAAA ATCAGCATAT ATACACCAAT TCTAAATAAG ATCTTTTACA
9001 CCGCTACTGC AATCAACCTC ATCAACAAAA TTCCCCTCTA GCATCCCTGG
9051 AGGCAAATCC TCACCTGGCC ATGGGTTCAA CCCTGCTTAA CATTTCTTAA
9101 TAATTTTAGT TGCTATAAAT TCTCATTTAT GCCCCTATAA TAATTCGGGA
9151 GTAAGTGCTA AAGATTCTCA ACTGCTCCAT CAGTGGTTTG AGCTTAGTCC
9201 TAGGGAAAGA TTGGCGATCG CCGTTGTGGT TAAGCCAGAA TAGGTCTCGG
9251 GTGGACAGAG AACGCTTTAT TCTTTGCCTC CATGGCGGCA TCCCACCTAG
9301 GTTCTCGGC ACTTATTGCC ATAATTATT ATTTGTCGTC TCAATTAAGG
9351 AGGCAATTCT GTGAATTCTT ATACTGTCGG TACCTATTTA GCGGAGCGGC
9401 TTGTCCAGAT TGGTCTCAAG CATCACTTCG CAGTCGCGGG CGACTACAAC
9451 CTCGTCCTTC TTGACAACCT GCTTTTGAAC AAAAACATGG AGCAGGTTTA
9501 TTGCTGTAAC GAACTGAACT GCGGTTTCAG TGCAGAAGGT TATGCTCGTG
9551 CCAAAGGCGC AGCAGCAGCC GTCGTTACCT ACAGCGTCGG TGCGCTTTCC
9601 GCATTTGATG CTATCGGTGG CGCCTATGCA GAAAACCTTC CGGTTATCCT
9651 GATCTCCGGT GCTCCGAACA ACAATGATCA CGCTGCTGGT CACGTGTTGC
```

Figure 6W(6)

```
9701  ATCACGCTCT TGGCAAAACC GACTATCACT ATCAGTTGGA AATGGCCAAG
9751  AACATCACGG CCGCAGCTGA AGCGATTTAC ACCCCAGAAG AAGCTCCGGC
9801  TAAAATCGAT CACGTGATTA AAACTGCTCT TCGTGAGAAG AAGCCGGTTT
9851  ATCTCGAAAT CGCTTGCAAC ATTGCTTCCA TGCCCTGCGC CGCTCCTGGA
9901  CCGGCAAGCG CATTGTTCAA TGACGAAGCC AGCGACGAAG CTTCTTTGAA
9951  TGCAGCGGTT GAAGAAACCC TGAAATTCAT CGCCAACCGC GACAAAGTTG
10001 CCGTCCTCGT CGGCAGCAAG CTGCGCGCAG CTGGTGCTGA AGAAGCTGCT
10051 GTCAAATTTG CTGATGCTCT CGGTGGCGCA GTTGCTACCA TGGCTGCTGC
10101 AAAAAGCTTC TTCCCAGAAG AAAACCCGCA TTACATCGGT ACCTCATGGG
10151 GTGAAGTCAG CTATCCGGGC GTTGAAAAGA CGATGAAAGA AGCCGATGCG
10201 GTTATCGCTC TGGCTCCTGT CTTCAACGAC TACTCCACCA CTGGTTGGAC
10251 GGATATTCCT GATCCTAAGA AACTGGTTCT CGCTGAACCG CGTTCTGTCG
10301 TCGTTAACGG CGTTCGCTTC CCCAGCGTTC ATCTGAAAGA CTATCTGACC
10351 CGTTTGGCTC AGAAAGTTTC CAAGAAAACC GGTGCTTTGG ACTTCTTCAA
10401 ATCCCTCAAT GCAGGTGAAC TGAAGAAAGC CGCTCCGGCT GATCCGAGTG
10451 CTCCGTTGGT CAACGCAGAA ATCGCCCGTC AGGTCGAAGC TCTTCTGACC
10501 CCGAACACGA CGGTTATTGC TGAAACCGGT GACTCTTGGT CAATGCTCA
10551 GCGCATGAAG CTCCCGAACG GTGCTCGCGT TGAATATGAA ATGCAGTGGG
10601 GTCACATCGG TTGGTCCGTT CCTGCCGCCT TCGGTTATGC CGTCGGTGCT
10651 CCGGAACGTC GCAACATCCT CATGGTTGGT GATGGTTCCT TCCAGCTGAC
10701 GGCTCAGGAA GTCGCTCAGA TGGTTCGCCT GAAACTGCCG GTTATCATCT
10751 TCTTGATCAA TAACTATGGT TACACCATCG AAGTTATGAT CCATGATGGT
10801 CCGTACAACA ACATCAAGAA CTGGGATTAT GCCGGTCTGA TGGAAGTGTT
10851 CAACGGTAAC GGTGGTTATG ACAGCGGTGC TGGTAAGGC CTGAAGGCTA
10901 AAACCGGTGG CGAACTGGCA GAAGCTATCA AGGTTGCTCT GGCAAACACC
10951 GACGGCCCAA CCCTGATCGA ATGCTTCATC GGTCGTGAAG ACTGCACTGA
11001 AGAATTGGTC AAATGGGGTA AGCGCGTTGC TGCCGCCAAC AGCCGTAAGC
11051 CTGTTAACAA GCTCCTCTAG TTTTTGGGGA TCAATTCGAG CTCGGTACCC
11101 AAACTAGTAT GTAGGGTGAG GTTATAGCTA TGGCTTCTTC AACTTTTTAT
11151 ATTCCTTTCG TCAACGAAAT GGGCGAAGGT TCGCTTGAAA AAGCAATCAA
11201 GGATCTTAAC GGCAGCGGCT TTAAAAATGC GCTGATCGTT TCTGATGCTT
11251 TCATGAACAA ATCCGGTGTT GTGAAGCAGG TTGCTGACCT GTTGAAAGCA
```

Figure 6W(7)

```
11301 CAGGGTATTA ATTCTGCTGT TTATGATGGC GTTATGCCGA ACCCGACTGT
11351 TACCGCAGTT CTGGAAGGCC TTAAGATCCT GAAGGATAAC AATTCAGACT
11401 TCGTCATCTC CCTCGGTGGT GGTTCTCCCC ATGACTGCGC CAAAGCCATC
11451 GCTCTGGTCG CAACCAATGG TGGTGAAGTC AAAGACTACG AAGGTATCGA
11501 CAAATCTAAG AAACCTGCCC TGCCTTTGAT GTCAATCAAC ACGACGGCTG
11551 GTACGGCTTC TGAAATGACG CGTTCTGCA TCATCACTGA TGAAGTCCGT
11601 CACGTTAAGA TGGCCATTGT TGACCGTCAC GTTACCCCGA TGGTTTCCGT
11651 CAACGATCCT CTGTTGATGG TTGGTATGCC AAAAGGCCTG ACCGCCGCCA
11701 CCGGTATGGA TGCTCTGACC CACGCATTTG AAGCTTATTC TTCAACGGCA
11751 GCTACTCCGA TCACCGATGC TTGCGCCTTG AAGGCTGCGT CCATGATCGC
11801 TAAGAATCTG AAGACCGCTT GCGACAACGG TAAGGATATG CCAGCTCGTG
11851 AAGCTATGGC TTATGCCCAA TTCCTCGCTG GTATGGCCTT CAACAACGCT
11901 TCGCTTGGTT ATGTCCATGC TATGGCTCAC CAGTTGGGCG GCTACTACAA
11951 CCTGCCGCAT GGTGTCTGCA ACGCTGTTCT GCTTCCGCAT GTTCTGGCTT
12001 ATAACGCCTC TGTCGTTGCT GGTCGTCTGA AGACGTTGG TGTTGCTATG
12051 GGTCTCGATA TCGCCAATCT CGGTGATAAA GAAGGCGCAG AAGCCACCAT
12101 TCAGGCTGTT CGCGATCTGG CTGCTTCCAT TGGTATTCCA GCAAATCTGA
12151 CCGAGCTGGG TGCTAAGAAA GAAGATGTGC CGCTTCTTGC TGACCACGCT
12201 CTGAAAGATG CTTGTGCTCT GACCAACCCG CGTCAGGGTG ATCAGAAAGA
12251 AGTTGAAGAA CTCTTCCTGA GCGCTTTCTA ATTTCAAAAC AGGAAAACGG
12301 TTTTCCGTCC TGTCTTGATT TTCAAGCAAA CAATGCCTCC GATTTCTAAT
12351 CGGAGGCATT TGTTTTTGTT TATTGCAAAA ACAAAAAATA TTGTTACAAA
12401 TTTTTACAGG CTATTAAGCC TACCGTCATA AATAATTTGC CATTTGGGGA
12451 TCCGATACGT AACGCGTCTG CA (SEQ ID NO:15)
```

Figure 6W(8)

| node | organism | taxanomy | accession | protein |
|---|---|---|---|---|
| Subclade A | | | | |
| Aca.ma_YP_001519107 | Acaryochloris marina MBIC11017 | Cyanobacteria | YP_001519107.1 | Zinc-containing alcohol dehydrogenase family protein |
| Cce7424_YP_002380432 | Cyanothece sp. PCC 7424 | Cyanobacteria | YP_002380432.1 | Alcohol dehydrogenase GroES domain protein |
| Cce7424_ZP_02976085 | Cyanothece sp. PCC 7424 | Cyanobacteria | ZP_02976085.1 | Alcohol dehydrogenase GroES domain protein |
| Cce7822_ZP_03154326 | Cyanothece sp. PCC 7822 | Cyanobacteria | ZP_03154326.1 | Alcohol dehydrogenase GroES domain protein |
| Cce8801_YP_002371662 | Cyanothece sp. PCC 8801 | Cyanobacteria | YP_002371662.1 | Alcohol dehydrogenase GroES domain protein |
| Cce8801_ZP_02941996 | Cyanothece sp. PCC 8801 | Cyanobacteria | ZP_02941996.1 | Alcohol dehydrogenase GroES domain protein |
| Cce8802_ZP_03143898 | Cyanothece sp. PCC 8802 | Cyanobacteria | ZP_03143898.1 | Alcohol dehydrogenase GroES domain protein |
| Mic.ch7420_EDX77810 | Microcoleus chthonoplastes PCC 7420 | Cyanobacteria | EDX77810.1 | Alcohol dehydrogenase GroES-like domain family |
| Mic.aeNIES843_YP_001659961 | Microcystis aeruginosa NIES-843 | Cyanobacteria | YP_001659961.1 | uncharacterized zinc-type alcohol dehydrogenase-like protein |
| Mic.ae7806_CAO90817 | Microcystis aeruginosa PCC 7806 | Cyanobacteria | CAO90817.1 | unnamed protein product |
| Subclade B | | | | |
| LimnoMED105_ZP_01914609 | Limnobacter sp. MED105 | Betaproteobacteria | ZP_01914609.1 | Alcohol dehydrogenase, zinc-binding protein |
| Syn6803_NP_443028 | Synechocystis sp. PCC 6803 | Cyanobacteria | NP_443028.1 | zinc-containing alcohol dehydrogenase family protein |

Figure 11B(1)

| Name | Organism | Class | Accession | Description |
|---|---|---|---|---|
| Alt.ma_YP_002126870 | Alteromonas macleodii 'Deep ecotype' | Gammaproteobacteria | YP_002126870.1 | zinc-containing alcohol dehydrogenase family protein |
| OceanRED65_ZP_01306627 | Oceanobacter sp. RED65 | Gammaproteobacteria | ZP_01306627.1 | zinc-containing alcohol dehydrogenase family protein |
| Psy.crK5_YP_581659 | Psychrobacter cryohalolentis K5 | Gammaproteobacteria | YP_581659.1 | alcohol dehydrogenase GroES-like protein |
| Sac.de_YP_529423 | Saccharophagus degradans 2-40 | Gammaproteobacteria | YP_529423.1 | zinc-containing alcohol dehydrogenase family protein |
| Ver.ba_EDY84203 | Verrucomicrobiae bacterium DG1235 | Verrucomicrobia | EDY84203.1 | Alcohol dehydrogenase GroES-like domain family |

Subclade C

| Name | Organism | Class | Accession | Description |
|---|---|---|---|---|
| ScoRS9916_ZP_01472751 | Synechococcus sp. RS9916 | Cyanobacteria | ZP_01472751.1 | zinc-containing alcohol dehydrogenase superfamily protein |
| Sco9917_ZP_01079933 | Synechococcus sp. RS9917 | Cyanobacteria | ZP_01079933.1 | Zinc-containing alcohol dehydrogenase superfamily protein |
| Sco5701_ZP_01085101 | Synechococcus sp. WH 5701 | Cyanobacteria | ZP_01085101.1 | Zinc-containing alcohol dehydrogenase superfamily protein |
| Sco7803_YP_001224538 | Synechococcus sp. WH 7803 | Cyanobacteria | YP_001224538.1 | Zn-dependent alcohol dehydrogenases |
| Sco7805_ZP_01125148 | Synechococcus sp. WH 7805 | Cyanobacteria | ZP_01125148.1 | zinc-containing alcohol dehydrogenase superfamily protein |

Figure 11B(2)

```
MIKAYAALEANGKLQPFEYDPGALGANEVEIEVQYCGVCHSDLSMINNEWGISNYPLVPGHE
VVGTVAAMGEGVNHVEVGDLVGLGWHSGYCMTCHSCLSGYHNLCATAESTIVGHYGGFGDRV
RAKGVSVVKLPKGIDLASAGPLFCGGITVFSPMVELSLKPTAKVAVIGIGGLGHLAVQFLRA
WGCEVTAFTSSARKQTEVLELGAHHILDSTNPEAIASAEGKFDYIISTVNLKLDWNLYISTL
APQGHFHFVGVVLEPLDLNLFPLLMGQRSVSASPVGSPATIATMLDFAVRHDIKPVVEQFSF
DQINEAIAHLESGKAHYRVVLSHSKN   (SEQ ID NO:16)
```

Figure 11C

```
MIKAFAADTAKGELKPFEYEVGELGSQEVEIEVHYCGVCHSDISMLDNEWGMTQYPFVPGHE
VAGLIKQVGAEVNHLKVGDRVGLGWQSGYCNHCENCMSGDHNLCGTAEMTIVGRHGGFADHV
RAQASSVVKLPDDIHMADAGPLFCGGVTVYNPMKQFDLKPTAKVAVIGIGGLGHMALQFLNS
WGCEVTAFTSTEEKRKEAIALGAHKTLNSRDEGELKGAAGSFDMIISTVNVSLNWEAYINTL
KAKGRLHFVGAVLEPIQVGVFPLMMGQRSISASPVGSPSTISQMLEFTARHQIKPQVELFQK
DQINDAINHVREGKARYRAVIQFKATSDNSA    (SEQ ID NO:17)
```

Figure 11D

```
MELIMINAYAAFEAKGPLKPFQYDPGELNAFDIEIDVDHCGICHSDVSMLDNDWGRAKYPMV
AGHEIIGRVSQVGSHVSHLAIGDVVGLGWHSGYCESCRMCMGGDHNLCSTAKGTIVGRHGGF
ADKVRAQAVSAVKIPAGVNPATAGPLLCGGITVYNPLVQFNISPQSKVAVIGVGGLGHMAVM
FLKAWGCEVTAFSSNVSKTDELLGMGAHHVLNSKDPDALKKAAGSFDLILSTVNVKLDWNAY
IGTLAPKGRLHFLGAVLEPLDIGVFGLMGQQRSISSSPVGSPRVIADMLKFAALHNIQPIVE
TYSFDQINEAVDKVRNGSPRFRVVLSR    (SEQ ID NO:18)
```

Figure 11E

```
MINAYAAKEKGGEFVPYQYDPGTLGDHEVEIEVHSCGICHSDLSMWQNEWGMTQYPFVGGHE
VAGKVLAKGKHVKHLELGDKVGLGWHKGYCNVCDLCIGGDHNLCPEQEGTIIGNHGGFADKV
RAKDTSVIKIPEGLDFNAVGPLLCGGVTVFNPLMQYDITPTSRVAVIGIGGLGHLALQFANA
WGCEVTAFTSESKMEEAKEMGAHHSLNSREDSEIEKAAGSFDLIISTVNVDMNWDVVIKTLR
PKGKLHFVGLLEAPLEISAAPMIMAQNSLSGSPVGSPSTLRKMLDFAARHNIQPVTETYKMS
EINEAFERLESGNARYRVVLERD    (SEQ ID NO:19)
```

Figure 11F

```
MIKAYATHTPGGKLEPFEYDPGELAPTDVEINVEHCGICHSDLSMLNNEWGMTTYPFVPGHE
VVGTIGAIGSDVKNLAPGQRVGLGWHSSYCTTCPSCLSGDHNLCQAAAGTIVGRHGGFADKV
RASALSVIPLPDSIDAAKAGPLFCGGITVFNPLIQYEVSPTAKVAVIGIGGLGHMALAFLNA
WGCEVTAFTTSEAKRQEALKLGAHHTLNSRDAAEIEAAAGRFDLILSTVNVGLDWNGYVNTL
KPKGRLHFLGAALEPIQIGAFSLIMAQRQISGSPVGSPATIAKMIEFAALHKIEPVTEHFKF
DQANEALAHLESGQARYRIVLSH (SEQ ID NO:20)
```

Figure 11G

```
MIKAYAAMEPGAALVPFEYEPGPLANNEVELKVESCGICHSDLSMLDNEWGFTQYPFVGGHE
VIGIVEAVGSSVNNVAVGQRVGLGWHSGYCNTCASCQSGDQNLCNSAQPTIAGHHGGFADKV
RADANAVVALPEGVNPDSAGPLFCGGITVFNPLVQFGIKPTSKVGVIGIGGLGHIALQFLNA
WGCEVTAFTSSESKKEEALKLGAHHVLNSSDAAQLEAAAGRFDFIISTVNVKLDWNEYLATL
APKGRLHFVGATLAPLDINVFQLIGSQREISGSPVGSPGTISQMLDFAALHNIQPVTEYFRF
DQINEALTKLREGKAHYRIVLTNK   (SEQ ID NO:21)
```

Figure 11H

```
MIYAYAAKEAGGKLEKFEYDPGELGAHDVEIDVESCGICHSDLSMLDNEWGITEFPFVPGHE
VVGTVSKIGDHVTSLKVGQRVGLGWHASYCNSCRTCEAGDHNLCAGATMTIGGRHGGFADKV
RAQARAVIPLPESIDSTKAGPLFCGGITVFNPLVQFNISPTSEVGVVGIGGLGHLALQFLNA
WGCKVVAFTSSESKEKEALSLGASETINSRDEDEIKKAQGRFDLIISTVNVKLDWNLYLSTL
APKGRLHFVGATLEPLDIGAFNLIGGQKSVSGSPVGSPATIKTMLDFAAHHDIEPVTETFKF
EDVNKAIDRLREGKAHYRIVLTR   (SEQ ID NO:22)
```

Figure 11I

```
MVNAYAAFEQGGVLQPFEYDPGPLGRQQVDIQVEYCGICHSDLSMIKNEWGMTQYPFVPGHE
IVGIVAEIGSEVTTLRVGQRVGLGWYSSSCMHCEWCMGGDHHLCLSAEGTIVGRPGGFADQV
RADQSWIVPIPESIDSAVAGPLFCAGITVFQPIIQCGVQPTDRVAVIGIGGLGHLALQFLNA
WGCEVTALSTQPDKEAEARRLGAHHFVNTRDPAALQAIANSCDYIISTVNVSLEWSIYLNAL
RPKGRLHLVGVAPDLSLPVFPLLAGQRSISGSPVGSPATITKMLNFVARHGLAPQTEVFPLA
QVNEALEKLRSQHPPYRLALKC   (SEQ ID NO:23)
```

Figure 11J

```
MIRAYAAHEPGGKLEPFEYEPGSLGDEEVDIKVEYCGICHSDLSMLKNDWGMTQYPFVPGHE
VVGVVEAVGSKVKNLQIGQKVGLGWYSRSCMTCEFCMSGNHNLCQDAEGTIVGRYGGFAEKV
RAHQGWVIPLPEGVNPVTAGPLFCGGITVFNPIVQFNIKPTDQVGVIGIGGLGHMALGFLRA
WGCEITAFSTSPDKEAEAKALGATHFVNSRDPEALKALTNSFDVILSTVNADLDWPTYIKLL
RPQGRLHLVGVIPNPLSVPIFPMILGQKSVSASPLGSPTTIAQMLNFAGRHHLEPIVEFFPL
EQVNEALERLQSNKARYRIILKMDH   (SEQ ID NO:24)
```

Figure 11K

MIRAYAAHEPGGKLEPFEYEPGSLGDEEVDIKVEYCGICHSDLSMLKNDWGMTQYPFVPGHE
VVGVVEAVGSKVKNLQIGQKVGLGWYSRSCMTCEFCMSGNHNLCQDAEGTIVGRYGGFAEKV
RAHQGWVIPLPEGVNPVTAGPLFCGGITVFNPIVQFNIKPTDQVGVIGIGGLGHMALGFLRA
WGCEITAFSTSPDKEAEAKALGATHFVNSRDPEALKALTNSFDVILSTVNADLDWPTYIKLL
RPQGRLHLVGVIPNPLSVPIFPMILGQKSVSASPLGSPTTIAQMLNFAGRHHLEPIVEFFPL
EQVNEALERLQSNKARYRIILKMDH    (SEQ ID NO:25)

Figure 11L

```
MIRAYAAHEPGGKLEPFEYDPGSLGDEDVEIQVEYCGICHSDLSMLNNEWGMTRYPFVPGHE
VVGTINAVGERVKHLQVGQRVGLGWYSRSCMTCEWCLSGNQNLCPQAEGTIVGRYGGFAEKV
RAHQGWVLPLPEKLNPLTAGPLFCGGITVFNPIVQFDVKPTDRVGVIGIGGLGHMALGFLAA
WGCEITAFSTSPDKEIEAKNLGANHFVNSRDPQALKALANSLDLILSTVNADLDWDTYISLL
RPKGRLHFVGVIPNPLSVQLFPLIGGQKSVSGSPLGSPVTLAQMLNFAGRHHVEPVVEFYPI
EQVNEAMERLKANKARYRIVLTFKNS    (SEQ ID NO:26)
```

Figure 11M

```
MIKAYAASEPGKELNSFEYDPGLLGEEDVEINVQYCGICHSDLSMLDNEWGITQYPFVPGHE
VVGTIGAVGSKVTTFQVGQTVGLWFSRSCFDCEWCLSGDQNLCQTAEGTIVGRPGGFADKV
RAHHRWVVPLPSGVNPETAGPLFCGGITVFNPIIQCGVKSTDRVGVIGIGGLGHLAIEFLHA
WGCEVTAFSSNPEKESEVKQLGADYFVNSRDPEAIKAVENSFDFIISTVNVSLDWNSYILAL
RPRGTLHFVGAVLNPISTQIFPLLMGQKTISGSPTGSPTTIAQMLDFAARHQIEPVTEIFPF
EQVNEAIDKLRHGQPRYRLVLKM   (SEQ ID NO:27)
```

Figure 11N

```
MRGERIVRSGVKEDILCNNAINTTIEVKVVIKAYAASEPGKELNSFEYDPGLLGEEDVEINV
QYCGICHSDLSMLDNEWGITQYPFVPGHEVVGTIGAVGSKVTTFQVGQTVGLGWFSRSCFDC
EWCLSGDQNLCQTAEGTIVGRPGGFADKVRAHHRWVVPLPSGVNPETAGPLFCGGITVFNPI
IQCGVKSTDRVGVIGIGGLGHLAIEFLHAWGCEVTAFSSNPEKESEVKQLGADYFVNSRDPE
AIKAVENSFDFIISTVNVSLDWNSYILALRPRGTLHFVGAVLNPISTQIFPLLMGQKTISGS
PTGSPTTIAQMLDFAARHQIEPVTEIFPFEQVNEAIDKLRHGQPRYRLVLKM   (SEQ ID
NO:28)
```

Figure 110

```
MRGERIVRSGVKEDILCNNAINTTIEVKVVIKAYAASEPGKELNSFEYDPGLLGEEDVEINV
QYCGICHSDLSMLDNEWGITQYPFVPGHEVVGTIGAVGSKVTTFQVGQTVGLGWFSRSCFDC
EWCLSGDQNLCQTAEGTIVGRPGGFADKVRAHHRWVVPLPSGVNPETAGPLFCGGITVFNPI
IQCGVKSTDRVGVIGIGGLGHLAIEFLHAWGCEVTAFSSNPEKESEVKQLGADYFVNSRDPE
AIKAVENSFDFIISTVNVSLDWNSYILALRPRGTLHFVGAVLNPISTQIFPLLMGQKTISGS
PTGSPTTIAQMLDFAARHQIEPVTEIFPFEQVNEAIDKLRHGQPRYRLVLKM   (SEQ ID
NO:29)
```

Figure 11P

```
MIKAYAAHEPGGQLQPFEYDPGTLGDEEVEIKVEYCGICHSDLSMLDNEWGMTDYPFVPGHE
VVGTIAALGDKVTTLNLGQRVGLGWFSGSCMTCEWCMSGNHNLCSNAEGTIVSRHGGFADKV
RADYSWVVPLPDGINPATAGPLFCGGITVFNPIVQFDIKPSDRVGVIGIGGLGHIALGFLQA
WGCEITAFSSSPDKEAEARELGATHFINSGDVNALESVQNSFDFILATANADLDWNAYIAAL
RPKGRLHFVGVIPNPLSTPIFPLILGQKSISASPVGSPATISQMINFAARQGVEPITETFSF
EQVNEAMEKLRHGKPRYRLVLKHS   (SEQ ID NO:30)
```

Figure 11Q

```
MIRAYAAREKGGKLEPFDYDPGILADEDVEIAVEYCGICHSDLSMLDNDWGLTTYPFVPGHE
VVGTIAALGAKVKELKLGQRVGLGWFSRSCSTCETCMSGDQNLCATAEGTIVGRHGGFADRV
RAHHSWLVPLGNQLDAAKAGPLFCGGITVFNPIVQFNIKPTARVGVIGIGGLGHIALKFLKA
WGCEVTAFSSSPDKETEAKELGATHFINSRDPEALQSVQNYFDFIISTVNVNLDWGLYIACL
RPKGRLHIVGAVLEPMATYAFPLIMGQKSISGSPLGSPSTINKMIEFASRHGIEPVTEIYPI
SQVNEAMEKLRTGQPKYRLVLQIK    (SEQ ID NO:31)
```

Figure 11R

```
MIRAYAAQEKGGKLEPFDYDPGILADEDVEIAVEYCGICHSDLSMLDNDWGLTTYPFVPGHE
VVGTIAALGAKVKELKLGQRVGLGWFSRSCSTCETCMSGDQNLCATAEGTIVGRHGGFAERV
RAHHSWLVPLPDQLDAAKAGPLFCGGITVFNPIVQFNIKPTARVGVIGIGGLGHIALKFLKA
WGCEVTAFSSSPDKETEAKELGATHFINSRDPEALQSVQNYFDFIISTVNVNLDWGLYIACL
RPKGRLHIVGAVLEPMATYAFPLIMGQKSISGSPLGSPSTVSKMIEFASRHGIEPVTETYPI
SRVNEAMEKLRTGQPKYRLVLQIK    (SEQ ID NO:32)
```

Figure 11S

```
MQITVWQALAKGGRLERSQATLLDPGPDEVLLEVLHCGLCHSDLSMLDNSWGISTYPLVPGH
EVVGRVAAVGAGVDSGLLGSIQGLGWIAGSCRHCDWCLGGNANLCPSLEASVVGRHGGFASH
VMAHQDWIVAIPDGVSAADAGPLFCGGITVFAPLFDEAVSPTSRVAVIGIGGLGHMALQFAR
AWGCEVTAVTTSPAKADEARRLGAHRVLALSELGDHPGVFDLIINTSNHDLDWPALIGSLAP
LGRLHQLGVPLSPLQIPAFPLIAGRRSVTGSPTSSPASLRRMVEFCARHGIAPLVEHLPMAE
INTAIERLRQGDVRYRFVLDGPA    (SEQ ID NO:33)
```

Figure 11T

```
MVVTITVWQAREAGAPLERAERAMLEPAAGELVLEVLHCGLCHSDLSMLDNNWGLSAYPLVP
GHEVVGRVVRVGEGVDPGVIGELRGLGWISGSCMHCALCLGGTANLCGSLEATIVGRQGGFA
SHVTARQDWAIRLPEGMDPAAAGPLFCGGITVFAPLVDEVVSPTAHVAVIGIGGLGHMALQF
ARAWGCEVTALTTHLAKAEEEAKRFGAHHVESLEELPDLAGRFDLVINTVNHALDWGAVMGSL
APLGRLHQLGAVLEPLQVSAFDLIMARRSITGSPTSSPASLMKMVEFCVRHNIRPQVEHLPM
DRLNEAIDRLRRGDVRYRFVLDSVAD (SEQ ID NO:34)

Figure 11U
```

```
MQITVWQALAKGGRLERSQATLLDPGPDEVLLEVLHCGLCHSDLSMLDNSWGISTYPLVPGH
EVVGRVAAVGAGVDSGLLGSIQGLGWIAGSCRHCDWCLGGNANLCPSLEASVVGRHGGFASH
VMAHQDWIVAIPDGVSAADAGPLFCGGITVFAPLFDEAVSPTSRVAVIGIGGLGHMALQFAR
AWGCEVTAVTTSPAKADEARRLGAHRVLALSELGDHPGVFDLIINTSNHDLDWPALIGSLAP
LGRLHQLGVPLSPLQIPAFPLIAGRRSVTGSPTSSPASLRRMVEFCARHGIAPLVEHLPMAE
INTAIERLRQGDVRYRFVLDGPA   (SEQ ID NO:35)
```

Figure 11V

```
MISVWQAPSAGAPLECGQRPAPEPAADELVLEVMHCGLCHSDLSMIGNHWGVSRYPLVPGHE
VIGRVTAVGEGVDPGLIGDVRGLGWISGSCNHCSLCLGGDQNLCTSLEATIVGRQGGFASHV
VARQDWAIPLPPGLDPADAGPLFCGGITVFAPLVDEAVSPTAHVAVVGIGGLGHIALQFARA
WGCEVTAITTNLAKAEQARRFGAHHVEELEMLPDLQSRFDLVINTVNHPLDWSAVMASLRPR
GRLHQLGAVLEPIQVGAFDLIPARRSITGSPTSSPASLQKMVEFCVRHNILPLVEHLPMDQV
NVAIQRLAKGDVRYRFVLDA    (SEQ ID NO:36)
```

Figure 11W

```
MISVWQAPSAGAPLECAQRPALQPVADELVLEVMHCGLCHSDLSMIGNHWGVSRYPLVPGHE
VIGRVTAVGEGVDPGVIGEVRGLGWISGSCNHCSLCLGGDQNLCSSLEATIVGRQGGFASHV
VARQDWTIPLPTGLDPAEAGPLFCGGVTVFAPLVDEAVSPTAHVAVVGIGGLGHIALQFARA
WGCEVTAITTNPAKTEQARRFGAHHVEELEALSDLQRRFDLVINTVNHPLDWSAVMASLKPR
GRLHQLGAVLEPIQVGAFDLISARRSITGSPTSSPASLLKMVEFCVRHNILPLVEHLPMDQV
NVAIERLAKGDVRYRFVLDA    (SEQ ID NO:37)

Figure 11X
```

| shaked Erlenmeyer flask (time course in days) | 0 | 5 | 6 | 7 | 9 | 12 | 13 | 14 | 15 | 16 | 19 |
|---|---|---|---|---|---|---|---|---|---|---|---|
| EtOH % (v/v) | | | | | | | | | | | |
| 6803-PisiA-ZmPDC-ADHII | 0 | 0,0172 | 0,021 | 0,026 | 0,0384 | 0,0429 | 0,0407 | 0,0401 | 0,0401 | 0,0354 | 0,0304 |
| 6803-PisiA-ZmPDC | 0 | 0,0216 | 0,0247 | 0,0303 | 0,0422 | 0,0541 | 0,057 | 0,0596 | 0,072 | 0,0733 | 0,0882 |
| 6803-PisiA-ZpPDC-ADHII | 0 | 0,0189 | 0,0224 | 0,029 | 0,043 | 0,0522 | 0,0497 | 0,0527 | 0,0549 | 0,0511 | 0,0459 |
| 6803-PisiA-ZpPDC | 0 | 0,0258 | 0,0303 | 0,0355 | 0,0504 | 0,0688 | 0,0682 | 0,0749 | 0,0826 | 0,0833 | 0,0911 |

Figure 12C

| shaked Erlenmeyer flask (time course in days) | 0 | 5 | 8 | 9 | 10 | 11 | 15 | 19 |
|---|---|---|---|---|---|---|---|---|
| EtOH % (v/v) | | | | | | | | |
| PpetJ-PDC | 0 | 0,0145 | 0,0191 | 0,0218 | 0,0225 | 0,0273 | 0,0323 | 0,0418 |
| PpetJ-PDC/SynADH | 0 | 0,0174 | 0,022 | 0,0267 | 0,0265 | 0,0306 | 0,0362 | 0,0426 |

Figure 12E

| aerated with 0,5% CO2 | | | | | | | |
|---|---|---|---|---|---|---|---|
| EtOH % (v/v) | 0 | 3 | 4 | 7 | 10 | 12 | 14 | 17 |
| PisiA-PDC/ADHII | 0 | 0,020 | 0,047 | 0,066 | 0,086 | 0,118 | 0,133 | 0,116 |
| PisiA-PDC | 0 | 0,012 | 0,031 | 0,052 | 0,087 | 0,108 | 0,134 | 0,127 |

Figure 12G

| aerated with 0,5% CO2 | | | | | | | | | | | | | | |
|---|---|---|---|---|---|---|---|---|---|---|---|---|---|---|
| EtOH % (v/v) | 0 | 1 | 2 | 3 | 4 | 7 | 8 | 10 | 11 | 14 | 15 | 16 | 17 | 18 |
| PpetJ-PDC/ADHII | 0 | 0,0028 | 0,0101 | 0,0208 | 0,0338 | 0,0655 | 0,0752 | 0,0896 | 0,1005 | 0,1096 | 0,1186 | 0,1169 | 0,126 | 0,1198 |
| PpetJ-PDC/SynADH | 0 | 0,0051 | 0,0126 | 0,0279 | 0,0456 | 0,0985 | 0,1325 | 0,1543 | 0,1726 | 0,2023 | 0,2194 | 0,2241 | 0,241 | 0,2494 |

Figure 12I

| promoter | constitutive | light conditions | stationary phase | nutrient status | heat stress | cold stress | salt /osmotic stress | oxidative stress |
|---|---|---|---|---|---|---|---|---|
| isiA | | high light | X | iron↓ | | | | X |
| nblA | | | | nitrogen↓ | | | | X |
| ntcA | (X) | | | nitrogen↓ | | | | |
| nirA | | | | NH₄ → NO₃ | | | | |
| petJ | | | | copper↓ | | | | |
| petE | | | | copper↑ | | | | |
| psaA | X | low light | | | | | | |
| psbA2 | (X) | high light | | | | | | X |
| rbcL | X | | | | | | | |
| lrtA | | darkness | | | | | | |
| crhC | | | | | | X | | |
| sigB | | | X | | X | | X | |
| ggpS | | | | | | | X | |
| htpG | | | | | X | | X | |
| hspA | | | | | X | X | X | X |
| clpB1 | | | | | X | X | X | X |
| hliB | | | | | X | X | X | X |

Figure 13A

SEQUENCE LISTING

```
<160> NUMBER OF SEQ ID NOS: 39

<210> SEQ ID NO 1
<211> LENGTH: 1216
<212> TYPE: DNA
<213> ORGANISM: Zymomonas mobilis

<400> SEQUENCE: 1
gagctctata tcaacaaaag gtagtcacca tgtcagccgc agatttgtcg actgacctct      60
atctctccga gatatatcaa caaaaggtag tcaccatgaa agcagccgtc ataactaaag     120
atcatacgat cgaagtgaaa gacaccaaat tacgccctct gaaatacggg gaagcgcttt     180
tggaaatgga atattgcggg gtatgtcata ccgatctcca cgtgaaaaac ggggattttg     240
gcgatgaaac cggcagaatt accggccatg aaggcatcgg tatcgtcaag caggtcgggg     300
aaggggttac ttctctgaaa gtcggtgacc gtgccagtgt tgcatggttc ttcaaaggct     360
gcggccattg cgaatattgt gtcagtggaa atgaaacgct ttgccgcaac gttgaaaatg     420
ccggttatac ggttgacggc gctatggcag aagaatgcat cgtcgttgcc gattactcgg     480
tcaaagtgcc agatggtctt gatcctgcgg ttgccagcag catcacttgc gcgggtgtaa     540
ccacctataa agcagtcaaa gtttctcaga tacagccggg acaatggctg gctatctatg     600
gcttgggcgg tttaggcaat ctagcccttc aaatatgcca agaatgtttt caacgccaag     660
tgatcgcgat cgatgtcaat gatgaacagc tcgcttttgc caaagagctg ggcgcagata     720
```

```
tggtcatcaa tccgaaaaac gaagatgctg ccaaaatcat tcaggaaaaa gtcggcggcg    780
cacatgcgac ggtggtgaca gctgttgcca aatccgcctt taactcggct gttgaggcta    840
tccgcgcggg tggccgtgtt gtcgccgttg gtctgcctcc tgaaaaaatg gatttgagca    900
ttcctcgctt ggtgcttgac ggtatcgaag tcttaggttc tttggtcgga acgcgggaag    960
atttgaaaga agccttccag tttgcagccg aaggtaaggt caaaccgaaa gtcaccaagc   1020
gtaaagtcga agaaatcaac caaatctttg acgaaatgga acatggtaaa ttcacaggcc   1080
gtatggttgt tgattttacc catcactagg tttccgtgaa ggcggaagca taaacggaaa   1140
aagcctttct cttaccagaa aggcttttc tttgtcgtct gataaaaatt ttcatacaga   1200
atttaataca ctgcag                                                   1216

<210> SEQ ID NO 2
<211> LENGTH: 337
<212> TYPE: PRT
<213> ORGANISM: Zymomonas mobilis

<400> SEQUENCE: 2

Met Lys Ala Ala Val Ile Thr Lys Asp His Thr Ile Glu Val Lys Asp
1               5                   10                  15

Thr Lys Leu Arg Pro Leu Lys Tyr Gly Glu Ala Leu Leu Glu Met Glu
            20                  25                  30

Tyr Cys Gly Val Cys His Thr Asp Leu His Val Lys Asn Gly Asp Phe
        35                  40                  45

Gly Asp Glu Thr Gly Arg Ile Thr Gly His Glu Gly Ile Gly Ile Val
    50                  55                  60

Lys Gln Val Gly Glu Gly Val Thr Ser Leu Lys Val Gly Asp Arg Ala
65                  70                  75                  80

Ser Val Ala Trp Phe Phe Lys Gly Cys Gly His Cys Glu Tyr Cys Val
                85                  90                  95

Ser Gly Asn Glu Thr Leu Cys Arg Asn Val Glu Asn Ala Gly Tyr Thr
            100                 105                 110

Val Asp Gly Ala Met Ala Glu Glu Cys Ile Val Val Ala Asp Tyr Ser
        115                 120                 125

Val Lys Val Pro Asp Gly Leu Asp Pro Ala Val Ala Ser Ser Ile Thr
    130                 135                 140

Cys Ala Gly Val Thr Thr Tyr Lys Ala Val Lys Val Ser Gln Ile Gln
145                 150                 155                 160

Pro Gly Gln Trp Leu Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Ala Phe Ala Lys Glu Leu Gly Ala Asp
        195                 200                 205

Met Val Ile Asn Pro Lys Asn Glu Asp Ala Ala Lys Ile Ile Gln Glu
    210                 215                 220

Lys Val Gly Gly Ala His Ala Thr Val Val Thr Ala Val Ala Lys Ser
225                 230                 235                 240

Ala Phe Asn Ser Ala Val Glu Ala Ile Arg Ala Gly Gly Arg Val Val
                245                 250                 255

Ala Val Gly Leu Pro Pro Glu Lys Met Asp Leu Ser Ile Pro Arg Leu
            260                 265                 270

Val Leu Asp Gly Ile Glu Val Leu Gly Ser Leu Val Gly Thr Arg Glu
        275                 280                 285
```

```
Asp Leu Lys Glu Ala Phe Gln Phe Ala Ala Glu Gly Lys Val Lys Pro
    290                 295                 300

Lys Val Thr Lys Arg Lys Val Glu Glu Ile Asn Gln Ile Phe Asp Glu
305                 310                 315                 320

Met Glu His Gly Lys Phe Thr Gly Arg Met Val Val Asp Phe Thr His
                325                 330                 335

His

<210> SEQ ID NO 3
<211> LENGTH: 1144
<212> TYPE: DNA
<213> ORGANISM: Synechocystis PCC6803

<400> SEQUENCE: 3
gagctctctg ataaaacta ataaactcta ttacccatga ttaaagccta cgctgccctg      60
gaagccaacg aaaactcca acctttgaa tacgaccccg gtgccctggg tgctaatgag     120
gtggagattg aggtgcagta ttgtggggtg tgccacagtg atttgtccat gattaataac     180
gaatggggca tttccaatta cccctagtg ccgggtcatg aggtggtggg tactgtggcc      240
gccatgggcg aagggtgaa ccatgttgag gtggggatt tagtggggct gggttggcat       300
tcgggctact gcatgacctg ccatagttgt ttatctggct accacaacct tgtgccacg      360 gcggaatcga ccattgtggg ccactacggt ggctttggcg atcgggttcg ggccaaggga     420
gtcagcgtgg tgaaattacc taaaggcatt gacctagcca gtgccgggcc ccttttctgt     480
ggaggaatta ccgttttcag tcctatggtg gaactgagtt taaagcccac tgcaaaagtg     540
gcagtgatcg gcattggggg cttgggccat ttagcggtgc aatttctccg gcctggggc      600 tgtgaagtga ctgcctttac ctccagtgcc aggaagcaaa cggaagtgtt ggaattgggc     660
gctcaccaca tactagattc caccaatcca gaggcgatcg ccagtgcgga aggcaaattt     720
gactatatta tctccactgt gaacctgaag cttgactgga acttatacat cagcacccctg    780 gcgccccagg acatttcca ctttgttggg gtggtgttgg agcctttgga tctaaatctt      840
tttccctttt tgatgggaca cgctccgtt tctgcctccc cagtgggtag tcccgccacc      900
attgccacca tgttggactt tgctgtgcgc catgacatta aacccgtggt ggaacaattt     960
agctttgatc agatcaacga ggcgatcgcc catctagaaa gcggcaaagc ccattatcgg    1020
gtagtgctca gccatagtaa aaattagctc tgcaaaggtt gcttctgggt ccgtggaatg    1080
gtcaaacgga gtcgatctca gttttgatac gctctatctg gaaagcttga cattcgatct    1140
gcag                                                                  1144

<210> SEQ ID NO 4
<211> LENGTH: 336
<212> TYPE: PRT
<213> ORGANISM: Synechocystis PCC6803

<400> SEQUENCE: 4

Met Ile Lys Ala Tyr Ala Ala Leu Glu Ala Asn Gly Lys Leu Gln Pro
1               5                   10                  15

Phe Glu Tyr Asp Pro Gly Ala Leu Gly Ala Asn Glu Val Glu Ile Glu
            20                  25                  30

Val Gln Tyr Cys Gly Val Cys His Ser Asp Leu Ser Met Ile Asn Asn
        35                  40                  45

Glu Trp Gly Ile Ser Asn Tyr Pro Leu Val Pro Gly His Glu Val Val
    50                  55                  60
```

```
Gly Thr Val Ala Ala Met Gly Glu Gly Val Asn His Val Glu Val Gly
 65                  70                  75                  80

Asp Leu Val Gly Leu Gly Trp His Ser Gly Tyr Cys Met Thr Cys His
                 85                  90                  95

Ser Cys Leu Ser Gly Tyr His Asn Leu Cys Ala Thr Ala Glu Ser Thr
            100                 105                 110

Ile Val Gly His Tyr Gly Gly Phe Gly Asp Arg Val Arg Ala Lys Gly
        115                 120                 125

Val Ser Val Val Lys Leu Pro Lys Gly Ile Asp Leu Ala Ser Ala Gly
130                 135                 140

Pro Leu Phe Cys Gly Gly Ile Thr Val Phe Ser Pro Met Val Glu Leu
145                 150                 155                 160

Ser Leu Lys Pro Thr Ala Lys Val Ala Val Ile Gly Ile Gly Gly Leu
                165                 170                 175

Gly His Leu Ala Val Gln Phe Leu Arg Ala Trp Gly Cys Glu Val Thr
            180                 185                 190

Ala Phe Thr Ser Ser Ala Arg Lys Gln Thr Glu Val Leu Glu Leu Gly
        195                 200                 205

Ala His His Ile Leu Asp Ser Thr Asn Pro Glu Ala Ile Ala Ser Ala
210                 215                 220

Glu Gly Lys Phe Asp Tyr Ile Ile Ser Thr Val Asn Leu Lys Leu Asp
225                 230                 235                 240

Trp Asn Leu Tyr Ile Ser Thr Leu Ala Pro Gln Gly His Phe His Phe
                245                 250                 255

Val Gly Val Val Leu Glu Pro Leu Asp Leu Asn Leu Phe Pro Leu Leu
            260                 265                 270

Met Gly Gln Arg Ser Val Ser Ala Ser Pro Val Gly Ser Pro Ala Thr
        275                 280                 285

Ile Ala Thr Met Leu Asp Phe Ala Val Arg His Asp Ile Lys Pro Val
290                 295                 300

Val Glu Gln Phe Ser Phe Asp Gln Ile Asn Glu Ala Ile Ala His Leu
305                 310                 315                 320

Glu Ser Gly Lys Ala His Tyr Arg Val Val Leu Ser His Ser Lys Asn
                325                 330                 335

<210> SEQ ID NO 5
<211> LENGTH: 2781
<212> TYPE: DNA
<213> ORGANISM: Escherichia coli

<400> SEQUENCE: 5
atgaattctg ctgttactaa tgtcgctgaa cttaacgcac tcgtagagcg tgtaaaaaaa      60
gcccagcgtg aatatgccag tttcactcaa gagcaagtag acaaaatctt ccgcgccgcc     120
gctctggctg ctgcagatgc tcgaatccca ctcgcgaaaa tggccgttgc cgaatccggc     180
atgggtatcg tcgaagataa agtgatcaaa accactttg cttctgaata tctctacaac      240
gcctataaag atgaaaaaac ctgtggtgtt ctgtctgaag acgacacttt tggtaccatc     300
actatcgctg aaccaatcgg tattatttgc ggtatcgttc cgaccactaa cccgacttca     360
actgctatct tcaaatcgct gatcagtctg aagacccgta acgccattat cttctccccg     420 caccccgcgtg caaaagatgc caccaacaaa gcggctgata tcgttctgca ggctgctatc     480
gctgccggtg ctccgaaaga tctgatcggc tggatcgatc aaccttctgt tgaactgtct     540
aacgcactga tgcaccaccc agacatcaac ctgatcctcg cgactggtgg tccgggcatg     600
gttaaagccg catacagctc cggtaaacca gctatcggtg taggcgcggg caacactcca     660
```

```
gttgttatcg atgaaactgc tgatatcaaa cgtgcagttg catctgtact gatgtccaaa      720
accttcgaca acggcgtaat ctgtgcttct gaacagtctg ttgttgttgt tgactctgtt      780
tatgacgctg tacgtgaacg ttttgcaacc cacggcggct atctgttgca gggtaaagag      840
ctgaaagctg ttcaggatgt tatcctgaaa aacggtgcgc tgaacgcggc tatcgttggt      900
cagccagcct ataaaattgc tgaactggca ggcttctctg taccagaaaa caccaagatt      960
ctgatcggtg aagtgaccgt tgttgatgaa agcgaaccgt tcgcacatga aaaactgtcc     1020
ccgactctgg caatgtaccg cgctaaagat ttcgaagacg cggtagaaaa agcagagaaa     1080
ctggttgcta tgggcggtat cggtcatacc tcttgcctgt acactgacca ggataaccaa     1140
ccggctcgcg tttcttactt cggtcagaaa atgaaaacgg cgcgtatcct gattaacacc     1200
ccagcgtctc agggtggtat cggtgacctg tataacttca aactcgcacc ttccctgact     1260
ctgggttgtg gttcttgggg tggtaactcc atctctgaaa acgttggtcc gaaacacctg     1320
atcaacaaga aaaccgttgc taagcgagct gaaaacatgt tgtggcacaa acttccgaaa     1380
tctatctact ccgccgtgg ctccctgcca atcgcgctgg atgaagtgat tactgatggc     1440
cacaaacgtg cgctcatcgt gactgaccgc ttcctgttca acaatggtta tgctgatcag     1500
atcacttccg tactgaaagc agcaggcgtt gaaactgaag tcttcttcga gtagaagcg      1560 gacccgaccc tgagcatcgt tcgtaaaggt gcagaactgg caaactcctt caaaccagac     1620
gtgattatcg cgctgggtgg tggttccccg atggacgccg cgaagatcat gtgggttatg     1680
tacgaacatc cggaaactca cttcgaagag ctggcgctgc gctttatgga tatccgtaaa     1740
cgtatctaca gttcccgaa atgggcgtg aaagcgaaaa tgatcgctgt caccaccact     1800
tctggtacag gttctgaagt cactccgttt gcggttgtaa ctgacgacgc tactggtcag     1860
aaatatccgc tggcagacta tgcgctgact ccggatatgg cgattgtcga cgccaacctg     1920
gttatggaca tgccgaagtc cctgtgtgct ttcggtggtc tggacgcagt aactcacgcc     1980
atggaagctt atgtttctgt actggcatct gagttctctg atggtcaggc tctgcaggca     2040
ctgaaactgc tgaaagaata tctgccagcg tcctaccacg aagggtctaa aaatccggta     2100
gcgcgtgaac gtgttcacag tgcagcgact atcgcgggta tcgcgtttgc gaacgccttc     2160
ctgggtgtat gtcactcaat ggcgcacaaa ctgggttccc agttccatat tccgcacggt     2220
ctggcaaacg ccctgctgat ttgtaacgtt attcgctaca atgcgaacga caacccgacc     2280
aagcagactg cattcagcca gtatgaccgt ccgcaggctc gccgtcgtta tgctgaaatt     2340
gccgaccact ggggtctgag cgcaccgggc gaccgtactg ctgctaagat cgagaaactg     2400
ctggcatggc tggaaacgct gaaagctgaa ctgggtattc cgaaatctat ccgtgaagct     2460
ggcgttcagg aagcagactt cctggcgaac gtggataaac tgtctgaaga tgcattcgat     2520
gaccagtgca ccggcgctaa cccgcgttac ccgctgatct ccgagctgaa acagattctg     2580
ctggatacct actacggtcg tgattatgta gaaggtgaaa ctgcagcgaa gaagaagct     2640 gctccggcta agctgagaa aaagcgaaa aatccgctt aatcagtagc gctgtctggc     2700
aacataaacg gccccttctg ggcaatgccg atcagttaag gattagttga ccgatcctta     2760
aactgaggca ctataggatc c                                               2781
```

<210> SEQ ID NO 6
<211> LENGTH: 893
<212> TYPE: PRT
<213> ORGANISM: Escherichia coli

<400> SEQUENCE: 6

```
Met Asn Ser Ala Val Thr Asn Val Ala Glu Leu Asn Ala Leu Val Glu
1               5                   10                  15

Arg Val Lys Lys Ala Gln Arg Glu Tyr Ala Ser Phe Thr Gln Glu Gln
            20                  25                  30

Val Asp Lys Ile Phe Arg Ala Ala Leu Ala Ala Asp Ala Arg
                35                  40                  45

Ile Pro Leu Ala Lys Met Ala Val Ala Glu Ser Gly Met Gly Ile Val
50                  55                  60

Glu Asp Lys Val Ile Lys Asn His Phe Ala Ser Glu Tyr Ile Tyr Asn
65                  70                  75                  80

Ala Tyr Lys Asp Glu Lys Thr Cys Gly Val Leu Ser Glu Asp Asp Thr
                85                  90                  95

Phe Gly Thr Ile Thr Ile Ala Glu Pro Ile Gly Ile Ile Cys Gly Ile
                100                 105                 110

Val Pro Thr Thr Asn Pro Thr Ser Thr Ala Ile Phe Lys Ser Leu Ile
                115                 120                 125

Ser Leu Lys Thr Arg Asn Ala Ile Ile Phe Ser Pro His Pro Arg Ala
                130                 135                 140

Lys Asp Ala Thr Asn Lys Ala Ala Asp Ile Val Leu Gln Ala Ala Ile
145                 150                 155                 160

Ala Ala Gly Ala Pro Lys Asp Leu Ile Gly Trp Ile Asp Gln Pro Ser
                165                 170                 175

Val Glu Leu Ser Asn Ala Leu Met His His Pro Asp Ile Asn Leu Ile
                180                 185                 190

Leu Ala Thr Gly Gly Pro Gly Met Val Lys Ala Ala Tyr Ser Ser Gly
                195                 200                 205

Lys Pro Ala Ile Gly Val Gly Ala Gly Asn Thr Pro Val Val Ile Asp
210                 215                 220

Glu Thr Ala Asp Ile Lys Arg Ala Val Ala Ser Val Leu Met Ser Lys
225                 230                 235                 240

Thr Phe Asp Asn Gly Val Ile Cys Ala Ser Glu Gln Ser Val Val Val
                245                 250                 255

Val Asp Ser Val Tyr Asp Ala Val Arg Glu Arg Phe Ala Thr His Gly
                260                 265                 270

Gly Tyr Leu Leu Gln Gly Lys Glu Leu Lys Ala Val Gln Asp Val Ile
                275                 280                 285

Leu Lys Asn Gly Ala Leu Asn Ala Ala Ile Val Gly Gln Pro Ala Tyr
290                 295                 300

Lys Ile Ala Glu Leu Ala Gly Phe Ser Val Pro Glu Asn Thr Lys Ile
305                 310                 315                 320

Leu Ile Gly Glu Val Thr Val Val Asp Glu Ser Glu Pro Phe Ala His
                325                 330                 335

Glu Lys Leu Ser Pro Thr Leu Ala Met Tyr Arg Ala Lys Asp Phe Glu
                340                 345                 350

Asp Ala Val Glu Lys Ala Glu Lys Leu Val Ala Met Gly Gly Ile Gly
                355                 360                 365

His Thr Ser Cys Leu Tyr Thr Asp Gln Asp Asn Gln Pro Ala Arg Val
                370                 375                 380

Ser Tyr Phe Gly Gln Lys Met Lys Thr Ala Arg Ile Leu Ile Asn Thr
385                 390                 395                 400

Pro Ala Ser Gln Gly Gly Ile Gly Asp Leu Tyr Asn Phe Lys Leu Ala
                405                 410                 415

Pro Ser Leu Thr Leu Gly Cys Gly Ser Trp Gly Gly Asn Ser Ile Ser
```

```
                420             425             430
Glu Asn Val Gly Pro Lys His Leu Ile Asn Lys Lys Thr Val Ala Lys
            435                 440                 445

Arg Ala Glu Asn Met Leu Trp His Lys Leu Pro Lys Ser Ile Tyr Phe
450                 455                 460

Arg Arg Gly Ser Leu Pro Ile Ala Leu Asp Glu Val Ile Thr Asp Gly
465                 470                 475                 480

His Lys Arg Ala Leu Ile Val Thr Asp Arg Phe Leu Phe Asn Asn Gly
                485                 490                 495

Tyr Ala Asp Gln Ile Thr Ser Val Leu Lys Ala Ala Gly Val Glu Thr
                500                 505                 510

Glu Val Phe Phe Glu Val Glu Ala Asp Pro Thr Leu Ser Ile Val Arg
                515                 520                 525

Lys Gly Ala Glu Leu Ala Asn Ser Phe Lys Pro Asp Val Ile Ile Ala
530                 535                 540

Leu Gly Gly Gly Ser Pro Met Asp Ala Ala Lys Ile Met Trp Val Met
545                 550                 555                 560

Tyr Glu His Pro Glu Thr His Phe Glu Glu Leu Ala Leu Arg Phe Met
                565                 570                 575

Asp Ile Arg Lys Arg Ile Tyr Lys Phe Pro Lys Met Gly Val Lys Ala
                580                 585                 590

Lys Met Ile Ala Val Thr Thr Thr Ser Gly Thr Gly Ser Glu Val Thr
                595                 600                 605

Pro Phe Ala Val Val Thr Asp Asp Ala Thr Gly Gln Lys Tyr Pro Leu
610                 615                 620

Ala Asp Tyr Ala Leu Thr Pro Asp Met Ala Ile Val Asp Ala Asn Leu
625                 630                 635                 640

Val Met Asp Met Pro Lys Ser Leu Cys Ala Phe Gly Gly Leu Asp Ala
                645                 650                 655

Val Thr His Ala Met Glu Ala Tyr Val Ser Val Leu Ala Ser Glu Phe
                660                 665                 670

Ser Asp Gly Gln Ala Leu Gln Ala Leu Lys Leu Leu Lys Glu Tyr Leu
                675                 680                 685

Pro Ala Ser Tyr His Glu Gly Ser Lys Asn Pro Val Ala Arg Glu Arg
690                 695                 700

Val His Ser Ala Ala Thr Ile Ala Gly Ile Ala Phe Ala Asn Ala Phe
705                 710                 715                 720

Leu Gly Val Cys His Ser Met Ala His Lys Leu Gly Ser Gln Phe His
                725                 730                 735

Ile Pro His Gly Leu Ala Asn Ala Leu Leu Ile Cys Asn Val Ile Arg
                740                 745                 750

Tyr Asn Ala Asn Asp Asn Pro Thr Lys Gln Thr Ala Phe Ser Gln Tyr
                755                 760                 765

Asp Arg Pro Gln Ala Arg Arg Arg Tyr Ala Glu Ile Ala Asp His Leu
                770                 775                 780

Gly Leu Ser Ala Pro Gly Asp Arg Thr Ala Ala Lys Ile Glu Lys Leu
785                 790                 795                 800

Leu Ala Trp Leu Glu Thr Leu Lys Ala Glu Leu Gly Ile Pro Lys Ser
                805                 810                 815

Ile Arg Glu Ala Gly Val Gln Glu Ala Asp Phe Leu Ala Asn Val Asp
                820                 825                 830

Lys Leu Ser Glu Asp Ala Phe Asp Asp Gln Cys Thr Gly Ala Asn Pro
                835                 840                 845
```

-continued

```
          Arg Tyr Pro Leu Ile Ser Glu Leu Lys Gln Ile Leu Leu Asp Thr Tyr
              850                 855                 860

Tyr Gly Arg Asp Tyr Val Glu Gly Glu Thr Ala Ala Lys Lys Glu Ala
          865                 870                 875                 880

Ala Pro Ala Lys Ala Glu Lys Lys Ala Lys Lys Ser Ala
                          885                 890

<210> SEQ ID NO 7
<211> LENGTH: 2747
<212> TYPE: DNA
<213> ORGANISM: Thermosynechococcus elongatus

<400> SEQUENCE: 7
atgaattccc caaccttgac cagtgacccc ccgttcaaa gccttgccga tctggaaggg      60
ctgattgagc gcgtccaacg ggcgcagagt cagtacgccc aatttaccca agagcaagtg    120
gatcacattt tccacgaagc agccatggcg gccaaccaag cccggattcc cctggccaaa    180
caagccgtag ccgaaacggg catggggtt gtcgaagata aagttattaa aaatcacttt    240
gcttcggaat acatctacaa caagtacaaa aatgagaaaa cctgcggcgt cattgaggat    300
gaccccatct ttggtatcca aaaaattgct gaaccggtgg ggatcattgc cggtgtggtg    360
ccggtcacga accccacttc aacgaccatc tttaaggcac tgattgccct gaagactcgc    420
aatggcatta tcttttcgcc ccaccccgg gcaaaggcct gtacggttgc agcggccaag    480
gtagtgttgg atgcagcggt cgctgccggc gcaccccccg atattattgg ctggattgat    540
gagccgacga ttgaactctc ccaagccctg atgcagcacc gcagatcaa gctgattttg    600 gccacggggg gaccaggtat ggtcaaggca gcctattcct ctggccatcc ggcgatcggg    660
gtcggggccg ggaatacccc cgtgctcatt gatgccacag ccgatattcc cacggcagtg    720
agttcgattc tcctcagtaa ggcctttgac aatggcatga tctgtgcctc ggagcaggca    780
gtgattgttg tggatgagat ttatgacgca cttaaagctg agtttcaacg gcgaggggcc    840
taccttctct cccctgagga acggcagcag gtggcacaac tactgctgaa ggatggtcgc    900
ctcaatgccg ccattgttgg tcaatcggcc gccaccattg ccgcaatggc caatatccaa    960
gtaccgccag aaacccgggt actcattggc gaggtgagtg aagtggggcc gcaggagcca   1020
ttttcctatg agaaactctg tccggtattg gcgttatatc gggcacccca gttccataaa   1080
ggggtggaga ttgcggccca gttggtgaat tttgggggca aggggcatac atctgtgctc   1140
tataccgatc ccgcaatca agatgatatt gcctatttca ataccgcat gcaaacggcg   1200 cgggttctga ttaacacccc ttcttcccag ggggcaattg gcgatctcta caacttcaag   1260
ttagatccgt cgctaaccct tggttgtggt acgtggggcg gcaacgtcac atcggaaaat   1320
gttggtcccc gtcacttgct gaatattaaa acggtgagcg atcgccggga aaatatgctt   1380
tggtttcggg tgccgcccaa gatctacttc aaacccggct gttttgcccat tgccctgcgg   1440 gagctggcgg ggaaaaaacg cgccttcctc gtgacggata accccctctt tgacttgggg   1500
atcactgaac cgattgtcca taccctcgaa gaactgggca tcaagtatga catcttccat   1560
gaagtggaac cagatccaac cctcagtacc gttaaccgcg tctagggtt gctgcggcaa   1620 tatcagccgg atgtgattgt tgctgtgggg ggtggctcac ctatggatgc agccaaggtg   1680
atgtggctgt gtatgagca tccggaggtg gagtttgacg gccttgcgat gcgcttcatg   1740
gatattcgca gcgggtgta tcaactgcct cccttgggtc aaaaggcaat cctggtggct   1800
attcccacca cctcggggac gggttcagag gtgacccct tgccgtggt taccgacgat   1860 cgcgtgggga ttaaatatcc cttggcagac tatgcccctta cgccaacgat ggcgattgtg   1920
```

```
gatcccgact tggtgctgca catgcccaag aaactgacgg cctacggtgg cattgatgcg      1980
ctgacccatg ccctggaggc ctatgtgtcg gtgctctcga cggagtttac ggagggactg      2040
gctctagagg ccattaaact gctctttacc tacctacccc gtgcctatcg cttgggggcg      2100
gcggatccgg aggcacggga aaggtccac tatgcggcga cgatcgctgg catggccttt       2160
gcgaatgcct tcttggggt ctgccactcg ctggcccaca aactaggctc caccttccac       2220
gtgccccacg gcttggcgaa tgcactcatg atttcccatg tgattcgcta caatgccacg      2280
gatgctcccc tgaagcaggc gattttcccg cagtacaagt atcccaagc gaaggagcgc       2340 tatgcccaaa ttgccgactt cctcgaattg ggggcacga ccccagagga aaaagtggag       2400
cgtctcattg cggcaattga ggatttgaaa gcccaattag aaattcccgc cacgattaag      2460
gaggccctca acagtgagga tcaagcgttc tatgagcagg tggagagcat ggccgaactg      2520
gcctttgacg atcagtgcac gggggccaat ccccgctatc cgctgatcca agacctcaag      2580
gagttgtata tcctggccta tatggggtgt cggcgggatg cggcagccta ctatggggg      2640 gaggcaacgg ggagttgatg tggcgttata ttcccccctt tgcagctcca gcgaaggtgc     2700
aaatggcggt ggattcctgg ctctggcagc ggagcgatcg cctgcag                   2747

<210> SEQ ID NO 8
<211> LENGTH: 885
<212> TYPE: PRT
<213> ORGANISM: Thermosynechococcus elongatus

<400> SEQUENCE: 8

Met Asn Ser Pro Thr Leu Thr Ser Asp Pro Pro Val Gln Ser Leu Ala
1               5                   10                  15

Asp Leu Glu Gly Leu Ile Glu Arg Val Gln Arg Ala Gln Ser Gln Tyr
            20                  25                  30

Ala Gln Phe Thr Gln Glu Gln Val Asp His Ile Phe His Glu Ala Ala
        35                  40                  45

Met Ala Ala Asn Gln Ala Arg Ile Pro Leu Ala Lys Gln Ala Val Ala
    50                  55                  60

Glu Thr Gly Met Gly Val Val Glu Asp Lys Val Ile Lys Asn His Phe
65                  70                  75                  80

Ala Ser Glu Tyr Ile Tyr Asn Lys Tyr Lys Asn Glu Lys Thr Cys Gly
                85                  90                  95

Val Ile Glu Asp Asp Pro Ile Phe Gly Ile Gln Lys Ile Ala Glu Pro
            100                 105                 110

Val Gly Ile Ile Ala Gly Val Val Pro Val Thr Asn Pro Thr Ser Thr
        115                 120                 125

Thr Ile Phe Lys Ala Leu Ile Ala Leu Lys Thr Arg Asn Gly Ile Ile
    130                 135                 140

Phe Ser Pro His Pro Arg Ala Lys Ala Cys Thr Val Ala Ala Ala Lys
145                 150                 155                 160

Val Val Leu Asp Ala Ala Val Ala Ala Gly Ala Pro Pro Asp Ile Ile
                165                 170                 175

Gly Trp Ile Asp Glu Pro Thr Ile Glu Leu Ser Gln Ala Leu Met Gln
            180                 185                 190

His Pro Gln Ile Lys Leu Ile Leu Ala Thr Gly Gly Pro Gly Met Val
        195                 200                 205

Lys Ala Ala Tyr Ser Ser Gly His Pro Ala Ile Gly Val Gly Ala Gly
    210                 215                 220

Asn Thr Pro Val Leu Ile Asp Ala Thr Ala Asp Ile Pro Thr Ala Val
```

```
                225                 230                 235                 240
Ser Ser Ile Leu Leu Ser Lys Ala Phe Asp Asn Gly Met Ile Cys Ala
                245                 250                 255

Ser Glu Gln Ala Val Ile Val Val Asp Glu Ile Tyr Asp Ala Leu Lys
                260                 265                 270

Ala Glu Phe Gln Arg Arg Gly Ala Tyr Leu Leu Ser Pro Glu Glu Arg
                275                 280                 285

Gln Gln Val Ala Gln Leu Leu Leu Lys Asp Gly Arg Leu Asn Ala Ala
                290                 295                 300

Ile Val Gly Gln Ser Ala Ala Thr Ile Ala Ala Met Ala Asn Ile Gln
305                 310                 315                 320

Val Pro Pro Glu Thr Arg Val Leu Ile Gly Glu Val Ser Glu Val Gly
                325                 330                 335

Pro Gln Glu Pro Phe Ser Tyr Glu Lys Leu Cys Pro Val Leu Ala Leu
                340                 345                 350

Tyr Arg Ala Pro Gln Phe His Lys Gly Val Glu Ile Ala Ala Gln Leu
                355                 360                 365

Val Asn Phe Gly Gly Lys Gly His Thr Ser Val Leu Tyr Thr Asp Pro
                370                 375                 380

Arg Asn Gln Asp Asp Ile Ala Tyr Phe Lys Tyr Arg Met Gln Thr Ala
385                 390                 395                 400

Arg Val Leu Ile Asn Thr Pro Ser Ser Gln Gly Ala Ile Gly Asp Leu
                405                 410                 415

Tyr Asn Phe Lys Leu Asp Pro Ser Leu Thr Leu Gly Cys Gly Thr Trp
                420                 425                 430

Gly Gly Asn Val Thr Ser Glu Asn Val Gly Pro Arg His Leu Leu Asn
                435                 440                 445

Ile Lys Thr Val Ser Asp Arg Arg Glu Asn Met Leu Trp Phe Arg Val
                450                 455                 460

Pro Pro Lys Ile Tyr Phe Lys Pro Gly Cys Leu Pro Ile Ala Leu Arg
465                 470                 475                 480

Glu Leu Ala Gly Lys Lys Arg Ala Phe Leu Val Thr Asp Lys Pro Leu
                485                 490                 495

Phe Asp Leu Gly Ile Thr Glu Pro Ile Val His Thr Leu Glu Glu Leu
                500                 505                 510

Gly Ile Lys Tyr Asp Ile Phe His Glu Val Glu Pro Asp Pro Thr Leu
                515                 520                 525

Ser Thr Val Asn Arg Gly Leu Gly Leu Leu Arg Gln Tyr Gln Pro Asp
                530                 535                 540

Val Ile Val Ala Val Gly Gly Gly Ser Pro Met Asp Ala Ala Lys Val
545                 550                 555                 560

Met Trp Leu Leu Tyr Glu His Pro Glu Val Glu Phe Asp Gly Leu Ala
                565                 570                 575

Met Arg Phe Met Asp Ile Arg Lys Arg Val Tyr Gln Leu Pro Pro Leu
                580                 585                 590

Gly Gln Lys Ala Ile Leu Val Ala Ile Pro Thr Thr Ser Gly Thr Gly
                595                 600                 605

Ser Glu Val Thr Pro Phe Ala Val Val Thr Asp Asp Arg Val Gly Ile
                610                 615                 620

Lys Tyr Pro Leu Ala Asp Tyr Ala Leu Thr Pro Thr Met Ala Ile Val
625                 630                 635                 640

Asp Pro Asp Leu Val Leu His Met Pro Lys Lys Leu Thr Ala Tyr Gly
                645                 650                 655
```

```
Gly Ile Asp Ala Leu Thr His Ala Leu Glu Ala Tyr Val Ser Val Leu
            660                 665                 670

Ser Thr Glu Phe Thr Glu Gly Leu Ala Leu Glu Ala Ile Lys Leu Leu
            675                 680                 685

Phe Thr Tyr Leu Pro Arg Ala Tyr Arg Leu Gly Ala Ala Asp Pro Glu
            690                 695                 700

Ala Arg Glu Lys Val His Tyr Ala Ala Thr Ile Ala Gly Met Ala Phe
705                 710                 715                 720

Ala Asn Ala Phe Leu Gly Val Cys His Ser Leu Ala His Lys Leu Gly
                725                 730                 735

Ser Thr Phe His Val Pro His Gly Leu Ala Asn Ala Leu Met Ile Ser
            740                 745                 750

His Val Ile Arg Tyr Asn Ala Thr Asp Ala Pro Leu Lys Gln Ala Ile
            755                 760                 765

Phe Pro Gln Tyr Lys Tyr Pro Gln Ala Lys Glu Arg Tyr Ala Gln Ile
            770                 775                 780

Ala Asp Phe Leu Glu Leu Gly Gly Thr Thr Pro Glu Glu Lys Val Glu
785                 790                 795                 800

Arg Leu Ile Ala Ala Ile Glu Asp Leu Lys Ala Gln Leu Glu Ile Pro
                805                 810                 815

Ala Thr Ile Lys Glu Ala Leu Asn Ser Glu Asp Gln Ala Phe Tyr Glu
            820                 825                 830

Gln Val Glu Ser Met Ala Glu Leu Ala Phe Asp Asp Gln Cys Thr Gly
            835                 840                 845

Ala Asn Pro Arg Tyr Pro Leu Ile Gln Asp Leu Lys Glu Leu Tyr Ile
            850                 855                 860

Leu Ala Tyr Met Gly Cys Arg Arg Asp Ala Ala Ala Tyr Tyr Gly Gly
865                 870                 875                 880

Glu Ala Thr Gly Ser
            885

<210> SEQ ID NO 9
<211> LENGTH: 1680
<212> TYPE: DNA
<213> ORGANISM: Zymobacter palmae

<400> SEQUENCE: 9
atgaattccg ttggtatgta cttggcagaa cgcctagccc agatcggcct gaaacaccac      60
tttgccgtgg ccggtgacta caacctggtg ttgcttgatc agctcctgct gaacaaagac     120
atggagcagg tctactgctg taacgaactt aactgcggct ttagcgccga aggttacgct     180
cgtgcacgtg gtgccgccgc tgccatcgtc acgttcagcg taggtgctat ctctgcaatg     240
aacgccatcg gtggcgccta tgcagaaaac ctgccggtca tcctgatctc tggctcaccg     300
aacaccaatg actacggcac aggccacatc ctgcaccaca ccattggtac tactgactat     360
aactatcagc tggaaatggt aaaacacgtt acctgcgcac gtgaaagcat cgtttctgcc     420
gaagaagcac cggcaaaaat cgaccacgtc atccgtacgg ctctacgtga acgcaaaccg     480
gcttatctgg aaatcgcatg caacgtcgct ggcgctgaat gtgttcgtcc gggcccgatc     540
aatagcctgc tgcgtgaact caagttgac cagaccagtg tcactgccgc tgtagatgcc     600
gccgtagaat ggctgcagga ccgccagaac gtcgtcatgc tggtcggtag caaactgcgt     660
gccgctgccg ctgaaaaaca ggctgttgcc ctagcggacc gcctgggctg cgctgtcacg     720
atcatggctg ccgaaaaagg cttcttcccg gaagatcatc cgaacttccg cggcctgtac     780
tggggtgaag tcagctccga aggtgcacag gaactggttg aaaacgccga tgccatcctg     840
```

```
tgtctggcac cggtattcaa cgactatgct accgttggct ggaactcctg gccgaaaggc    900
gacaatgtca tggtcatgga caccgaccgc gtcactttcg caggacagtc cttcgaaggt    960
ctgtcattga gcaccttcgc cgcagcactg gctgagaaag caccttctcg cccggcaacg   1020
actcaaggca ctcaagcacc ggtactgggt attgaggccg cagagcccaa tgcaccgctg   1080
accaatgacg aaatgacgcg tcagatccag tcgctgatca cttccgacac tactctgaca   1140
gcagaaacag gtgactcttg gttcaacgct ctcgcatgc cgattcctgg cggtgctcgt    1200
gtcgaactgg aaatgcaatg gggtcatatc ggttggtccg taccttctgc attcggtaac   1260
gccgttggtt ctccggagcg tcgccacatc atgatggtcg gtgatggctc tttccagctg   1320
actgctcaag aagttgctca gatgatccgc tatgaaatcc cggtcatcat cttcctgatc   1380
aacaaccgcg gttacgtcat cgaaatcgct atccatgacg cccttacaa ctacatcaaa    1440
aactggaact acgctggcct gatcgacgtc ttcaatgacg aagatggtca tggcctgggt   1500
ctgaaagctt ctactggtgc agaactagaa ggcgctatca gaaagcact cgacaatcgt    1560
cgcggtccga cgctgatcga atgtaacatc gctcaggacg actgcactga accctgatt    1620
gcttggggta acgtgtagc agctaccaac tctcgcaaac cacaagcgta agttgagctc    1680
```

<210> SEQ ID NO 10
<211> LENGTH: 556
<212> TYPE: PRT
<213> ORGANISM: Zymobacter palmae

<400> SEQUENCE: 10

```
Met Asn Ser Val Gly Met Tyr Leu Ala Glu Arg Leu Ala Gln Ile Gly
 1               5                  10                  15

Leu Lys His His Phe Ala Val Ala Gly Asp Tyr Asn Leu Val Leu Leu
            20                  25                  30

Asp Gln Leu Leu Leu Asn Lys Asp Met Glu Gln Val Tyr Cys Cys Asn
        35                  40                  45

Glu Leu Asn Cys Gly Phe Ser Ala Glu Gly Tyr Ala Arg Ala Arg Gly
    50                  55                  60

Ala Ala Ala Ala Ile Val Thr Phe Ser Val Gly Ala Ile Ser Ala Met
65                  70                  75                  80

Asn Ala Ile Gly Gly Ala Tyr Ala Glu Asn Leu Pro Val Ile Leu Ile
                85                  90                  95

Ser Gly Ser Pro Asn Thr Asn Asp Tyr Gly Thr Gly His Ile Leu His
            100                 105                 110

His Thr Ile Gly Thr Thr Asp Tyr Asn Tyr Gln Leu Glu Met Val Lys
        115                 120                 125

His Val Thr Cys Ala Arg Glu Ser Ile Val Ser Ala Glu Glu Ala Pro
    130                 135                 140

Ala Lys Ile Asp His Val Ile Arg Thr Ala Leu Arg Glu Arg Lys Pro
145                 150                 155                 160

Ala Tyr Leu Glu Ile Ala Cys Asn Val Ala Gly Ala Glu Cys Val Arg
                165                 170                 175

Pro Gly Pro Ile Asn Ser Leu Leu Arg Glu Leu Glu Val Asp Gln Thr
            180                 185                 190

Ser Val Thr Ala Ala Val Asp Ala Ala Val Glu Trp Leu Gln Asp Arg
        195                 200                 205

Gln Asn Val Val Met Leu Val Gly Ser Lys Leu Arg Ala Ala Ala Ala
    210                 215                 220

Glu Lys Gln Ala Val Ala Leu Ala Asp Arg Leu Gly Cys Ala Val Thr
```

```
                225                 230                 235                 240
Ile Met Ala Ala Glu Lys Gly Phe Phe Pro Glu Asp His Pro Asn Phe
                    245                 250                 255

Arg Gly Leu Tyr Trp Gly Glu Val Ser Ser Glu Gly Ala Gln Glu Leu
                260                 265                 270

Val Glu Asn Ala Asp Ala Ile Leu Cys Leu Ala Pro Val Phe Asn Asp
            275                 280                 285

Tyr Ala Thr Val Gly Trp Asn Ser Trp Pro Lys Gly Asp Asn Val Met
        290                 295                 300

Val Met Asp Thr Asp Arg Val Thr Phe Ala Gly Gln Ser Phe Glu Gly
305                 310                 315                 320

Leu Ser Leu Ser Thr Phe Ala Ala Leu Ala Glu Lys Ala Pro Ser
                325                 330                 335

Arg Pro Ala Thr Thr Gln Gly Thr Gln Ala Pro Val Leu Gly Ile Glu
                340                 345                 350

Ala Ala Glu Pro Asn Ala Pro Leu Thr Asn Asp Glu Met Thr Arg Gln
            355                 360                 365

Ile Gln Ser Leu Ile Thr Ser Asp Thr Thr Leu Thr Ala Glu Thr Gly
        370                 375                 380

Asp Ser Trp Phe Asn Ala Ser Arg Met Pro Ile Pro Gly Gly Ala Arg
385                 390                 395                 400

Val Glu Leu Glu Met Gln Trp Gly His Ile Gly Trp Ser Val Pro Ser
                405                 410                 415

Ala Phe Gly Asn Ala Val Gly Ser Pro Glu Arg Arg His Ile Met Met
                420                 425                 430

Val Gly Asp Gly Ser Phe Gln Leu Thr Ala Gln Glu Val Ala Gln Met
            435                 440                 445

Ile Arg Tyr Glu Ile Pro Val Ile Ile Phe Leu Ile Asn Asn Arg Gly
        450                 455                 460

Tyr Val Ile Glu Ile Ala Ile His Asp Gly Pro Tyr Asn Tyr Ile Lys
465                 470                 475                 480

Asn Trp Asn Tyr Ala Gly Leu Ile Asp Val Phe Asn Asp Glu Asp Gly
                485                 490                 495

His Gly Leu Gly Leu Lys Ala Ser Thr Gly Ala Glu Leu Glu Gly Ala
                500                 505                 510

Ile Lys Lys Ala Leu Asp Asn Arg Gly Pro Thr Leu Ile Glu Cys
            515                 520                 525

Asn Ile Ala Gln Asp Asp Cys Thr Glu Thr Leu Ile Ala Trp Gly Lys
        530                 535                 540

Arg Val Ala Ala Thr Asn Ser Arg Lys Pro Gln Ala
545                 550                 555

<210> SEQ ID NO 11
<211> LENGTH: 5711
<212> TYPE: DNA
<213> ORGANISM: Artificial
<220> FEATURE:
<223> OTHER INFORMATION: pSK10 cloning vector

<400> SEQUENCE: 11
gtcgacatat gtttctcggc aaaaattaat tatcgattgg ctggaacctg gtcaaaccag       60
ggcttttcat ccattggaaa agcgattttg atcatctagg gtcaggagca aagatctgat      120
caaatattga tcattatta ggaaagctga actttcacca ctttattttt ggcttcctct       180
actttgggca aagtcaaagt taggataccg gcatcgtaat tagctttaac ttctgtgttt      240
```

```
tggattgctc caggtacagg aataacccgg cggaaactgc catagcggaa ctctgtgcgc    300
cgcaccccat cttttcggt  gctatgggta tcctggcgat cgccgctgac ggtcaccgca    360
tccctggcgg cttggatgtc caaattatcg gggtccatgc caggtaattc tagtttgagc    420
acataggctt cttcagtttc agttagttct gctttaggat taaacccttg gcgatcgccg    480
tggcggtccg tagggacaaa aacttcttca aacagttggt tcatctgctg ctggaaatta    540
tccatttccc gcaggggatt gtaaagaatg agagacataa tgttaactcc tgatgtgtgg    600
aaggaattga ttacccttga atggttctat cttaaaattt ccccttccag gttagattcg    660
gttttcagga aagaaggtgg ggggattgcc gaaattacat ttctagccgc aatttttagt    720 aaaaaaaga  tgagttttta cctcaccttta gtaaatatt  tgagtggcaa acaaaatgg    780 taaaaatagc taagcttcca ccgccctatg gattttttgga aggaagtctt aggttgtgaa    840
aaactataaa aaccaaccat aggaatggag acctttaccc aacaagttga cccctaggta    900
acaaatccaa accaccgtaa aaccgctggc ggccaaaata gcgggcttgc ggccttgcca    960 accttttggta atgcgggcat ggagataggc ggcaaatact agccaggtga ttagggcccg   1020
gtacccagct tttgttccct ttagtgaggg ttaatttcga gcttggcgta atcatggtca   1080 tagctgttttc ctgtgtgaaa ttgttatccg ctcacaattc cacacaacat acgagccgga   1140
agcataaagt gtaaagcctg gggtgcctaa tgagtgagct aactcacatt aattgcgttg   1200
cgctcactgc ccgctttcca gtcgggaaac ctgtcgtgcc agctgcatta atgaatcggc   1260
caacgcgcgg ggagaggcgg tttgcgtatt gggcgctctt ccgcttcctc gctcactgac   1320
tcgctgcgct cggtcgttcg gctgcggcga gcggtatcag ctcactcaaa ggcggtaata   1380
cggttatcca cagaatcagg ggataacgca ggaaagaaca tgtgagcaaa aggccagcaa   1440
aaggccagga accgtaaaaa ggccgcgttg ctggcgtttt tccataggct ccgcccccct   1500
gacgagcatc acaaaaatcg acgctcaagt cagaggtggc gaaacccgac aggactataa   1560
agataccagg cgtttccccc tggaagctcc ctcgtgcgct ctcctgttcc gaccctgccg   1620
cttaccggat acctgtccgc ctttctccct tcgggaagcg tggcgctttc tcatagctca   1680
cgctgtaggt atctcagttc ggtgtaggtc gttcgctcca agctgggctg tgtgcacgaa   1740
ccccccgttc agcccgaccg ctgcgcctta tccggtaact atcgtcttga gtccaacccg   1800
gtaagacacg acttatcgcc actggcagca gccactggta acaggattag cagagcgagg   1860
tatgtaggcg gtgctacaga gttcttgaag tggtggccta actacggcta cactagaagg   1920
acagtatttg gtatctgcgc tctgctgaag ccagttacct tcggaaaaag agttggtagc   1980
tcttgatccg gcaaacaaac caccgctggt agcggtggtt ttttttgtttg caagcagcag   2040 attacgcgca gaaaaaaagg atctcaagaa gatcctttga tcttttctac ggggtctgac   2100
gctcagtgga acgaaaactc acgttaaggg attttggtca tgagattatc aaaaaggatc   2160
ttcacctaga tccttttaaa ttaaaaatga agttttaaat caatctaaag tatatatgag   2220
taaacttggt ctgacagtta ccaatgctta atcagtgagg cacctatctc agcgatctgt   2280
ctatttcgtt catccatagt tgcctgactc cccgtcgtgt agataactac gatacgggag   2340
ggcttaccat ctggccccag tgctgcaatg ataccgcgag acccacgctc accggctcca   2400
gatttatcag caataaacca gccagccgga agggccgagc gcagaagtgg tcctgcaact   2460
ttatccgcct ccatccagtc tattaattgt tgccgggaag ctagagtaag tagttcgcca   2520
gttaatagtt tgcgcaacgt tgttgccatt gctacaggca tcgtggtgtc acgctcgtcg   2580
tttggtatgg cttcattcag ctccggttcc caacgatcaa ggcgagttac atgatccccc   2640
```

```
atgttgtgca aaaaagcggt tagctccttc ggtcctccga tcgttgtcag aagtaagttg    2700
gccgcagtgt tatcactcat ggttatggca gcactgcata attctcttac tgtcatgcca    2760
tccgtaagat gcttttctgt gactggtgag tactcaacca agtcattctg agaatagtgt    2820
atgcggcgac cgagttgctc ttgcccggcg tcaatacggg ataataccgc gccacatagc    2880
agaactttaa aagtgctcat cattggaaaa cgttcttcgg ggcgaaaact ctcaaggatc    2940
ttaccgctgt tgagatccag ttcgatgtaa cccactcgtg cacccaactg atcttcagca    3000
tcttttactt tcaccagcgt ttctgggtga gcaaaaacag gaaggcaaaa tgccgcaaaa    3060
aagggaataa gggcgacacg gaaatgttga atactcatac tcttcctttt tcaatattat    3120
tgaagcattt atcagggtta ttgtctcatg agcggataca tatttgaatg tatttagaaa    3180
aataaacaaa taggggttcc gcgcacattt ccccgaaaag tgccacctaa attgtaagcg    3240
ttaatatttt gttaaaattc gcgttaaatt tttgttaaat cagctcattt tttaaccaat    3300
aggccgaaat cggcaaaatc ccttataaat caaaagaata accgagata  ggggttgagtg    3360 ttgttccagt ttggaacaag agtccactat taaagaacgt ggactccaac gtcaaagggc    3420
gaaaaaccgt ctatcagggc gatggcccac tacgtgaacc atcaccctaa tcaagttttt    3480
tggggtcgag gtgccgtaaa gcactaaatc ggaaccctaa agggagcccc cgatttagag    3540
cttgacgggg aaagccggcg aacgtggcga gaaaggaagg gaagaaagcg aaaggagcgg    3600
gcgctagggc gctggcaagt gtagcggtca cgctgcgcgt aaccaccaca cccgccgcgc    3660
ttaatgcgcc gctacaggge gcgtcccatt cgccattcag gctgcgcaac tgttgggaag    3720
ggcgatcggt gcgggcctct tcgctattac gccagctggc gaaaggggga tgtgctgcaa    3780
ggcgattaag ttgggtaacg ccagggtttt cccagtcacg acgttgtaaa acgacggcca    3840
gtgaattgta atacgactca ctatagggcg aattggaggc cagtgctgga ggaatatgat    3900
tttgtcatcc tcgactgtgc ccctggttat aatctgttga cccgcagtgg cattgcggcc    3960
agcgactttt atctgttgcc ggctcgtcct gaaccectat cggtggtggg gatgcagtta    4020
ctggaaagaa gaattgagaa actgaaggaa agccataagg cctccgatga tccectgaat    4080 atcaatctga tcggagtggt gtttattctg tccggcggcg gtttgatgag tcgctactat    4140
aaccaggtaa tgcggcgggt acaaacggat ttcaccccgg acaacttttt tcagcagtcc    4200
attcccatgg atgtcaatgt ggctaaggca gtggatagct ttatgccggt ggttacctcc    4260
atgcccaata cggcgggttc aaaagctttt attaaattaa cccaggaatt tttacagaaa    4320
gtagaagctt ttggctaaag caaagccccc attgattaac aacggagggg gtaccgaggt    4380
gctgctgaag ttgcccgcaa cagagagtgg aaccaaccgg tagtgcatct aacgcttgag    4440
ttaagccgcg ccgcgaagcg gcgtcggctt gaacgaattg ttagacatta tttgccgact    4500
accttggtga tctcgccttt cacgtagtgg acaaattctt ccaactgatc tgcgcgcgag    4560
gccaagcgat cttcttcttg tccaagataa ggctgtctag cttcaagtat gacgggctga    4620
tactgggccg gcaggcgctc cattgcccag tcggcagcga catccttcgg cgcgattttg    4680
ccggttactg cgctgtacca aatgcgggac aacgtaagca ctacatttcg ctcatcgcca    4740
gcccagtcgg gcggcgagtt ccatagcgtt aaggtttcat ttagcgcctc aaatagatcc    4800
tgttcaggaa ccggatcaaa gagttcctcc gccgctggac ctaccaaggc aacgctatgt    4860
tctcttgctt ttgtcagcaa gatagccaga tcaatgtcga tcgtggctgg ctcgaagata    4920
cctgcaagaa tgtcattgcg ctgccattct ccaaattgca gttcgcgctt agctggataa    4980
cgccacggaa tgatgtcgtc gtgcacaaca atggtgactt ctacagcgcg gagaatctcg    5040
```

```
ctctctccag gggaagccga agtttccaaa aggtcgttga tcaaagctcg ccgcgttgtt    5100
tcatcaagcc ttacggtcac cgtaaccagc aaatcaatat cactgtgtgg cttcaggccg    5160
ccatccactg cggagccgta caaatgtacg gccagcaacg tcggttcgag atggcgctcg    5220
atgacgccaa ctacctctga tagttgagtc gatacttcgg cgatcaccgc ttccctcatg    5280
atgtttaact ttgttttagg gcgactgccc tgctgcgtaa catcgttgct gctccataac    5340
atcaaacatc gacccacggc gtaacgcgct tgctgcttgg atgcccgagg catagactgt    5400
accccaaaaa aacagtcata caagccatg  aaaaccgcca ctgcgccgtt accaccgctg    5460
cgttcggtca aggttctgga ccagttgcgt gagcgcatac gctacttgca ttacagctta    5520
cgaaccgaac aggcttatgt ccactgggtt cgtgccttca tccgtttcca cggtgtgcgt    5580
cacccggcaa ccttgggcag cagcgaagtc gaggcatttc tgtcctggct ggcgaacgag    5640
cgcaaggttt cggtctccac gcatcgtcag gcattggcgg ccttgctgtt cttctagaca    5700
aggctgcagt t                                                         5711

<210> SEQ ID NO 12
<211> LENGTH: 397
<212> TYPE: DNA
<213> ORGANISM: Anabaena PCC7120

<400> SEQUENCE: 12
gtcgactcta gaaagatgcc actagcacca gacgactagt tagcgatagt ctatccacca     60
ttgttcgttt tgtaggtttt gcttttatag cgatcggttt tgtatttgc ggtaacttca    120 tcaattttt aggggctggt aattttaac atatctcacg gggtgcaatc ttcgcgcccc     180
tactagtcca tcgaatcgtc atttccaact attaatatta aagtttagag aaattggatt    240
atatgtaacc tgtactctgt taagattcac cattgggta ttcgctatca gtcttggcgc    300
tactgcccat cccgccctc aaacctttgt ccgtccgcct aagactgata ccgctactgg    360
tgacaggccg atgttatatc tggagttcta tgaattc                             397

<210> SEQ ID NO 13
<211> LENGTH: 359
<212> TYPE: DNA
<213> ORGANISM: Anabaena PCC7120

<400> SEQUENCE: 13 gtcgacttt ttgctgaggt actgagtaca cagctaataa aattgggcaa tctccgcgcc     60
tctatgactt gaaggagagt gtaggggtat agggaaaga tatcttttat ctacatcaca    120
taaataaaaa atttaatttg tcgctctggc tgcatatatt gatgtatttt tagccataag    180
ttttttagtg ccatgtaatt atagtgattt ttagcgatcg cagagcattt ttccctggat    240
ttatcgcgat ctcaaaaaaa atttgcccga agtatgacag attgtcatat tggtgtcga    300 tttatttaa aatgaaataa gaaaataaa actacaggtt aggagaacgc catgaattc      359

<210> SEQ ID NO 14
<211> LENGTH: 13102
<212> TYPE: DNA
<213> ORGANISM: Artificial
<220> FEATURE:
<223> OTHER INFORMATION: sequence of plasmid pRL593-PisiAPDC-ADHII

<400> SEQUENCE: 14
atcgataatt aattttttgcc gagaaacata tgtcgacttt tttgctgagg tactgagtac     60
acagctaata aaattgggca atctccgcgc ctctatgact tgaaggagag tgtaggggta    120
```

```
tagggaaaag atatctttta tctacatcac ataaataaaa aatttaattt gtcgctctgg    180
ctgcatatat tgatgtattt ttagccataa gttttttagt gccatgtaat tatagtgatt    240
tttagcgatc gcagagcatt tttccctgga tttatcgcga tctcaaaaaa aatttgcccg    300
aagtatgaca gattgtcata tttggtgtcg atttttattta aaatgaaata agaaaaataa    360
aactacaggt taggagaacg ccatgaattc ttatactgtc ggtacctatt tagcggagcg    420
gcttgtccag attggtctca agcatcactt cgcagtcgcg ggcgactaca acctcgtcct    480
tcttgacaac ctgcttttga acaaaaacat ggagcaggtt tattgctgta acgaactgaa    540
ctgcggtttc agtgcagaag gttatgctcg tgccaaaggc gcagcagcag ccgtcgttac    600
ctacagcgtc ggtgcgcttt ccgcatttga tgctatcggt ggcgcctatg cagaaaacct    660
tccggttatc ctgatctccg gtgctccgaa caacaatgat cacgctgctg gtcacgtgtt    720
gcatcacgct cttggcaaaa ccgactatca ctatcagttg gaaatggcca agaacatcac    780
ggccgcagct gaagcgattt acaccccaga agaagctccg gctaaaatcg atcacgtgat    840
taaaactgct cttcgtgaga agaagccggt ttatctcgaa atcgcttgca acattgcttc    900
catgccctgc gccgctcctg gaccggcaag cgcattgttc aatgacgaag ccagcgacga    960
agcttctttg aatgcagcgg ttgaagaaac cctgaaattc atcgccaacc gcgacaaagt   1020
tgccgtcctc gtcggcagca agctgcgcgc agctggtgct gaagaagctg ctgtcaaatt   1080
tgctgatgct ctcggtggcg cagttgctac catggctgct gcaaaagct tcttcccaga   1140 agaaaacccg cattacatcg gtacctcatg gggtgaagtc agctatccgg gcgttgaaaa   1200
gacgatgaaa gaagccgatg cggttatcgc tctggctcct gtcttcaacg actactccac   1260
cactggttgg acgatattc ctgatcctaa gaaactggtt ctcgctgaac gcgttctgt   1320 cgtcgttaac ggcgttcgct tccccagcgt tcatctgaaa gactatctga cccgtttggc   1380
tcagaaagtt tccaagaaaa ccggtgcttt ggacttcttc aaatcccctca atgcaggtga   1440 actgaagaaa gccgctccgg ctgatccgag tgctccgttg gtcaacgcag aaatcgcccg   1500
tcaggtcgaa gctcttctga ccccgaacac gacggttatt gctgaaaccg gtgactcttg   1560
gttcaatgct cagcgcatga agctcccgaa cggtgctcgc gttgaatatg aaatgcagtg   1620
gggtcacatc ggttggtccg ttcctgccgc cttcggttat gccgtcggtg ctccggaacg   1680
tcgcaacatc ctcatggttg gtgatggttc cttccagctg acggctcagg aagtcgctca   1740
gatggttcgc ctgaaactgc cggttatcat cttcttgatc aataactatg gttacaccat   1800
cgaagttatg atccatgatg gtccgtacaa caacatcaag aactgggatt atgccggtct   1860
gatggaagtg ttcaacggta acggtggtta tgacagcggt gctggtaaag gcctgaaggc   1920
taaaaccggt ggcgaactgg cagaagctat caaggttgct ctggcaaaca ccgacggccc   1980
aaccctgatc gaatgcttca tcggtcgtga agactgcact gaagaattgg tcaaatgggg   2040
taagcgcgtt gctgccgcca acagccgtaa gcctgttaac aagctcctct agttttggg   2100 gatcaattcg agctcggtac ccaaactagt atgtagggtg aggttatagc tatggcttct   2160 tcaactttt atattccttt cgtcaacgaa atgggcgaag gttcgcttga aaaagcaatc   2220
aaggatctta acggcagcgg ctttaaaaat gcgctgatcg tttctgatgc tttcatgaac   2280
aaatccggtt ttgtgaagca ggttgctgac ctgttgaaag cacagggtat taattctgct   2340
gtttatgatg gcgttatgcc gaacccgact gttaccgcag ttctggaagg ccttaagatc   2400
ctgaaggata caaattcaga cttcgtcatc tccctcggtg gtggttctcc ccatgactgc   2460
gccaaagcca tcgctctggt cgcaaccaat ggtggtgaag tcaaagacta cgaaggtatc   2520
```

```
gacaaatcta agaaacctgc cctgcctttg atgtcaatca acacgacggc tggtacggct    2580
tctgaaatga cgcgtttctg catcatcact gatgaagtcc gtcacgttaa gatggccatt    2640
gttgaccgtc acgttacccc gatggtttcc gtcaacgatc ctctgttgat ggttggtatg    2700
ccaaaaggcc tgaccgccgc caccggtatg gatgctctga cccacgcatt tgaagcttat    2760
tcttcaacgg cagctactcc gatcaccgat gcttgcgcct gaaggctgc gtccatgatc     2820
gctaagaatc tgaagaccgc ttgcgacaac ggtaaggata tgccagctcg tgaagctatg    2880
gcttatgccc aattcctcgc tggtatggcc ttcaacaacg cttcgcttgg ttatgtccat    2940
gctatggctc accagttggg cggctactac aacctgccgc atggtgtctg caacgctgtt    3000
ctgcttccgc atgttctggc ttataacgcc tctgtcgttg ctggtcgtct gaaagacgtt    3060
ggtgttgcta tgggtctcga tatcgccaat ctcggtgata agaaggcgc agaagccacc     3120
attcaggctg ttcgcgatct ggctgcttcc attggtattc cagcaaatct gaccgagctg    3180
ggtgctaaga agaagatgt gccgcttctt gctgaccacg ctctgaaaga tgcttgtgct     3240
ctgaccaacc cgcgtcaggg tgatcagaaa gaagttgaag aactcttcct gagcgctttc    3300
taatttcaaa acaggaaaac ggttttccgt cctgtcttga ttttcaagca acaatgcct     3360
ccgatttcta atcggaggca tttgtttttg tttattgcaa aaacaaaaaa tattgttaca    3420
aattttaca ggctattaag cctaccgtca taaataattt gccatttggg gatcccggta     3480
gagggaaacc gttgtggtct ccctatagtg agtcgtatta atttcgcggg atcgagatcc    3540
tttttgataa tctcatgacc aaaatccctt aacgtgagtt ttcgttccac tgagcgtcag    3600
accccgtaga aagatcaaa ggatcttctt gagatccttt ttttctgcgc gtaatctgct     3660
gcttgcaaac aaaaaaacca ccgctaccag cggtggtttg tttgccggat caagagctac    3720
caactctttt tccgaaggta actggcttca gcagagcgca gataccaaat actgtccttc    3780
tagtgtagcc gtagttaggc caccacttca agaactctgt agcaccgcct acatacctcg    3840
ctctgctaat cctgttacca gtggctgctg ccagtggcga taagtcgtgt cttaccgggt    3900
tggactcaag acgatagtta ccggataagg cgcagcggtc gggctgaacg ggggggtcgt    3960
gcacacagcc cagcttggag cgaacgacct acaccgaact gagataccta cagcgtgagc    4020
attgagaaag cgccacgctt cccgaaggga gaaaggcgga caggtatccg gtaagcggca    4080
gggtcggaac aggagagcgc acgagggagc ttcagggggg aaacgcctgg tatctttata    4140
gtcctgtcgg gtttcgccac ctctgacttg agcgtcgatt tttgtgatgc tcgtcagggg    4200
ggcggagcct atgaaaaac gccagcaacg cggccttttt acggttcctg gccttttgct     4260
ggccttttgc tcacatgttc tttcctgcgt tatcccctga ttctgtggat aaccgtatta    4320
ccgcctttga gtgagctgat accgctcgcc gcagccgaac gaccgagcgc agcgagtcag    4380
tgagcgagga agcggaagag cgcctgatgc ggtattttct ccttacgcat ctgtgcggta    4440
tttcacaccg catatggtgc actctcagta caatctgctc tgatgccgca tagttaagcc    4500
agtatacact ccgctatcgc tacgtgactg ggtcatggct gcgccccgac acccgccaac    4560
acccgctgac gcgccctgac gggcttgtct gctcccggca tccgcttaca dcaagctgt     4620
gaccgtctcc gggagctgca tgtgtcagag gttttcaccg tcatcaccga aacgcgcgag    4680
gcagctgcgt aaagctcat cagcgtggtc gtgaagcgat tcacagatgt ctgcctgttc     4740
atccgcgtcc agctcgttga gtttctccag aagcgttaat gtctggcttc tgataaagcg    4800
ggccatgccac cataccccacg ccgaaacaag cgctcatgag cccgaagtgg cgagcccgat   4860
cttccccatc ggtgatgtcg gcgatatcct cgtgatgatc agtgatggaa aaagcactgt    4920
```

```
aattcccttg gttttttggct gaaagtttcg gactcagtag acctaagtac agagtgatgt    4980
caacgccttc aagctagacg ggaggcggct tttgccatgg ttcagcgatc gctcctcatc    5040
ttcaataagc agggcatgag ccagcgttaa gcaaatcaaa tcaaatctcg cttctgggct    5100
tcaataaatg gttccgattg atgataggtt gattcatgca agcttggagc acaggatgac    5160
gcctaacaat tcattcaagc cgacaccgct tcgcggcgcg gcttaattca ggagttaaac    5220
atcatgaggg aagcggtgat cgccgaagta tcgactcaac tatcagaggt agttggcgtc    5280
atcgagcgcc atctcgaacc gacgttgctg gccgtacatt tgtacggctc cgcagtggat    5340
ggcggcctga agccacacag tgatattgat ttgctggtta cggtgaccgt aaggcttgat    5400
gaaacaacgc ggcgagcttt gatcaacgac cttttggaaa cttcggcttc ccctggagag    5460
agcgagattc tccgcgctgt agaagtcacc attgttgtgc acgacgacat cattccgtgg    5520
cgttatccag ctaagcgcga actgcaattt ggagaatggc agcgcaatga cattcttgca    5580
ggtatcttcg agccagccac gatcgacatt gatctggcta tcttgctgac aaaagcaaga    5640
gaacatagcg ttgccttggt aggtccagcg gcggaggaac tctttgatcc ggttcctgaa    5700
caggatctat ttgaggcgct aaatgaaacc ttaacgctat ggaactcgcc gcccgactgg    5760
gctggcgatg agcgaaatgt agtgcttacg ttgtcccgca tttggtacag cgcagtaacc    5820
ggcaaaatcg cgccgaagga tgtcgctgcc gactgggcaa tggagcgcct gccggcccag    5880
tatcagcccg tcatacttga agctaggcag gcttatcttg acaagaaga tcgcttggcc    5940
tcgcgcgcag atcagttgga agaatttgtt cactacgtga aaggcgagat caccaaggta    6000
gtcggcaaat aatgtctaac aattcgttca agccgacgcc gcttcgcggc gcggcttaac    6060
tcaagcgtta gagagctggg gaagactatg cgcgatctgt tgaaggtggt tctaagcctc    6120
gtacttgcga tggcatcggg gcaggcactt gctgacctgc caattgtttt agtggatgaa    6180
gctcgtcttc cctatgacta ctccccatcc aactacgaca tttctccaag caactacgac    6240
aactccataa gcaattacga caatagtcca tcaaattacg acaactctga gagcaactac    6300
gataatagtt catccaatta cgacaatagt cgcaacggaa atcgtaggct tatatatagc    6360
gcaaatgggt ctcgcacttt cgccggctac tacgtcattg ccaacaatgg gacaacgaac    6420
ttctttttcca catctggcaa aaggatgttc tacaccccaa aagggggggcg cggcgtctat    6480
ggcggcaaag atgggagctt ctgcggggca ttggtcgtca taaatggcca attttcgctt    6540
gccctgacag ataacggcct gaagatcatg tatctaagca actagcctgc tctctaataa    6600
aatgttaggc ctcaacatct agtcgcaagc tgagggggaac cactagcagc acgccatagt    6660
gactggcgat gctgtcggaa tggacgatat ctagacttat atagacacta atatagacaa    6720
tagtttatac tgctatctat acaagtatag acattatcta atcatggcag acaaaactct    6780
agccactttt cgtattgact ccgaagaatg ggagtctttt aaaaaccttg ctagttctga    6840
aagttccaac gcctcagcac tgttaacaga atttgttcgt tggtatttgg caggtaacag    6900
gtttaatact cccacttctc acactcccac ccatctagac acatccctcg aacagcgtat    6960
agacaatatt gaacaacgtc tagataaagt cacaactaat aatctagaca atatagatga    7020
atttatagac aagcgtatag aagataatct agcaacacgt ctagacaaac ttcaatcgca    7080
actggaggaa ctgcgggaa atcgaaagc ccggtagttc aggcagaagg acaagctacc    7140
gggcaagaca gaaagaatat agacaatagt atagacaatc tagacaaatt ggaggcaacc    7200
cgcgatcgca ccctcaataa gctaaaaatg ggtaggcagt cagccgccgg gaaagccatc    7260
gacgcgtttta tcaaagagtt gctttcttca ggagacaaca taagctgaag ttatcaaaat    7320
```

```
tctgtcctta cgtcgaaagc ctgatttttac cgtgcaacga ttgataagct tggctaaact    7380
agcactggct ttcaacagaa agcatacgaa gaatcaatag atatagccac caattccaca    7440
aaatgcagat aacgtgtaga gtattggaat gcttaatctg taagggttat gaaggttaac    7500
ggcaacggac gagccaaaat actcacctcc gacgaactca ggcgactgtt tagcgacgga    7560
ttcaccacac cgcgcgatcg cgttttgttt ggcatctgtc tattcaccgg ttgccgcgtt    7620
agtgaagctc tagcactcca aacaacggac attaaaggcg aaacactaac ctttaggaag    7680
tctaccacca aagggaaact caaaacccgc gtggttgaca tccagccagg actagccgca    7740
ctcatggctg actatcaccc caaaccggga accctgttcc ctggcatgag gggagtcagc    7800
gataggctca cgcgatacgc ggcggataaa atcttgcgcg atgcagccaa aagaatcggg    7860
ctagaaggca tcagtaccca cagtttccgc cgtactgccc tcaaccaaat gtctagcgcc    7920
ggtatcccgt tgcgacacat tcaagagata tccggtcaca atgaccttgg cacactgcaa    7980
cgctatcttg aagttacacc cgaacagcga cgcaaagctg tatccgtgat ggcttctaa    8040
tgtacgccaa cgctgtttag acccctatgg gtgctaaaaa aagacgcagc ctaaacacac    8100
gctctacact tgaggatact tttaaagtat ccatcggttc tagaactctg cacacgttcc    8160
ggactttgga aacgttatac ctttccctgt gttgcagaat gctgcaatat ttcttcgaca    8220
agttaacttg tgactggttt aatattttct caaattgccc caaaacaaca cgcctaaatc    8280
cttagacgtt tctgtggaaa cctattaggt ttttatcgcc gttgttttag tggtaaaccc    8340
aaagggtttg tatattcttg tatgaagttc gactctgagg gttaagaaga atggctcgcc    8400
gaattttta caagtggaaa ccgattaaag gttaagggtc aatcgggacg atgaatattt    8460
tctaattgtg accttctcca tctaataagc tttctttggg gttaaggtcg aagaaagtac    8520
tacgcatgat ctgcatacga tctctattgc caaaaagccg cgaccctata ggctctcggt    8580
catgctgcac tagttcgtgt cgatcactat actggttgcc gcagcatttc acgctaaaaa    8640
aaaattctta aaaatgtcct tcatatctcg ccagagtggc aacctattac aaaacggttg    8700
cctacccgac cggctcgatt ttcgctgaag tggcactgtg acagtttgaa atggtacttc    8760
cgccgtgctg ctgacatcgt tgttagggtg aattgttcgc ggtagatgtt gcaccgattc    8820
atgaacacct tgtcacccac tttgaataat cgaccgtcaa attcagtcgc gtcaatttgg    8880
taagtgttgg gctgtctctt tttggctcca ggggcaatgc catcagaaaa cacaaccgcg    8940
tcacccataa cttgataacc gatatcagtt ttggttccag tgaaagccca aaattcagac    9000
gcgtcattat tccgagcgtg ccggagttga ttgtactcaa ttttggcttg caaagttga    9060
cggcgattca tgcccagctg cttttgatgt cgtcgcactg tgcgcttgtg aatacccaac    9120
tcacagctga cagcttttg agatgtacca tagtggatga aacttttga gacgaatatc    9180
cgcgacgaac taatgtgaag tacacaaggt acttccccct ctggcgattt aagagaggat    9240
tgccttgtgt cctcactag ctcgttcggg tgtggcgctc caaaaagttt tctgtactct    9300
ggtttaagtt gtctgttggc cgcatagcgg ctcttttgtt gaaagctttg tgtgactatg    9360
ccagtggtca gtgagcgtaa atcgcttaac acttggacta aaggcactac tgcaacatca    9420
ccccatcttt ttaaatttag gttgtaacaa acttgaaaca taccgcccaa gtagacggtt    9480
atcattcctg ctttaatttt gtagcggcgg aatgctccta tttttttcc atcctgtaac    9540
caacggtaaa cagacttatc actacaatct aagaacgtct gtactacagg caatggcaat    9600
gttaaatgac cagaccccatc cttatcaagc gctcgacaca aataccacaa ccgcgcacaa    9660
ggttctcgac caatgcgagt gtgtaccctg accgtgtaag tgccaagaat tatttcagtt    9720
```

```
tgtagttccc ttgtaagcag ggttagtgat acatttgtat ttaagctttc tgggctgatc   9780
atttggaaat gtctcagtcc agtacctatt gaatgttatt tgcttaacct gaagctaaat   9840
aaaacttgtt aactcaccc attaattgat aaattcaaag cacgttttt ctgtttggtg    9900 tttggtgtgg taacaattct gtgtatgtgt gttttattta gcttcggtta agtagcataa   9960 caaccccccaa gcactgaact tttttaata ggtaatttaa actttgccta tcggcaaaat  10020
tttcaatcaa ttgtacgcca aagtgttgca tgatcaacgt ttgacttatt tttgtattta  10080
ctaaatactg aatttcgccg tgacgctttt tacagatgga aattcacggc aaaatgtttt  10140
ttgctaactt tgctatgtaa aacaagaaac ttggcactcg gttattacta aataaactgg  10200
taaaaaataa ccattagaac caaaagaac gaaaaccagt acacccttgc cagttttcaa   10260
gcttttgcta tgacgactct aataatcggg tttaacacca ttccgctttg agaaaattat  10320
ccttgtacag caagtaacag tcaatgctaa accgcaccgc tacaaatcct taagttttc   10380 cagtagcgat ttaccttctt ggtaacgccc gccttgatag cccaaaattt ctttaatcac  10440
cttactttct gaaaacccg cttccagaca ggcttttacc acttttgcta gggtttcatc    10500
tcttggttct gggagggatg aaacgggctg taatgcttgt tctgaggtcg gttgagccgt   10560
ttggagtggc tgaaaactgg ttacagactg taaccggggc ataaccattt tgtaactgct   10620
tacatctggt aactgacacg gcatatcatc caccatgcag cgatatttcc ccgactttaa   10680
ccactccaca agggcaaggt ctttaagga cttggcgtgg ctaactgcaa acttacccag    10740
gcgtaacatc ctaaaacact tacgacacc gccttcaccc tcgataccta aggtcttgac    10800
attatcatct tgagtcagcc caataacaaa acgcttgggc ttgcggccgc gcctggcgtg   10860
tttgatgagc cattcggttg ctatctcgac ttcatctctc agcagtggca gttcttcagc   10920
aattaaaacg ctttctttc ctgctagtgc cttatcccca gactcacccc gtagctcaat    10980
ccggcgctgc aattcctcca ggtcagcagc catgcccgac tgtatagcct caaagtcacc   11040
acggcggcca atgacattta accccgtcca ctcgtccggt gcagcgtcag cgtcatagac   11100
tgtcacctca cccccgactt gataagcaag ccattgggct atggtgcttt tgccagttcc   11160
cgtatcccca actattaaac agtgcttacc agacagagct tgcatcaagt cggtgatgat   11220
tccctctggt tcgaccgcaa gggtgacggc ggtagtgtca atgatagccg cgccgtaagt   11280
gccagcatag ggcaattggt cgtaaacttt gaccaagttg tatacagact gtctacacca   11340
cttcaccact gttaacgctg tttgcaaagc gtaagacgtg gcatcaaata aaaatatgct   11400
ggcactaaaa gttaatcgcc ccaatcccca cagtaaaaac ctgcctagct gttgacgact   11460
aggcaagtgc atttcaatcc agtcatttgc cataaatcac cccgtctta aagccttgca    11520 gttgagcgcg acaggtattt aactgtgctt gtaactctgt ttgctggttt tgataccaca   11580
gactgacggc ggcggccgcc agtcctaaaa atagaaactg gcgatcgctc attattgact   11640
tactccctgt tgattagcgt ggtagtgagt catagccgca ttgaccgctt cttgggcttg    11700
gggtgttctg ccaagattgg gttttgtagg gtcatcgttg gctacgacta aggacgcttg   11760
ttcggctatc gcttgcggga caccaacttt agttaactct gtcaaggata cttggtaaag   11820
tcgctcgttc attagccgat tctccggtac ataaaactgt tgctggcagt cccttcattg   11880
gcgacgagtt cttcagccgg agtatcagcg ataatgtcag cccagccggt gacattatta   11940
ttaataatgt tttgttcggc aattgcaccc aagccaggac gcgccgtttc aaactcagag   12000
atgacttgct gctctttctc ggtgagtggt ctatctgtca tgataattat gtccttcatt   12060
atgtaggcga ttccagtggg tgtttacgag gcagtccaca ggaatcagtg cgattcacct   12120
```

```
ttaaggtgaa tcgtcatcaa aaaatcactc ggtagcaacg acccgaaccg accaggattg   12180
atttcccggt tctcagttcg caggcttttg agcgcgtcac cttgaccatt gggtaactgc   12240
catcagccga taagctaaac gggctgtata gcggtaaagc atcccacaca gtcgggctgg   12300
catcaacttt gcaggaatag ctcacgtcac tcatctcact cgcgcctggg ttggatggca   12360
gcgaaggcag attacgacgc agttttttac tggcactttt acccgcatta aaacgggta    12420 cagtgccatt gttgacggtc tgtacttcgg tcatatactc ggtgtacact aatacactc    12480 tatactatta ctgccgatta gtacatttgt caatcactct ttgcacaagg tgtatgatat   12540
ggactcagga gtacaccaaa cgtcatgcca accaataaag ggagaatagc agtcactcta   12600
gaagctgaaa tttaccaatg gattgctaac cgagcgtctg aggaaggaag accgttggct   12660
aatcttgccg ctttcttact cacacgagtt gttaaagaac aaatggaaca agaagccaag   12720
gacaaccaag acaagcaggg ggcagcatga gcgaagacag actagccaga atagaagctg   12780
cgttagacag ccaagttgca gtgaatgccg acctccgcac atcggttaca gaactccgcg   12840
caaccgcaga agcattgttg caaacagttc aaatccatca gcagaacttt gaaattctta   12900
ccgctaggca attacaaacc gaagcacggc ttgatgagta ccaacgtacc actagcgcgg   12960
cactcgacag aattggcgcg gtcttagact acctcgttag gcagcaaaac ggttgaggtg   13020
agggatgagc gatgactatc tagacggata tcccgcaaga ggcccttcg  tcttcaagaa   13080 ttctcatgtt tgacagctta tc                                           13102

<210> SEQ ID NO 15
<211> LENGTH: 12472
<212> TYPE: DNA
<213> ORGANISM: Artificial
<220> FEATURE:
<223> OTHER INFORMATION: sequence of plasmid pRL593-PisiA-PDC-ADHII

<400> SEQUENCE: 15
ctagcgctat atgcgttgat gcaatttcta tgcgcacccg ttctcggagc actgtccgac     60
cgctttggcc gccgcccagt cctgctcgct tcgctacttg gagccactat cgactacgcg    120
atcatggcga ccacacccgt cctgtggatc actaccgggc gtattttttg agttatcgag    180
attttcagga gctaaggaag ctaaaatgga gaaaaaaatc actggatata ccaccgttga    240
tatatcccaa tggcatcgta aagaacattt tgaggcattt cagtcagttg ctcaatgtac    300
ctataaccag accgttcagc tggatattac ggcctttttta aagaccgtaa agaaaaataa    360
gcacaagttt tatccggcct ttattcacat tcttgcccgc ctgatgaatg ctcatccgga    420
attccgtatg gcaatgaaag acggtgagct ggtgatatgg gatagtgttc acccttgtta    480
caccgttttc catgagcaaa ctgaaacgtt ttcatcgctc tggagtgaat accacgacga    540
tttccggcag tttctacaca tatattcgca agatgtggcg tgttacggtg aaaacctggc    600
ctatttccct aaagggttta ttgagaatat gttttttcgtc tcagccaatc cctgggtgag    660
tttcaccagt tttgatttaa acgtggccaa tatggacaac ttcttcgccc ccgttttcac    720
catgggcaaa tattatacgc aaggcgacaa ggtgctgatg ccgctggcga ttcaggttca    780
tcatgccgtt tgtgatggct tccatgtcgg cagaatgctt aatgaattac aacagtactg    840
cgatgagtgg cagggcgggg cgtaattttt taaggcagt tattggtgcc cttaaacgcc    900
tggtgctacg cctgaataag tgataataag cggatgaatg gcagaaattc gaaagcaaat   960
tcgacccggt cgtcggttca gggcagggtc gttaaatagc cgcttatgtc tattgctggt   1020
ttaccggttt attgactacc ggaagcagtg tgaccgtgtg cttctcaaat gcctgaggcc   1080
```

```
agtttgctca ggctctcccc gtggaggtaa taattgacga tatgatcctc tacgccggac   1140
gcatcgtggc cggcatcacc ggcgataagc ttcacgctgc cgcaagcact cagggcgcaa   1200
gggctgctaa aggaagcgga acacgtagaa agccagtccg cagaaacggt gctgaccccg   1260
gatgaatgtc agctactggg ctatctggac aagggaaaac gcaagcgcaa agagaaagca   1320
ggtagcttgc agtgggctta catggcgata gctagactgg gcggttttat ggacagcaag   1380
cgaaccggaa ttgccagctg gggcgccctc tggtaaggtt gggaagccct gcaaagtaaa   1440
ctggatggct tcttgccgc caaggatctg atggcgcagg ggatcaagat ctgatcaaga    1500
gacaggatga ggatcgtttc gcatgattga acaagatgga ttgcacgcag gttctccggc   1560
cgcttgggtg gagaggctat tcggctatga ctgggcacaa cagacaatcg gctgctctga   1620
tgccgccgtg ttccggctgt cagcgcaggg gcgcccggtt cttttttgtca agaccgacct   1680
gtccggtgcc ctgaatgaac tgcaggacga ggcagcgcgg ctatcgtggc tggccacgac   1740
gggcgttcct tgcgcagctg tgctcgacgt tgtcactgaa gcgggaaggg actggctgct   1800
attgggcgaa gtgccggggc aggatctcct gtcatctcac cttgctcctg ccgagaaagt   1860
atccatcatg gctgatgcaa tgcggcggct gcatacgctt gatccggcta cctgcccatt   1920
cgaccaccaa gcgaaacatc gcatcgagcg agcacgtact cggatggaag ccggtcttgt   1980
cgatcaggat gatctggacg aagagcatca ggggctcgcg ccagccgaac tgttcgccag   2040
gctcaaggcg cgcatgcccg acggcgagga tctcgtcgtg acccatggcg atgcctgctt   2100
gccgaatatc atggtggaaa atggccgctt ttctggattc atcgactgtg gccggctggg   2160
tgtggcggac cgctatcagg acatagcgtt ggctacccgt gatattgctg aagagcttgg   2220
cggcgaatgg gctgaccgct tcctcgtgct ttacggtatc gccgctcccg attcgcagcg   2280
catcgccttc tatcgccttc ttgacgagtt cttctgagcg ggactctggg gttcgaaatg   2340
accgaccaag cgacgcccaa cctgccatca cgagatttcg attccaccgc cgccttctat   2400
gaaaggttgg gcttcggaat cgttttccgg gacgccggct ggatgatcct ccagcgcggg   2460
gatctcatgc tggagttctt cgcccacccc aacgatctga tagagaaggg tttgctcggg   2520
tcggtggctc tggtaacgac cagtatcccg atcccggctg gccgtcctgg ccgccacatg   2580
aggcatgttc cgcgtccttg caatactgtg tttacataca gtctatcgct tagcggaaag   2640
ttcttttacc ctcagccgaa atgcctgccg ttgctagaca ttgccagcca gtgcccgtca   2700
ctcccgtact aactgtcacg aaccctgca ataactgtca cgcccctg caataactgt     2760
cacgaacccc tgcaataact gtcacgcccc aaacctgca acccagcag ggcgggggc     2820
tggcggggtg ttggaaaaat ccatccatga ttatctaaga ataatccact aggcgcggtt   2880
atcagcgccc ttgtggggcg ctgctgccct tgcccaatat gcccggccag aggccggata   2940
gctggtctat tcgctgcgct aggctacaca ccgccccacc gctgcgcggc aggggaaag    3000
gcgggcaaag cccgctaaac cccacaccaa acccgcaga aatacgctgg agcgcttta    3060
gccgctttag cggccttcc ccctacccga agggtggggg cgcgtgtgca gccccgcagg   3120
gcctgtctcg gtcgatcatt cagcccggct catccttctg gcgtggcggc agaccgaaca   3180
aggcgcggtc gtggtcgcgt tcaaggtacg catccattgc cgccatgagc cgatcctccg   3240
gccactcgct gctgttcacc ttggccaaaa tcatggcccc caccagcacc ttgcgccttg   3300
tttcgttctt gcgctcttgc tgctgttccc ttgcccgctc ccgctgaatt tcggcattga   3360
ttcgcgctcg ttgttcttcg agcttggcca gccgatccgc cgccttgttg ctccccttaa   3420
ccatcttgac accccattgt taatgtgctg tctcgtaggc tatcatggag gcacagcggc   3480
```

```
ggcaatcccg accctacttt gtaggggagg gcgcacttac cggtttctct tcgagaaact   3540
ggccctaacg gccacccttc gggcggtgcg ctctccgagg gccattgcat ggagccgaaa   3600
agcaaaagca acagcgaggc agcatggcga tttatcacct tacggcgaaa accggcagca   3660
ggtcgggcgg ccaatcggcc agggccaagg ccgactacat ccagcgcgaa ggcaagtatg   3720
cccgcgacat ggatgaagtc ttgcacgccg aatccgggca catgccggag ttcgtcgagc   3780
ggcccgccga ctactgggat gctgccgacc tgtatgaacg cgccaatggg cggctgttca   3840
aggaggtcga atttgccctg ccggtcgagc tgaccctcga ccagcagaag gcgctggcgt   3900
ccgagttcgc ccagcacctg accggtgccg agcgcctgcc gtatacgctg gccatccatg   3960
ccggtggcgg cgagaacccg cactgccacc tgatgatctc cgagcggatc aatgacggca   4020
tcgagcggcc cgccgctcag tggttcaagc ggtacaacgg caagaccccg gagaagggcg   4080
ggcacagaa gaccgaagcg ctgaagccca aggcatggct tgagcagacc cgcgaggcat   4140
gggccgacca tgccaaccgg gcattagagc gggctggcca cgacgcccgc attgaccaca   4200
gaacacttga ggcgcagggc atcgagcgcc tgcccggtgt tcacctgggg ccgaacgtgg   4260
tggagatgga aggccgggc atccgcaccg accgggcaga cgtggccctg aacatcgaca   4320
ccgccaacgc ccagatcatc gacttacagg aataccggga ggcaatagac catgaacgca   4380
atcgacagag tgaagaaatc cagaggcatc aacgagttag cggagcagat cgaaccgctg   4440
gcccagagca tggcgacact ggccgacgaa gcccggcagg tcatgagcca gaccaagcag   4500
gccagcgagg cgcaggcggc ggagtggctg aaagcccagc gccagacagg ggcggcatgg   4560
gtggagctgg ccaaagagtt gcgggaggta ccgccgagg tgagcagcgc cgcgcagagc   4620
gcccggagcg cgtcgcgggg gtggcactgg aagctatggc taaccgtgat gctggcttcc   4680
atgatgccta cggtggtgct gctgatcgca tcgttgctct tgctcgacct gacgccactg   4740
acaaccgagg acggctcgat ctggctgcgc ttggtggccc gatgaagaac gacaggactt   4800
tgcaggccat aggccgacag ctcaaggcca tgggctgtga gcgcttcgat atcggcgtca   4860
gggacgcacc caccgccag atgatgaacc gggaatggtc agccgccgaa gtgctccaga   4920
acacgccatg gctcaagcgg atgaatgccc agggcaatga cgtgtatatc aggcccgccg   4980
agcaggagcg gcatggtctg gtgctggtgg acgacctcag cgagtttgac ctggatgaca   5040
tgaaagccga gggccgggag cctgccctgg tagtggaaac cagcccgaag aactatcagg   5100
catgggtcaa ggtggccgac gccgcaggcg gtgaacttcg ggggcagatt gcccggacgc   5160
tggccagcga gtacgacgcc gacccggcca gcgccgacag ccgccactat ggccgcttgg   5220
cgggcttcac caaccgcaag gacaagcaca ccacccgcgc cggttatcag ccgtgggtgc   5280
tgctgcgtga atccaaggc aagaccgcca ccgctggccc ggcgctggtg cagcaggctg   5340
gccagcagat cgagcaggcc cagcggcagc aggagaaggc ccgcaggctg ccagcctcg   5400
aactgcccga gcgcagctt agccgccacc ggcgcacggc gctggacgag taccgcagcg   5460
agatggccgg gctggtcaag cgcttcggtc atgacctcag caagtgcgac tttatcgccg   5520
cgcagaagct ggccagccgg ggccgcagtg ccgaggaaat cggcaaggcc atggccgagg   5580
ccagcccagc gctggcagag cgcaagcccg gccacgaagc ggattacatc gagcgcaccg   5640
tcagcaaggt catgggtctg cccagcgtcc agcttgcgcg ggccgagctg gcacgggcac   5700
cggcacccg ccagcgaggc atggacaggg gcgggccaga tttcagcatg tagtgcttgc   5760
gttggtactc acgcctgtta tactatgagt actcacgcac agaagggggt tttatggaat   5820
acgaaaaaag cgcttcaggg tcggtctacc tgatcaaaag tgacaaggc tattggttgc   5880
```

```
ccggtggctt tggttatacg tcaaacaagg ccgaggctgg ccgcttttca gtcgctgata    5940
tggccagcct taaccttgac ggctgcacct tgtccttgtt ccgcgaagac aagcctttcg    6000
gccccggcaa gtttctcggt gactgatatg aaagaccaaa aggacaagca gaccggcgac    6060
ctgctggcca gccctgacgc tgtacgccaa gcgcgatatg ccgagcgcat gaaggccaaa    6120
gggatgcgtc agcgcaagtt ctggctgacc gacgacgaat acgaggcgct gcgcgagtgc    6180
ctggaagaac tcagagcggc gcagggcggg ggtagtgacc ccgccagcgc ctaaccacca    6240
actgcctgca aaggaggcaa tcaatggcta cccataagcc tatcaatatt ctggaggcgt    6300
tcgcagcagc gccgccaccg ctggactacg ttttgcccaa catggtggcc ggtacggtcg    6360
gggcgctggt gtcgcccggt ggtgccggta atccatgct ggccctgcaa ctggccgcac     6420
agattgcagg cgggccggat ctgctggagg tgggcgaact gcccaccggc ccggtgatct    6480
acctgcccgc cgaagacccg cccaccgcca ttcatcaccg cctgcacgcc cttggggcgc    6540
acctcagcgc cgaggaacgg caagccgtgg ctgacggcct gctgatccag ccgctgatcg    6600
gcagcctgcc caacatcatg gccccggagt ggttcgacgg cctcaagcgc gccgccgagg    6660
gccgccgcct gatggtgctg acacgctgc gccggttcca catcgaggaa gaaaacgcca     6720
gcggccccat ggcccaggtc atcggtcgca tggaggccat cgccgccgat accgggtgct    6780
ctatcgtgtt cctgcaccat gccagcaagg gcgcggccat gatgggcgca ggcgaccagc    6840
agcaggccag ccggggcagc tcggtactgg tcgataacat ccgctggcag tcctacctgt    6900
cgagcatgac cagcgccgag gccgaggaat ggggtgtgga cgacgaccag cgccggttct    6960
tcgtccgctt cggtgtgagc aaggccaact atggcgcacc gttcgctgat cggtggttca    7020
ggcggcatga cggcggggtg ctcaagcccg ccgtgctgga gaggcagcgc aagagcaagg    7080
gggtgccccg tggtgaagcc taagaacaag cacagcctca gccacgtccg gcacgacccg    7140
gcgcactgtc tggccccggg cctgttccgt gccctcaagc ggggcgagcg caagcgcagc    7200
aagctggacg tgacgtatga ctacggcgac ggcaagcgga tcgagttcag cggcccggag    7260
ccgctgggcg ctgatgatct gcgcatcctg caagggctgg tggccatggc tgggcctaat    7320
ggcctagtgc ttggcccgga acccaagacc gaaggcggac ggcagctccg gctgttcctg    7380
gaacccaagt gggaggccgt caccgctgaa tgccatgtgg tcaaaggtag ctatcgggcg    7440
ctggcaaagg aaatcgggc agaggtcgat agtggtgggg cgctcaagca catacaggac    7500
tgcatcgagc gcctttggaa ggtatccatc atcgcccaga atggccgcaa gcggcagggg    7560
tttcggctgc tgtcggagta cgccagcgac gaggcggacg ggcgcctgta cgtggccctg    7620
aaccccttga tcgcgcaggc cgtcatgggt ggcggccagc atgtgcgcat cagcatggac    7680
gaggtagcgg gcgctggaca gcgaaaccgc ccgcctgctg caccagcggc tgtgtggctg    7740
gatcgacccc ggcaaaaccg gcaaggcttc catagatacc ttgtgcggct atgtctggcc    7800
gtcagaggcc agtggttcga ccatgcgcaa gcgccgcaag cgggtgcgcg agcgttgccg    7860
gagctggtcg cgctgggctg acggtaacc gagttcgcgg cggcaagta cgacatcacc      7920 cggcccaagg cggcaggctg accccccca ctctattgta aacaacacat ttttatcttt     7980
tatattcaat ggcttatttt cctgctaatt ggtaatacca tgaaaatac catgctcaga     8040 aaaggcttaa caatattttg aaaaattgcc tactgagcgc tgccgcacag ctccataggc    8100
cgcttttcag gctttgcttc cagatgtatg ctcttctgct cctgcagttc attcagggca    8160
ccggacaggt cggtcttgac aaaaagaacc gggcgcccct gcgctgacag ccggaacacg    8220
gcggcatcag agcagccgat tgtctgttgt gcccagtcat agccgaatag cctctccacc    8280
```

-continued

```
caagcggccg gagaacctgc gtgcaatcca tcttgttcaa tcatgcgaaa cgatcctcat    8340
cctgtctctt gatcattgat cccctgcgcc atcagatcct tggcggcaag aaagccatcc    8400
agtttacttt gcagggcttc ccaaccttac cagagggcgc cccagctggc aattccggtt    8460
cgcttgctgt ccataaaacc gcccagtcta gctatcgcca tgtaagccca ctgcaagcta    8520
cctgctttct ctttgcgctt gcgttttccc ttgtccagat agcccagtag ctgacattca    8580
tccggggtca gcaccgtttc tgcggactgg cttttctacgt gttccgcttc ctttagcagc    8640
ccttgcgccc tgagtgcttg cggcagcgtg aagcttatcg attcacaaaa aataggcaca    8700
cgaaaaacaa gttaagggat gcagtttatg cactagccta ggctcgagaa gcttgtcgac    8760
cttccagcac cacgtcaact ttgtttaact gctcccggag ttgtcttttcc gctttggcaa    8820 tgtgcccggg ataccattgg attaaagcca tgagttgttc acttttttac tgacgagggc    8880
ttccggaggc cacgctccca cccataacag cttgccacat ccccgtcgga agttacgtta    8940
cccttgggcg atcgccaaaa atcagcatat atacaccaat tctaaataag atcttttaca    9000
ccgctactgc aatcaacctc atcaacaaaa ttcccctcta gcatccctgg aggcaaatcc    9060
tcacctggcc atgggttcaa ccctgcttaa catttcttaa taattttagt tgctataaat    9120
tctcatttat gccctataa taattcggga gtaagtgcta aagattctca actgctccat    9180
cagtggtttg agcttagtcc tagggaaaga ttggcgatcg ccgttgtggt taagccagaa    9240
taggtctcgg gtggacagag aacgctttat tctttgcctc catggcggca tcccacctag    9300
gtttctcggc acttattgcc ataatttatt atttgtcgtc tcaattaagg aggcaattct    9360
gtgaattctt atactgtcgg tacctattta gcggagcggc ttgtccagat tggtctcaag    9420
catcacttcg cagtcgcggg cgactacaac ctcgtccttc ttgacaacct gcttttgaac    9480
aaaaacatgg agcaggttta ttgctgtaac gaactgaact gcggtttcag tgcagaaggt    9540
tatgctcgtg ccaaaggcgc agcagcagcc gtcgttacct acagcgtcgg tgcgctttcc    9600
gcatttgatg ctatcggtgg cgcctatgca gaaaaccttc cggttatcct gatctccggt    9660
gctccgaaca acaatgatca cgctgctggt cacgtgttgc atcacgctct tggcaaaacc    9720
gactatcact atcagttgga aatggccaag aacatcacgg ccgcagctga agcgatttac    9780
accccagaag aagctccggc taaaatcgat cacgtgatta aaactgctct tcgtgagaag    9840
aagccggttt atctcgaaat cgcttgcaac attgcttcca tgccctgcgc cgctcctgga    9900
ccggcaagcg cattgttcaa tgacgaagcc agcgacgaag cttctttgaa tgcagcggtt    9960
gaagaaaccc tgaaattcat cgccaaccgc gacaaagttg ccgtcctcgt cggcagcaag    10020
ctgcgcgcag ctggtgctga agaagctgct gtcaaatttg ctgatgctct cggtggcgca    10080
gttgctacca tggctgctgc aaaaagcttc ttcccagaag aaaacccgca ttacatcggt    10140
acctcatggg gtgaagtcag ctatccgggc gttgaaaaga cgatgaaaga agccgatgcg    10200
gttatcgctc tggctcctgt cttcaacgac tactccacca ctggttggac ggatattcct    10260
gatcctaaga aactggttct cgctgaaccg cgttctgtcg tcgttaacgg cgttcgcttc    10320
cccagcgttc atctgaaaga ctatctgacc cgtttggctc agaaagtttc caagaaaacc    10380
ggtgctttgg acttcttcaa atccctcaat gcaggtgaac tgaagaaagc cgctccggct    10440
gatccgagtc ctccgttggt caacgcagaa atcgcccgtc aggtcgaagc tcttctgacc    10500
ccgaacacga cggttattgc tgaaaccggt gactcttggt tcaatgctca gcgcatgaag    10560
ctcccgaacg gtgctcgcgt tgaatatgaa atgcagtggg gtcacatcgg ttggtccgtt    10620
cctgccgcct tcggttatgc cgtcggtgct ccggaacgtc gcaacatcct catggttggt    10680
```

```
gatggttcct tccagctgac ggctcaggaa gtcgctcaga tggttcgcct gaaactgccg    10740
gttatcatct tcttgatcaa taactatggt tacaccatcg aagttatgat ccatgatggt    10800
ccgtacaaca acatcaagaa ctgggattat gccggtctga tggaagtgtt caacggtaac    10860
ggtggttatg acagcggtgc tggtaaaggc ctgaaggcta aaaccggtgg cgaactggca    10920
gaagctatca aggttgctct ggcaaacacc gacggcccaa ccctgatcga atgcttcatc    10980
ggtcgtgaag actgcactga agaattggtc aaatggggta gcgcgttgc tgccgccaac    11040
agccgtaagc ctgttaacaa gctcctctag ttttgggga tcaattcgag ctcggtaccc    11100
aaactagtat gtagggtgag ttatagcta tggcttcttc aacttttat attcctttcg    11160
tcaacgaaat gggcgaaggt tcgcttgaaa aagcaatcaa ggatcttaac ggcagcggct    11220
ttaaaaatgc gctgatcgtt tctgatgctt catgaacaa tccggtgtt gtgaagcagg    11280
ttgctgacct gttgaaagca cagggtatta ttctgctgt ttatgatggc gttatgccga    11340
acccgactgt taccgcagtt ctggaaggcc ttaagatcct gaaggataac aattcagact    11400
tcgtcatctc cctcggtggt ggttctcccc atgactgcgc caaagccatc gctctggtcg    11460
caaccaatgg tggtgaagtc aaagactacg aaggtatcga caaatctaag aaacctgccc    11520
tgcctttgat gtcaatcaac acgacggctg gtacggcttc tgaaatgacg cgtttctgca    11580
tcatcactga tgaagtccgt cacgttaaga tggccattgt tgaccgtcac gttaccccga    11640
tggtttccgt caacgatcct ctgttgatgg ttggtatgcc aaaaggcctg accgccgcca    11700
ccggtatgga tgctctgacc cacgcatttg aagcttattc ttcaacggca gctactccga    11760
tcaccgatgc ttgcgccttg aaggctgcgt ccatgatcgc taagaatctg aagaccgctt    11820
gcgacaacgg taaggatatg ccagctcgtg aagctatggc ttatgcccaa ttcctcgctg    11880
gtatggcctt caacaacgct tcgcttggtt atgtccatgc tatggctcac cagttgggcg    11940
gctactacaa cctgccgcat ggtgtctgca acgctgttct gcttccgcat gttctggctt    12000
ataacgcctc tgtcgttgct ggtcgtctga agacgttgg tgttgctatg ggtctcgata    12060
tcgccaatct cggtgataaa gaaggcgcag aagccaccat tcaggctgtt cgcgatctgg    12120
ctgcttccat tggtattcca gcaaatctga ccgagctggg tgctaagaaa gaagatgtgc    12180
cgcttcttgc tgaccacgct ctgaaagatg cttgtgctct gaccaacccg cgtcagggtg    12240
atcagaaaga agttgaagaa ctcttcctga gcgctttcta atttcaaaac aggaaaacgg    12300
ttttccgtcc tgtcttgatt ttcaagcaaa caatgcctcc gatttctaat cggaggcatt    12360
tgttttgtt tattgcaaaa acaaaaaata ttgttacaaa tttttacagg ctattaagcc    12420
taccgtcata ataatttgc catttgggga tccgatacgt aacgcgtctg ca              12472
```

<210> SEQ ID NO 16
<211> LENGTH: 336
<212> TYPE: PRT
<213> ORGANISM: Synechocystis PCC6803

<400> SEQUENCE: 16

Met Ile Lys Ala Tyr Ala Ala Leu Glu Ala Asn Gly Lys Leu Gln Pro
1               5                   10                  15

Phe Glu Tyr Asp Pro Gly Ala Leu Gly Ala Asn Glu Val Glu Ile Glu
                20                  25                  30

Val Gln Tyr Cys Gly Val Cys His Ser Asp Leu Ser Met Ile Asn Asn
            35                  40                  45

Glu Trp Gly Ile Ser Asn Tyr Pro Leu Val Pro Gly His Glu Val Val
        50                  55                  60

```
Gly Thr Val Ala Ala Met Gly Glu Gly Val Asn His Val Glu Val Gly
 65                  70                  75                  80

Asp Leu Val Gly Leu Gly Trp His Ser Gly Tyr Cys Met Thr Cys His
                 85                  90                  95

Ser Cys Leu Ser Gly Tyr His Asn Leu Cys Ala Thr Ala Glu Ser Thr
            100                 105                 110

Ile Val Gly His Tyr Gly Gly Phe Gly Asp Arg Val Arg Ala Lys Gly
        115                 120                 125

Val Ser Val Val Lys Leu Pro Lys Gly Ile Asp Leu Ala Ser Ala Gly
    130                 135                 140

Pro Leu Phe Cys Gly Gly Ile Thr Val Phe Ser Pro Met Val Glu Leu
145                 150                 155                 160

Ser Leu Lys Pro Thr Ala Lys Val Ala Val Ile Gly Ile Gly Gly Leu
                165                 170                 175

Gly His Leu Ala Val Gln Phe Leu Arg Ala Trp Gly Cys Glu Val Thr
            180                 185                 190

Ala Phe Thr Ser Ser Ala Arg Lys Gln Thr Glu Val Leu Glu Leu Gly
        195                 200                 205

Ala His His Ile Leu Asp Ser Thr Asn Pro Glu Ala Ile Ala Ser Ala
    210                 215                 220

Glu Gly Lys Phe Asp Tyr Ile Ile Ser Thr Val Asn Leu Lys Leu Asp
225                 230                 235                 240

Trp Asn Leu Tyr Ile Ser Thr Leu Ala Pro Gln Gly His Phe His Phe
                245                 250                 255

Val Gly Val Val Leu Glu Pro Leu Asp Leu Asn Leu Phe Pro Leu Leu
            260                 265                 270

Met Gly Gln Arg Ser Val Ser Ala Ser Pro Val Gly Ser Pro Ala Thr
        275                 280                 285

Ile Ala Thr Met Leu Asp Phe Ala Val Arg His Asp Ile Lys Pro Val
    290                 295                 300

Val Glu Gln Phe Ser Phe Asp Gln Ile Asn Glu Ala Ile Ala His Leu
305                 310                 315                 320

Glu Ser Gly Lys Ala His Tyr Arg Val Val Leu Ser His Ser Lys Asn
                325                 330                 335

<210> SEQ ID NO 17
<211> LENGTH: 341
<212> TYPE: PRT
<213> ORGANISM: Oceanobacter sp. Red65

<400> SEQUENCE: 17

Met Ile Lys Ala Phe Ala Ala Asp Thr Ala Lys Gly Glu Leu Lys Pro
1               5                   10                  15

Phe Glu Tyr Glu Val Gly Glu Leu Gly Ser Gln Glu Val Glu Ile Glu
                20                  25                  30

Val His Tyr Cys Gly Val Cys His Ser Asp Ile Ser Met Leu Asp Asn
            35                  40                  45

Glu Trp Gly Met Thr Gln Tyr Pro Phe Val Pro Gly His Glu Val Ala
        50                  55                  60

Gly Leu Ile Lys Gln Val Gly Ala Glu Val Asn His Leu Lys Val Gly
 65                  70                  75                  80

Asp Arg Val Gly Leu Gly Trp Gln Ser Gly Tyr Cys Asn His Cys Glu
                 85                  90                  95

Asn Cys Met Ser Gly Asp His Asn Leu Cys Gly Thr Ala Glu Met Thr
            100                 105                 110
```

Ile Val Gly Arg His Gly Gly Phe Ala Asp His Val Arg Ala Gln Ala
            115                 120                 125

Ser Ser Val Val Lys Leu Pro Asp Asp Ile His Met Ala Asp Ala Gly
    130                 135                 140

Pro Leu Phe Cys Gly Gly Val Thr Val Tyr Asn Pro Met Lys Gln Phe
145                 150                 155                 160

Asp Leu Lys Pro Thr Ala Lys Val Ala Val Ile Gly Ile Gly Gly Leu
                165                 170                 175

Gly His Met Ala Leu Gln Phe Leu Asn Ser Trp Gly Cys Glu Val Thr
                180                 185                 190

Ala Phe Thr Ser Thr Glu Glu Lys Arg Lys Glu Ala Ile Ala Leu Gly
            195                 200                 205

Ala His Lys Thr Leu Asn Ser Arg Asp Glu Gly Glu Leu Lys Gly Ala
        210                 215                 220

Ala Gly Ser Phe Asp Met Ile Ile Ser Thr Val Asn Val Ser Leu Asn
225                 230                 235                 240

Trp Glu Ala Tyr Ile Asn Thr Leu Lys Ala Lys Gly Arg Leu His Phe
                245                 250                 255

Val Gly Ala Val Leu Glu Pro Ile Gln Val Gly Val Phe Pro Leu Met
            260                 265                 270

Met Gly Gln Arg Ser Ile Ser Ala Ser Pro Val Gly Ser Pro Ser Thr
        275                 280                 285

Ile Ser Gln Met Leu Glu Phe Thr Ala Arg His Gln Ile Lys Pro Gln
    290                 295                 300

Val Glu Leu Phe Gln Lys Asp Gln Ile Asn Asp Ala Ile Asn His Val
305                 310                 315                 320

Arg Glu Gly Lys Ala Arg Tyr Arg Ala Val Ile Gln Phe Lys Ala Thr
                325                 330                 335

Ser Asp Asn Ser Ala
            340

<210> SEQ ID NO 18
<211> LENGTH: 337
<212> TYPE: PRT
<213> ORGANISM: Limnobacter sp. MED105

<400> SEQUENCE: 18

Met Glu Leu Ile Met Ile Asn Ala Tyr Ala Ala Phe Glu Ala Lys Gly
1               5                   10                  15

Pro Leu Lys Pro Phe Gln Tyr Asp Pro Gly Glu Leu Asn Ala Phe Asp
            20                  25                  30

Ile Glu Ile Asp Val Asp His Cys Gly Ile Cys His Ser Asp Val Ser
        35                  40                  45

Met Leu Asp Asn Asp Trp Gly Arg Ala Lys Tyr Pro Met Val Ala Gly
    50                  55                  60

His Glu Ile Ile Gly Arg Val Ser Gln Val Gly Ser His Val Ser His
65                  70                  75                  80

Leu Ala Ile Gly Asp Val Val Gly Leu Gly Trp His Ser Gly Tyr Cys
                85                  90                  95

Glu Ser Cys Arg Met Cys Met Gly Gly Asp His Asn Leu Cys Ser Thr
            100                 105                 110

Ala Lys Gly Thr Ile Val Gly Arg His Gly Gly Phe Ala Asp Lys Val
        115                 120                 125

Arg Ala Gln Ala Val Ser Ala Val Lys Ile Pro Ala Gly Val Asn Pro
    130                 135                 140

```
Ala Thr Ala Gly Pro Leu Leu Cys Gly Gly Ile Thr Val Tyr Asn Pro
145                 150                 155                 160

Leu Val Gln Phe Asn Ile Ser Pro Gln Ser Lys Val Ala Val Ile Gly
                165                 170                 175

Val Gly Gly Leu Gly His Met Ala Val Met Phe Leu Lys Ala Trp Gly
            180                 185                 190

Cys Glu Val Thr Ala Phe Ser Ser Asn Val Ser Lys Thr Asp Glu Leu
            195                 200                 205

Leu Gly Met Gly Ala His His Val Leu Asn Ser Lys Asp Pro Asp Ala
        210                 215                 220

Leu Lys Lys Ala Ala Gly Ser Phe Asp Leu Ile Leu Ser Thr Val Asn
225                 230                 235                 240

Val Lys Leu Asp Trp Asn Ala Tyr Ile Gly Thr Leu Ala Pro Lys Gly
                245                 250                 255

Arg Leu His Phe Leu Gly Ala Val Leu Glu Pro Leu Asp Ile Gly Val
            260                 265                 270

Phe Gly Leu Met Gly Gln Gln Arg Ser Ile Ser Ser Pro Val Gly
        275                 280                 285

Ser Pro Arg Val Ile Ala Asp Met Leu Lys Phe Ala Ala Leu His Asn
290                 295                 300

Ile Gln Pro Ile Val Glu Thr Tyr Ser Phe Asp Gln Ile Asn Glu Ala
305                 310                 315                 320

Val Asp Lys Val Arg Asn Gly Ser Pro Arg Phe Arg Val Val Leu Ser
                325                 330                 335

Arg

<210> SEQ ID NO 19
<211> LENGTH: 333
<212> TYPE: PRT
<213> ORGANISM: Psychrobacter cryohalolentis K5

<400> SEQUENCE: 19

Met Ile Asn Ala Tyr Ala Ala Lys Glu Lys Gly Gly Glu Phe Val Pro
1               5                   10                  15

Tyr Gln Tyr Asp Pro Gly Thr Leu Gly Asp His Glu Val Glu Ile Glu
            20                  25                  30

Val His Ser Cys Gly Ile Cys His Ser Asp Leu Ser Met Trp Gln Asn
        35                  40                  45

Glu Trp Gly Met Thr Gln Tyr Pro Phe Val Gly Gly His Glu Val Ala
    50                  55                  60

Gly Lys Val Leu Ala Lys Gly Lys His Val Lys His Leu Glu Leu Gly
65                  70                  75                  80

Asp Lys Val Gly Leu Gly Trp His Lys Gly Tyr Cys Asn Val Cys Asp
                85                  90                  95

Leu Cys Ile Gly Asp His Asn Leu Cys Pro Glu Gln Glu Gly Thr
            100                 105                 110

Ile Ile Gly Asn His Gly Gly Phe Ala Asp Lys Val Arg Ala Lys Asp
        115                 120                 125

Thr Ser Val Ile Lys Ile Pro Glu Gly Leu Asp Phe Asn Ala Val Gly
130                 135                 140

Pro Leu Leu Cys Gly Gly Val Thr Val Phe Asn Pro Leu Met Gln Tyr
145                 150                 155                 160

Asp Ile Thr Pro Thr Ser Arg Val Ala Val Ile Gly Ile Gly Gly Leu
                165                 170                 175

Gly His Leu Ala Leu Gln Phe Ala Asn Ala Trp Gly Cys Glu Val Thr
```

```
                    180                 185                 190
Ala Phe Thr Ser Glu Ser Lys Met Glu Glu Ala Lys Glu Met Gly Ala
        195                 200                 205

His His Ser Leu Asn Ser Arg Glu Asp Ser Glu Ile Glu Lys Ala Ala
    210                 215                 220

Gly Ser Phe Asp Leu Ile Ile Ser Thr Val Asn Val Asp Met Asn Trp
225                 230                 235                 240

Asp Val Val Ile Lys Thr Leu Arg Pro Lys Gly Lys Leu His Phe Val
                245                 250                 255

Gly Leu Leu Glu Ala Pro Leu Glu Ile Ser Ala Ala Pro Met Ile Met
            260                 265                 270

Ala Gln Asn Ser Leu Ser Gly Ser Pro Val Gly Ser Pro Ser Thr Leu
        275                 280                 285

Arg Lys Met Leu Asp Phe Ala Ala Arg His Asn Ile Gln Pro Val Thr
    290                 295                 300

Glu Thr Tyr Lys Met Ser Glu Ile Asn Glu Ala Phe Glu Arg Leu Glu
305                 310                 315                 320

Ser Gly Asn Ala Arg Tyr Arg Val Val Leu Glu Arg Asp
                325                 330

<210> SEQ ID NO 20
<211> LENGTH: 333
<212> TYPE: PRT
<213> ORGANISM: Verrucomicrobiae bacterium DG1235

<400> SEQUENCE: 20

Met Ile Lys Ala Tyr Ala Thr His Thr Pro Gly Gly Lys Leu Glu Pro
1               5                   10                  15

Phe Glu Tyr Asp Pro Gly Glu Leu Ala Pro Thr Asp Val Glu Ile Asn
                20                  25                  30

Val Glu His Cys Gly Ile Cys His Ser Asp Leu Ser Met Leu Asn Asn
            35                  40                  45

Glu Trp Gly Met Thr Thr Tyr Pro Phe Val Pro Gly His Glu Val Val
        50                  55                  60

Gly Thr Ile Gly Ala Ile Gly Ser Asp Val Lys Asn Leu Ala Pro Gly
65                  70                  75                  80

Gln Arg Val Gly Leu Gly Trp His Ser Ser Tyr Cys Thr Thr Cys Pro
                85                  90                  95

Ser Cys Leu Ser Gly Asp His Asn Leu Cys Gln Ala Ala Gly Thr
            100                 105                 110

Ile Val Gly Arg His Gly Gly Phe Ala Asp Lys Val Arg Ala Ser Ala
        115                 120                 125

Leu Ser Val Ile Pro Leu Pro Asp Ser Ile Asp Ala Ala Lys Ala Gly
    130                 135                 140

Pro Leu Phe Cys Gly Gly Ile Thr Val Phe Asn Pro Leu Ile Gln Tyr
145                 150                 155                 160

Glu Val Ser Pro Thr Ala Lys Val Ala Val Ile Gly Ile Gly Gly Leu
                165                 170                 175

Gly His Met Ala Leu Ala Phe Leu Asn Ala Trp Gly Cys Glu Val Thr
            180                 185                 190

Ala Phe Thr Thr Ser Glu Ala Lys Arg Gln Glu Ala Leu Lys Leu Gly
        195                 200                 205

Ala His His Thr Leu Asn Ser Arg Asp Ala Ala Glu Ile Glu Ala Ala
    210                 215                 220

Ala Gly Arg Phe Asp Leu Ile Leu Ser Thr Val Asn Val Gly Leu Asp
```

```
                225                 230                 235                 240
Trp Asn Gly Tyr Val Asn Thr Leu Lys Pro Lys Gly Arg Leu His Phe
                    245                 250                 255

Leu Gly Ala Ala Leu Glu Pro Ile Gln Ile Gly Ala Phe Ser Leu Ile
            260                 265                 270

Met Ala Gln Arg Gln Ile Ser Gly Ser Pro Val Gly Ser Pro Ala Thr
        275                 280                 285

Ile Ala Lys Met Ile Glu Phe Ala Ala Leu His Lys Ile Glu Pro Val
    290                 295                 300

Thr Glu His Phe Lys Phe Asp Gln Ala Asn Glu Ala Leu Ala His Leu
305                 310                 315                 320

Glu Ser Gly Gln Ala Arg Tyr Arg Ile Val Leu Ser His
                325                 330

<210> SEQ ID NO 21
<211> LENGTH: 334
<212> TYPE: PRT
<213> ORGANISM: Saccharophagus degradans 2-40

<400> SEQUENCE: 21

Met Ile Lys Ala Tyr Ala Ala Met Glu Pro Gly Ala Ala Leu Val Pro
1               5                   10                  15

Phe Glu Tyr Glu Pro Gly Pro Leu Ala Asn Asn Glu Val Glu Leu Lys
            20                  25                  30

Val Glu Ser Cys Gly Ile Cys His Ser Asp Leu Ser Met Leu Asp Asn
        35                  40                  45

Glu Trp Gly Phe Thr Gln Tyr Pro Phe Val Gly His Glu Val Ile
    50                  55                  60

Gly Ile Val Glu Ala Val Gly Ser Ser Val Asn Asn Val Ala Val Gly
65                  70                  75                  80

Gln Arg Val Gly Leu Gly Trp His Ser Gly Tyr Cys Asn Thr Cys Ala
                85                  90                  95

Ser Cys Gln Ser Gly Asp Gln Asn Leu Cys Asn Ser Ala Gln Pro Thr
            100                 105                 110

Ile Ala Gly His His Gly Gly Phe Ala Asp Lys Val Arg Ala Asp Ala
        115                 120                 125

Asn Ala Val Val Ala Leu Pro Glu Gly Val Asn Pro Asp Ser Ala Gly
    130                 135                 140

Pro Leu Phe Cys Gly Gly Ile Thr Val Phe Asn Pro Leu Val Gln Phe
145                 150                 155                 160

Gly Ile Lys Pro Thr Ser Lys Val Gly Val Ile Gly Ile Gly Gly Leu
                165                 170                 175

Gly His Ile Ala Leu Gln Phe Leu Asn Ala Trp Gly Cys Glu Val Thr
            180                 185                 190

Ala Phe Thr Ser Ser Glu Ser Lys Lys Glu Glu Ala Leu Lys Leu Gly
        195                 200                 205

Ala His His Val Leu Asn Ser Ser Asp Ala Ala Gln Leu Glu Ala Ala
    210                 215                 220

Ala Gly Arg Phe Asp Phe Ile Ile Ser Thr Val Asn Val Lys Leu Asp
225                 230                 235                 240

Trp Asn Glu Tyr Leu Ala Thr Leu Ala Pro Lys Gly Arg Leu His Phe
                245                 250                 255

Val Gly Ala Thr Leu Ala Pro Leu Asp Ile Asn Val Phe Gln Leu Ile
            260                 265                 270

Gly Ser Gln Arg Glu Ile Ser Gly Ser Pro Val Gly Ser Pro Gly Thr
```

```
                275                 280                 285
Ile Ser Gln Met Leu Asp Phe Ala Ala Leu His Asn Ile Gln Pro Val
            290                 295                 300

Thr Glu Tyr Phe Arg Phe Asp Gln Ile Asn Glu Ala Leu Thr Lys Leu
305                 310                 315                 320

Arg Glu Gly Lys Ala His Tyr Arg Ile Val Leu Thr Asn Lys
                325                 330

<210> SEQ ID NO 22
<211> LENGTH: 333
<212> TYPE: PRT
<213> ORGANISM: Alteromonas macleodii

<400> SEQUENCE: 22

Met Ile Tyr Ala Tyr Ala Ala Lys Glu Ala Gly Gly Lys Leu Glu Lys
1               5                   10                  15

Phe Glu Tyr Asp Pro Gly Glu Leu Gly Ala His Asp Val Glu Ile Asp
            20                  25                  30

Val Glu Ser Cys Gly Ile Cys His Ser Asp Leu Ser Met Leu Asp Asn
        35                  40                  45

Glu Trp Gly Ile Thr Glu Phe Pro Phe Val Pro Gly His Glu Val Val
50                  55                  60

Gly Thr Val Ser Lys Ile Gly Asp His Val Thr Ser Leu Lys Val Gly
65                  70                  75                  80

Gln Arg Val Gly Leu Gly Trp His Ala Ser Tyr Cys Asn Ser Cys Arg
                85                  90                  95

Thr Cys Glu Ala Gly Asp His Asn Leu Cys Ala Gly Ala Thr Met Thr
            100                 105                 110

Ile Gly Gly Arg His Gly Gly Phe Ala Asp Lys Val Arg Ala Gln Ala
        115                 120                 125

Arg Ala Val Ile Pro Leu Pro Glu Ser Ile Asp Ser Thr Lys Ala Gly
130                 135                 140

Pro Leu Phe Cys Gly Gly Ile Thr Val Phe Asn Pro Leu Val Gln Phe
145                 150                 155                 160

Asn Ile Ser Pro Thr Ser Glu Val Gly Val Val Gly Ile Gly Gly Leu
                165                 170                 175

Gly His Leu Ala Leu Gln Phe Leu Asn Ala Trp Gly Cys Lys Val Val
            180                 185                 190

Ala Phe Thr Ser Ser Glu Ser Lys Glu Lys Glu Ala Leu Ser Leu Gly
        195                 200                 205

Ala Ser Glu Thr Ile Asn Ser Arg Asp Glu Asp Glu Ile Lys Lys Ala
210                 215                 220

Gln Gly Arg Phe Asp Leu Ile Ile Ser Thr Val Asn Val Lys Leu Asp
225                 230                 235                 240

Trp Asn Leu Tyr Leu Ser Thr Leu Ala Pro Lys Gly Arg Leu His Phe
                245                 250                 255

Val Gly Ala Thr Leu Glu Pro Leu Asp Ile Gly Ala Phe Asn Leu Ile
            260                 265                 270

Gly Gly Gln Lys Ser Val Ser Gly Ser Pro Val Gly Ser Pro Ala Thr
        275                 280                 285

Ile Lys Thr Met Leu Asp Phe Ala Ala His His Asp Ile Glu Pro Val
290                 295                 300

Thr Glu Thr Phe Lys Phe Glu Asp Val Asn Lys Ala Ile Asp Arg Leu
305                 310                 315                 320

Arg Glu Gly Lys Ala His Tyr Arg Ile Val Leu Thr Arg
                325                 330
```

<210> SEQ ID NO 23
<211> LENGTH: 332
<212> TYPE: PRT
<213> ORGANISM: Acaryochloris marina MBIC11017

<400> SEQUENCE: 23

Met Val Asn Ala Tyr Ala Ala Phe Glu Gln Gly Gly Val Leu Gln Pro
1               5                   10                  15

Phe Glu Tyr Asp Pro Gly Pro Leu Gly Arg Gln Gln Val Asp Ile Gln
            20                  25                  30

Val Glu Tyr Cys Gly Ile Cys His Ser Asp Leu Ser Met Ile Lys Asn
        35                  40                  45

Glu Trp Gly Met Thr Gln Tyr Pro Phe Val Pro Gly His Glu Ile Val
    50                  55                  60

Gly Ile Val Ala Glu Ile Gly Ser Glu Val Thr Thr Leu Arg Val Gly
65                  70                  75                  80

Gln Arg Val Gly Leu Gly Trp Tyr Ser Ser Ser Cys Met His Cys Glu
                85                  90                  95

Trp Cys Met Gly Gly Asp His His Leu Cys Leu Ser Ala Glu Gly Thr
            100                 105                 110

Ile Val Gly Arg Pro Gly Gly Phe Ala Asp Gln Val Arg Ala Asp Gln
        115                 120                 125

Ser Trp Ile Val Pro Ile Pro Glu Ser Ile Asp Ser Ala Val Ala Gly
    130                 135                 140

Pro Leu Phe Cys Ala Gly Ile Thr Val Phe Gln Pro Ile Ile Gln Cys
145                 150                 155                 160

Gly Val Gln Pro Thr Asp Arg Val Ala Val Ile Gly Ile Gly Gly Leu
                165                 170                 175

Gly His Leu Ala Leu Gln Phe Leu Asn Ala Trp Gly Cys Glu Val Thr
            180                 185                 190

Ala Leu Ser Thr Gln Pro Asp Lys Glu Ala Glu Ala Arg Arg Leu Gly
        195                 200                 205

Ala His His Phe Val Asn Thr Arg Asp Pro Ala Ala Leu Gln Ala Ile
    210                 215                 220

Ala Asn Ser Cys Asp Tyr Ile Ile Ser Thr Val Asn Val Ser Leu Glu
225                 230                 235                 240

Trp Ser Ile Tyr Leu Asn Ala Leu Arg Pro Lys Gly Arg Leu His Leu
                245                 250                 255

Val Gly Val Ala Pro Asp Leu Ser Leu Pro Val Phe Pro Leu Leu Ala
            260                 265                 270

Gly Gln Arg Ser Ile Ser Gly Ser Pro Val Gly Ser Pro Ala Thr Ile
        275                 280                 285

Thr Lys Met Leu Asn Phe Val Ala Arg His Gly Leu Ala Pro Gln Thr
    290                 295                 300

Glu Val Phe Pro Leu Ala Gln Val Asn Glu Ala Leu Glu Lys Leu Arg
305                 310                 315                 320

Ser Gln His Pro Pro Tyr Arg Leu Ala Leu Lys Cys
                325                 330

<210> SEQ ID NO 24
<211> LENGTH: 335
<212> TYPE: PRT
<213> ORGANISM: Cyanothece sp. PCC 7424

<400> SEQUENCE: 24

```
Met Ile Arg Ala Tyr Ala Ala His Glu Pro Gly Gly Lys Leu Glu Pro
1               5                   10                  15

Phe Glu Tyr Glu Pro Gly Ser Leu Gly Asp Glu Val Asp Ile Lys
            20                  25                  30

Val Glu Tyr Cys Gly Ile Cys His Ser Asp Leu Ser Met Leu Lys Asn
            35                  40                  45

Asp Trp Gly Met Thr Gln Tyr Pro Phe Val Pro Gly His Glu Val Val
50                  55                  60

Gly Val Val Glu Ala Val Gly Ser Lys Val Lys Asn Leu Gln Ile Gly
65                  70                  75                  80

Gln Lys Val Gly Leu Gly Trp Tyr Ser Arg Ser Cys Met Thr Cys Glu
                85                  90                  95

Phe Cys Met Ser Gly Asn His Asn Leu Cys Gln Asp Ala Glu Gly Thr
            100                 105                 110

Ile Val Gly Arg Tyr Gly Gly Phe Ala Glu Lys Val Arg Ala His Gln
            115                 120                 125

Gly Trp Val Ile Pro Leu Pro Glu Gly Val Asn Pro Val Thr Ala Gly
130                 135                 140

Pro Leu Phe Cys Gly Gly Ile Thr Val Phe Asn Pro Ile Val Gln Phe
145                 150                 155                 160

Asn Ile Lys Pro Thr Asp Gln Val Gly Val Ile Gly Ile Gly Gly Leu
            165                 170                 175

Gly His Met Ala Leu Gly Phe Leu Arg Ala Trp Gly Cys Glu Ile Thr
            180                 185                 190

Ala Phe Ser Thr Ser Pro Asp Lys Glu Ala Glu Ala Lys Ala Leu Gly
            195                 200                 205

Ala Thr His Phe Val Asn Ser Arg Asp Pro Glu Ala Leu Lys Ala Leu
            210                 215                 220

Thr Asn Ser Phe Asp Val Ile Leu Ser Thr Val Asn Ala Asp Leu Asp
225                 230                 235                 240

Trp Pro Thr Tyr Ile Lys Leu Leu Arg Pro Gln Gly Arg Leu His Leu
            245                 250                 255

Val Gly Val Ile Pro Asn Pro Leu Ser Val Pro Ile Phe Pro Met Ile
            260                 265                 270

Leu Gly Gln Lys Ser Val Ser Ala Ser Pro Leu Gly Ser Pro Thr Thr
            275                 280                 285

Ile Ala Gln Met Leu Asn Phe Ala Gly Arg His His Leu Glu Pro Ile
            290                 295                 300

Val Glu Phe Phe Pro Leu Glu Gln Val Asn Glu Ala Leu Glu Arg Leu
305                 310                 315                 320

Gln Ser Asn Lys Ala Arg Tyr Arg Ile Ile Leu Lys Met Asp His
            325                 330                 335

<210> SEQ ID NO 25
<211> LENGTH: 335
<212> TYPE: PRT
<213> ORGANISM: Cyanothece sp. PCC 7424

<400> SEQUENCE: 25

Met Ile Arg Ala Tyr Ala Ala His Glu Pro Gly Gly Lys Leu Glu Pro
1               5                   10                  15

Phe Glu Tyr Glu Pro Gly Ser Leu Gly Asp Glu Val Asp Ile Lys
            20                  25                  30

Val Glu Tyr Cys Gly Ile Cys His Ser Asp Leu Ser Met Leu Lys Asn
            35                  40                  45
```

```
Asp Trp Gly Met Thr Gln Tyr Pro Phe Val Pro Gly His Glu Val Val
        50                  55                  60
Gly Val Val Glu Ala Val Gly Ser Lys Val Lys Asn Leu Gln Ile Gly
 65                  70                  75                  80
Gln Lys Val Gly Leu Gly Trp Tyr Ser Arg Ser Cys Met Thr Cys Glu
                 85                  90                  95
Phe Cys Met Ser Gly Asn His Asn Leu Cys Gln Asp Ala Glu Gly Thr
                100                 105                 110
Ile Val Gly Arg Tyr Gly Gly Phe Ala Glu Lys Val Arg Ala His Gln
                115                 120                 125
Gly Trp Val Ile Pro Leu Pro Glu Gly Val Asn Pro Val Thr Ala Gly
        130                 135                 140
Pro Leu Phe Cys Gly Gly Ile Thr Val Phe Asn Pro Ile Val Gln Phe
145                 150                 155                 160
Asn Ile Lys Pro Thr Asp Gln Val Gly Val Ile Gly Ile Gly Gly Leu
                165                 170                 175
Gly His Met Ala Leu Gly Phe Leu Arg Ala Trp Gly Cys Glu Ile Thr
                180                 185                 190
Ala Phe Ser Thr Ser Pro Asp Lys Glu Ala Glu Ala Lys Ala Leu Gly
                195                 200                 205
Ala Thr His Phe Val Asn Ser Arg Asp Pro Glu Ala Leu Lys Ala Leu
        210                 215                 220
Thr Asn Ser Phe Asp Val Ile Leu Ser Thr Val Asn Ala Asp Leu Asp
225                 230                 235                 240
Trp Pro Thr Tyr Ile Lys Leu Leu Arg Pro Gln Gly Arg Leu His Leu
                245                 250                 255
Val Gly Val Ile Pro Asn Pro Leu Ser Val Pro Ile Phe Pro Met Ile
                260                 265                 270
Leu Gly Gln Lys Ser Val Ser Ala Ser Pro Leu Gly Ser Pro Thr Thr
                275                 280                 285
Ile Ala Gln Met Leu Asn Phe Ala Gly Arg His His Leu Glu Pro Ile
        290                 295                 300
Val Glu Phe Phe Pro Leu Glu Gln Val Asn Glu Ala Leu Glu Arg Leu
305                 310                 315                 320
Gln Ser Asn Lys Ala Arg Tyr Arg Ile Ile Leu Lys Met Asp His
                325                 330                 335

<210> SEQ ID NO 26
<211> LENGTH: 336
<212> TYPE: PRT
<213> ORGANISM: Cyanothece sp. PCC 7822

<400> SEQUENCE: 26

Met Ile Arg Ala Tyr Ala Ala His Glu Pro Gly Gly Lys Leu Glu Pro
1                5                  10                  15
Phe Glu Tyr Asp Pro Gly Ser Leu Gly Asp Glu Asp Val Glu Ile Gln
                20                  25                  30
Val Glu Tyr Cys Gly Ile Cys His Ser Asp Leu Ser Met Leu Asn Asn
                35                  40                  45
Glu Trp Gly Met Thr Arg Tyr Pro Phe Val Pro Gly His Glu Val Val
        50                  55                  60
Gly Thr Ile Asn Ala Val Gly Glu Arg Val Lys His Leu Gln Val Gly
 65                  70                  75                  80
Gln Arg Val Gly Leu Gly Trp Tyr Ser Arg Ser Cys Met Thr Cys Glu
                 85                  90                  95
```

```
Trp Cys Leu Ser Gly Asn Gln Asn Leu Cys Pro Gln Ala Glu Gly Thr
            100                 105                 110

Ile Val Gly Arg Tyr Gly Gly Phe Ala Glu Lys Val Arg Ala His Gln
        115                 120                 125

Gly Trp Val Leu Pro Leu Pro Glu Lys Leu Asn Pro Leu Thr Ala Gly
    130                 135                 140

Pro Leu Phe Cys Gly Gly Ile Thr Val Phe Asn Pro Ile Val Gln Phe
145                 150                 155                 160

Asp Val Lys Pro Thr Asp Arg Val Gly Val Ile Gly Ile Gly Gly Leu
                165                 170                 175

Gly His Met Ala Leu Gly Phe Leu Ala Ala Trp Gly Cys Glu Ile Thr
            180                 185                 190

Ala Phe Ser Thr Ser Pro Asp Lys Glu Ile Glu Ala Lys Asn Leu Gly
        195                 200                 205

Ala Asn His Phe Val Asn Ser Arg Asp Pro Gln Ala Leu Lys Ala Leu
    210                 215                 220

Ala Asn Ser Leu Asp Leu Ile Leu Ser Thr Val Asn Ala Asp Leu Asp
225                 230                 235                 240

Trp Asp Thr Tyr Ile Ser Leu Leu Arg Pro Lys Gly Arg Leu His Phe
                245                 250                 255

Val Gly Val Ile Pro Asn Pro Leu Ser Val Gln Leu Phe Pro Leu Ile
            260                 265                 270

Gly Gly Gln Lys Ser Val Ser Gly Ser Pro Leu Gly Ser Pro Val Thr
        275                 280                 285

Leu Ala Gln Met Leu Asn Phe Ala Gly Arg His His Val Glu Pro Val
    290                 295                 300

Val Glu Phe Tyr Pro Ile Glu Gln Val Asn Glu Ala Met Glu Arg Leu
305                 310                 315                 320

Lys Ala Asn Lys Ala Arg Tyr Arg Ile Val Leu Thr Phe Lys Asn Ser
                325                 330                 335

<210> SEQ ID NO 27
<211> LENGTH: 333
<212> TYPE: PRT
<213> ORGANISM: Cyanothece sp. PCC 8801

<400> SEQUENCE: 27

Met Ile Lys Ala Tyr Ala Ala Ser Glu Pro Gly Lys Glu Leu Asn Ser
1               5                   10                  15

Phe Glu Tyr Asp Pro Gly Leu Leu Gly Glu Asp Val Glu Ile Asn
                20                  25                  30

Val Gln Tyr Cys Gly Ile Cys His Ser Asp Leu Ser Met Leu Asp Asn
            35                  40                  45

Glu Trp Gly Ile Thr Gln Tyr Pro Phe Val Pro Gly His Glu Val Val
    50                  55                  60

Gly Thr Ile Gly Ala Val Gly Ser Lys Val Thr Thr Phe Gln Val Gly
65                  70                  75                  80

Gln Thr Val Gly Leu Gly Trp Phe Ser Arg Ser Cys Phe Asp Cys Glu
                85                  90                  95

Trp Cys Leu Ser Gly Asp Gln Asn Leu Cys Gln Thr Ala Glu Gly Thr
            100                 105                 110

Ile Val Gly Arg Pro Gly Gly Phe Ala Asp Lys Val Arg Ala His His
        115                 120                 125

Arg Trp Val Val Pro Leu Pro Ser Gly Val Asn Pro Glu Thr Ala Gly
    130                 135                 140
```

-continued

```
Pro Leu Phe Cys Gly Gly Ile Thr Val Phe Asn Pro Ile Ile Gln Cys
145                 150                 155                 160

Gly Val Lys Ser Thr Asp Arg Val Gly Val Ile Gly Ile Gly Gly Leu
            165                 170                 175

Gly His Leu Ala Ile Glu Phe Leu His Ala Trp Gly Cys Glu Val Thr
        180                 185                 190

Ala Phe Ser Ser Asn Pro Glu Lys Glu Ser Glu Val Lys Gln Leu Gly
    195                 200                 205

Ala Asp Tyr Phe Val Asn Ser Arg Asp Pro Glu Ala Ile Lys Ala Val
210                 215                 220

Glu Asn Ser Phe Asp Phe Ile Ile Ser Thr Val Asn Val Ser Leu Asp
225                 230                 235                 240

Trp Asn Ser Tyr Ile Leu Ala Leu Arg Pro Arg Gly Thr Leu His Phe
                245                 250                 255

Val Gly Ala Val Leu Asn Pro Ile Ser Thr Gln Ile Phe Pro Leu Leu
            260                 265                 270

Met Gly Gln Lys Thr Ile Ser Gly Ser Pro Thr Gly Ser Pro Thr Thr
        275                 280                 285

Ile Ala Gln Met Leu Asp Phe Ala Ala Arg His Gln Ile Glu Pro Val
    290                 295                 300

Thr Glu Ile Phe Pro Phe Glu Gln Val Asn Glu Ala Ile Asp Lys Leu
305                 310                 315                 320

Arg His Gly Gln Pro Arg Tyr Arg Leu Val Leu Lys Met
                325                 330

<210> SEQ ID NO 28
<211> LENGTH: 362
<212> TYPE: PRT
<213> ORGANISM: Cyanothece sp. PCC 8801

<400> SEQUENCE: 28

Met Arg Gly Glu Arg Ile Val Arg Ser Gly Val Lys Glu Asp Ile Leu
1               5                   10                  15

Cys Asn Asn Ala Ile Asn Thr Thr Ile Glu Val Lys Val Val Ile Lys
            20                  25                  30

Ala Tyr Ala Ala Ser Glu Pro Gly Lys Glu Leu Asn Ser Phe Glu Tyr
        35                  40                  45

Asp Pro Gly Leu Leu Gly Glu Glu Asp Val Glu Ile Asn Val Gln Tyr
    50                  55                  60

Cys Gly Ile Cys His Ser Asp Leu Ser Met Leu Asp Asn Glu Trp Gly
65                  70                  75                  80

Ile Thr Gln Tyr Pro Phe Val Pro Gly His Glu Val Val Gly Thr Ile
                85                  90                  95

Gly Ala Val Gly Ser Lys Val Thr Thr Phe Gln Val Gly Gln Thr Val
            100                 105                 110

Gly Leu Gly Trp Phe Ser Arg Ser Cys Phe Asp Cys Glu Trp Cys Leu
        115                 120                 125

Ser Gly Asp Gln Asn Leu Cys Gln Thr Ala Glu Gly Thr Ile Val Gly
    130                 135                 140

Arg Pro Gly Gly Phe Ala Asp Lys Val Arg Ala His His Arg Trp Val
145                 150                 155                 160

Val Pro Leu Pro Ser Gly Val Asn Pro Glu Thr Ala Gly Pro Leu Phe
                165                 170                 175

Cys Gly Gly Ile Thr Val Phe Asn Pro Ile Ile Gln Cys Gly Val Lys
            180                 185                 190
```

```
Ser Thr Asp Arg Val Gly Val Ile Gly Ile Gly Gly Leu Gly His Leu
        195                 200                 205

Ala Ile Glu Phe Leu His Ala Trp Gly Cys Glu Val Thr Ala Phe Ser
    210                 215                 220

Ser Asn Pro Glu Lys Glu Ser Glu Val Lys Gln Leu Gly Ala Asp Tyr
225                 230                 235                 240

Phe Val Asn Ser Arg Asp Pro Glu Ala Ile Lys Ala Val Glu Asn Ser
                245                 250                 255

Phe Asp Phe Ile Ile Ser Thr Val Asn Val Ser Leu Asp Trp Asn Ser
                260                 265                 270

Tyr Ile Leu Ala Leu Arg Pro Arg Gly Thr Leu His Phe Val Gly Ala
        275                 280                 285

Val Leu Asn Pro Ile Ser Thr Gln Ile Phe Pro Leu Leu Met Gly Gln
        290                 295                 300

Lys Thr Ile Ser Gly Ser Pro Thr Gly Ser Pro Thr Thr Ile Ala Gln
305                 310                 315                 320

Met Leu Asp Phe Ala Ala Arg His Gln Ile Glu Pro Val Thr Glu Ile
                325                 330                 335

Phe Pro Phe Glu Gln Val Asn Glu Ala Ile Asp Lys Leu Arg His Gly
                340                 345                 350

Gln Pro Arg Tyr Arg Leu Val Leu Lys Met
        355                 360

<210> SEQ ID NO 29
<211> LENGTH: 362
<212> TYPE: PRT
<213> ORGANISM: Cyanothece sp. PCC 8802

<400> SEQUENCE: 29

Met Arg Gly Glu Arg Ile Val Arg Ser Gly Val Lys Glu Asp Ile Leu
1               5                   10                  15

Cys Asn Asn Ala Ile Asn Thr Thr Ile Glu Val Lys Val Val Ile Lys
                20                  25                  30

Ala Tyr Ala Ala Ser Glu Pro Gly Lys Glu Leu Asn Ser Phe Glu Tyr
            35                  40                  45

Asp Pro Gly Leu Leu Gly Glu Glu Asp Val Glu Ile Asn Val Gln Tyr
50                  55                  60

Cys Gly Ile Cys His Ser Asp Leu Ser Met Leu Asp Asn Glu Trp Gly
65                  70                  75                  80

Ile Thr Gln Tyr Pro Phe Val Pro Gly His Glu Val Val Gly Thr Ile
                85                  90                  95

Gly Ala Val Gly Ser Lys Val Thr Thr Phe Gln Val Gly Gln Thr Val
            100                 105                 110

Gly Leu Gly Trp Phe Ser Arg Ser Cys Phe Asp Cys Glu Trp Cys Leu
        115                 120                 125

Ser Gly Asp Gln Asn Leu Cys Gln Thr Ala Glu Gly Thr Ile Val Gly
    130                 135                 140

Arg Pro Gly Gly Phe Ala Asp Lys Val Arg Ala His His Arg Trp Val
145                 150                 155                 160

Val Pro Leu Pro Ser Gly Val Asn Pro Glu Thr Ala Gly Pro Leu Phe
                165                 170                 175

Cys Gly Gly Ile Thr Val Phe Asn Pro Ile Ile Gln Cys Gly Val Lys
            180                 185                 190

Ser Thr Asp Arg Val Gly Val Ile Gly Ile Gly Gly Leu Gly His Leu
        195                 200                 205
```

-continued

Ala Ile Glu Phe Leu His Ala Trp Gly Cys Glu Val Thr Ala Phe Ser
    210                 215                 220

Ser Asn Pro Glu Lys Glu Ser Glu Val Lys Gln Leu Gly Ala Asp Tyr
225                 230                 235                 240

Phe Val Asn Ser Arg Asp Pro Glu Ala Ile Lys Ala Val Glu Asn Ser
                245                 250                 255

Phe Asp Phe Ile Ile Ser Thr Val Asn Val Ser Leu Asp Trp Asn Ser
            260                 265                 270

Tyr Ile Leu Ala Leu Arg Pro Arg Gly Thr Leu His Phe Val Gly Ala
        275                 280                 285

Val Leu Asn Pro Ile Ser Thr Gln Ile Phe Pro Leu Leu Met Gly Gln
    290                 295                 300

Lys Thr Ile Ser Gly Ser Pro Thr Gly Ser Pro Thr Thr Ile Ala Gln
305                 310                 315                 320

Met Leu Asp Phe Ala Ala Arg His Gln Ile Glu Pro Val Thr Glu Ile
                325                 330                 335

Phe Pro Phe Glu Gln Val Asn Glu Ala Ile Asp Lys Leu Arg His Gly
            340                 345                 350

Gln Pro Arg Tyr Arg Leu Val Leu Lys Met
        355                 360

<210> SEQ ID NO 30
<211> LENGTH: 334
<212> TYPE: PRT
<213> ORGANISM: Microcoleus chthonoplastes PCC 7420

<400> SEQUENCE: 30

Met Ile Lys Ala Tyr Ala Ala His Glu Pro Gly Gly Gln Leu Gln Pro
1               5                   10                  15

Phe Glu Tyr Asp Pro Gly Thr Leu Gly Asp Glu Glu Val Glu Ile Lys
            20                  25                  30

Val Glu Tyr Cys Gly Ile Cys His Ser Asp Leu Ser Met Leu Asp Asn
        35                  40                  45

Glu Trp Gly Met Thr Asp Tyr Pro Phe Val Pro Gly His Glu Val Val
    50                  55                  60

Gly Thr Ile Ala Ala Leu Gly Asp Lys Val Thr Thr Leu Asn Leu Gly
65                  70                  75                  80

Gln Arg Val Gly Leu Gly Trp Phe Ser Gly Ser Cys Met Thr Cys Glu
                85                  90                  95

Trp Cys Met Ser Gly Asn His Asn Leu Cys Ser Asn Ala Glu Gly Thr
            100                 105                 110

Ile Val Ser Arg His Gly Gly Phe Ala Asp Lys Val Arg Ala Asp Tyr
        115                 120                 125

Ser Trp Val Val Pro Leu Pro Asp Gly Ile Asn Pro Ala Thr Ala Gly
    130                 135                 140

Pro Leu Phe Cys Gly Gly Ile Thr Val Phe Asn Pro Ile Val Gln Phe
145                 150                 155                 160

Asp Ile Lys Pro Ser Asp Arg Val Gly Val Ile Gly Ile Gly Gly Leu
                165                 170                 175

Gly His Ile Ala Leu Gly Phe Leu Gln Ala Trp Gly Cys Glu Ile Thr
            180                 185                 190

Ala Phe Ser Ser Ser Pro Asp Lys Glu Ala Glu Ala Arg Glu Leu Gly
        195                 200                 205

Ala Thr His Phe Ile Asn Ser Gly Asp Val Asn Ala Leu Glu Ser Val
    210                 215                 220

```
Gln Asn Ser Phe Asp Phe Ile Leu Ala Thr Ala Asn Ala Asp Leu Asp
225                 230                 235                 240

Trp Asn Ala Tyr Ile Ala Ala Leu Arg Pro Lys Gly Arg Leu His Phe
                245                 250                 255

Val Gly Val Ile Pro Asn Pro Leu Ser Thr Pro Ile Phe Pro Leu Ile
            260                 265                 270

Leu Gly Gln Lys Ser Ile Ser Ala Ser Pro Val Gly Ser Pro Ala Thr
        275                 280                 285

Ile Ser Gln Met Ile Asn Phe Ala Ala Arg Gln Gly Val Glu Pro Ile
290                 295                 300

Thr Glu Thr Phe Ser Phe Glu Gln Val Asn Glu Ala Met Glu Lys Leu
305                 310                 315                 320

Arg His Gly Lys Pro Arg Tyr Arg Leu Val Leu Lys His Ser
                325                 330
```

<210> SEQ ID NO 31
<211> LENGTH: 334
<212> TYPE: PRT
<213> ORGANISM: Microcystis aeruginosa NIES-843

<400> SEQUENCE: 31

```
Met Ile Arg Ala Tyr Ala Ala Arg Glu Lys Gly Gly Lys Leu Glu Pro
1               5                   10                  15

Phe Asp Tyr Asp Pro Gly Ile Leu Ala Asp Glu Asp Val Glu Ile Ala
                20                  25                  30

Val Glu Tyr Cys Gly Ile Cys His Ser Asp Leu Ser Met Leu Asp Asn
            35                  40                  45

Asp Trp Gly Leu Thr Thr Tyr Pro Phe Val Pro Gly His Glu Val Val
50                  55                  60

Gly Thr Ile Ala Ala Leu Gly Ala Lys Val Lys Glu Leu Lys Leu Gly
65                  70                  75                  80

Gln Arg Val Gly Leu Gly Trp Phe Ser Arg Ser Cys Ser Thr Cys Glu
                85                  90                  95

Thr Cys Met Ser Gly Asp Gln Asn Leu Cys Ala Thr Ala Glu Gly Thr
            100                 105                 110

Ile Val Gly Arg His Gly Gly Phe Ala Asp Arg Val Arg Ala His His
        115                 120                 125

Ser Trp Leu Val Pro Leu Gly Asn Gln Leu Asp Ala Ala Lys Ala Gly
130                 135                 140

Pro Leu Phe Cys Gly Gly Ile Thr Val Phe Asn Pro Ile Val Gln Phe
145                 150                 155                 160

Asn Ile Lys Pro Thr Ala Arg Val Gly Val Ile Gly Ile Gly Gly Leu
                165                 170                 175

Gly His Ile Ala Leu Lys Phe Leu Lys Ala Trp Gly Cys Glu Val Thr
            180                 185                 190

Ala Phe Ser Ser Ser Pro Asp Lys Glu Thr Glu Ala Lys Glu Leu Gly
        195                 200                 205

Ala Thr His Phe Ile Asn Ser Arg Asp Pro Glu Ala Leu Gln Ser Val
210                 215                 220

Gln Asn Tyr Phe Asp Phe Ile Ile Ser Thr Val Asn Val Asn Leu Asp
225                 230                 235                 240

Trp Gly Leu Tyr Ile Ala Cys Leu Arg Pro Lys Gly Arg Leu His Ile
                245                 250                 255

Val Gly Ala Val Leu Glu Pro Met Ala Thr Tyr Ala Phe Pro Leu Ile
            260                 265                 270
```

```
Met Gly Gln Lys Ser Ile Ser Gly Ser Pro Leu Gly Ser Pro Ser Thr
            275                 280                 285

Ile Asn Lys Met Ile Glu Phe Ala Ser Arg His Gly Ile Glu Pro Val
            290                 295                 300

Thr Glu Ile Tyr Pro Ile Ser Gln Val Asn Glu Ala Met Glu Lys Leu
305                 310                 315                 320

Arg Thr Gly Gln Pro Lys Tyr Arg Leu Val Leu Gln Ile Lys
                325                 330
```

<210> SEQ ID NO 32
<211> LENGTH: 334
<212> TYPE: PRT
<213> ORGANISM: Microcystis aeruginosa PCC 7806

<400> SEQUENCE: 32

```
Met Ile Arg Ala Tyr Ala Ala Gln Glu Lys Gly Gly Lys Leu Glu Pro
1               5                   10                  15

Phe Asp Tyr Asp Pro Gly Ile Leu Ala Asp Glu Asp Val Glu Ile Ala
            20                  25                  30

Val Glu Tyr Cys Gly Ile Cys His Ser Asp Leu Ser Met Leu Asp Asn
            35                  40                  45

Asp Trp Gly Leu Thr Thr Tyr Pro Phe Val Pro Gly His Glu Val Val
        50                  55                  60

Gly Thr Ile Ala Ala Leu Gly Ala Lys Val Lys Glu Leu Lys Leu Gly
65                  70                  75                  80

Gln Arg Val Gly Leu Gly Trp Phe Ser Arg Ser Cys Ser Thr Cys Glu
                85                  90                  95

Thr Cys Met Ser Gly Asp Gln Asn Leu Cys Ala Thr Ala Glu Gly Thr
            100                 105                 110

Ile Val Gly Arg His Gly Gly Phe Ala Glu Arg Val Arg Ala His His
            115                 120                 125

Ser Trp Leu Val Pro Leu Pro Asp Gln Leu Asp Ala Ala Lys Ala Gly
        130                 135                 140

Pro Leu Phe Cys Gly Gly Ile Thr Val Phe Asn Pro Ile Val Gln Phe
145                 150                 155                 160

Asn Ile Lys Pro Thr Ala Arg Val Gly Val Ile Gly Ile Gly Gly Leu
                165                 170                 175

Gly His Ile Ala Leu Lys Phe Leu Lys Ala Trp Gly Cys Glu Val Thr
            180                 185                 190

Ala Phe Ser Ser Ser Pro Asp Lys Glu Thr Glu Ala Lys Glu Leu Gly
            195                 200                 205

Ala Thr His Phe Ile Asn Ser Arg Asp Pro Glu Ala Leu Gln Ser Val
        210                 215                 220

Gln Asn Tyr Phe Asp Phe Ile Ile Ser Thr Val Asn Val Asn Leu Asp
225                 230                 235                 240

Trp Gly Leu Tyr Ile Ala Cys Leu Arg Pro Lys Gly Arg Leu His Ile
                245                 250                 255

Val Gly Ala Val Leu Glu Pro Met Ala Thr Tyr Ala Phe Pro Leu Ile
            260                 265                 270

Met Gly Gln Lys Ser Ile Ser Gly Ser Pro Leu Gly Ser Pro Ser Thr
            275                 280                 285

Val Ser Lys Met Ile Glu Phe Ala Ser Arg His Gly Ile Glu Pro Val
            290                 295                 300

Thr Glu Thr Tyr Pro Ile Ser Arg Val Asn Glu Ala Met Glu Lys Leu
305                 310                 315                 320
```

```
Arg Thr Gly Gln Pro Lys Tyr Arg Leu Val Leu Gln Ile Lys
            325                 330

<210> SEQ ID NO 33
<211> LENGTH: 333
<212> TYPE: PRT
<213> ORGANISM: Synechococcus sp. WH 5701

<400> SEQUENCE: 33

Met Gln Ile Thr Val Trp Gln Ala Leu Ala Lys Gly Gly Arg Leu Glu
1               5                   10                  15

Arg Ser Gln Ala Thr Leu Leu Asp Pro Gly Pro Asp Glu Val Leu Leu
            20                  25                  30

Glu Val Leu His Cys Gly Leu Cys His Ser Asp Leu Ser Met Leu Asp
        35                  40                  45

Asn Ser Trp Gly Ile Ser Thr Tyr Pro Leu Val Pro Gly His Glu Val
    50                  55                  60

Val Gly Arg Val Ala Ala Val Gly Ala Gly Val Asp Ser Gly Leu Leu
65                  70                  75                  80

Gly Ser Ile Gln Gly Leu Gly Trp Ile Ala Gly Ser Cys Arg His Cys
                85                  90                  95

Asp Trp Cys Leu Gly Gly Asn Ala Asn Leu Cys Pro Ser Leu Glu Ala
            100                 105                 110

Ser Val Val Gly Arg His Gly Gly Phe Ala Ser His Val Met Ala His
        115                 120                 125

Gln Asp Trp Ile Val Ala Ile Pro Asp Gly Val Ser Ala Ala Asp Ala
    130                 135                 140

Gly Pro Leu Phe Cys Gly Gly Ile Thr Val Phe Ala Pro Leu Phe Asp
145                 150                 155                 160

Glu Ala Val Ser Pro Thr Ser Arg Val Ala Val Ile Gly Ile Gly Gly
                165                 170                 175

Leu Gly His Met Ala Leu Gln Phe Ala Arg Ala Trp Gly Cys Glu Val
            180                 185                 190

Thr Ala Val Thr Thr Ser Pro Ala Lys Ala Asp Glu Ala Arg Arg Leu
        195                 200                 205

Gly Ala His Arg Val Leu Ala Leu Ser Glu Leu Gly Asp His Pro Gly
    210                 215                 220

Val Phe Asp Leu Ile Ile Asn Thr Ser Asn His Asp Leu Asp Trp Pro
225                 230                 235                 240

Ala Leu Ile Gly Ser Leu Ala Pro Leu Gly Arg Leu His Gln Leu Gly
                245                 250                 255

Val Pro Leu Ser Pro Leu Gln Ile Pro Ala Phe Pro Leu Ile Ala Gly
            260                 265                 270

Arg Arg Ser Val Thr Gly Ser Pro Thr Ser Ser Pro Ala Ser Leu Arg
        275                 280                 285

Arg Met Val Glu Phe Cys Ala Arg His Gly Ile Ala Pro Leu Val Glu
    290                 295                 300

His Leu Pro Met Ala Glu Ile Asn Thr Ala Ile Glu Arg Leu Arg Gln
305                 310                 315                 320

Gly Asp Val Arg Tyr Arg Phe Val Leu Asp Gly Pro Ala
                325                 330

<210> SEQ ID NO 34
<211> LENGTH: 336
<212> TYPE: PRT
<213> ORGANISM: Synechococcus sp. RS9917
```

<400> SEQUENCE: 34

```
Met Val Val Thr Ile Thr Val Trp Gln Ala Arg Glu Ala Gly Ala Pro
1               5                   10                  15
Leu Glu Arg Ala Glu Arg Ala Met Leu Glu Pro Ala Ala Gly Glu Leu
            20                  25                  30
Val Leu Glu Val Leu His Cys Gly Leu Cys His Ser Asp Leu Ser Met
        35                  40                  45
Leu Asp Asn Asn Trp Gly Leu Ser Ala Tyr Pro Leu Val Pro Gly His
    50                  55                  60
Glu Val Val Gly Arg Val Val Arg Val Gly Gly Val Asp Pro Gly
65                  70                  75                  80
Val Ile Gly Glu Leu Arg Gly Leu Gly Trp Ile Ser Gly Ser Cys Met
                85                  90                  95
His Cys Ala Leu Cys Leu Gly Gly Thr Ala Asn Leu Cys Gly Ser Leu
            100                 105                 110
Glu Ala Thr Ile Val Gly Arg Gln Gly Gly Phe Ala Ser His Val Thr
        115                 120                 125
Ala Arg Gln Asp Trp Ala Ile Arg Leu Pro Glu Gly Met Asp Pro Ala
    130                 135                 140
Ala Ala Gly Pro Leu Phe Cys Gly Gly Ile Thr Val Phe Ala Pro Leu
145                 150                 155                 160
Val Asp Glu Val Val Ser Pro Thr Ala His Val Ala Val Ile Gly Ile
                165                 170                 175
Gly Gly Leu Gly His Met Ala Leu Gln Phe Ala Arg Ala Trp Gly Cys
            180                 185                 190
Glu Val Thr Ala Leu Thr Thr His Leu Ala Lys Ala Glu Glu Ala Lys
        195                 200                 205
Arg Phe Gly Ala His His Val Glu Ser Leu Glu Glu Leu Pro Asp Leu
    210                 215                 220
Ala Gly Arg Phe Asp Leu Val Ile Asn Thr Val Asn His Ala Leu Asp
225                 230                 235                 240
Trp Gly Ala Val Met Gly Ser Leu Ala Pro Leu Gly Arg Leu His Gln
                245                 250                 255
Leu Gly Ala Val Leu Glu Pro Leu Gln Val Ser Ala Phe Asp Leu Ile
            260                 265                 270
Met Ala Arg Arg Ser Ile Thr Gly Ser Pro Thr Ser Ser Pro Ala Ser
        275                 280                 285
Leu Met Lys Met Val Glu Phe Cys Val Arg His Asn Ile Arg Pro Gln
    290                 295                 300
Val Glu His Leu Pro Met Asp Arg Leu Asn Glu Ala Ile Asp Arg Leu
305                 310                 315                 320
Arg Arg Gly Asp Val Arg Tyr Arg Phe Val Leu Asp Ser Val Ala Asp
                325                 330                 335
```

<210> SEQ ID NO 35
<211> LENGTH: 333
<212> TYPE: PRT
<213> ORGANISM: Synechococcus sp. WH 5701

<400> SEQUENCE: 35

```
Met Gln Ile Thr Val Trp Gln Ala Leu Ala Lys Gly Gly Arg Leu Glu
1               5                   10                  15
Arg Ser Gln Ala Thr Leu Leu Asp Pro Gly Pro Asp Glu Val Leu Leu
            20                  25                  30
```

```
Glu Val Leu His Cys Gly Leu Cys His Ser Asp Leu Ser Met Leu Asp
            35                  40                  45

Asn Ser Trp Gly Ile Ser Thr Tyr Pro Leu Val Pro Gly His Glu Val
 50                  55                  60

Val Gly Arg Val Ala Ala Val Gly Ala Gly Val Asp Ser Gly Leu Leu
 65                  70                  75                  80

Gly Ser Ile Gln Gly Leu Gly Trp Ile Ala Gly Ser Cys Arg His Cys
                 85                  90                  95

Asp Trp Cys Leu Gly Gly Asn Ala Asn Leu Cys Pro Ser Leu Glu Ala
                100                 105                 110

Ser Val Val Gly Arg His Gly Gly Phe Ala Ser His Val Met Ala His
                115                 120                 125

Gln Asp Trp Ile Val Ala Ile Pro Asp Gly Val Ser Ala Ala Asp Ala
130                 135                 140

Gly Pro Leu Phe Cys Gly Gly Ile Thr Val Phe Ala Pro Leu Phe Asp
145                 150                 155                 160

Glu Ala Val Ser Pro Thr Ser Arg Val Ala Val Ile Gly Ile Gly Gly
                165                 170                 175

Leu Gly His Met Ala Leu Gln Phe Ala Arg Ala Trp Gly Cys Glu Val
                180                 185                 190

Thr Ala Val Thr Thr Ser Pro Ala Lys Ala Asp Glu Ala Arg Arg Leu
            195                 200                 205

Gly Ala His Arg Val Leu Ala Leu Ser Glu Leu Gly Asp His Pro Gly
210                 215                 220

Val Phe Asp Leu Ile Ile Asn Thr Ser Asn His Asp Leu Asp Trp Pro
225                 230                 235                 240

Ala Leu Ile Gly Ser Leu Ala Pro Leu Gly Arg Leu His Gln Leu Gly
                245                 250                 255

Val Pro Leu Ser Pro Leu Gln Ile Pro Ala Phe Pro Leu Ile Ala Gly
                260                 265                 270

Arg Arg Ser Val Thr Gly Ser Pro Thr Ser Ser Pro Ala Ser Leu Arg
            275                 280                 285

Arg Met Val Glu Phe Cys Ala Arg His Gly Ile Ala Pro Leu Val Glu
290                 295                 300

His Leu Pro Met Ala Glu Ile Asn Thr Ala Ile Glu Arg Leu Arg Gln
305                 310                 315                 320

Gly Asp Val Arg Tyr Arg Phe Val Leu Asp Gly Pro Ala
                325                 330

<210> SEQ ID NO 36
<211> LENGTH: 330
<212> TYPE: PRT
<213> ORGANISM: Synechococcus sp. WH 7803

<400> SEQUENCE: 36

Met Ile Ser Val Trp Gln Ala Pro Ser Ala Gly Ala Pro Leu Glu Cys
  1               5                  10                  15

Gly Gln Arg Pro Ala Pro Glu Pro Ala Ala Asp Glu Leu Val Leu Glu
                 20                  25                  30

Val Met His Cys Gly Leu Cys His Ser Asp Leu Ser Met Ile Gly Asn
             35                  40                  45

His Trp Gly Val Ser Arg Tyr Pro Leu Val Pro Gly His Glu Val Ile
 50                  55                  60

Gly Arg Val Thr Ala Val Gly Glu Gly Val Asp Pro Gly Leu Ile Gly
 65                  70                  75                  80
```

```
Asp Val Arg Gly Leu Gly Trp Ile Ser Gly Ser Cys Asn His Cys Ser
                 85                  90                  95

Leu Cys Leu Gly Gly Asp Gln Asn Leu Cys Thr Ser Leu Glu Ala Thr
            100                 105                 110

Ile Val Gly Arg Gln Gly Gly Phe Ala Ser His Val Val Ala Arg Gln
            115                 120                 125

Asp Trp Ala Ile Pro Leu Pro Pro Gly Leu Asp Pro Ala Asp Ala Gly
        130                 135                 140

Pro Leu Phe Cys Gly Gly Ile Thr Val Phe Ala Pro Leu Val Asp Glu
145                 150                 155                 160

Ala Val Ser Pro Thr Ala His Val Ala Val Gly Ile Gly Gly Leu
                165                 170                 175

Gly His Ile Ala Leu Gln Phe Ala Arg Ala Trp Gly Cys Glu Val Thr
            180                 185                 190

Ala Ile Thr Thr Asn Leu Ala Lys Ala Glu Gln Ala Arg Arg Phe Gly
            195                 200                 205

Ala His His Val Glu Glu Leu Glu Met Leu Pro Asp Leu Gln Ser Arg
        210                 215                 220

Phe Asp Leu Val Ile Asn Thr Val Asn His Pro Leu Asp Trp Ser Ala
225                 230                 235                 240

Val Met Ala Ser Leu Arg Pro Arg Gly Arg Leu His Gln Leu Gly Ala
                245                 250                 255

Val Leu Glu Pro Ile Gln Val Gly Ala Phe Asp Leu Ile Pro Ala Arg
            260                 265                 270

Arg Ser Ile Thr Gly Ser Pro Thr Ser Pro Ala Ser Leu Gln Lys
            275                 280                 285

Met Val Glu Phe Cys Val Arg His Asn Ile Leu Pro Leu Val Glu His
        290                 295                 300

Leu Pro Met Asp Gln Val Asn Val Ala Ile Gln Arg Leu Ala Lys Gly
305                 310                 315                 320

Asp Val Arg Tyr Arg Phe Val Leu Asp Ala
            325                 330

<210> SEQ ID NO 37
<211> LENGTH: 330
<212> TYPE: PRT
<213> ORGANISM: Synechococcus sp. WH 7805

<400> SEQUENCE: 37

Met Ile Ser Val Trp Gln Ala Pro Ser Ala Gly Ala Pro Leu Glu Cys
1               5                   10                  15

Ala Gln Arg Pro Ala Leu Gln Pro Val Ala Asp Glu Leu Val Leu Glu
            20                  25                  30

Val Met His Cys Gly Leu Cys His Ser Asp Leu Ser Met Ile Gly Asn
        35                  40                  45

His Trp Gly Val Ser Arg Tyr Pro Leu Val Pro Gly His Glu Val Ile
    50                  55                  60

Gly Arg Val Thr Ala Val Gly Glu Gly Val Asp Pro Gly Val Ile Gly
65              70                  75                  80

Glu Val Arg Gly Leu Gly Trp Ile Ser Gly Ser Cys Asn His Cys Ser
                85                  90                  95

Leu Cys Leu Gly Gly Asp Gln Asn Leu Cys Ser Ser Leu Glu Ala Thr
            100                 105                 110

Ile Val Gly Arg Gln Gly Gly Phe Ala Ser His Val Val Ala Arg Gln
            115                 120                 125
```

```
Asp Trp Thr Ile Pro Leu Pro Thr Gly Leu Asp Pro Ala Glu Ala Gly
    130                 135                 140

Pro Leu Phe Cys Gly Gly Val Thr Val Phe Ala Pro Leu Val Asp Glu
145                 150                 155                 160

Ala Val Ser Pro Thr Ala His Val Ala Val Val Gly Ile Gly Gly Leu
                165                 170                 175

Gly His Ile Ala Leu Gln Phe Ala Arg Ala Trp Gly Cys Glu Val Thr
            180                 185                 190

Ala Ile Thr Thr Asn Pro Ala Lys Thr Glu Gln Ala Arg Arg Phe Gly
        195                 200                 205

Ala His His Val Glu Glu Leu Glu Ala Leu Ser Asp Leu Gln Arg Arg
    210                 215                 220

Phe Asp Leu Val Ile Asn Thr Val Asn His Pro Leu Asp Trp Ser Ala
225                 230                 235                 240

Val Met Ala Ser Leu Lys Pro Arg Gly Arg Leu His Gln Leu Gly Ala
                245                 250                 255

Val Leu Glu Pro Ile Gln Val Gly Ala Phe Asp Leu Ile Ser Ala Arg
            260                 265                 270

Arg Ser Ile Thr Gly Ser Pro Thr Ser Ser Pro Ala Ser Leu Leu Lys
        275                 280                 285

Met Val Glu Phe Cys Val Arg His Asn Ile Leu Pro Leu Val Glu His
    290                 295                 300

Leu Pro Met Asp Gln Val Asn Val Ala Ile Glu Arg Leu Ala Lys Gly
305                 310                 315                 320

Asp Val Arg Tyr Arg Phe Val Leu Asp Ala
                325                 330

<210> SEQ ID NO 38
<211> LENGTH: 27
<212> TYPE: DNA
<213> ORGANISM: Synechocystis PCC6803

<400> SEQUENCE: 38
ctctaggatc catgattaaa gcctacg                                          27

<210> SEQ ID NO 39
<211> LENGTH: 28
<212> TYPE: DNA
<213> ORGANISM: Synechocystis PCC6803

<400> SEQUENCE: 39
cacggaccca gcggccgcct ttgcagag                                         28
```

SELECTION OF ADH IN GENETICALLY MODIFIED CYANOBACTERIA FOR THE PRODUCTION OF ETHANOL

CROSS-REFERENCE TO RELATED APPLICATIONS

The present application claims priority to U.S. provisional application 61/065,292, filed Feb. 8, 2008, which is incorporated by reference in its entirety. The present application is related to a PCT application titled "GENETICALLY MODIFIED PHOTOAUTOTROPHIC ETHANOL PRODUCING HOST CELLS, METHOD FOR PRODUCING THE HOST CELLS, CONSTRUCTS FOR THE TRANSFORMATION OF THE HOST CELLS, METHOD FOR TESTING A PHOTOAUTOTROPHIC STRAIN FOR A DESIRED GROWTH PROPERTY AND METHOD OF PRODUCING ETHANOL USING THE HOST CELLS," filed on even day with the present application and claiming priority to U.S. provisional application 61/065,292, which PCT application is incorporated by reference in its entirety.

FIELD OF THE INVENTION

This invention is related to the field of direct production of ethanol from carbon dioxide and water using genetically modified cyanobacteria.

This application refers to a "Sequence Listing" listed below, which is provided as a text document. The document is entitled "12368160SeqList.txt" (140,000 bytes, created Sep. 3, 2009) and is hereby incorporated by reference in its entirety herein.

BACKGROUND OF THE INVENTION

There is a current need to find alternate energy sources to substitute for the use of fossil fuels for transportation applications. Biologically produced ethanol has been proposed as an alternative to petroleum-derived liquid fuels. There are different ways to generate ethanol through biological means. Obtaining ethanol from grains and seeds has been criticized for contributing to rising food prices and leading to deforestation. The disadvantages of obtaining ethanol from grain and cellulosic sources are further explained in paragraph [0007] of published U.S. patent application 20090017512 [H. D. May, T. Shimotori]. The present invention is addressed to the direct production of ethanol from carbon dioxide and water using genetically-modified cyanobacteria and overcomes problems associated with grain or cellulosic sources of ethanol.

Further, the present invention discloses the capability to produce ethanol using desert lands and salt water and resolves problems associated with demand on food-producing land and water resources. Moreover, the ethanol productivity of the present invention is higher than for corn-based ethanol. The present invention has projected productivity of 6,000 gallons (22,700 liter) ethanol per acre compared to 370 gallons (1,400 liter) ethanol for corn ethanol. [Bryan Walsh, "Biofuels: the New Alchemy," TIME magazine, http://www.time.com/time/specials/packages/aricle/0,28804,18721 10_1872133_1872143-1,00.html; see also Emily Waltz, "Biotech's Green Gold," 27 Nature Biotechnology 15-18 (2009)].

The present invention improves upon work disclosed by Woods et al. in U.S. Pat. Nos. 6,306,639 and 6,699,696, which taught the genetic modification of Cyanobacteria by incorporating the genetic information encoding for pyruvate decarboxylase (pdc) and alcohol dehydrogenase (adh). Specifically, the coding sequences of pyruvate decarboxylase (pdc) and alcohol dehydrogenase II (adh) from the bacterium *Zymomonas mobilis* were cloned into the shuttle vector pCB4 and then used to transform the cyanobacterium *Synechococcus* sp. strain PCC 7942. The pdc and adh genes were expressed at high levels, and the transformed cyanobacterium synthesized ethanol, which diffused from the cells into the culture medium. See also Deng and Coleman, Applied and Environmental Microbiology, February 1999, p. 523-528, Vol. 65, No. 2.

Methods to improve ethanol production in such ethanologenic organisms are needed to facilitate commercial implementation of this ethanol source. The ability to modify the genetics of specific species has been stated to be currently limiting progress. E. T. Johnson and C. Schmidt-Dannert, "Light Energy Conversion in Engineered Microorganisms, Trends in Biotechnology, Volume 26, Issue 12, December 2008, Pages 682-689. The problem of genetic engineering is complicated. Some of the obstacles to achieving high yields of products are a result of the interdependence of metabolic networks, which are strongly influenced by the global levels of a handful of metabolites: ATP/ADP, NAD+/NADH, NADP+/NADPH, and acyl-CoAs. ( . . . ) The incorporation of new pathways for biofuel synthesis can destabilize the balance of these important metabolites, leading to the production of undesirable byproducts and a decrease in yield. Sung Kuk Lee, Howard Chou, Timothy S Ham, Taek Soon Lee, Jay D Keasling, Current Opinion in Biotechnology, Volume 19, Issue 6, December 2008, Pages 556-563. Generally, on biochemistry, see Biochemistry. Fifth Edition. Berg J M, Tymoczko J L, and Stryer L. New York. W.H. Freeman and Company. 2002.

One way to increase ethanol production in a microbial host cell is to optimize the activity of the adh enzyme. The initial work of Woods et al. disclosed the use of alcohol dehydrogenase II (adh) from the bacterium *Zymomonas mobilis*. The present invention discloses how different selections of adh can be successfully made to increase ethanol production over that disclosed in the art.

SUMMARY OF THE INVENTION

The present invention discloses genetically-modified cyanobacteria with ethanol-production capabilities enhanced over the currently-reported art, and methods of making such cyanobacteria. An embodiment of the invention provides a genetically modified photoautotrophic, ethanol producing host cell comprising an overexpressed pyruvate decarboxylase enzyme converting pyruvate to acetaldehyde and an overexpressed Zn2+ dependent alcohol dehydrogenase enzyme converting acetaldehyde to ethanol. A preferred embodiment provides a genetically modified, photoautotrophic cyanobacterial host cell wherein the alcohol dehydrogenase enzyme is a Zn2+-dependent dehydrogenase. A more preferred embodiment utilizes adh from *Synechocystis*. In a further embodiment of this invention the Zn2+ dependent alcohol dehydrogenase enzyme is selected from a member of the Zinc-binding GroES-like domain alcohol dehydrogenases and furthermore has at least 70%, preferably 80% most preferred at least 90% sequence identity to the amino acid sequence of the *Synechocystis* Adh. The Zn2+ dependent alcohol dehydrogenase enzyme can furthermore be selected from a group of Zn2+ dependent alcohol dehydrogenase enzymes identified from a phylogenetic tree constructed with MEGA version 3.1 using the neighbor-joining method with Poisson correction substitution model and 100 bootstrap replicates assuming uniform heterogeneity among sites, as more fully described below.

A separate embodiment of the invention provides a genetically modified photoautotrophic, ethanol producing cyanobacterial host cell comprising an overexpressed pyruvate decarboxylase enzyme converting pyruvate to acetaldehyde and an endogenous Zn2+ dependent alcohol dehydrogenase enzyme converting acetaldehyde to ethanol. Furthermore, with the recognition that different adh enzymes perform differently in the production of ethanol with genetically-modified cyanobacteria (including the finding that the adh of *Zymomonas mobilis* has a higher enzymatic activity than the adh of *Synechocystis* for the unwanted back reaction of ethanol to acetaldehyde), an embodiment of the invention is a method to evaluate the utility of different adh enzymes for use in ethanol production.

BRIEF DESCRIPTION OF THE DRAWINGS

FIG. 1A presents the nucleotide sequence of the adhA gene from *Zymomonas mobilis* ZM4. (SEQ ID NO:1)

FIG. 1B presents the amino acid sequence for the ZmAdhI protein sequence (AAV89860). (SEQ ID NO:2)

FIG. 2A presents the nucleotide sequence of SynAdh, the adh gene (slr1192) of *Synechocystis* sp. PCC 6803. (SEQ ID NO:3)

FIG. 2B presents the amino acid sequence of SynAdh (protein sequence BAA18840) of *Synechocystis* sp. PCC 6803. (SEQ ID NO:4)

FIG. 3A presents the nucleotide sequence of EcAdhE, the adhE gene from *E. coli* K12. (SEQ ID NO:5)

FIG. 3B presents the amino acid sequence of EcAdhE (protein sequence NP_415757). (SEQ ID NO:6)

FIG. 4A presents the nucleotide sequence of ThAdhE, the adhE gene (tlr0227) from *Thermosynechococcus elongatus* BP-1. (SEQ ID NO:7)

FIG. 4B presents the amino acid sequence of ThAdhE (protein sequence BAC07780). (SEQ ID NO:8)

FIG. 5A presents the nucleotide sequence of ZpPdcpdc gene from *Zymobacter palmae* ATCC 51623 (SEQ ID NO:9)

FIG. 5B presents the amino acid sequence of ZpPdc (protein sequence AAM49566). (SEQ ID NO:10)

FIG. 6A presents the nucleotide sequence of pSK10 cloning vector (derivate of pSK9 [V. V. Zinchenko, Moscow, Russia; unpublished]). (SEQ ID NO:11)

FIG. 6O is a schematic representation of the gene organization of the construct pSK10-PisiA-PDC-ThAdhE.

FIG. 6R presents the nucleotide sequence of the crhC promoter (*Anabaena* sp. PCC7120) (crhC gene: alr4718, RNA helicase crhC cold shock inducible) (SEQ ID NO:12).

FIG. 6S presents the nucleotide sequence of the petE promoter (*Anabaena* sp. PCC7120) petE gene: all0258, plastocyanin precursor (petE) induced by addition of Cu (SEQ ID NO:13)

FIG. 6U presents the nucleotide sequence of plasmid pRL1049-PpetE-PDC-ADHII (SEQ ID NO:14).

FIG. 6W presents the nucleotide sequence of plasmid pRL593-PisiA-PDC-ADHII (SEQ ID NO:15).

FIG. 11B presents in tabular form all genes identified by the Zn-binding, SynADH clade.

FIG. 11C presents the amino acid sequence of a zinc-containing alcohol dehydrogenase family protein of Synechocystis sp. PCC 6803, identified by Genbank Accession No. NP_443028.1. (SEQ ID NO:16)

FIG. 11D presents the amino acid sequence of a zinc-containing alcohol dehydrogenase family protein of Oceanobacter sp. RED65, identified by Genbank Accession No. ZP_01306627.1. (SEQ ID NO:17)

FIG. 11E presents the amino acid sequence of an alcohol dehydrogenase, zinc-binding protein of Limnobacter sp. MED105, identified by Genbank Accession No. ZP_01914609.1. (SEQ ID NO:18)

FIG. 11F presents the amino acid sequence of an alcohol dehydrogenase GroES-like protein of Psychrobacter cryohalolentis K5, identified by Genbank Accession No. YP_581659.1. (SEQ ID NO:19)

FIG. 11G presents the amino acid sequence of an alcohol dehydrogenase GroES-like domain family of Verrucomicrobiae bacterium DG1235, identified by Genbank Accession No. EDY84203.1. (SEQ ID NO:20)

FIG. 11H presents the amino acid sequence of a zinc-containing alcohol dehydrogenase family protein of Saccharophagus degradans 2-40, identified by Genbank Accession No. YP_529423.1. (SEQ ID NO:21)

FIG. 11I presents the amino acid sequence of a zinc-containing alcohol dehydrogenase family protein of Alteromonas macleodii 'Deep ecotype', identified by Genbank Accession No. YP_002126870.1. (SEQ ID NO:22)

FIG. 11J presents the amino acid sequence of a zinc-containing alcohol dehydrogenase family protein of Acaryochloris marina MBIC11017, identified by Genbank Accession No. YP 001519107.1. (SEQ ID NO:23)

FIG. 11K presents the amino acid sequence of an alcohol dehydrogenase GroES domain protein of Cyanothece sp. PCC 7424, identified by Genbank Accession No. YP_002380432.1. (SEQ ID NO:24)

FIG. 11L presents the amino acid sequence of an alcohol dehydrogenase GroES domain protein of Cyanothece sp. PCC 7424, identified by Genbank Accession No. ZP_02976085.1. (SEQ ID NO:25)

FIG. 11M presents the amino acid sequence of an alcohol dehydrogenase GroES domain protein of Cyanothece sp. PCC 7822, identified by Genbank Accession No. ZP_03154326.1. (SEQ ID NO:26)

FIG. 11N presents the amino acid sequence of an alcohol dehydrogenase GroES domain protein of Cyanothece sp. PCC 8801, identified by Genbank Accession No. YP_002371662.1. (SEQ ID NO:27)

FIG. 11O presents the amino acid sequence of an alcohol dehydrogenase GroES domain protein of Cyanothece sp. PCC 8801, identified by Genbank Accession No. ZP_02941996.1. (SEQ ID NO:28)

FIG. 11P presents the amino acid sequence of an alcohol dehydrogenase GroES domain protein of Cyanothece sp. PCC 8802, identified by Genbank Accession No. ZP_03143898.1. (SEQ ID NO:29)

FIG. 11Q presents the amino acid sequence of an alcohol dehydrogenase GroES-like domain family of Microcoleus chthonoplastes PCC 7420, identified by Genbank Accession No. EDX77810.1. (SEQ ID NO:30)

FIG. 11R presents the amino acid sequence of an uncharacterized zinc-type alcohol dehydrogenase-like protein of Microcystis aeruginosa NIES-843, identified by Genbank Accession No. YP_001659961.1. (SEQ ID NO:31)

FIG. 11S presents the amino acid sequence of an unnamed protein product of Microcystis aeruginosa PCC 7806, identified by Genbank Accession No. CA090817.1. (SEQ ID NO:32)

FIG. 11T presents the amino acid sequence of a zinc-containing alcohol dehydrogenase superfamily protein of Synechococcus sp. WH 5701, identified by Genbank Accession No. ZP_01085101.1. (SEQ ID NO:33)

FIG. 11U presents the amino acid sequence of a zinc-containing alcohol dehydrogenase superfamily protein of Synechococcus sp. RS9917, identified by Genbank Accession No. ZP_01079933.1. (SEQ ID NO:34)

FIG. 11V presents the amino acid sequence of a zinc-containing alcohol dehydrogenase superfamily protein of Synechococcus sp. WH 5701, identified by Genbank Accession No. ZP_01085101.1. (SEQ ID NO:35)

FIG. 11W presents the amino acid sequence of a zn-dependent alcohol dehydrogenase of Synechococcus sp. WH 7803, identified by Genbank Accession No. YP_001224538.1. (SEQ ID NO:36)

FIG. 11X presents the amino acid sequence of a zinc-containing alcohol dehydrogenase superfamily protein of Synechococcus sp. WH 7805, identified by Genbank Accession No. ZP_01125148.1. (SEQ ID NO:37)

FIG. 12C is a tabular presentation of data for an ethanol concentration time course under limiting CO2 conditions; these data are presented graphically in FIG. 12D.

FIG. 12E is a tabular presentation of data for an ethanol concentration time course under limiting CO2 conditions; these data are presented graphically in FIG. 12F.

FIG. 12G is a tabular presentation of data for an ethanol concentration time course under limiting CO2 conditions; these data are presented graphically in FIG. 12H.

FIG. 12I is a tabular presentation of data for an ethanol concentration time course under limiting CO2 conditions; these data are presented graphically in FIG. 12J.

FIG. 13A is a tabular presentation of cyanobacterial promoters used to express ethanologenic enzymes in Synechocystis 6803.

FIG. 13O is a graphic depiction of ethanol production of Synechocystis 6803 pVZ321 b-PhspA-PDC, pVZ321 b-PhtpG-PDC, pVZ321 b-PhliB-PDC and pVZ321 b-PclpB1-PDC.

Figure 14A:
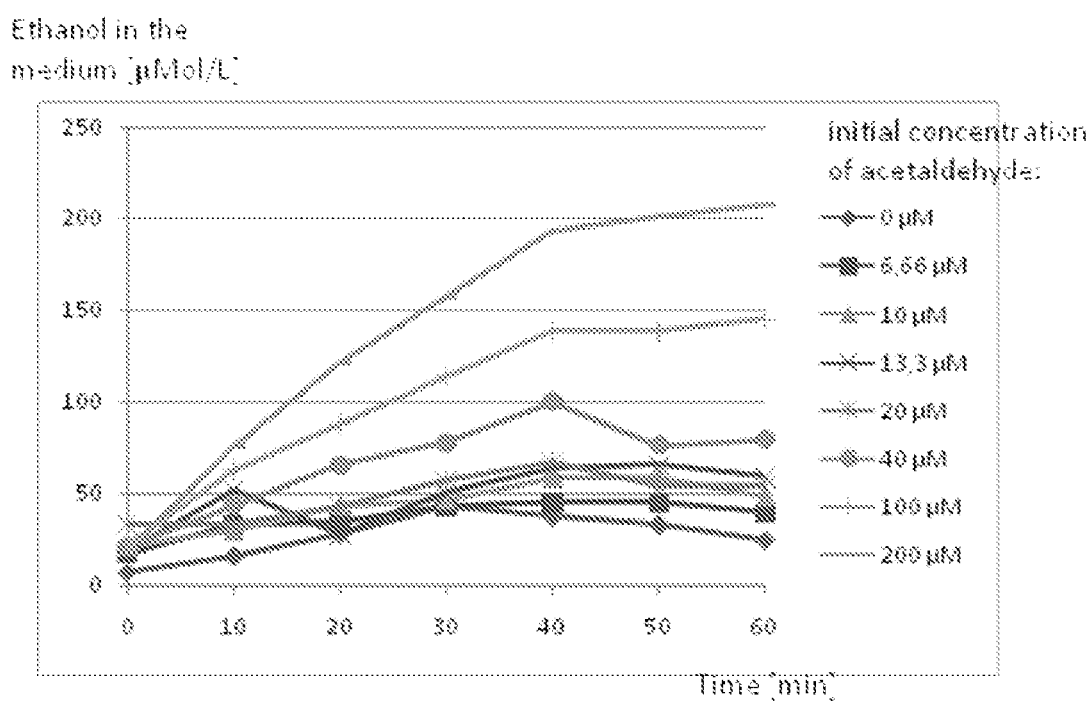
FIG. 14A is a graphic representation of ethanol production after the addition of acetaldehyde. Different acetaldehyde concentrations were added to a culture of strain 6803pVZPisiA, and the ethanol content in the medium was measured for 60 minutes.
Figure 14B:
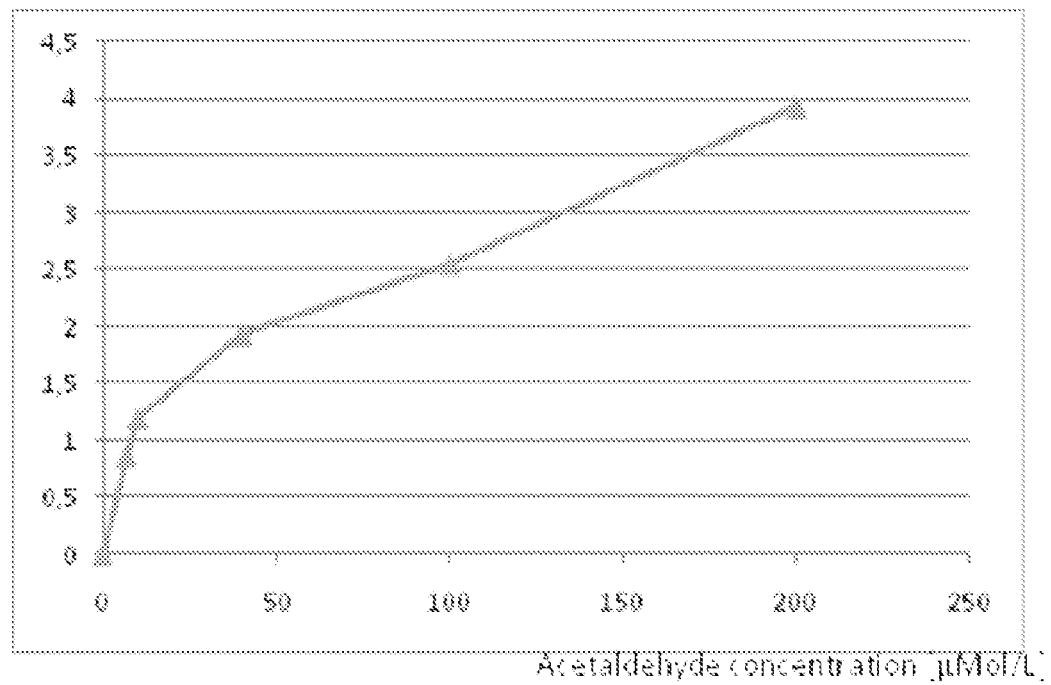
FIG. 14B is a graphic representation of the correlation of ethanol production rate and acetaldehyde concentration. Given are the initial ethanol rates (calculated with FIG. 14A) in correlation to the initial acetaldehyde concentrations.
Figure 14C:
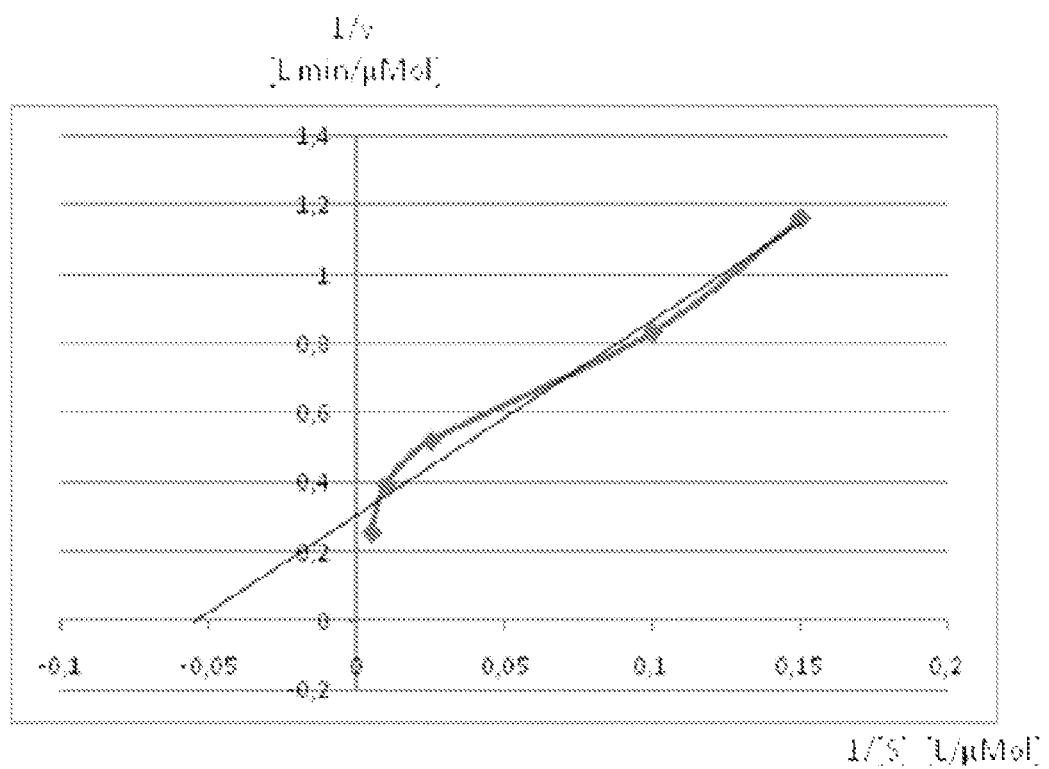
FIG. 14C (Lineweaver-Burk-Plot) is a graphic representation of the reciprocal of the initial velocity versus the reciprocal of the acetaldehyde concentration. Intact cells were used.
Figure 14D:
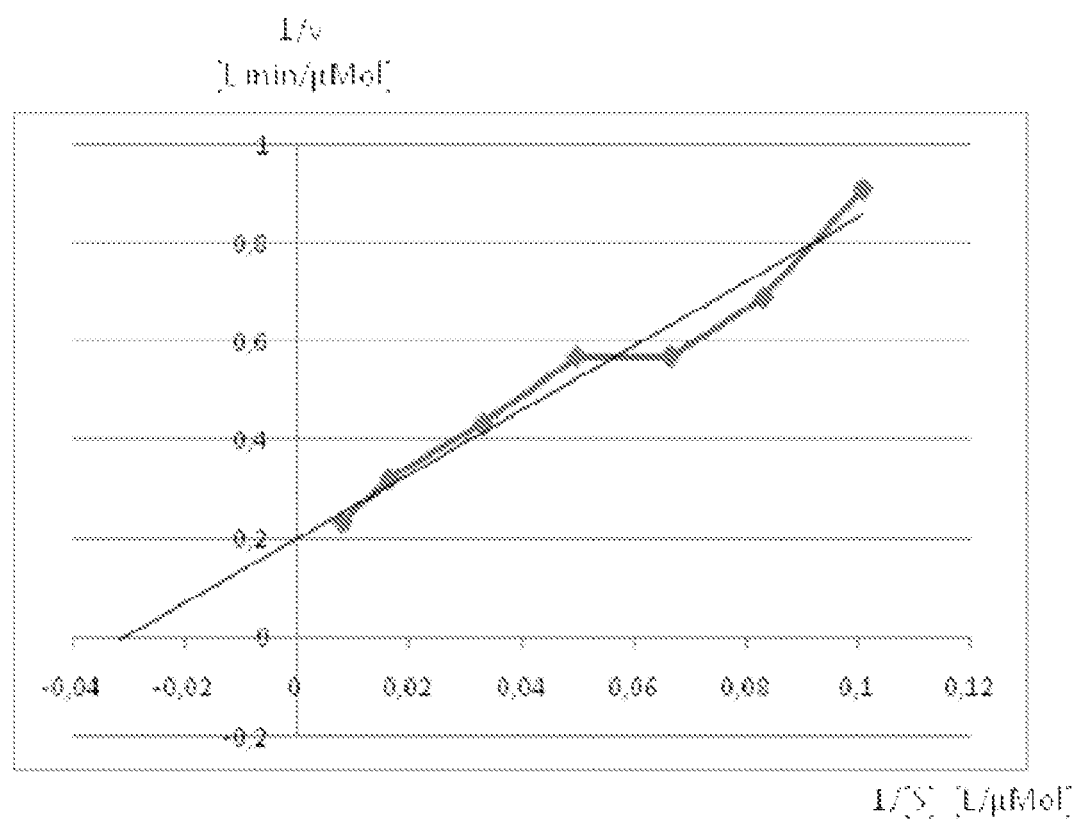
FIG. 14D (Lineweaver-Burk-Plot) is a graphic representation of the reciprocal of the initial velocity versus the reciprocal of the acetaldehyde concentration. The results shown are from a repeat of the experiment with intact cells.
Figure 14E:
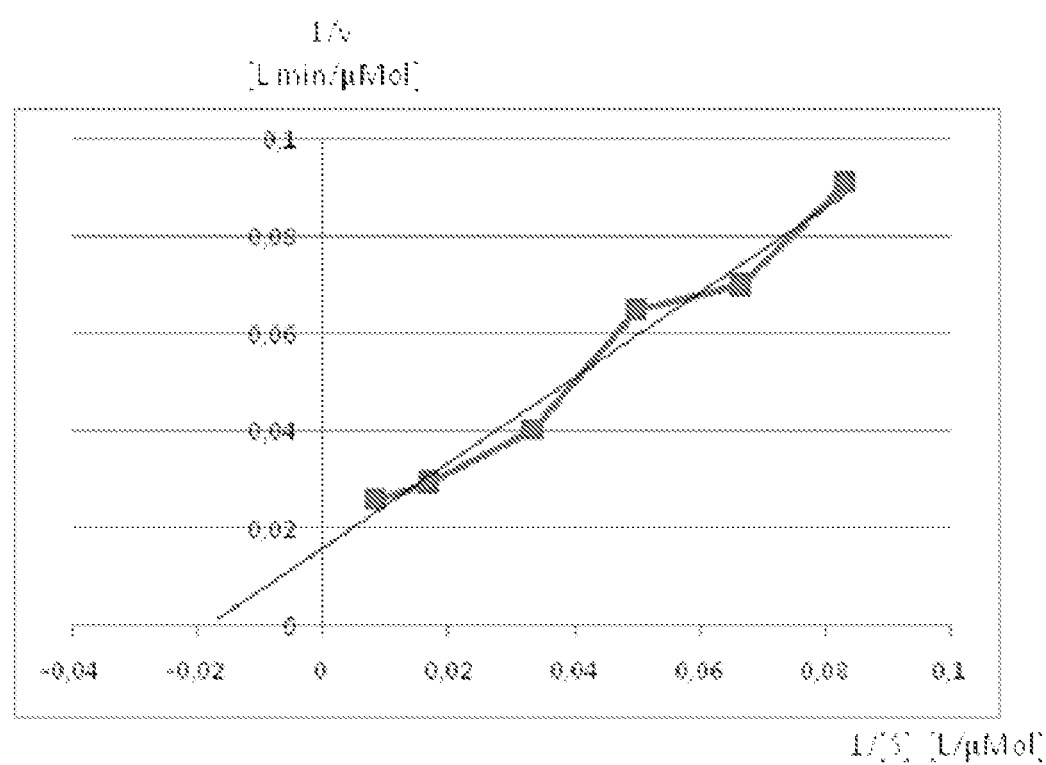

FIG. 14E (Lineweaver-Burk-Plot) is a graphic representation of the Adh activities of a crude extract of strain 6803PVZ-PisiA were measured in presence of different concentration of acetaldehyde. In contrast to the experiments with intact cells in this experiment NADH was added in excess. Shown is the reciprocal of the initial velocity versus reciprocal of the concentration of acetaldehyde.

Figure 14F:
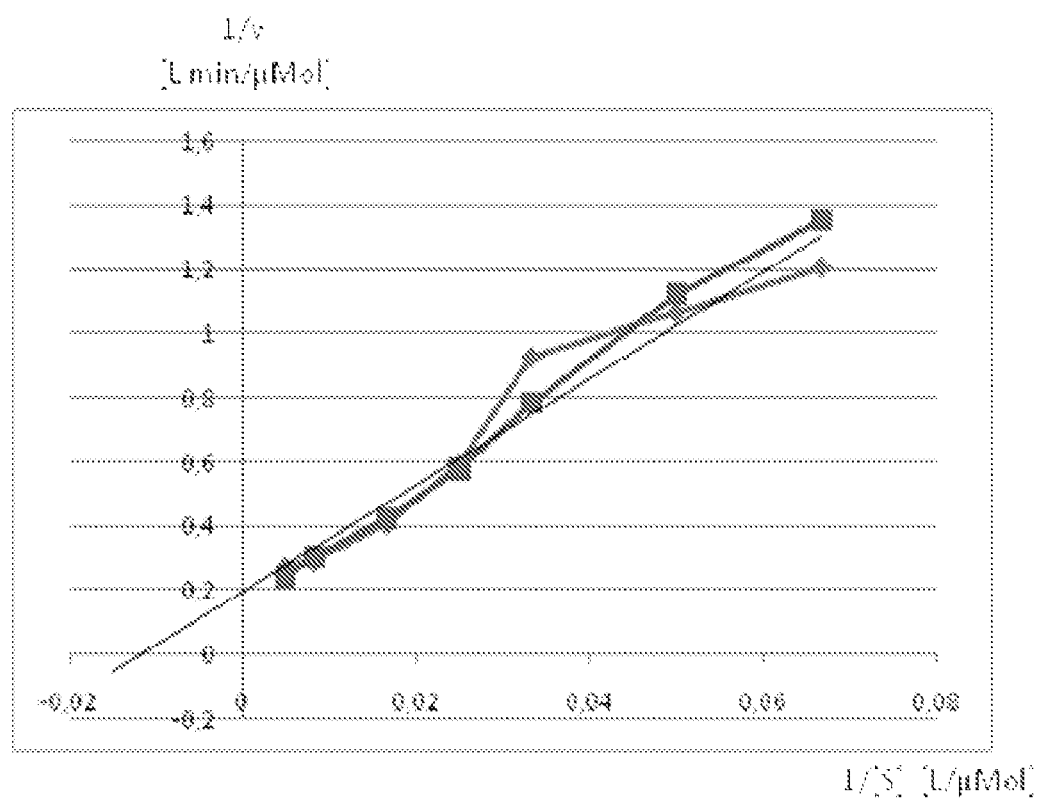

FIG. 14F (Lineweaver-Burk-Plot) Similar to the experiment summarized in FIG. 14E, Adh activities of a crude extract of strain 6803PVZPisiA were measured in the presence of different concentrations of acetaldehyde. The assays contained an over excess either of NADH or of NADPH. Substantial differences between NADH and NADPH were not observed.

DETAILED DESCRIPTION

Overview

The introduction of a pyruvate decarboxylase (Pdc) and an alcohol dehydrogenase (Adh) into cyanobacteria, as disclosed by Woods et al in U.S. Pat. No. 6,306,639, enables a light driven production of ethanol in autophototrophic bacteria by directing carbon fixed via photosynthesis into ethanol production. The substrate for the Pdc enzyme is pyruvate that is converted by decarboxylation into acetaldehyde and $CO_2$.

The product, acetaldehyde, is then converted by an Adh enzyme into the desired end-product ethanol.

Woods disclosed the use of adhi and adhII from the bacterium *Zymomonas mobilis*. Many organisms contain adh, and there are adh enzymes with a variety of properties. The present invention discloses benefits associated with the use of adh from *Synechocystis* PCC6803. One benefit associated with the use of adh from *Synechocystis* PCC6803, relative to adh from *Zymomonas mobilis*, is the significantly decreased back reaction of ethanol to acetaldehyde under conditions of relevance to ethanol production.

Section P.2 (below) discloses information on genetically modified photoautotrophic host cells comprising *Zymomonas* PDC and ADHII. Section P.3 discloses information on genetically modified host cells comprising *Zymomonas* PDC and *Synechocystis* ADH. Section P.4 discloses information on photoautotrophic host cells comprising *Zymomonas* PDC and various wild type as well as mutant ADHE enzymes. Section P.5 discloses information on genetically modified photoautotrophic host cells comprising *Zymomonas* PDC and different ADH enzymes. There is a section on the phylogenetic analysis of ADH from *Synechocystis*. Section P.6 discloses information on genetically modified photoautotrophic host cells comprising *Zymomonas* PDC as the only genetic modification. Section P.7 discloses information on genetically modified host cells comprising *Zymomonas* PDC with the host cell harboring PDC in conjunction with various ADH enzymes. Section P.9 discloses results under various growth conditions. There is a section disclosing various embodiments of this invention.

Experimental Section

Introduction of Alternative Ethanologenic Genes to ZmPdc and ZmAdhII Into the Existing pVZ-Expression Constructs (Point 1)

In order to create expression constructs as described above (point 1) but with different alcohol dehydrogenases, the adh encoding sequence was cut out by SacI/PstI digestion of the corresponding pVZ-Pxxx-pdc/adh construct (xxx for isiA, nblA, ntcA). The new adh sequence containing the restriction sites SacI/PstI (introduced by used primer) was ligated into the "adh free" pVZ construct resulting in a construct that expresses the ZmPdc together with new Adh.

Remark: In all following nt sequences of genes, there is designation of restriction sites for clonings as well as translation starts (start codons) and translation stops (stop codons)

In this context, new alcohol dehydrogenases include the following:

(1) FIG. 1A presents the nucleotide sequence for ZmADHI (adhA gene from *Zymomonas mobilis* ZM4) and FIG. 1B presents the amino acid sequence for ZmAdhI AAV89860

Figure 1C:
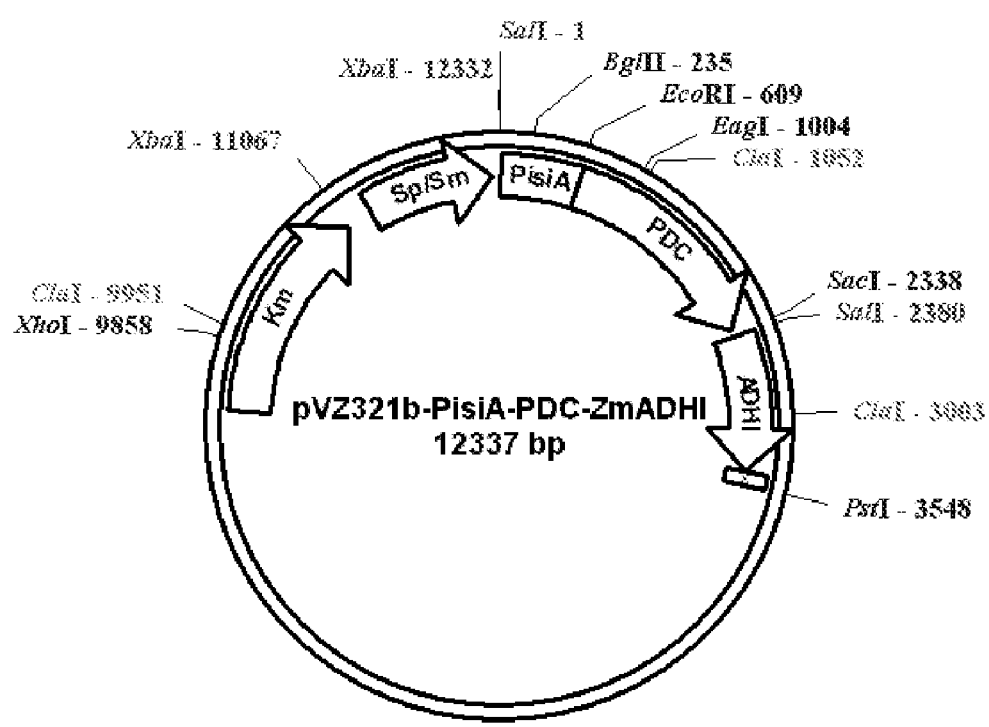
FIG. 1C is a schematic presentation of the gene organization for construct pVZ321b-PisiA-PDC-ADHI.
Figure 1D:
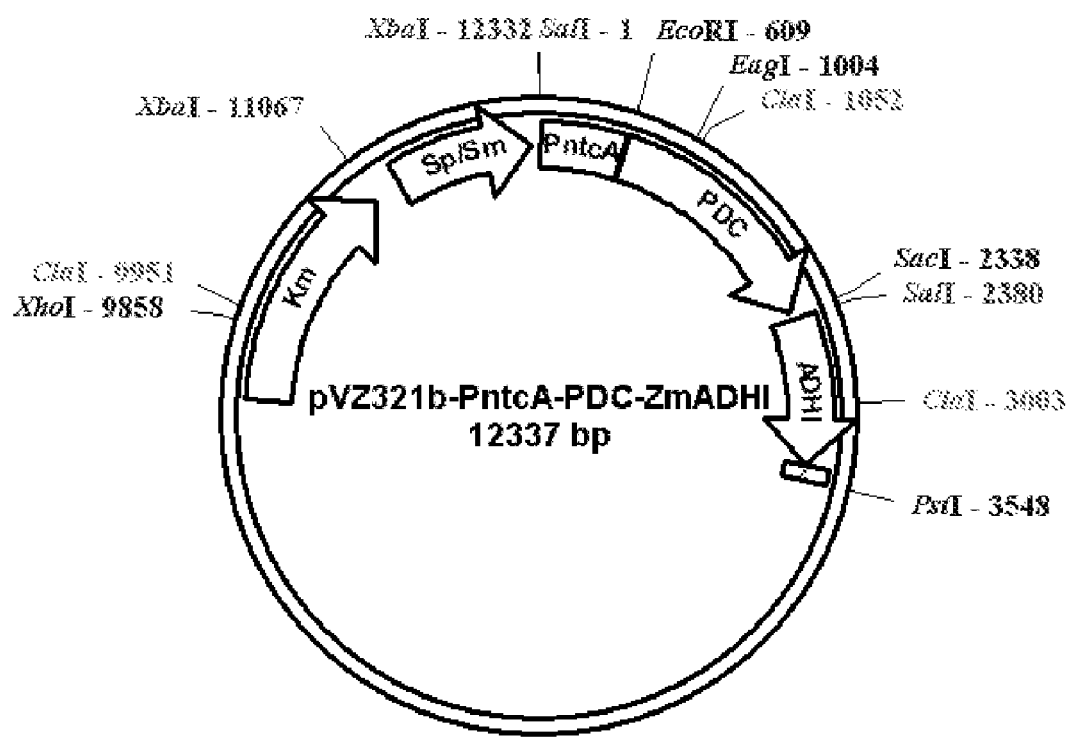
FIG. 1D is a schematic presentation of the gene organization for construct pVZ321b-PntcA-PDC-ZmADHI.
Figure 1E:
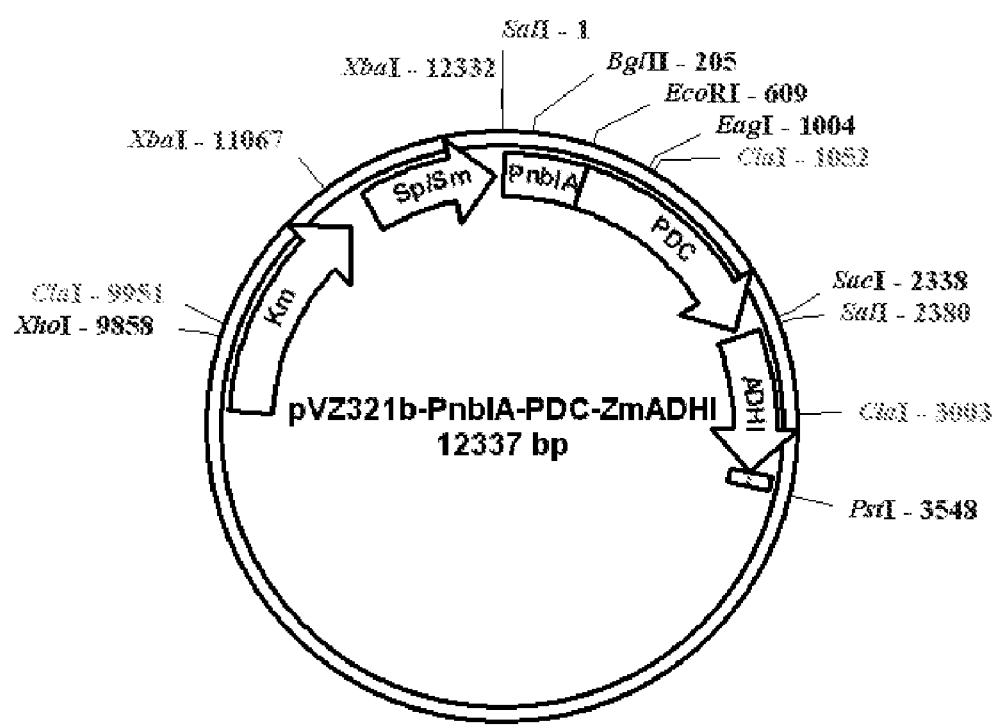
FIG. 1E is a schematic presentation of the gene organization for construct pVZ321b-PnblA-PDC-ZmADHI.

FIG. 1C presents a schematic representation of the plasmid pVZ321 b-PisiA-PDC-ZmADH1. FIG. 1D presents a schematic representation of the plasmid pVZ321 b-PntcA-PDC-ZmAH1. FIG. 1E presents a schematic representation of the plasmid pVZ321 b-PnblA-PDC-ZmADH1.

(2) The nucleotide sequence of SynAdh (adh gene (slr1192) *Synechocystis* sp. PCC 6803) is presented in FIG. 2A. The amino acid sequence of this protein (SynAdh protein sequence BAA18840) is presented in FIG. 2B.

Figure 2C:
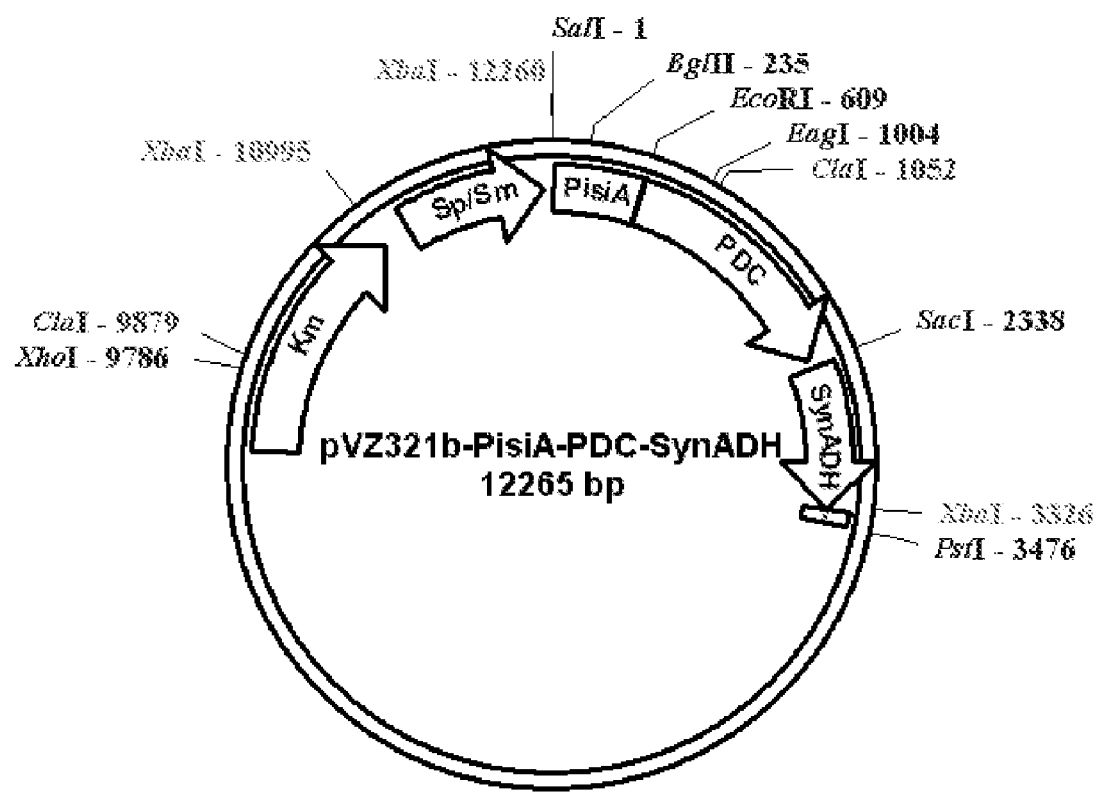
FIG. 2C is a schematic representation of the gene organization for construct pVZ321 b-PisiA-PDC-SynADH.
Figure 2D:
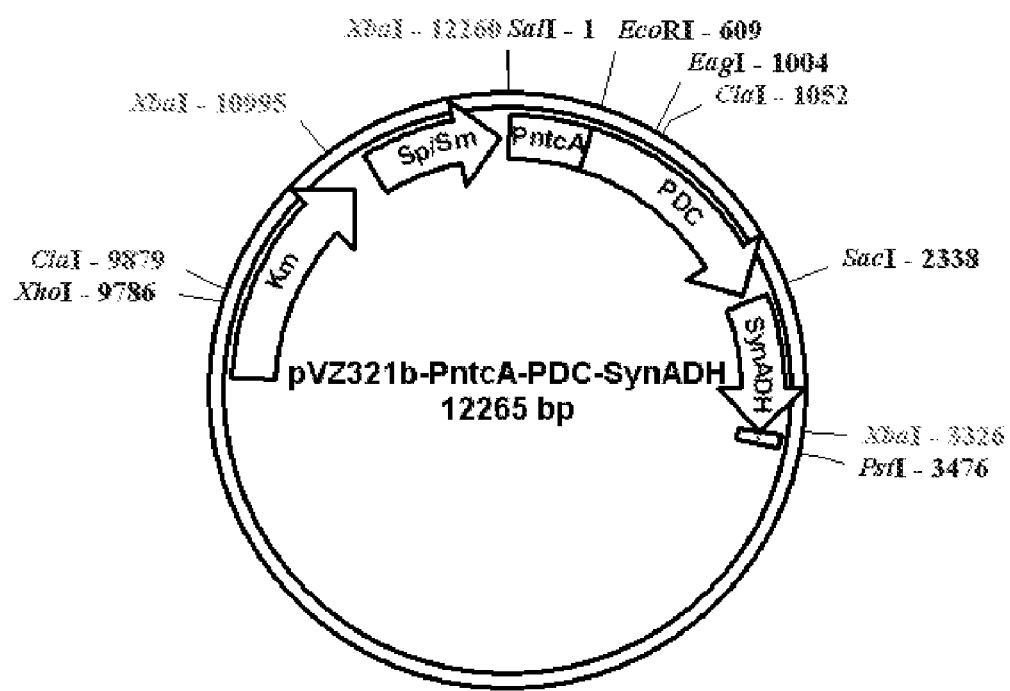
FIG. 2D is a schematic representation of the gene organization for construct pVZ321 b-PntcA-PDC-SynADH.
Figure 2E:
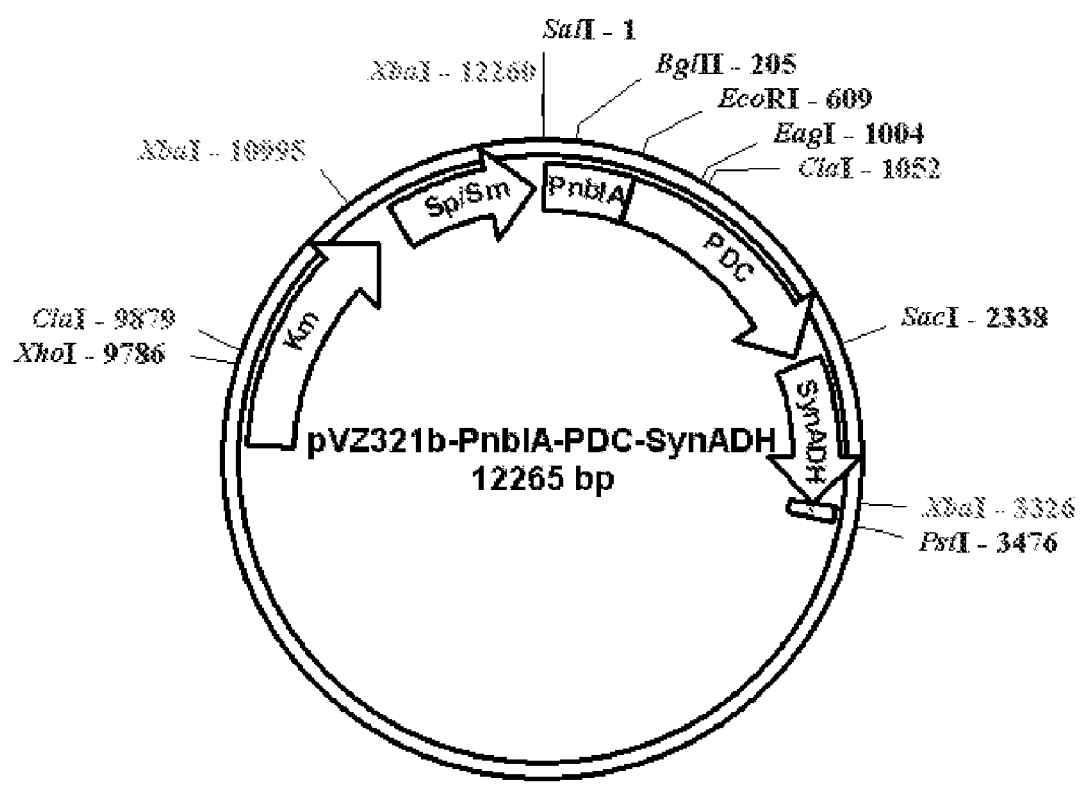
FIG. 2E is a schematic representation of the gene organization for construct pVZ321 b-PnblA-PDC-SynADH.

FIG. 2C presents a schematic representation of the plasmid pVZ321 b-PisiA-PDC-SynADH. FIG. 2D presents a schematic representation of the plasmid pVZ321 b-PntcA-PDC-SynADH. FIG. 2E presents a schematic representation of the plasmid pVZ321 b-PnblA-PDC-SynADH.

In order to create expression constructs as described above (point 1) but with AdhE-type alcohol dehydrogenases, the pdc/adh encoding sequence was cut out by EcoRI/BamHI and EcoRI/PstI digestion resp. of the corresponding pVZ-Pxxx-pdc/adh construct (xxx for isiA, ntcA, nblA). The adhE sequence of *E. coli* and *Thermosynechococcus elongatus* resp. containing the restriction sites EcoRI/BamHI and EcoRI/PstI resp. (introduced by used primer) were ligated into the "pdc/adh free" pVZ construct resulting in constructs that express the AdhE-type alcohol dehydrogenases.

(3) The nucleotide sequence for EcAdhE (adhE gene from *E. coli* K12) is presented in FIG. 3A. The amino acid sequence for this protein (EcAdhE protein sequence NP_415757) is presented in FIG. 3B.

Figure 3C:
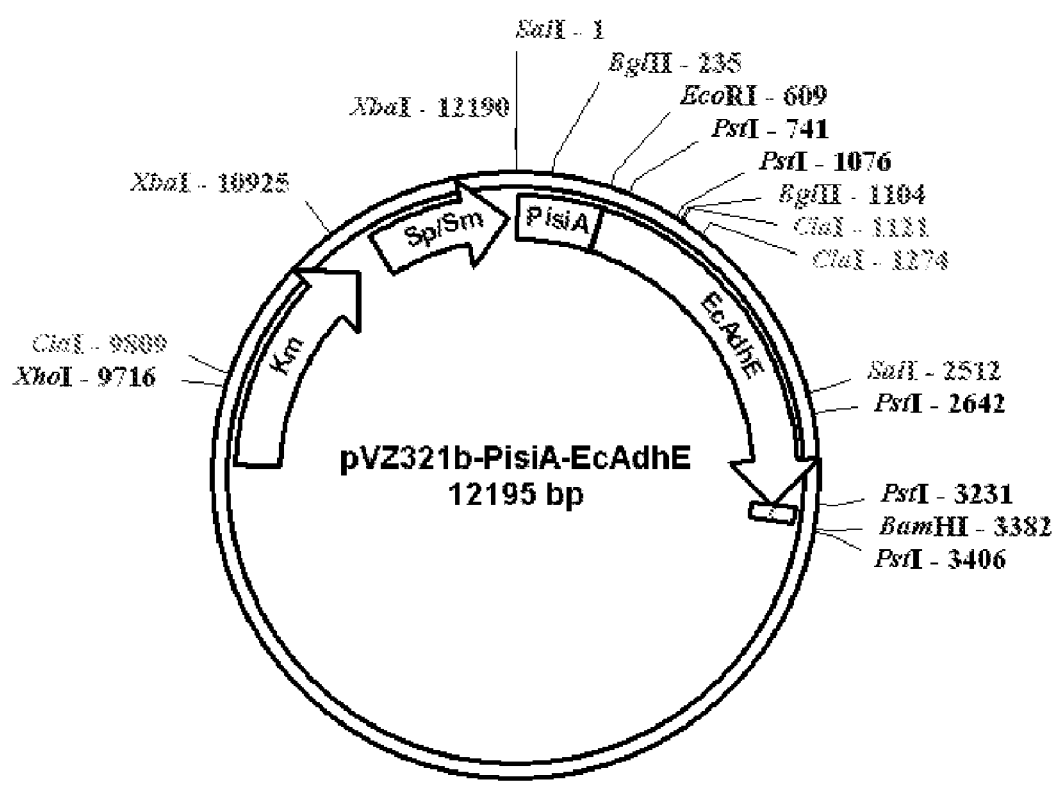
FIG. 3C is a schematic representation of the gene organization for construct pVZ321 b-PisiA-PDC-EcAdhE.
Figure 3D:
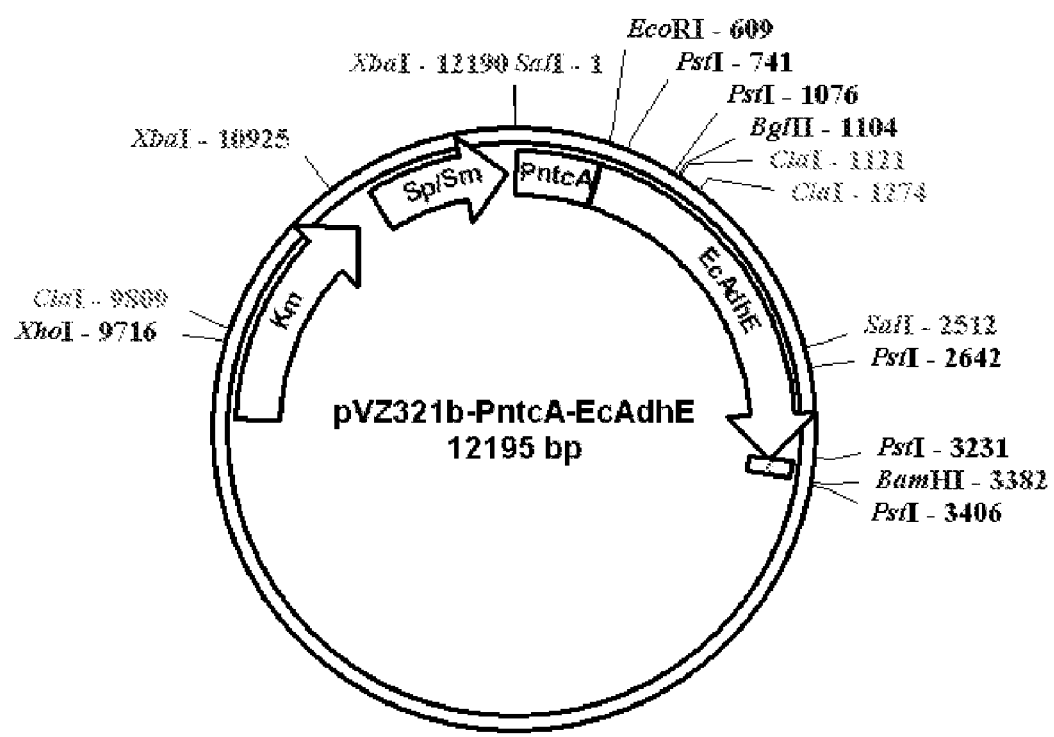
FIG. 3D is a schematic representation of the gene organization for construct pVZ321 b-PntcA-PDC-EcAdhE.
Figure 3E:
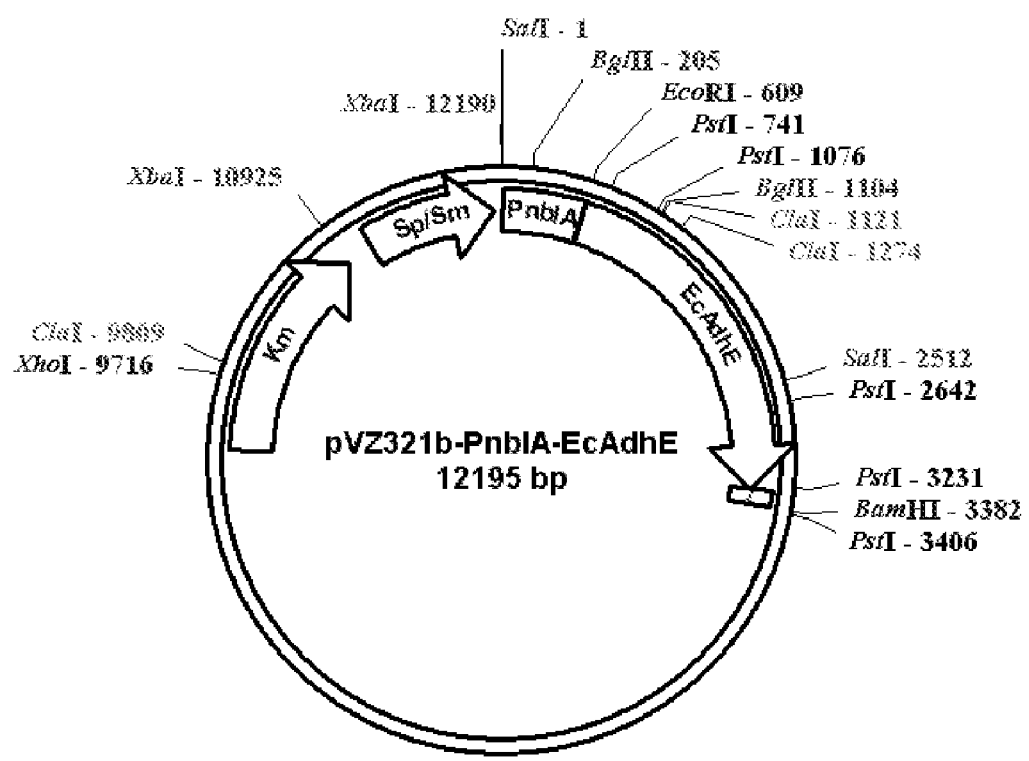
FIG. 3E is a schematic representation of the gene organization for construct pVZ321 b-PnblA-PDC-EcAdhE.

FIG. 3C presents a schematic representation of the plasmid pVZ321 b-PisiA-PDC-EcAdhE. FIG. 3D depicts a schematic representation of the plasmid pVZ321 b-PntcA-PDC-EcAdhE. FIG. 3E presents a schematic representation of the plasmid pVZ321 b-PnblA-PDC-EcAdhE.

(4) The nucleotide sequence for the ThAdhE gene (adhE gene (tlr0227) from *Thermosynechococcus elongatus* BP-1) is presented in FIG. 4A, and the amino acid sequence for this protein (ThAdhE protein sequence BAC07780) is presented in FIG. 4B.

Figure 4C:
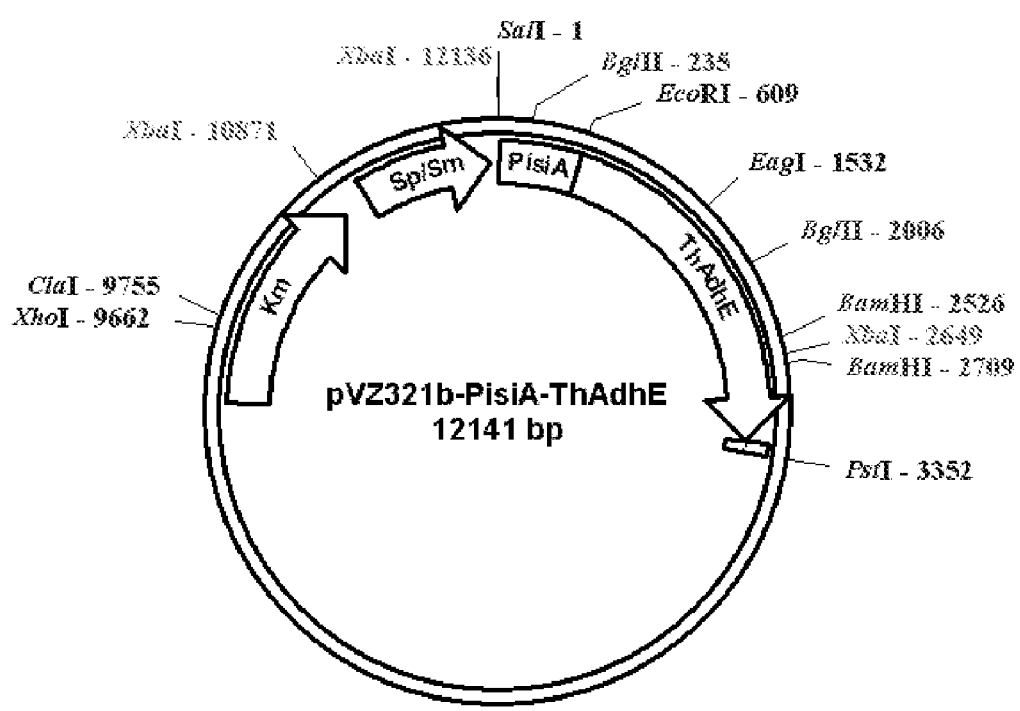
FIG. 4C is a schematic representation of the gene organization for the construct pVZ321 b-PisiA-ThAdhE.
Figure 4D:
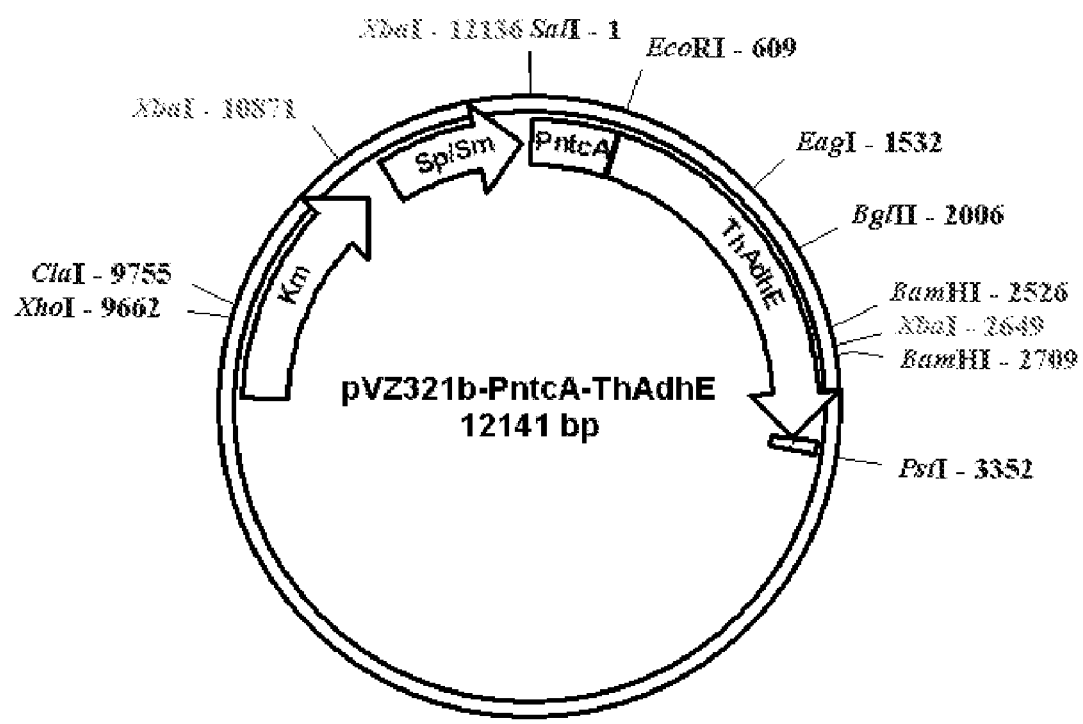
FIG. 4D is a schematic representation of the gene organization for the construct pVZ321 b-PntcA-ThAdhE.
Figure 4E:
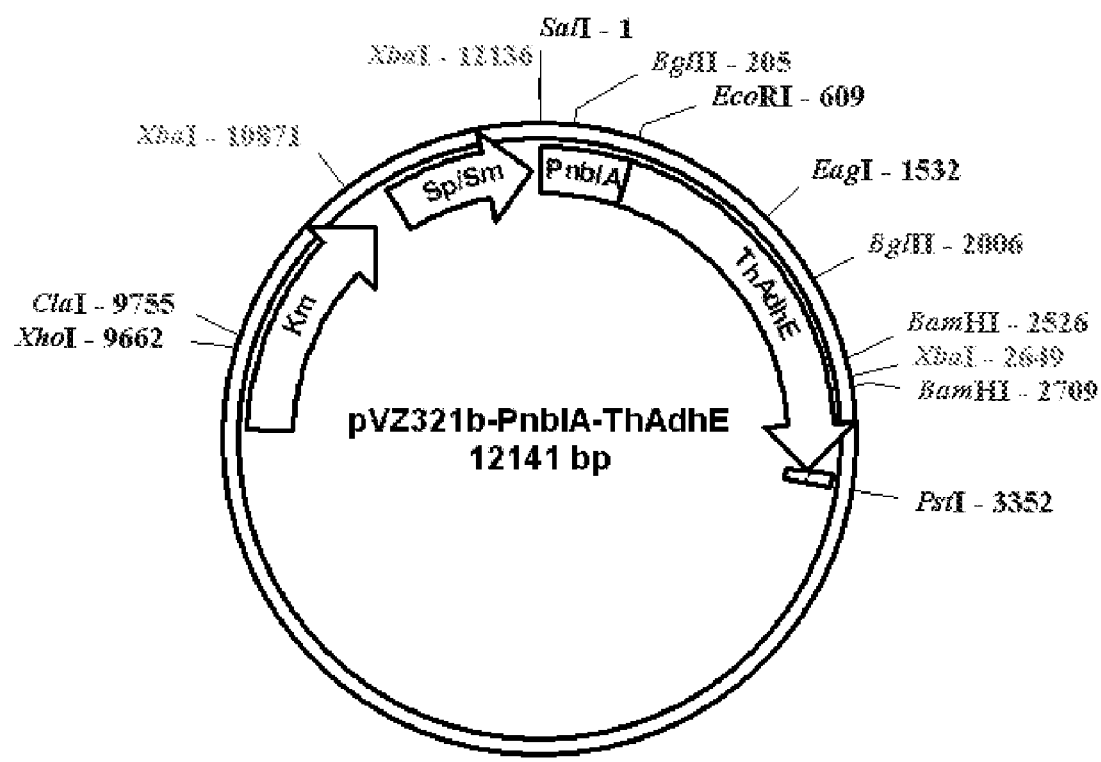
FIG. 4E is a schematic representation of the gene organization for the construct pVZ321 b-PnblA-ThAdhE.

FIG. 4C presents a schematic representation of the plasmid pVZ321 b-PisiA-PDC-ThAdhE. FIG. 4D presents a schematic representation of the plasmid pVZ321 b-PntcA-PDC-ThAdhE. FIG. 4E presents a schematic representation of the plasmid pVZ321 b-PnblA-PDC-ThAdhE.

In order to create expression constructs as described above (point 1) but with an alternative pyruvate decarboxylase to the *Zymomonas* mobilis enzyme, the Pdc encoding sequence was cut out by EcoRI/SacI digestion of the corresponding pVZ-Pxxx-pdc/adh construct (xxx for isiA, ntcA, nblA). The pdc sequence from *Zymobacter palmae* containing the restriction sites EcoRI/SacI (introduced by used primer) was ligated into the "pdc free" pVZ construct resulting in a construct that express the Pdc from *Zymobacter palmae* together with the preexisting Adh.

FIG. 5A presents the nucleotide sequence for ZpPdc (pdc gene from *Zymobacter palmae* ATCC 51623), and the amino acid sequence for this protein (ZpPdc protein sequence AAM49566) is presented in FIG. 5B.

Construction of Chromosome Integrative pSK-Vectors

In order to create plasmids for stable chromosome integration in cyanobacteria the whole inserts from the described pVZ constructs (point 1 and 3) containing the promoter sequence and the coding region of the ethanologenic enzymes (Pdc and Adh) were cut out by SalI/PstI digestion. The resulting inserts were ligated into the pSK10, a derivate of the pSK9 (a kind gift of V. V. Zinchenko and described in Dühring et al., submitted 16th of December 2007, Plant Physiology) using the SalI/PstI restriction sites. In some cases other restriction sites were used, e.g. in case of pVZ321 b-Pxxx-pdc-adhI the restriction sites XbaI/PstI were used, in case of pVZ321 b-Pxxx-Ecdhe the restriction sites XbaI/BamHI were used.

Figure 6B:
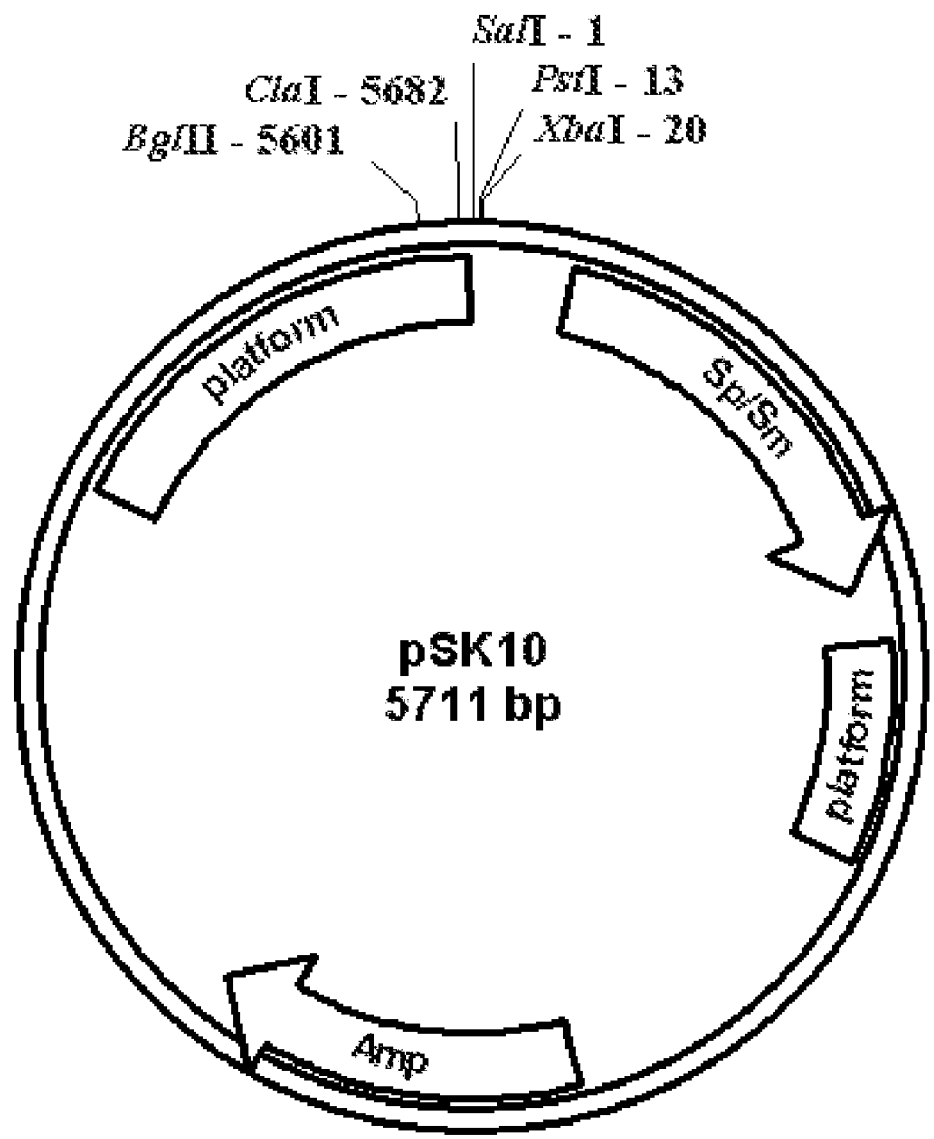
FIG. 6B is a schematic representation of the gene organization for the plasmid pSK10.

FIG. 6A presents the nucleotide sequence of the pSK10 cloning vector (derivate of pSK9 [V. V. Zinchenko, Moscow, Russia]). FIG. 6B presents a schematic representation of this plasmid.

Several pSK10 constructs with ZmPdc/ZmAdhII were obtained.

Figure 6C:
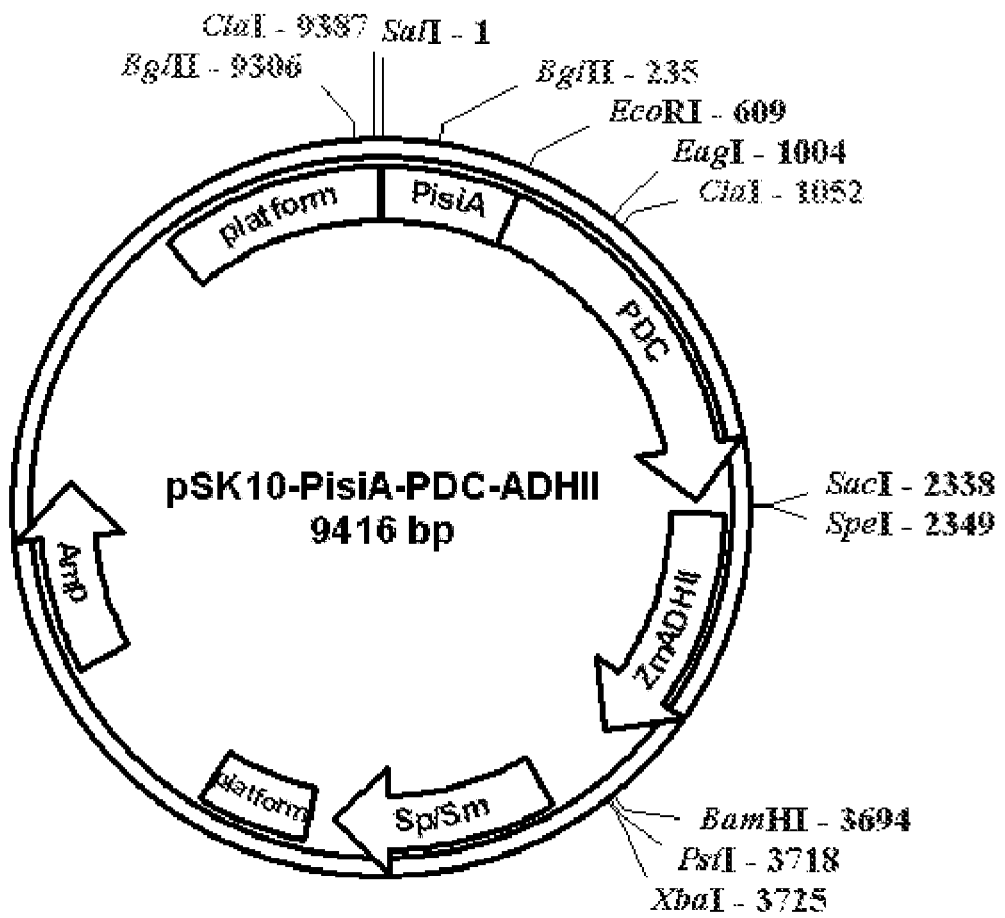
FIG. 6C is a schematic representation of the gene organization of the construct pSK10-PisiA-PDC-ADHII.

FIG. 6C presents a schematic diagram of pSK10-PisiA-PDC-ADHII.

Figure 6D:
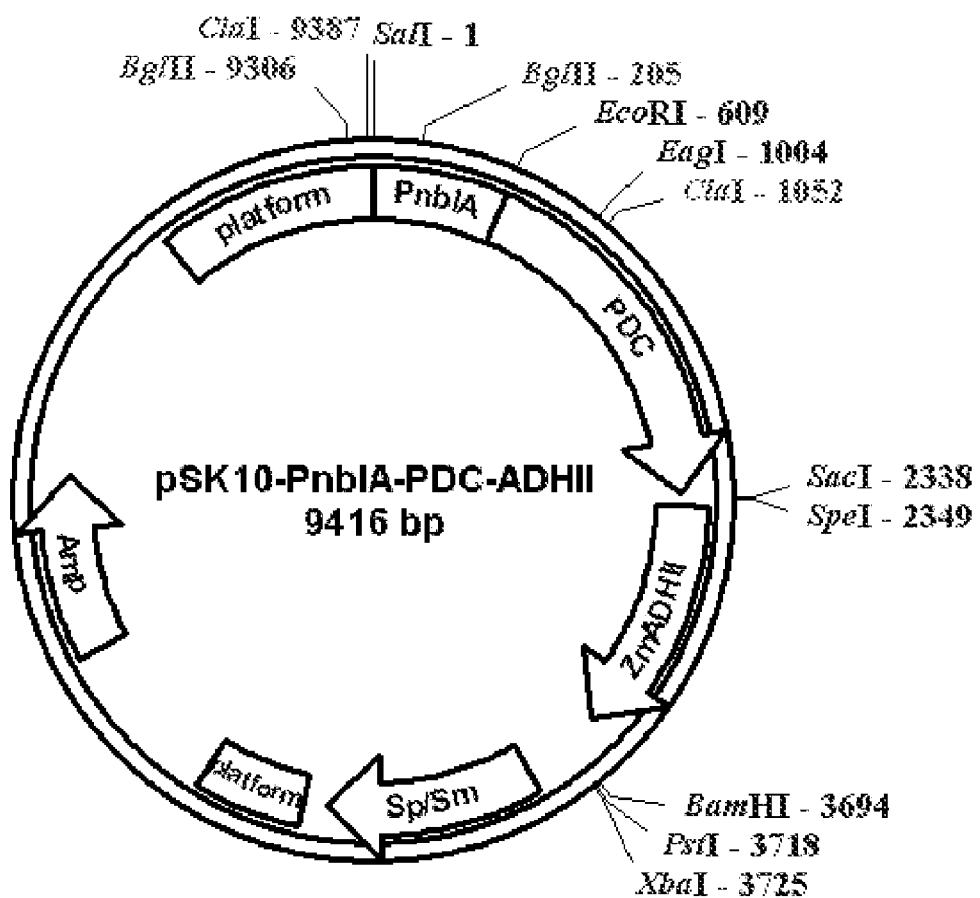
FIG. 6D is a schematic representation of the gene organization of the construct pSK10-PnblA-PDC-ADHII.

FIG. 6D presents a schematic diagram of pSK10-PnblA-PDC-ADHII.

Figure 6E:
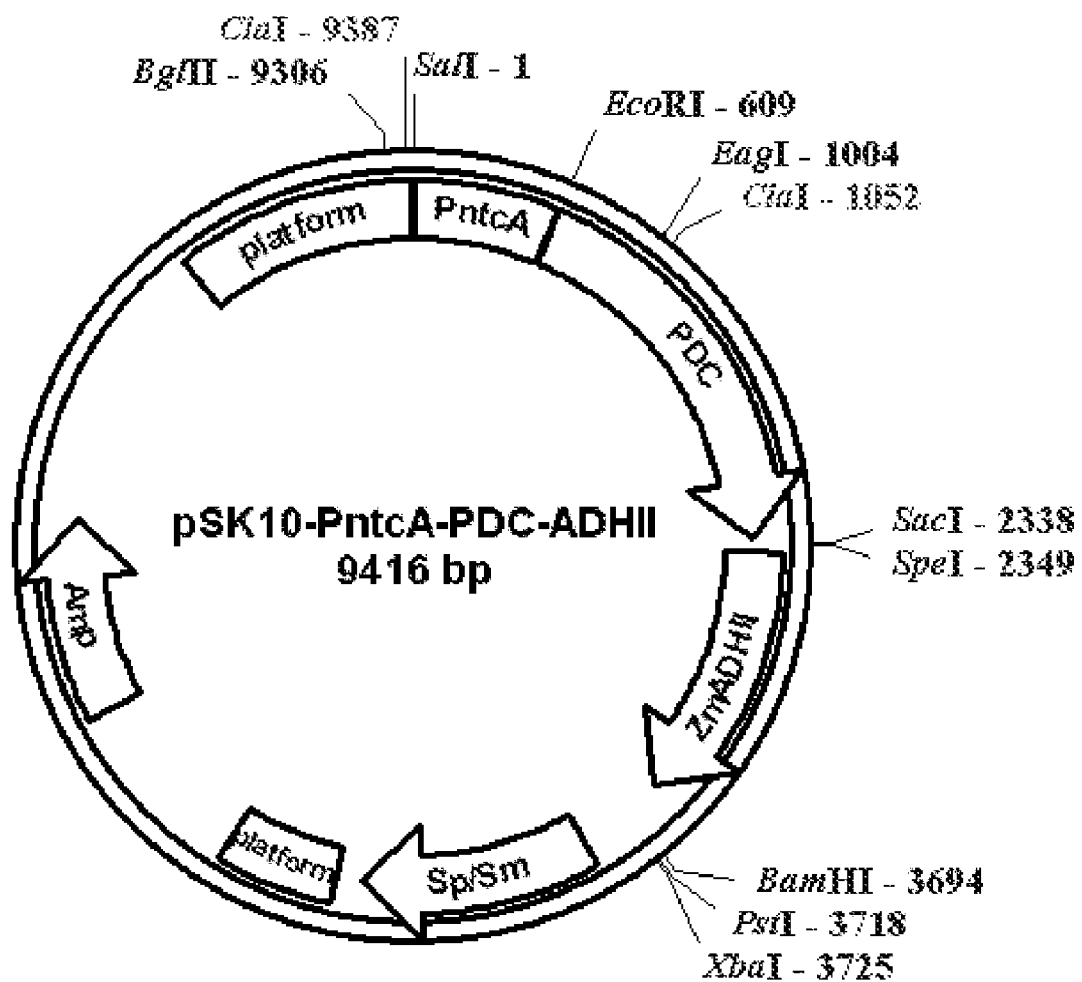
FIG. 6E is a schematic representation of the gene organization of the construct pSK10-PntcA-PDC-ADHII.

FIG. 6E presents a schematic diagram of pSK10-PntcA-PDC-ADHII.

Several pSK10 constructs with ZmPdc/ZmAdhI were obtained.

Figure 6F:
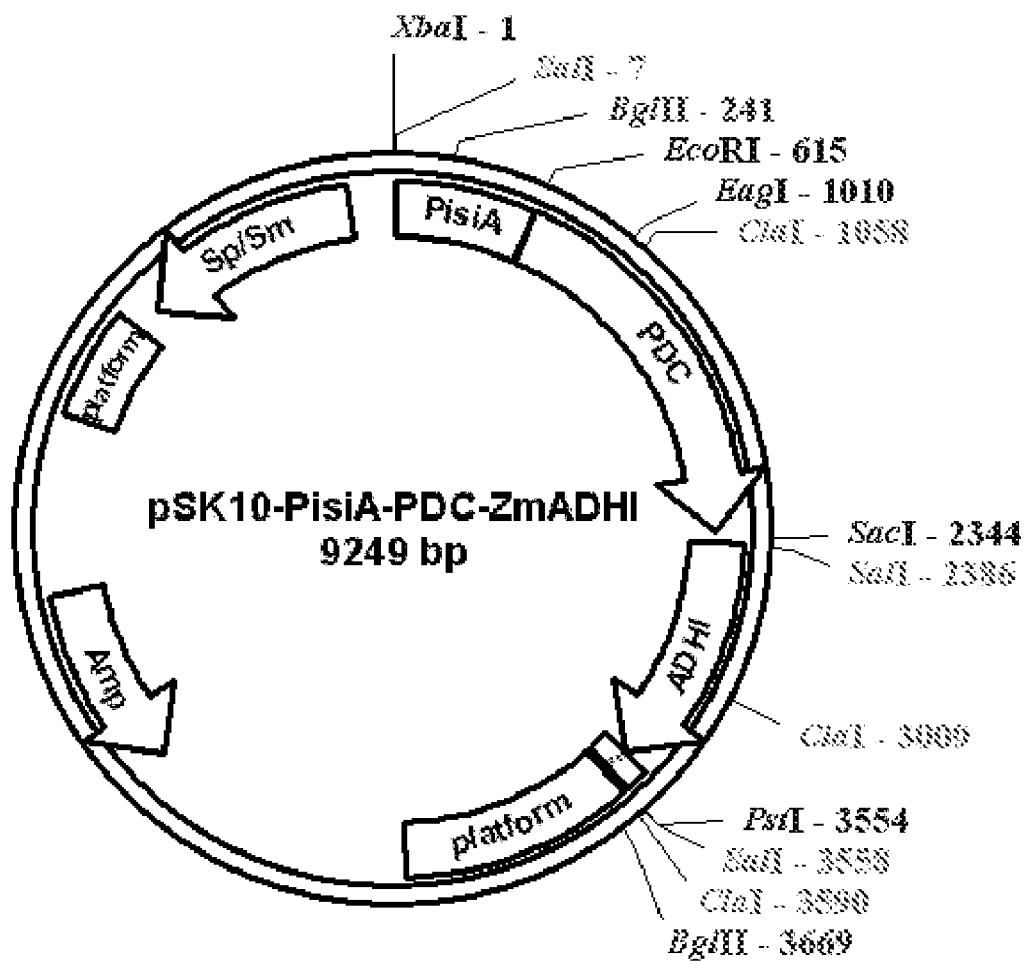
FIG. 6F is a schematic representation of the gene organization of the construct pSK10-PisiA-PDC-ADHI.

FIG. 6F presents a schematic diagram of pSK10-PisiA-PDC-ADHI.

Figure 6G:
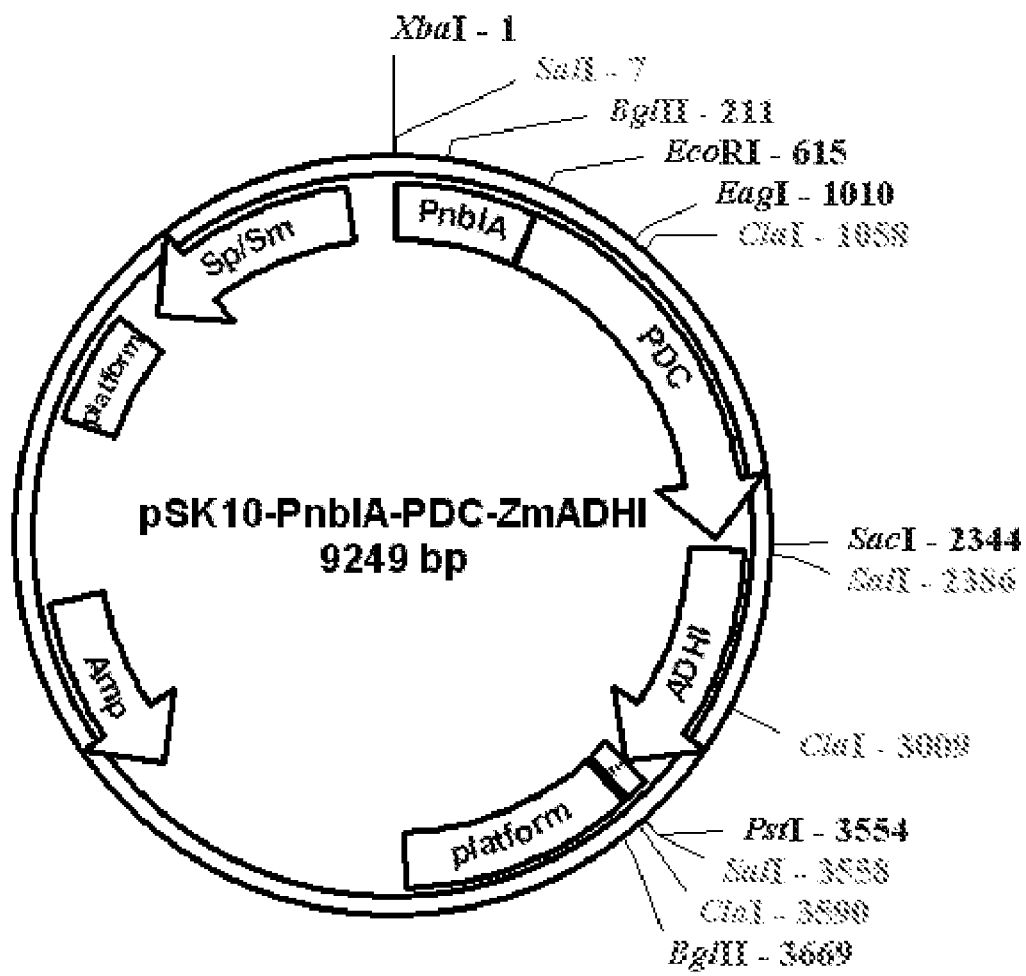
FIG. 6G is a schematic representation of the gene organization of the construct pSK10-PnblA-PDC-ADHI.

FIG. 6G presents a schematic diagram of pSK10-PnblA-PDC-ADHI.

Figure 6H:
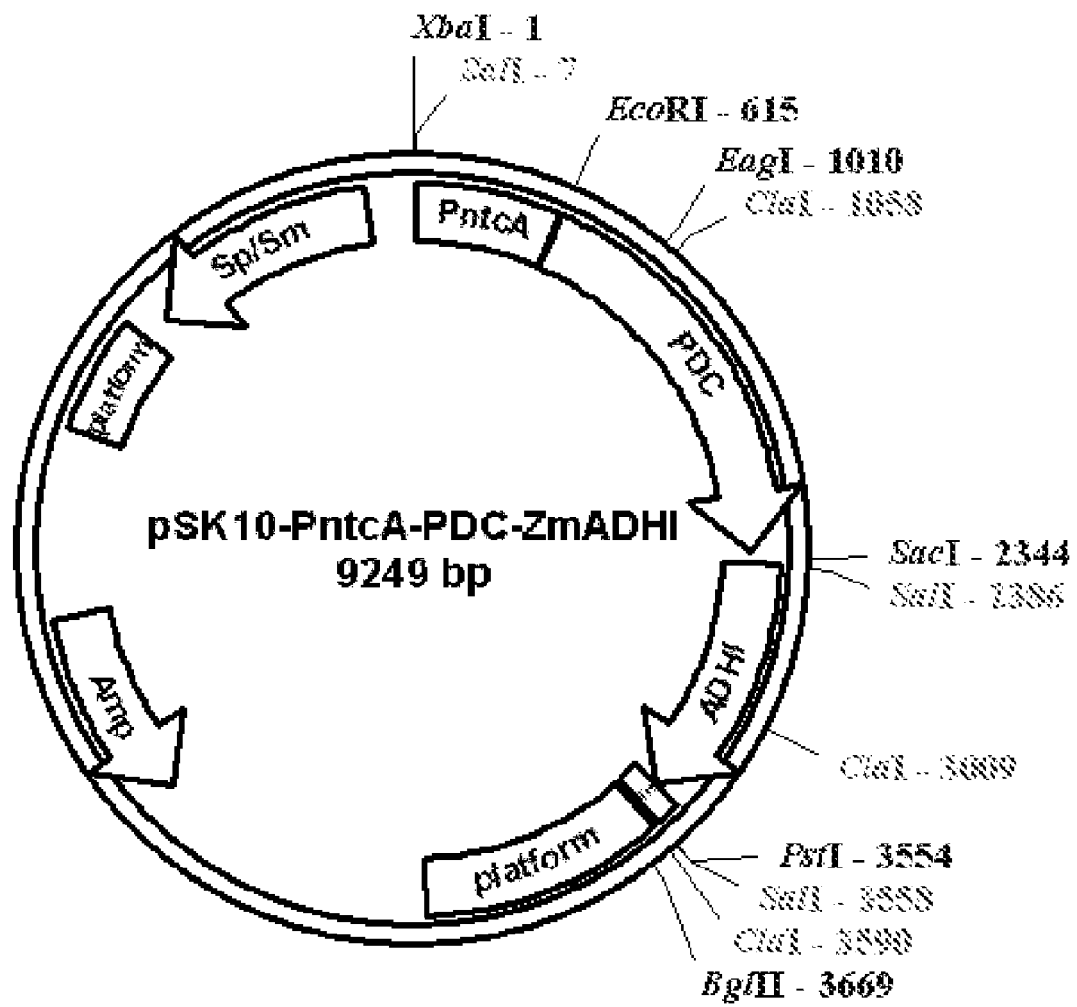
FIG. 6H is a schematic representation of the gene organization of the construct pSK10-PntcA-PDC-ADHI.

FIG. 6H presents a schematic diagram of pSK10-PntcA-PDC-ADHI.

Several pSK10 constructs with ZmPdc/SynAdh were obtained.

Figure 6I:
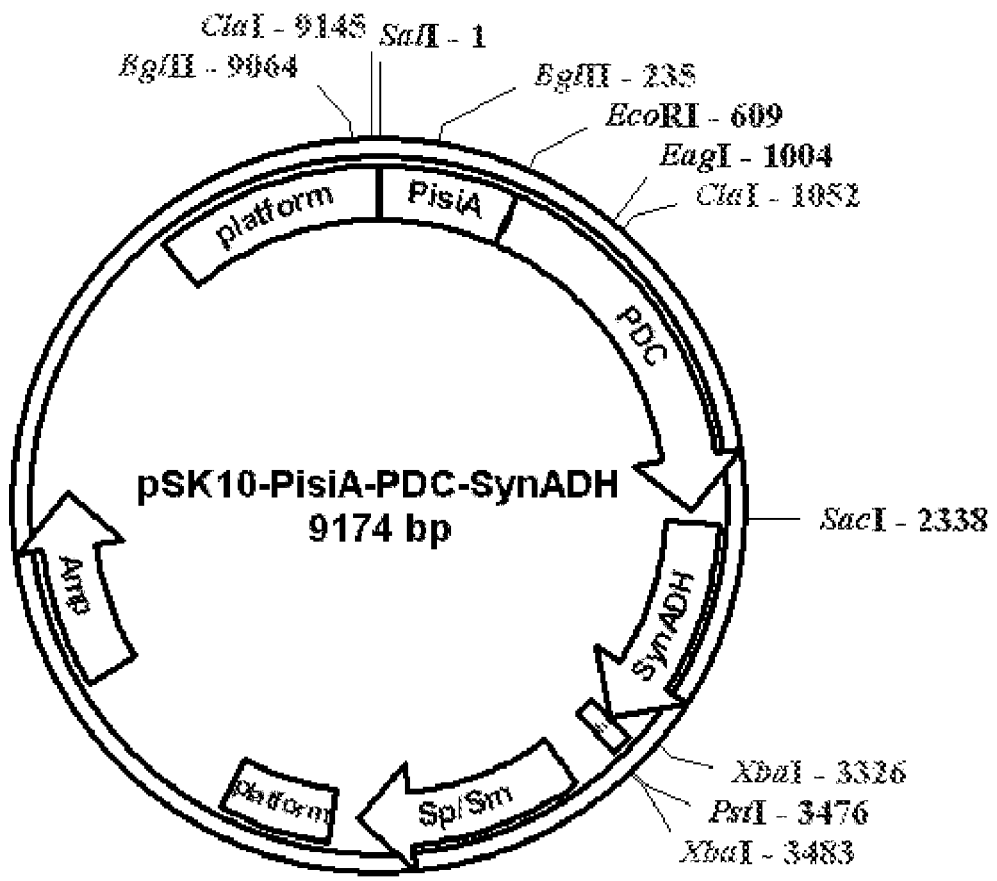
FIG. 6I is a schematic representation of the gene organization of the construct pSK10-PisiA-PDC-SynADH.

FIG. 6I presents a schematic diagram of pSK10-PisiA-PDC-SynADH.

Figure 6J:
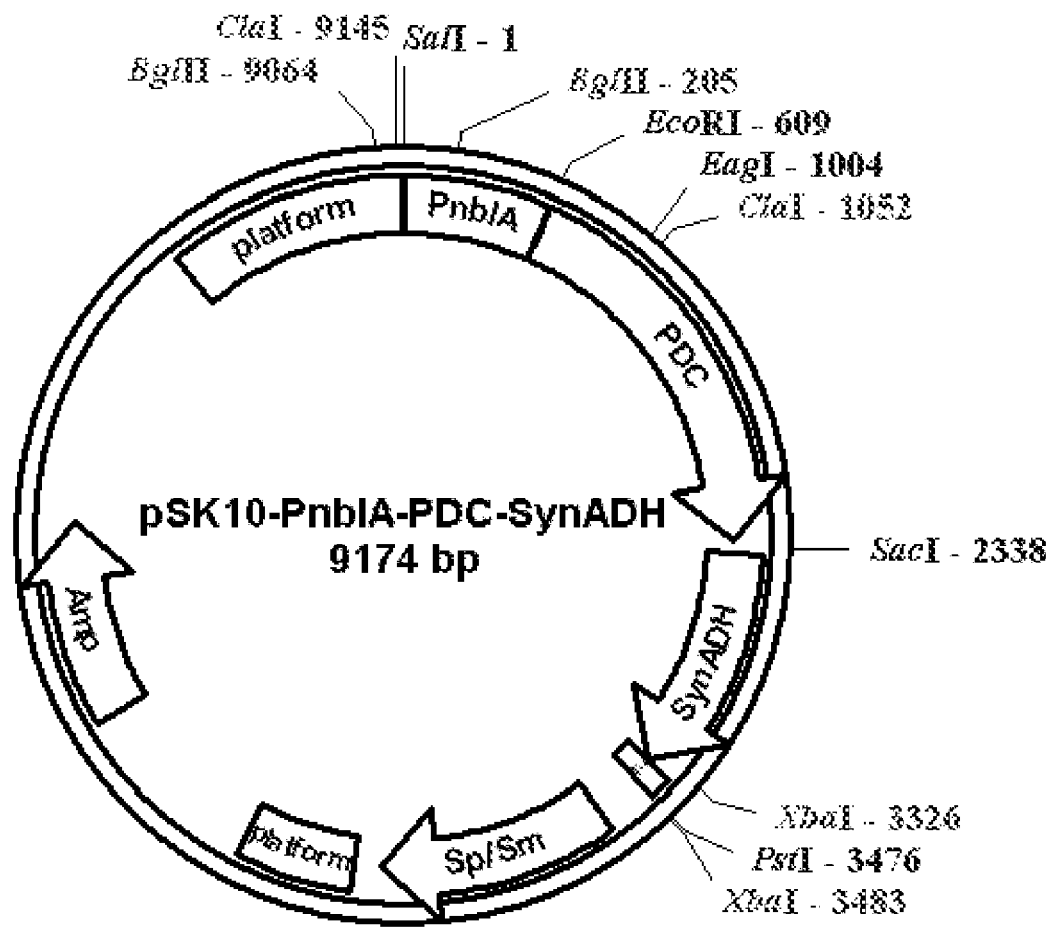
FIG. 6J is a schematic representation of the gene organization of the construct pSK10-PnblA-PDC-SynADH.

FIG. 6J presents a schematic diagram of pSK10-PnblA-PDC-SynADH.

Figure 6K:
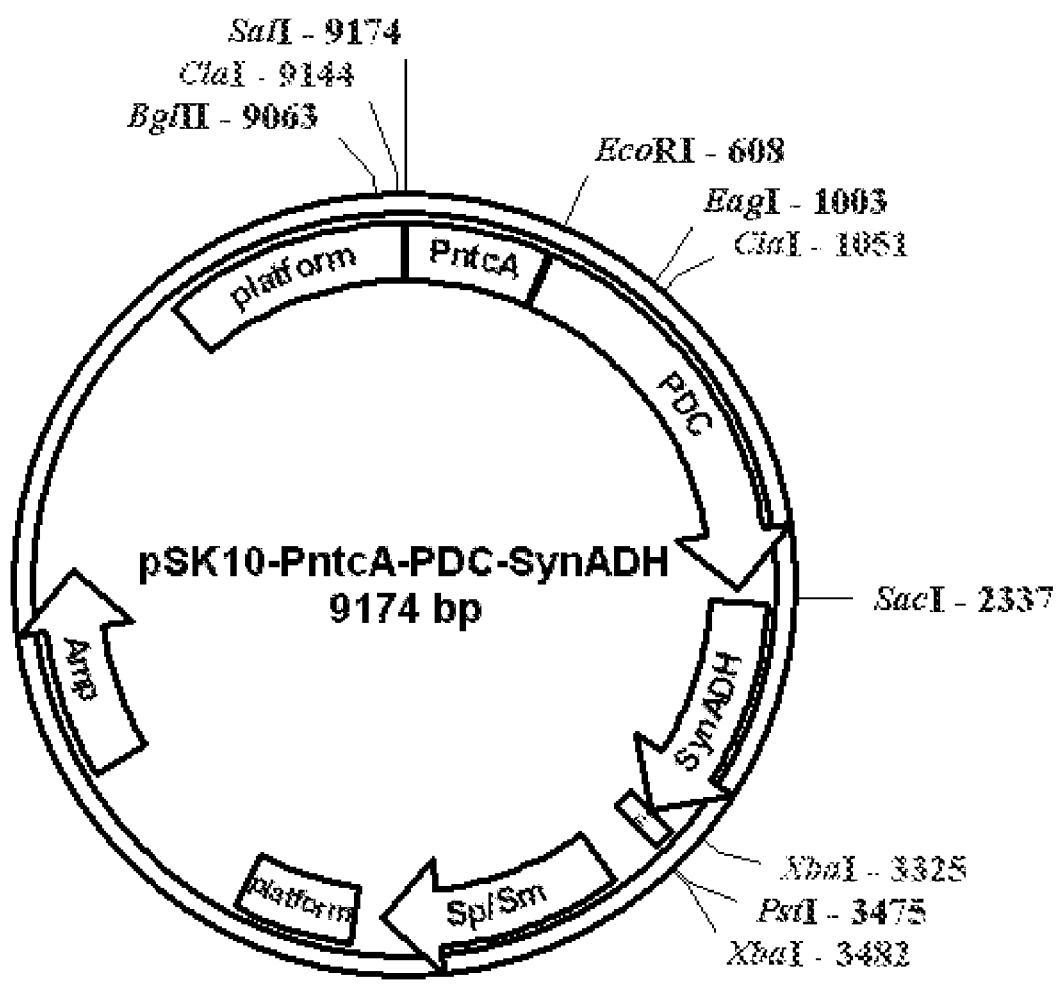
FIG. 6K is a schematic representation of the gene organization of the construct pSK10-PntcA-PDC-SynADH.

FIG. 6K presents a schematic diagram of pSK10-PntcA-PDC-SynADH.

Several pSK10 constructs with EcAdhE were obtained.

Figure 6L:
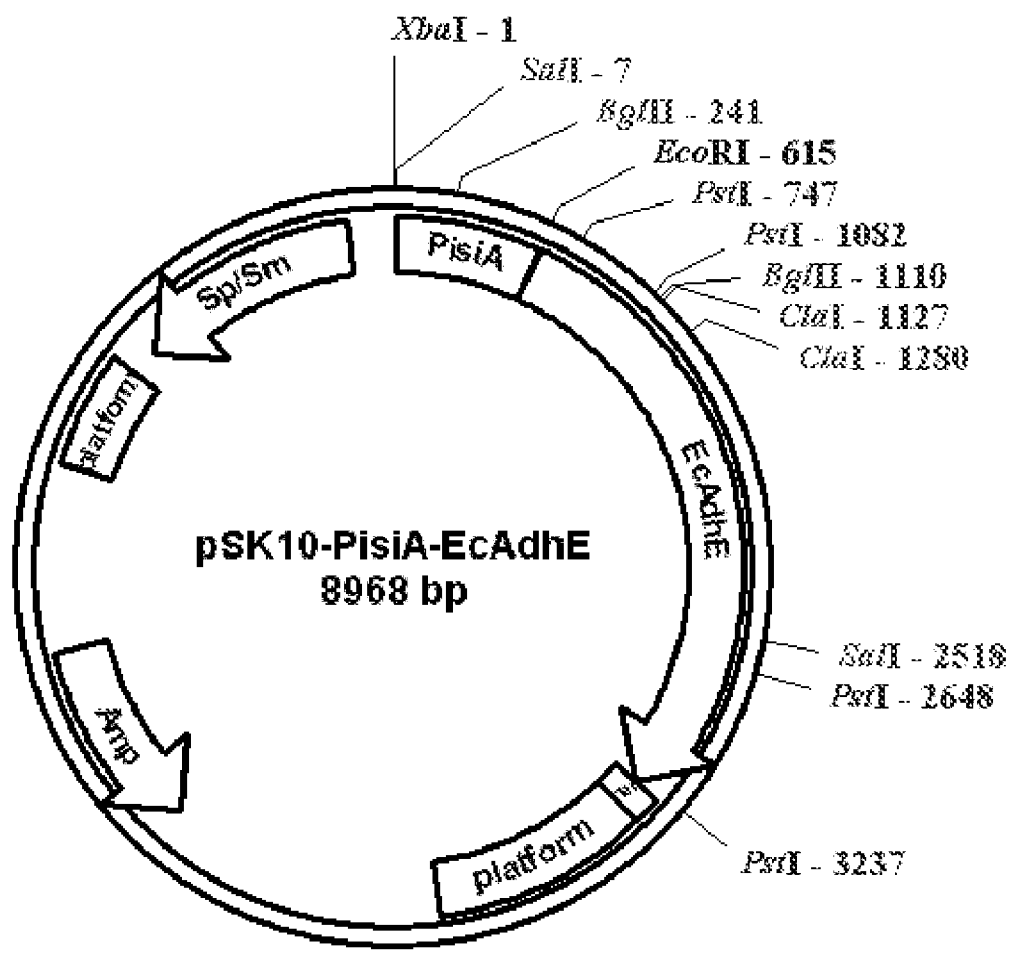
FIG. 6L is a schematic representation of the gene organization of the construct pSK10-PisiA-PDC-EcAdhE.

FIG. 6L presents a schematic diagram of pSK10-PisiA-PDC-EcAdhE.

Figure 6M:
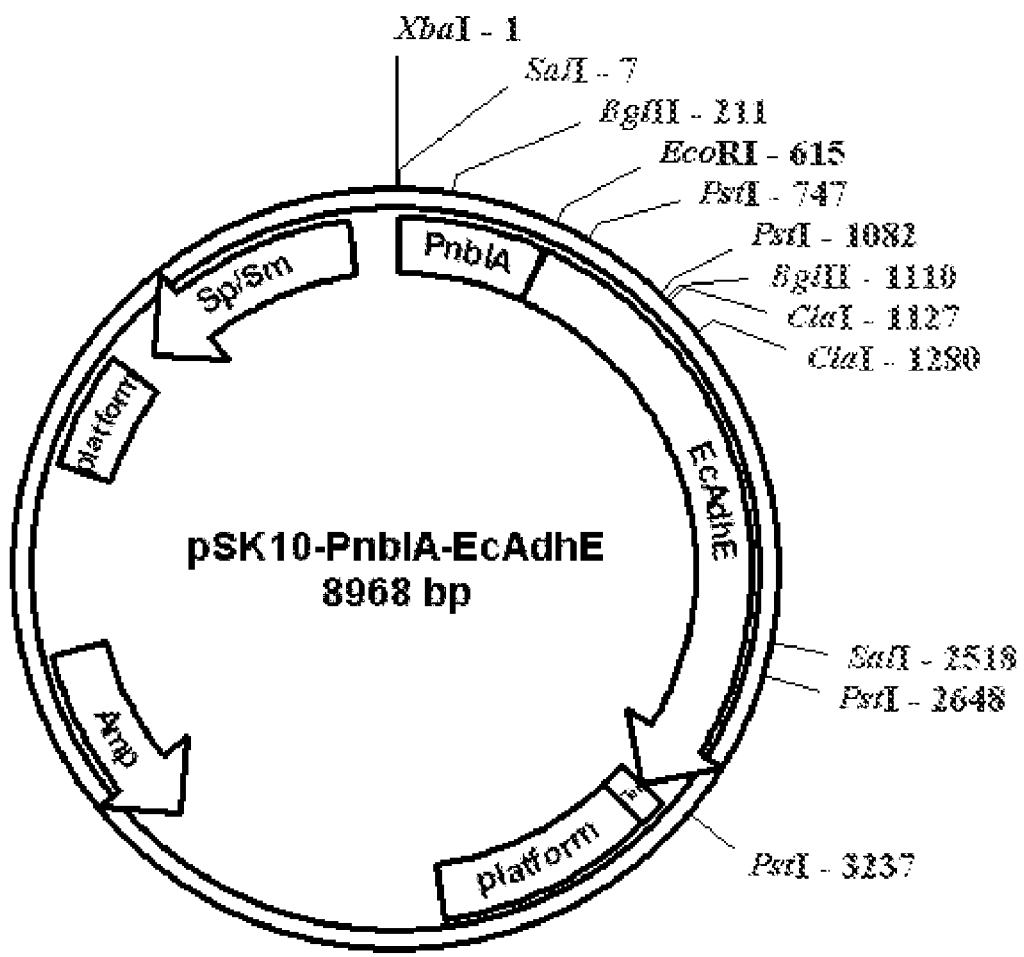
FIG. 6M is a schematic representation of the gene organization of the construct pSK10-PnblA-PDC-EcAdhE.

FIG. 6M presents a schematic diagram of pSK10-PnblA-PDC-EcAdhE.

Figure 6N:
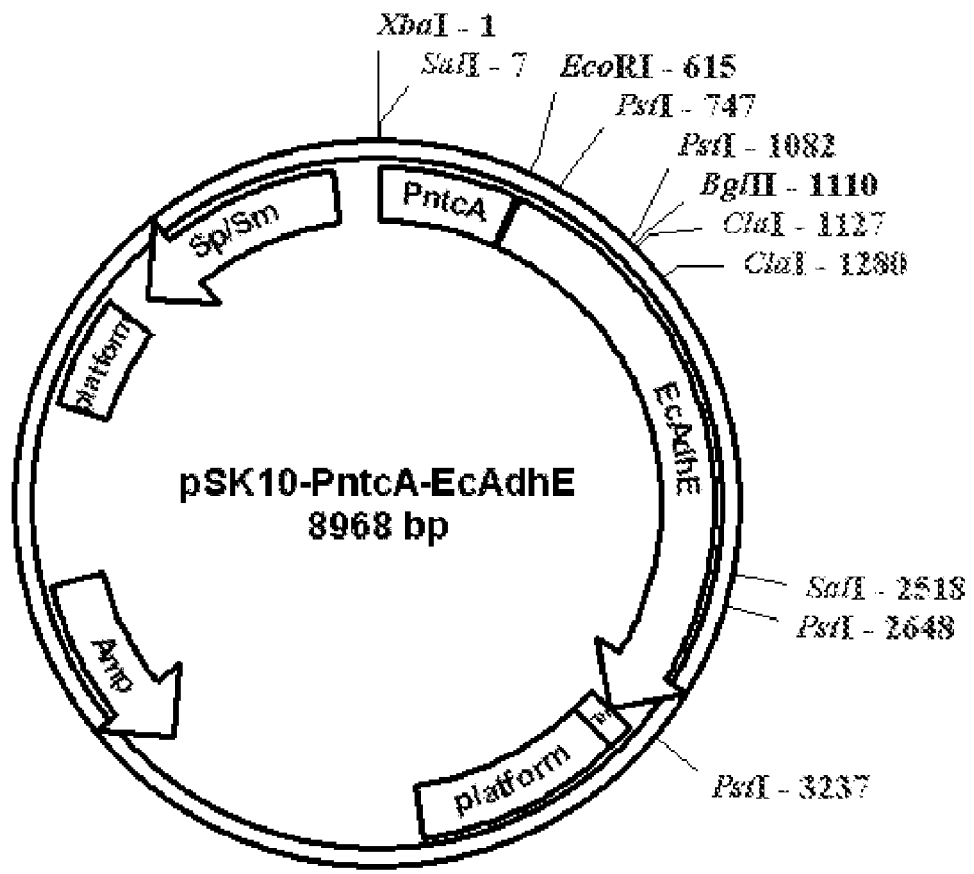
FIG. 6N is a schematic representation of the gene organization of the construct pSK10-PntcA-PDC-EcAdhE.
Figure 60:
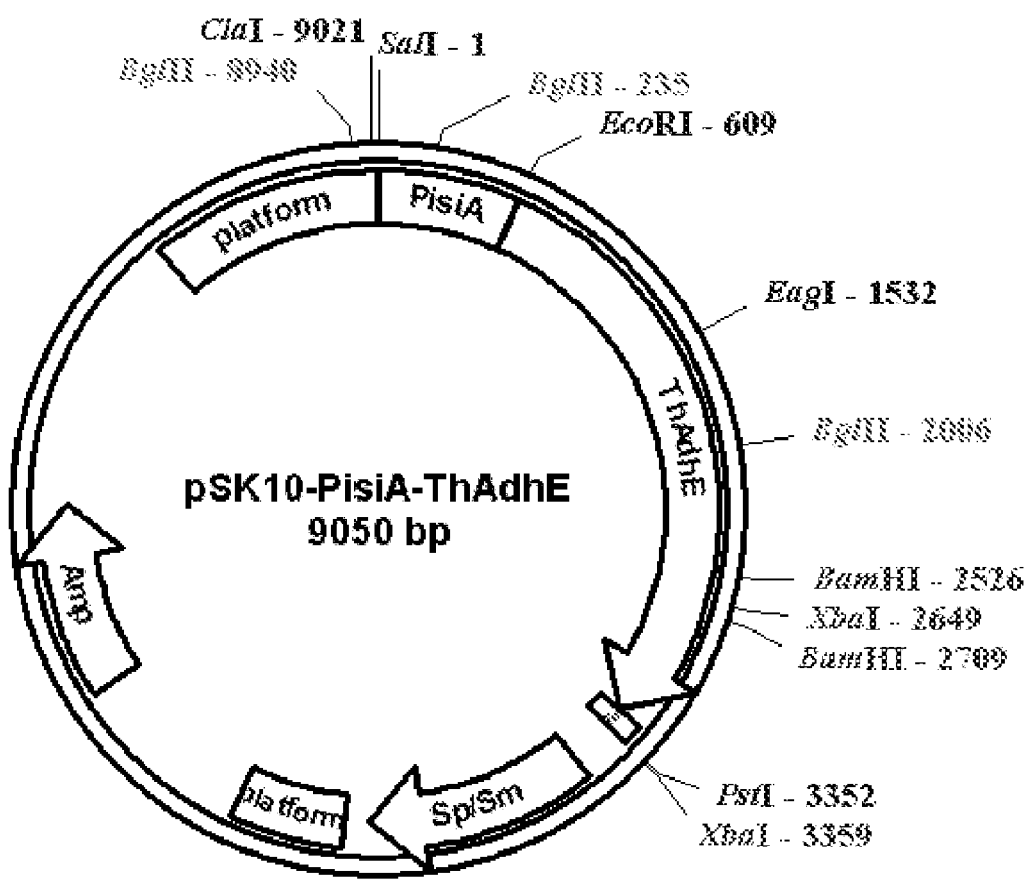

FIG. 6N presents a schematic diagram of pSK10-PntcA-PDC-EcAdhE.

Several pSK10 constructs with ThAdhE were obtained.

FIG. 6O presents a schematic diagram of pSK10-PisiA-PDC-ThAdhE.

Figure 6P:
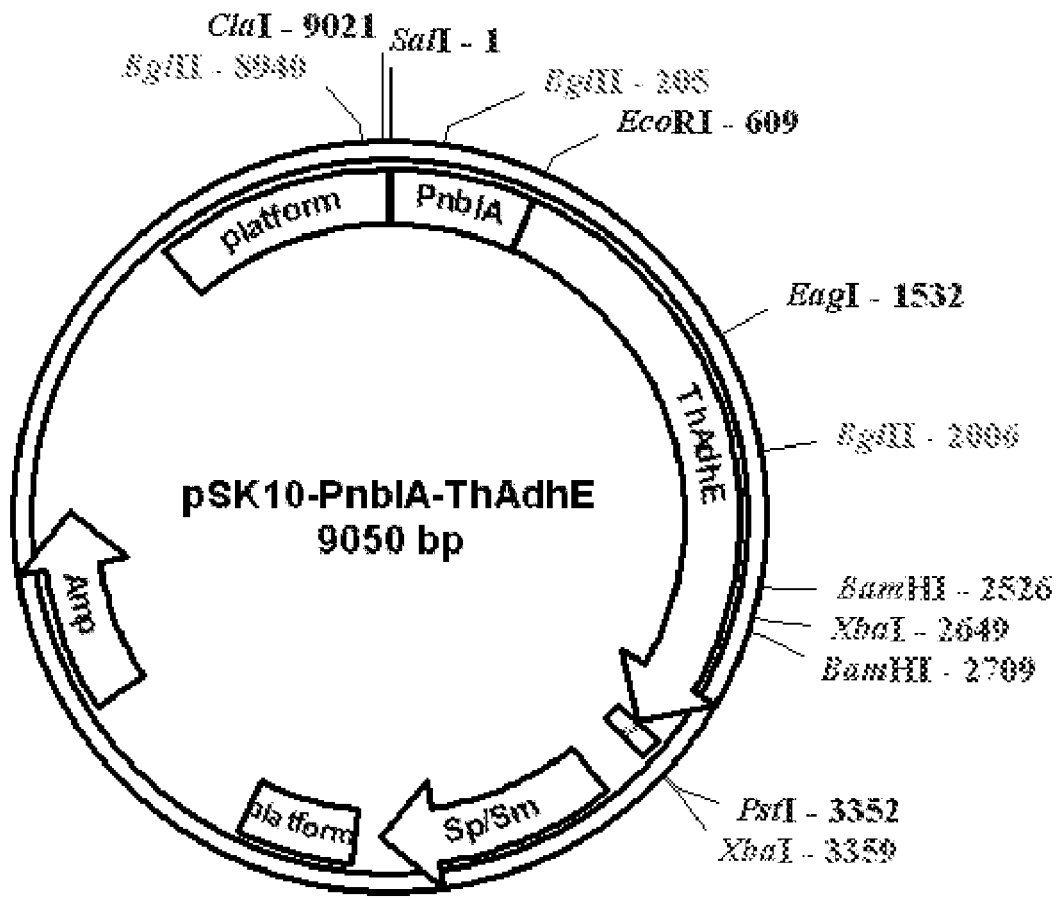
FIG. 6P is a schematic representation of the gene organization of the construct pSK10-PnblA-PDC-ThAdhE.

FIG. 6P presents a schematic diagram of pSK10-PnblA-PDC-ThAdhE.

Figure 6Q:
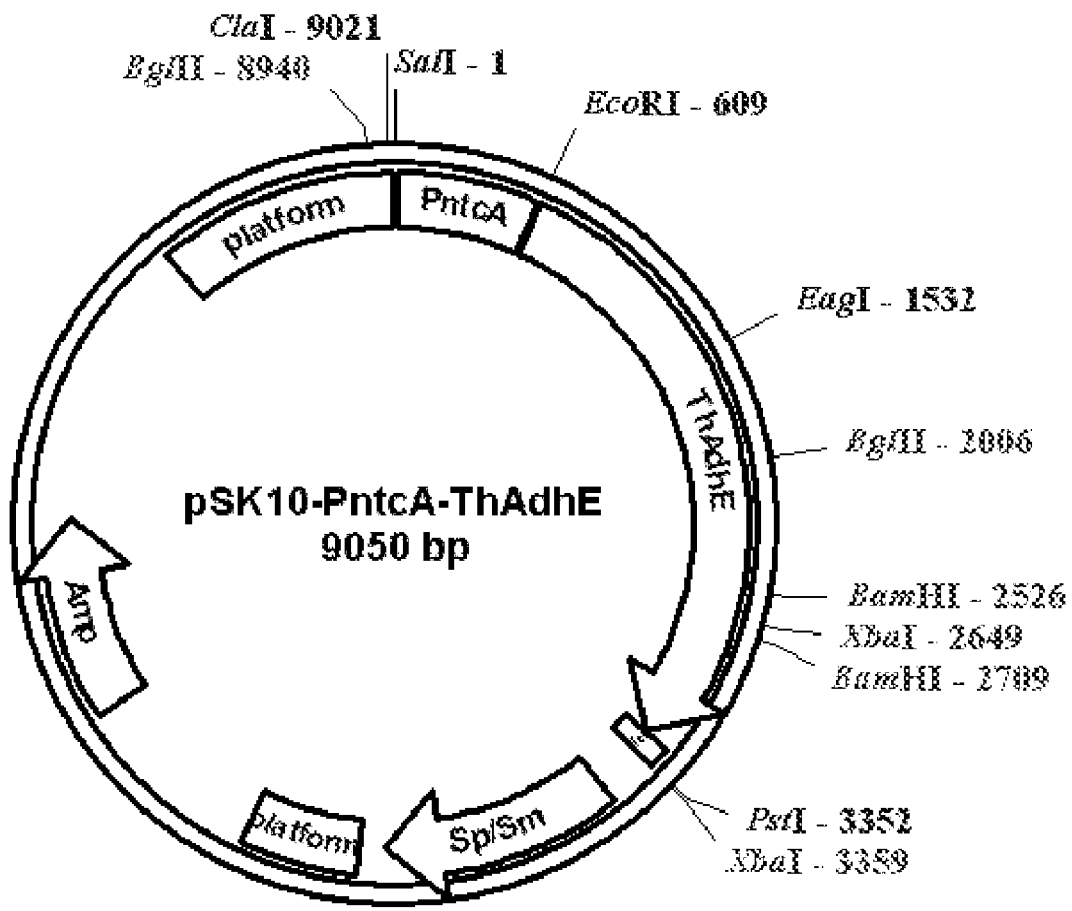
FIG. 6Q is a schematic representation of the gene organization of the construct pSK10-PntcA-PDC-ThAdhE.
Figure 6T:
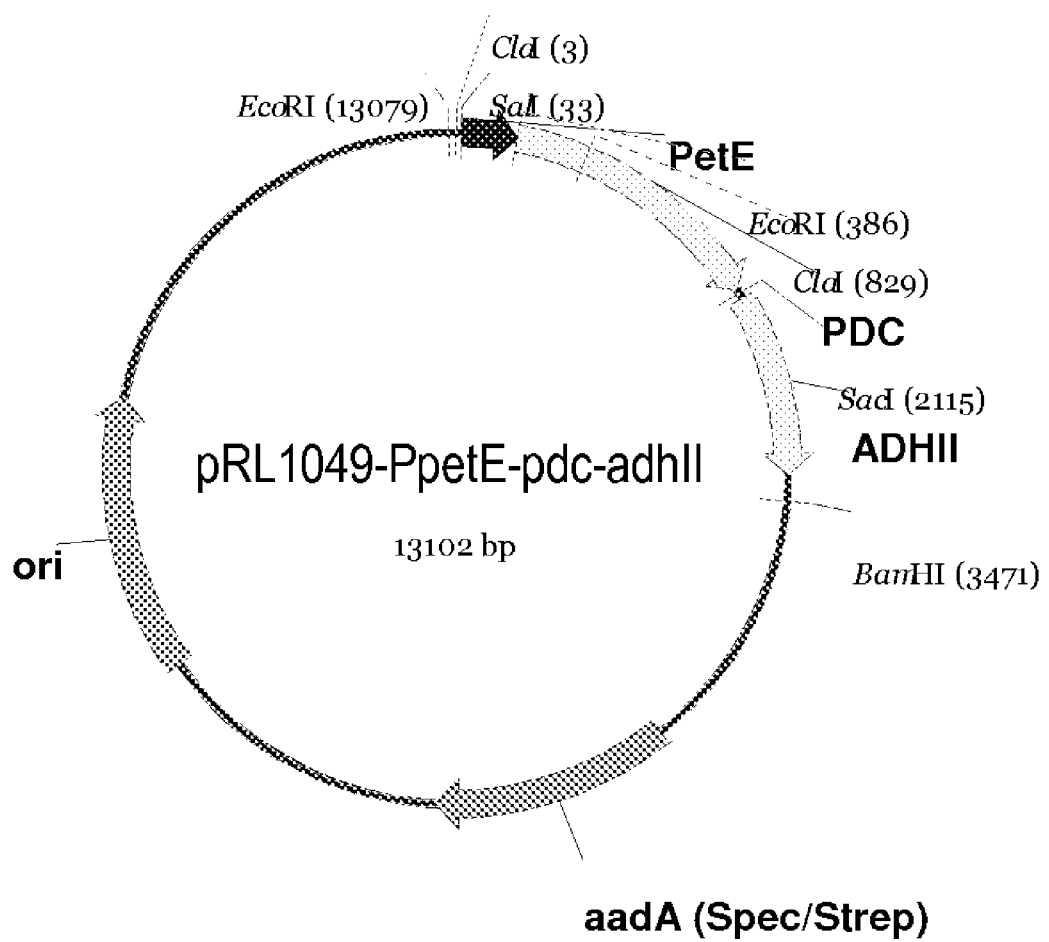
FIG. 6T presents the gene organization of plasmid pRL1049-PpetE-PDC-ADHII.
Figure 6V:
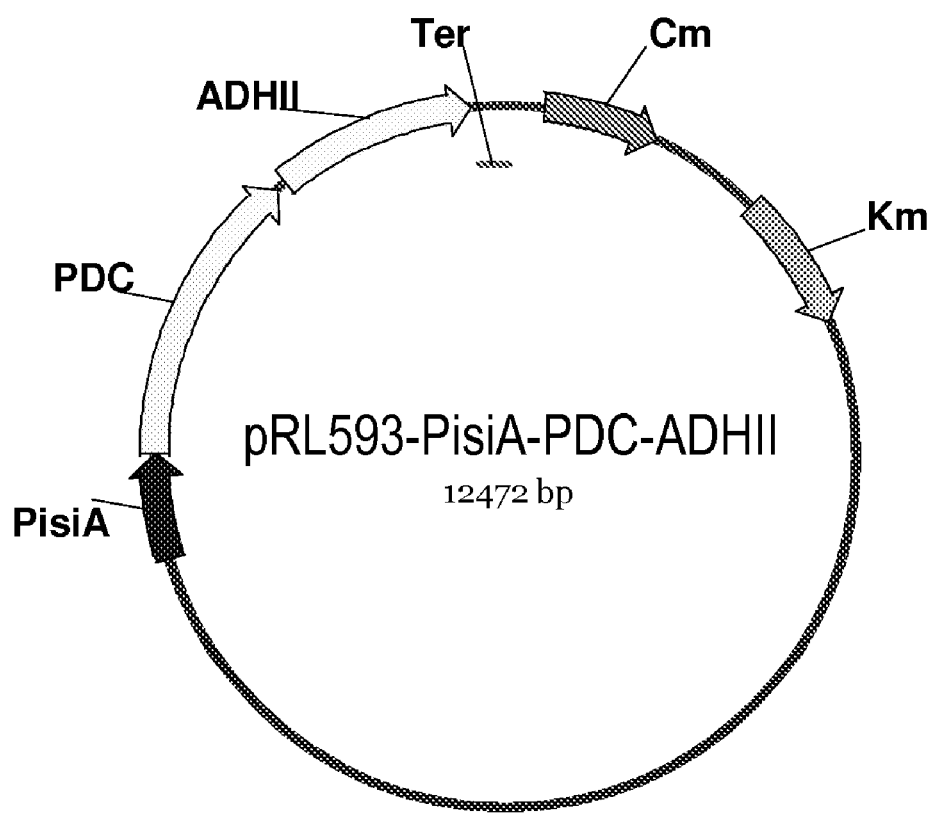
FIG. 6V depicts the gene organization of plasmid pRL593-PisiA-PDC-ADHII.
Figure 6X:
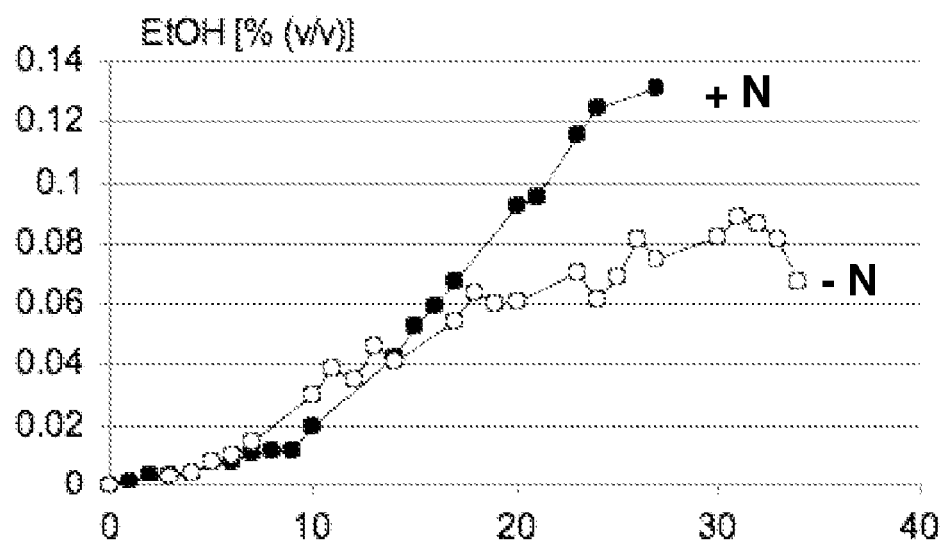
FIG. 6X is a graphic depiction of ethanol production rate in *Anabaena* PCC7120 harboring pRL593-PisiA-PDC-ADHII following induction by iron starvation was measured in BG11 medium (+N) and in medium lacking combined nitrogen (—N) in day (12 h)/night (12 h) cycle.
Figure 6Y:
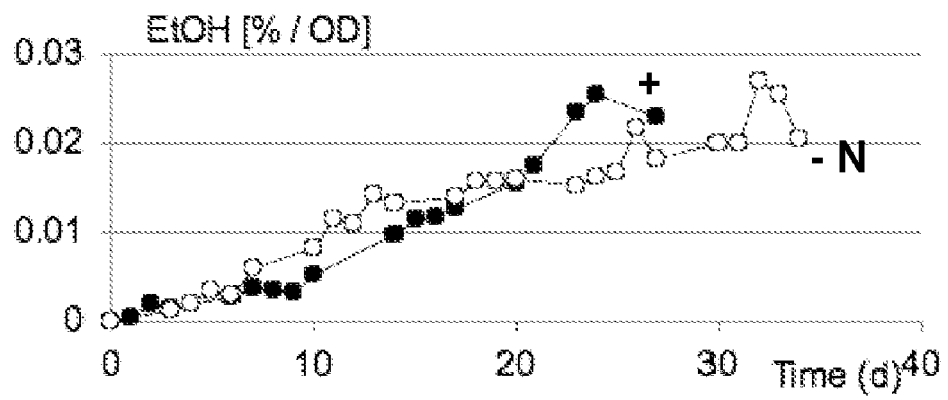
FIG. 6Y is a graphic depiction of ethanol production rate in *Anabaena* PCC7120 harboring pRL593-PisiA-PDC-ADHII following induction by iron starvation was measured in BG11 medium (+N) and in medium lacking combined nitrogen (—N) in day (12 h)/night (12 h) cycle, wherein values are normalized for optical density.
Figure 7A:
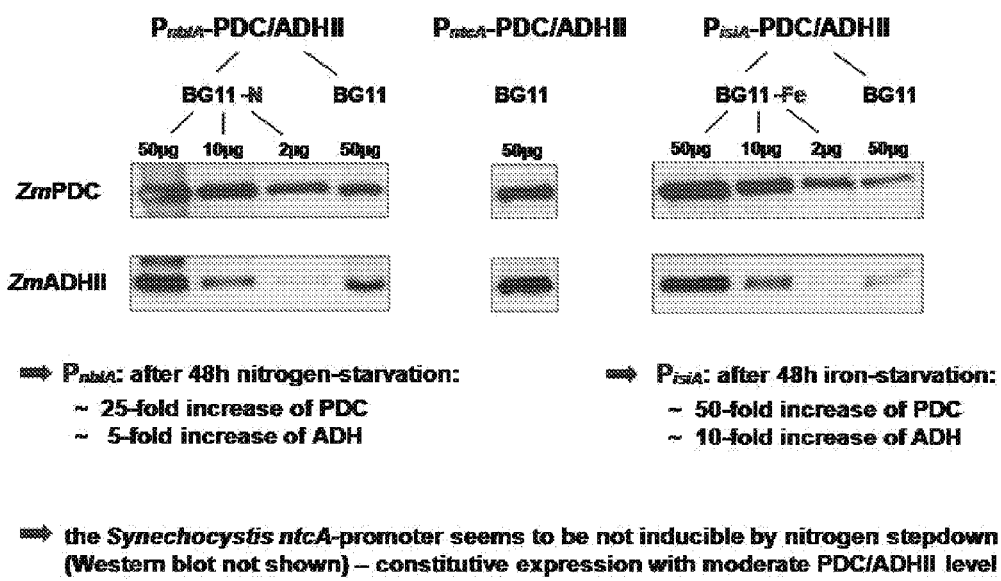
FIG. 7A is a photographic depiction of a Western Blot that was used to quantify the induction rate of the used promoters by determining the relative abundance of the *Z. mobilis* ADHII and PDC enzymes expressed in *Synechocystis* with and without nutrient starvation.
Figure 7B:
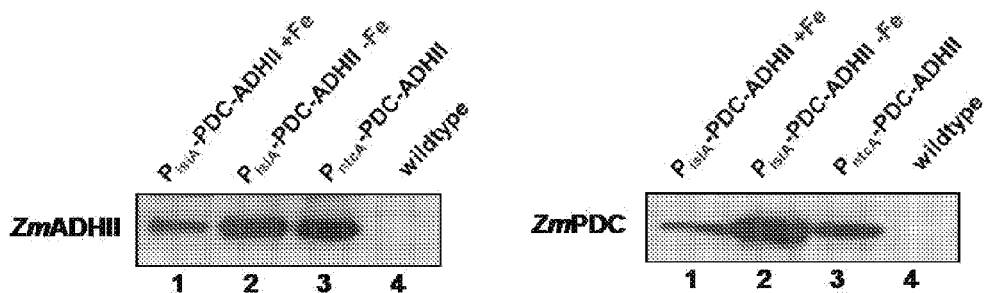
FIG. 7B is a photograph of a Western Blot that was used to determine the relative abundance of the Z. mobilis ADHII and PDC enzymes expressed in Synechocystis with and without nutrient starvation.

FIG. 6Q presents a schematic diagram of pSK10-PntcA-PDC-ThAdhE.

Figure 8A:
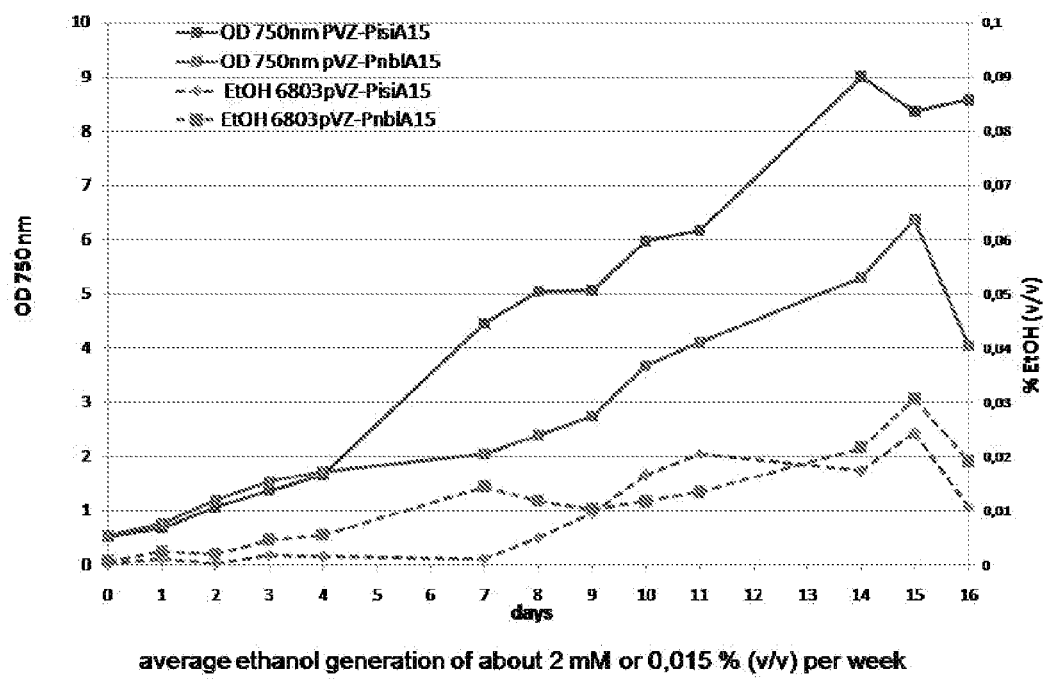
FIG. 8A is a graphic representation of ethanol production rates of genetically modified photoautotrophic host cells containing Zymomonas mobilis PDC and ADHII as a second genetic modification.
Figure 8B:
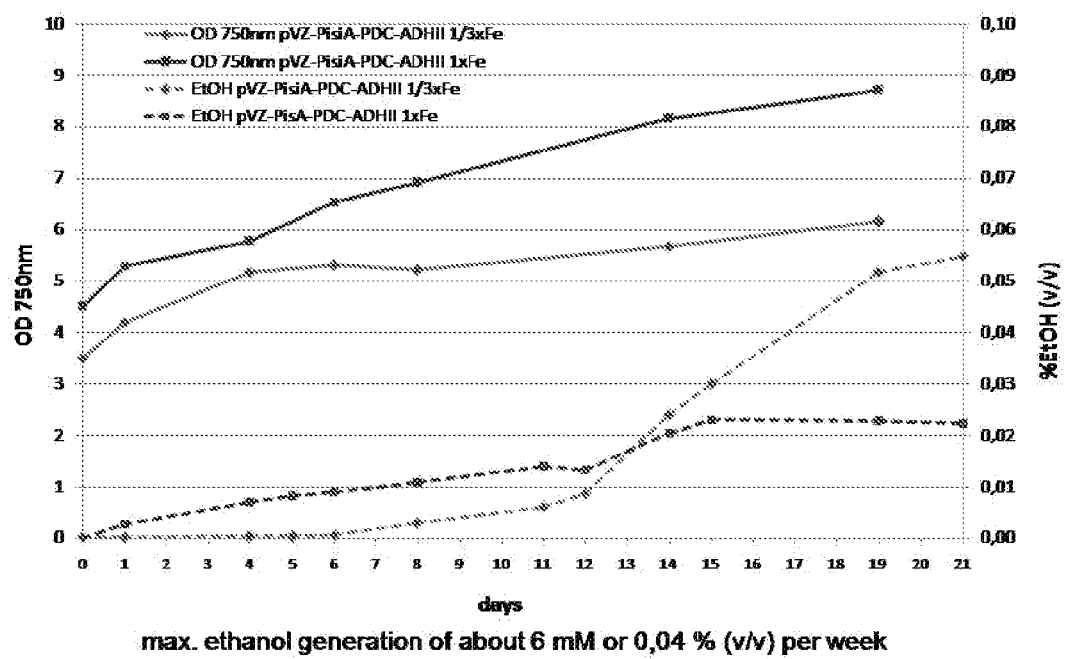
FIG. 8B is a graphic representation of ethanol production in Synechocystis pVZ mutants having ZmPdC and ZmADHII under the control of isiA, and iron-dependent promoter.
Figure 8C:
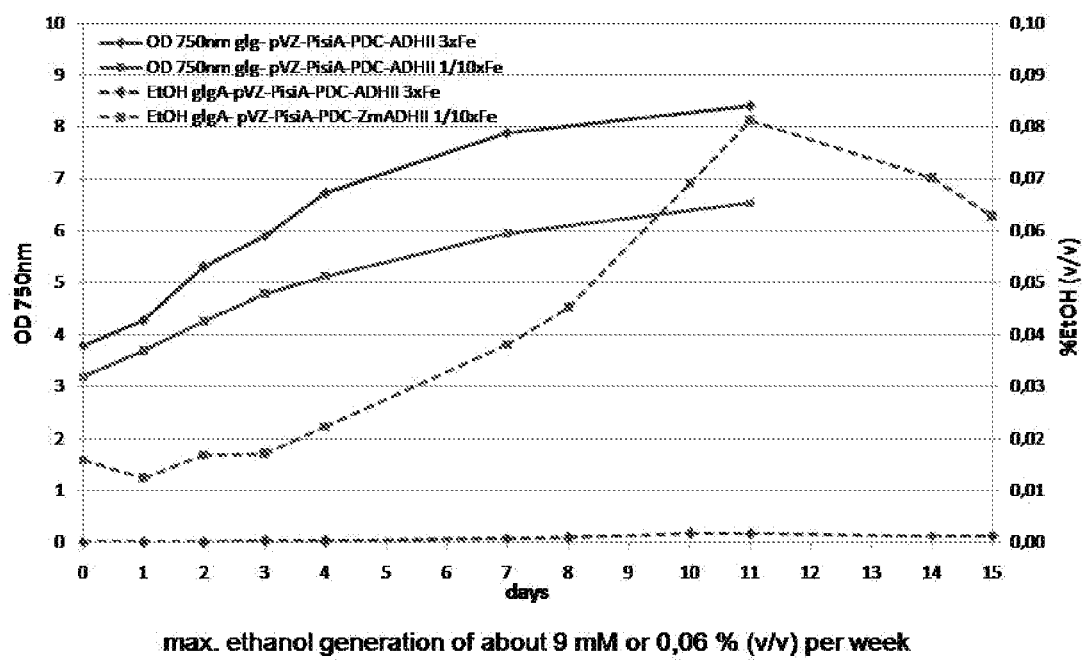
FIG. 8C is a graphic presentation of ethanol production in glycogen deficient Synechocystis pVZ mutants having ZmPdC and ZmADHII under the control of isiA, an iron-dependent promoter.

P.2 Ethanol Production Rates of Genetically Modified Photoautotrophic Host Cells Containing *Zymomonas Mobilis* PDC and ADHII as a Second Genetic Modification Ethanol production rates and $OD_{750\ nm}$ values were determined as described above and are shown in FIGS. 8A, 8B and 8C.

The concentration of ethanol in the growth medium was determined using a standard UV-ethanol assay purchased from R-Biopharm AG. In particular the assay is based on the UV detection of NADH at 340 nm. It is based on the detection of generated NADH according to the following enzymatic reaction catalyzed by alcohol dehydrogenase and aldehyde dehydrogenase:

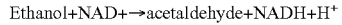

Ethanol+NAD+→acetaldehyde+NADH+H⁺

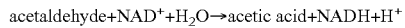

acetaldehyde+NAD⁺+H₂O→acetic acid+NADH+H⁺

Figure 8D:
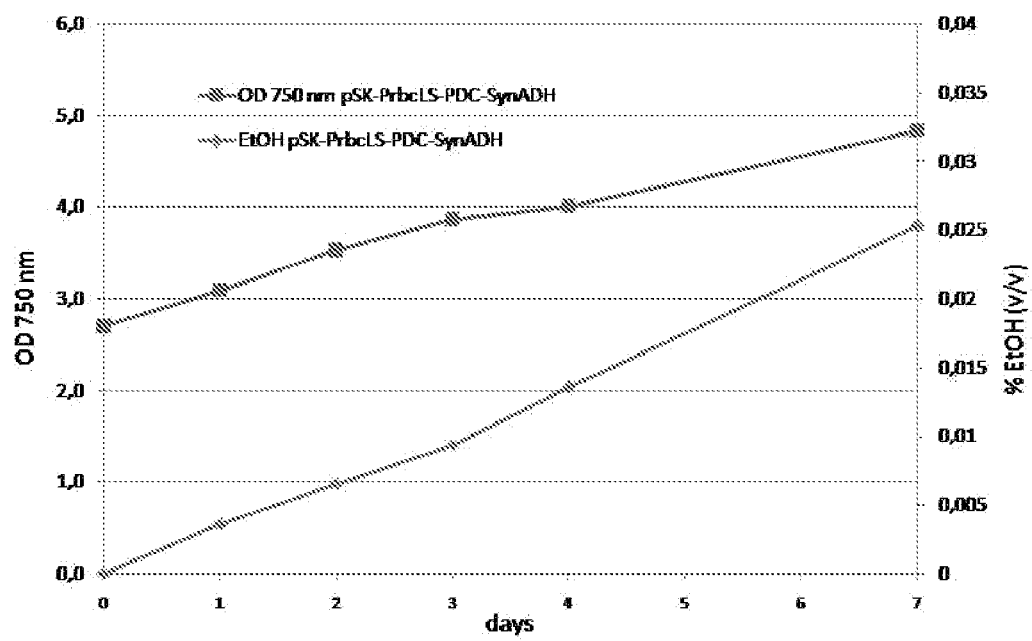
FIG. 8D is a graphic presentation of ethanol production in Synechocystis pVZ mutants having ZmPdC and SynADH under the control of rbcLS, a constitutive promoter.

P.3 Ethanol Production Rates of Genetically Modified Photoautotrophic Host Cells Containing *Zymomonas Mobilis* Pdc and *Synechocystis* Adh as a Second Genetic Modification Further the ethanol production rates of *Synechocystis* cultures transformed with *Zymomonas mobilis* Pdc and an endogenous *Synechocystis* Adh were also determined as described above. Results are presented in FIG. 8D.

P.4 Ethanol Production Rates of Genetically Modified Photoautotrophic Host Cells Containing *Zymomonas Mobilis* Pdc and Various Wildtype as Well as Mutant AdhE Enzymes as a Second Genetic Modification Background:

The use of so called AdhE-type alcohol dehydrogenases (Adh), which contain two enzymatic activities, namely a CoA-dependent aldehyde dehydrogenase and an iron-dependent alcohol dehydrogenase activity would allow the production of ethanol in genetically modified cyanobacteria without requirement of a pyruvate decarboxylase (Pdc). The substrate for this dual enzyme is acetylCoA that is converted via two steps (by forming acetaldehyde as transient intermediate) into ethanol. AcetylCoA is similar to pyruvate a central metabolite in the cell which might be a well convertible precursor for the ethanol production, too. Interestingly, besides the group of enterobacteria where an AdhE is very common, also some cyanobacteria contain such an AdhE enzyme, e.g. *Thermosynechococcus elongatus* BP-1, *Microcystis aeruginosa* and some *Aponinum* species.

Therefore, besides the approach to use the Pdc together with a conventional Adh, the over-expression of AdhE could also be convenient for ethanol production in cyanobacteria. For this purpose, the well characterized AdhE from *E. coli* and the corresponding enzyme from *Thermosynechococcus* were chosen.

Mutant Generation:

Several plasmids to over-express both AdhE's were constructed and respective mutants in *Synechocystis* 6803 were created (see above described plasmid maps). Furthermore specific activity-enhancing point-mutations were created in the adhE-gene from *E. coli* K12 wild-type strain, which lead to specific amino acid exchanges.

The AdhEs were over-expressed on a self-replicating extra-chromosomal plasmid, pVZ321b, under control of the copper-dependent petJ-promoter. Mutants were selected on streptomycin plates and grown in BG11 medium containing the appropriate antibiotics (kanamycin 100 mg/l and streptomycin 10 mg/l).

The following pVZ321b mutants were generated:
6803 pVZ321 b-PpetJ-EcAdhE (wt)
6803 pVZ321 b-PpetJ-EcAdhE (E568K, exchange from glutamic acid at position 568 to lysine)
6803 pVZ321 b-PpetJ-EcAdhE (A267T/E568K, exchange of alanine at position 267 to threonine and in addition E568K)
6803 pVZ321 b-PpetJ-ThAdhE (AdhE from *Thermosynechococcus*)

Growth Conditions:

Mutants and *Synechocystis* wild-type strains were grown at 28° C., under constant light (50 μE m−2 s−1) on a shaker (100 rpm). The initial $OD_{750}$ was about 3 in a total culture volume of 50 ml in a 100 ml Erlenmeyer flask. The ethanol concentration was determined as described.

Figure 9:
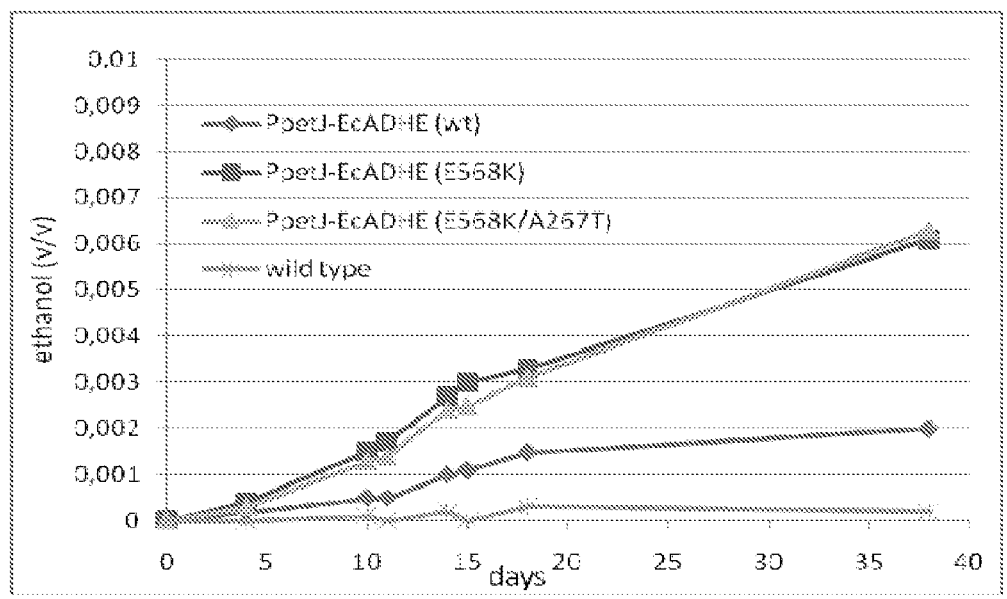
FIG. 9 is a graphic presentation of ethanol production in Synechocystis expressing different 3 variants of E. coli AdhE compared to wild-type.

Results are presented in FIG. 9, wherein ethanol production of *Synechocystis* mutants that express AdhE of *E. coli* (3 different variants) are compared to *Synechocystis* wild type.

Results and Conclusions:

Exemplarily shown are ethanol production rates of the AdhEs of *E. coli*. Compared to the wild type over the cultivation time of about 5 weeks significant amounts of ethanol were produced by the mutants. All over-expression mutants showed a significant ethanol production. The exchange from glutamic acid at position 568 to lysine (E568K), which shall reduce the oxygen sensitivity seems to enhance the efficiency of the *E. coli* AdhE (EcAdhE in *Synechocystis* compared to the *E. coli* wild-type enzyme. The further exchange of alanine at position 267 to threonine (A267T) did not lead to an additional improvement of the first point mutation (E568K), although it is might increase the acetaldehyde dehydrogenase activity of the *E. coli* enzyme. But for both modified EcAdhE variants an about 3-fold increase in ethanol accumulation was observed. Therefore, it is possible to improve the AdhE enzyme by site-directed mutations in order to reach better production rates in cyanobacteria.

*Synechocystis* mutants that express the cyanobacterial thermophilic AdhE (ThAdhE) from *Thermosynechococcus* show a similar ethanol production rate to the mutants, which express the improved variants of the EcAdhE (data not shown). Thus, if this enzyme can be optimized in the same way, it might be even better than the *E. coli* enzyme. In general the application of AdhE-type alcohol dehydrogenases to produce ethanol in cyanobacteria is possible. The potential to improve this kind of enzymes as shown for the *E. coli* enzyme may allow for a large scale application for future ethanol production processes.

P.5 Characterization of Genetically Modified Photoautotrophic Host Cells Containing *Zymomonas Mobilis* Pdc and Different Adh Enzymes as a Second Genetic Modification Background:

The introduction of a pyruvate decarboxylase (Pdc) and an alcohol dehydrogenase (Adh) into cyanobacteria enables a light driven production of ethanol in these phototrophic bacteria by directing carbon fixed via photosynthesis into ethanol production. The substrate for the Pdc enzyme is pyruvate that is converted by decarboxylation into acetaldehyde and $CO_2$. The generated acetaldehyde is then converted by an Adh enzyme into the end-product ethanol.

In contrast to the Pdc almost all organisms contain Adhs leading a huge number of Adh enzymes with quite different characteristics. Interestingly, in *Zymomonas mobilis* two different Adhs are present, which are not related to each other and originate from different ancestors. The AdhI from *Zymomonas mobilis* is a so-called Zn-dependent, oxygen insensitive alcohol dehydrogenase, whereas the AdhII is Fe-dependent and oxygen-sensitive. Both are quite effective with high affinities for their substrates, acetaldehyde and NADH and outstanding due to their high maximum velocities. Therefore both Adhs from *Zymomonas* seem to be well suited, however the AdhI exhibits substrate inhibition at elevated ethanol concentrations and the AdhII might be partially inactive in cyanobacteria, since they produce large amounts of oxygen by photosynthesis.

Therefore three different Adhs were analyzed for their suitability for the ethanol production in cyanobacteria. Besides the well characterized *Zymomonas* Adhs, a Zn-dependent Adh from *Synechocystis* PCC6803 (SynAdh) was chosen, since this enzyme should be also oxygen-insensitive and therefore active in cyanobacteria.

Mutant Generation:

Several plasmids to overexpress all three Adhs together with the Pdc from *Zymomonas mobilis* (Zm) were constructed and the respective mutants were created in *Synechocystis* 6803 (see above described plasmid maps).

To over-express each Pdc/Adh combination a self-replicating extra-chromosomal plasmid, the pVZ321b, was used on which the regarding pdc/adh-genes are expressed under control of the copper-dependent petJ-promoter. Mutants were selected on streptomycin plates and grown in BG11 medium containing the appropriate antibiotics (kanamycin 100 mg/l and streptomycin 10 mg/l).

The following pVZ321b mutants were generated:
6803 pVZ321 b-PpetJ-ZmPdc/ZmAdhI
6803 pVZ321b-PpetJ-ZmPdc/ZmAdhII
6803 pVZ321 b-PpetJ-ZmPdc/SynAdh Growth Conditions:

Mutants were grown in BG11 medium without copper at 28° C. and constant light conditions (100 µE m−2 s−1). The initial $OD_{750}$ was about 1.5 in a total culture volume of about 150 ml in a culture vessel aerated with $CO_2$-enriched air (0.5% $CO_2$). The ethanol concentration was determined as described above and the growth was determined by measurements of the optical density at 750 nm. At the 11th day the cultures were diluted by addition of 1 volume of new BG11 medium without copper.

Figure 10A:
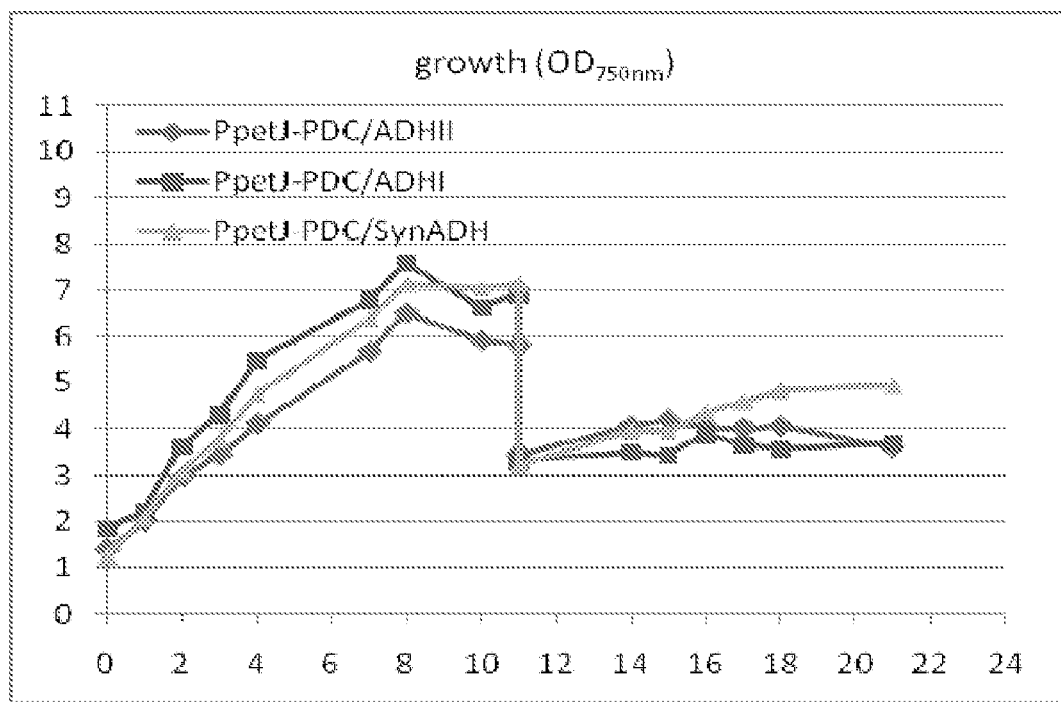
FIG. 10A is a graphic representation of growth over time for the captioned mutant strains.
Figure 10B:
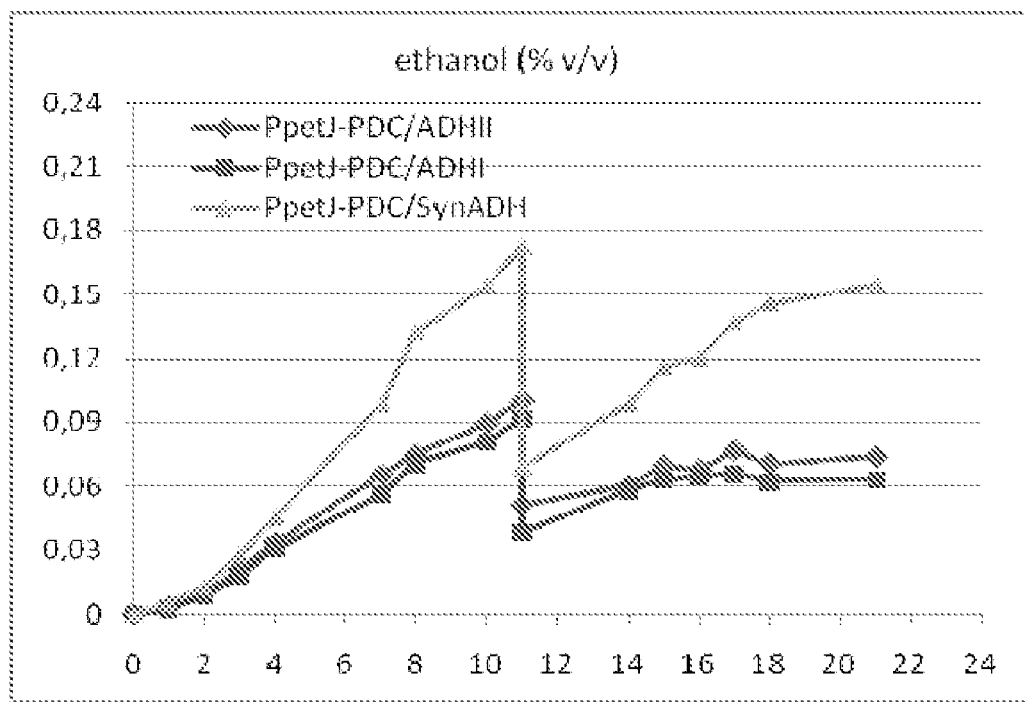
FIG. 10B is a graphic representation of ethanol production over time (% v/v) for the captioned mutant strains.
Figure 10C:
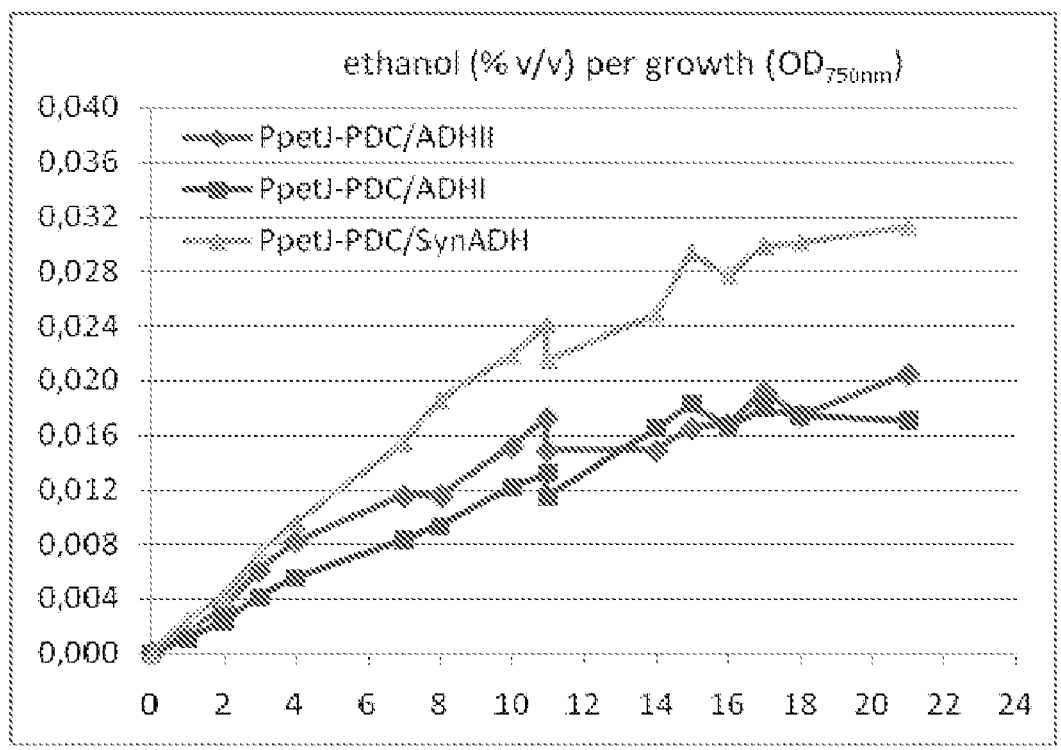
FIG. 10C is a graphic representation of ethanol production per growth for the captioned mutant strains.

FIGS. 10A, 10B and 10C present results of growth, ethanol accumulation and ethanol production per growth of *Synechocystis* mutants that express ZmPdc/ZmAdhI (squares), ZmPdc/ZmAdhII(diamonds) and ZmPdc/SynAdh (triangles), respectively.

Results and Conclusions:

All three PDC/ADH expressing *Synechocystis* mutants were able to produce ethanol efficiently with similar production rates (FIGS. 10A, 10B and 10C). Thus, all three Adh enzymes seem to convert the generated acetaldehyde, produced by the PDC into ethanol. In general each of the three Adhs can be used for the ethanol production in cyanobacteria.

Figure 10D:
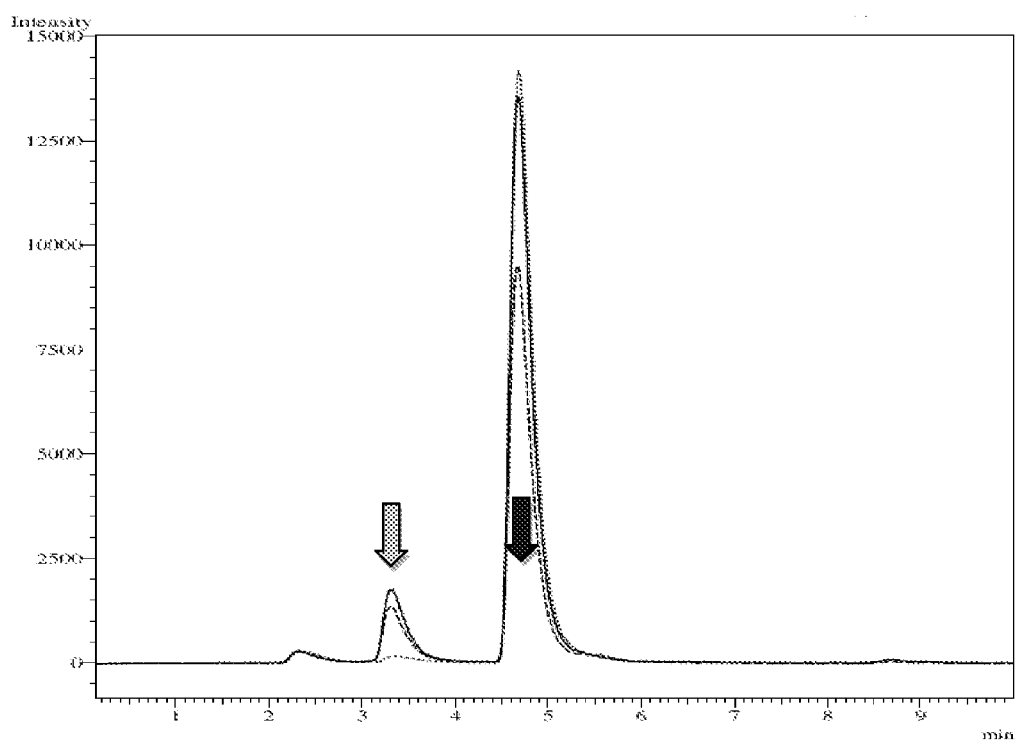
FIG. 10D is a graphic representation of measurements on outgas samples of Synechocystis mutants that express ZmPdc/ZmAdhI (dashed line), ZmPdc/ZmAdhII (solid line) and ZmPdc/SynAdh (dotted line) analysed by gas chromatography. The grey arrow indicates the acetaldehyde, and the black arrow indicates the ethanol peak.

Interestingly, the growth rate of the different mutants is very similar at least for the first 10 days of cultivation, then after addition of new BG11-medium the mutant expressing Pdc/SynAdh looks more healthy and seems to grow faster than the mutants expressing the *Zymomonas mobilis* Adhs, which rather have stopped growing (although new nutrients were added). This is probably due to the decreased vitality of respective ethanol producing cells (visible by yellow pigmentation and bleaching as well as by the reduced oxygen evolution), since a small amount of the generated ethanol is reconverted to acetaldehyde by both *Zymomonas* Adhs. This back-reaction decreased the yield of ethanol on one hand and on the other hand is harmful for the cells, because of the toxicity of the accumulating acetaldehyde. The Adh of *Synechocystis* does not exhibit this back-reaction (under the conditions studied), since in contrast to mutants expressing ZmAdhI or ZmAdhII no acetaldehyde was detectable in the gas-phase of a SynAdh expressing mutant culture (determined by gas chromatography, see FIG. 10D). FIG. 10D presents measurements for outgas samples of *Synechocystis* mutants that express ZmPdc/ZmAdhI (dashed line), ZmPdc/ZmAdhII (solid line) and ZmPdc/SynAdh (dotted line) analyzed by gas chromatography. The grey arrow indicates the acetaldehyde, the black arrow the ethanol peak. This finding makes the ZmPdc/SynAdh expressing mutant a more efficient ethanol producer, because this mutant is healthier during the period of ethanol production and is able to maintain the initial ethanol production rate over a longer time scale as visible in FIGS. 10A, 10B and 10C.

Due to the fact that the ZmPdc/SynAdh expressing mutants do not convert the produced ethanol back into acetaldehyde, there is no loss in the production process. This is clearly visible in the increased ethanol accumulation of these mutants. Both mutants expressing the respective *Zymomonas* Adhs exhibit a lower ethanol yield. Already after 10 days of cultivation there is a significant difference in the ethanol content of the cultures, which indicates that the loss by the back-reaction is not marginal.

Although each of the three Adhs could be used to make ethanol from genetically modified cyanobacteria, the adh of *Synechocystis*, and functionally related adhs, offer clear advantages. With the aim of long-term commercial ethanol production with maximal yields it can be summarized the Adh of *Synechocystis* is obviously advantageous and well suited for the production process because of the lack of the observed disadvantageous back-reaction.

Further experiments were prepared in which the acetaldehyde formation in presence of different amounts of ethanol was monitored. These experiments showed that cells expressing Pdc and Adh I of *Zymomonas mobilis* produced more acetaldehyde when more ethanol was added to the growth medium. It is therefore concluded, that the acetaldehyde is formed by a back reaction from ethanol and is not formed by a Pdc enzyme, which produces too much acetaldehyde to be completely further converted into ethanol by the Adh enzyme.

These results indicate a method to select for desirable adh comprising the steps of
1. adding ethanol to a cyanobacterial cells expressing Pdc and Adh
2. monitoring for the formation of acetaldehyde, and
3. selecting cells which do not form acetaldehyde.

Analysis of ethanol and acetaldehyde by gas chromatography (GC) was performed under following conditions. Gas chromatograph: Shimadzu GC-2014; column: SGE ID-BP634 3.0, 30 m×0.53 mm; carrier gas: helium; temperature: 40° C. constant. An acetaldehyde standard eluted under this conditions at 3.2 min. For the standard, acetaldehyde (Carl Roth) was diluted to 1 mg/ml in water, 25 µl were injected into a 250 ml gas sampling tube, the acetaldehyde was vaporized (30 min, 60° C.). After cooling different volumes were analyzed by GC. A calibration curve was obtained by plotting the integrated peak area against the amount of acetaldehyde.

The gas phase over the cultures was sampled with a gas tight syringe pierced into the tubing at the outlet and 250 µl were injected into the GC.

For measurement of the acetaldehyde production from ethanol *Synechocystis* cells were pelleted, repeatedly washed with BG-11 and dissolved to 10 µg Chl/ml in BG-11 medium. 2 ml of the cultures were mixed with ethanol in clear gas vials (4 ml total volume) closed with rubber seals. The samples were incubated at room temperature for defined time periods in the light (approx. 1000 µE/s*m2). 250 µl of the gas phase were sampled with a gas tight syringe and analyzed. Chlorophyll was determined as in described in Tandeau De Marsac, N. and Houmard, J. in: Methods in Enzymology, Vol. 169, 318-328. L. Packer, ed., Academic Press, 198.

TABLE 1

Ethanol and acetaldehyde in the gas phase above ethanol producing strains.

|  | acetaldehyde gas phase [µmol/L] | ethanol gas phase [µmol/L] | ethanol medium [µmol/L] |
|---|---|---|---|
| PCC6803 wild type | n.d. | n.d. | n.d. |
| ZmPdc/ZmADH I | 0.70 | 4.5 | 8670 |
| ZmPdc/ZmADH II | 0.62 | 3.5 | 5134 |
| ZpPdc/ZmADH II | 0.33 | 3.3 | — |
| ZmPdc/native ADH | n.d. | 4.0 | 7777 |
| ZpPdc/native ADH | n.d. | 2.8 | — |
| Pdc/SynADH | n.d. | 5.1 | 9767 |

Figure 10E:
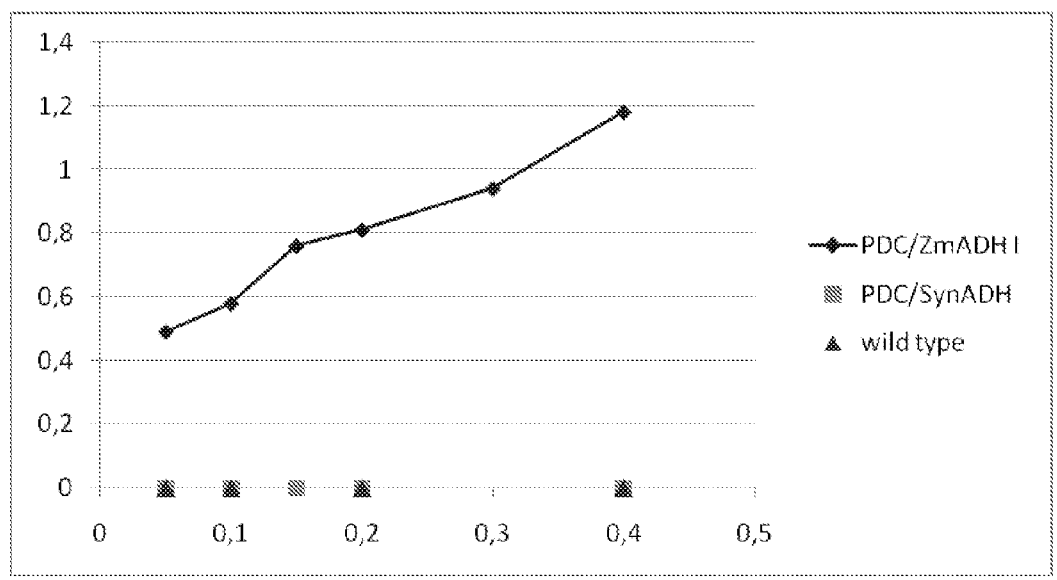
FIG. 10E is a graphic depiction of acetaldehyde production after addition of ethanol in different concentrations. Wild type and ethanol producing transgenic cells are presented.

The gas phase above transgenic strains of *Synechocystis* PCC6803 expressing different Pdcs and Adhs using the plasmid pVZ323 PpetJ was analyzed for ethanol and acetaldehyde content. As a control the ethanol was also quantified in the culture medium.
ZmPdc, Pdc of *Zymomonas mobilis*; ZpPdc, Pdc of *Zymobacter palmae*; ZmAdh I, Adh I of *Zymomonas mobilis*; ZmAdh II, Adh II of *Zymomonas mobilis*; native Adh, no expression of an heterologous Adh, the native Adh of *Synechocystis* is present; SynAdh, Adh of *Synechocystis* is overexpressed; n.d. not detectable; —, not measured FIG. 10E shows the acetaldehyde production after addition of ethanol in different concentrations. Wild type and ethanol producing transgenic cells *Synechocystis* PCC6803, overexpressing different Pdcs and Adhs enzymes (see text) were incubated for 30 min under illumination with 0.05% to 0.4% (v/v) of ethanol. The y-axis of FIG. 10E denotes the acetaldehyde concentration in the gas phase (in µmol/l) and the x-axis shows the ethanol concentration in % (v/v).

FIG. 10E shows that only for the *Synechocystis* strain transformed with pVZ323 PpetJ Pdc/ZmADH I, the amount of acetaldehyde in the gas phase could be increased by adding more ethanol to the growth medium. For the *Synechocystis* PCC6803 strains transformed with pVZ323 PpetJ Pdc/SynAdh no increase in acetaldehyde could be detected upon addition of ethanol.

The Adh enzyme from *Synechocystis* was further characterized by preparing crude cell extracts from *Synechocystis* PCC6803 overexpressing SynAdh. For the reason of comparison crude cell extracts from *Synechocystis* cells overexpressing *Zymomonas mobilis* Adh II were prepared as well.

For preparation of crude extracts, cells were pelleted, dissolved in buffer supplemented with 1 mM DTT and broken (beadbeater, 2×10 min, glass beads with 100 µm diameter). The supernatant of a centrifugation (15 min, 14000 rpm, 4° C., Micro 200R, Hettich) was used for the experiments.

*Synechocystis* or *Zymomonas mobilis* Adh enzyme activity was measured either as ethanol oxidation or as acetaldehyde reduction, i.e. in the direction of ethanol formation. The assays for ethanol oxidation contained in a total volume of 800 µl 30 mM Tris/HCl (pH 8.5), 1 mM NAD+ or 1 mM NADP+, 1 M ethanol and the crude extract. The Adh activity was measured as rate of the increase of the absorbance at 340 nm. For measurement of the acetaldehyde reduction, the assays contained 30 mM MES/KOH (pH 6.2), 0.3 mM NADH or 0.3 mM NADPH, and crude extracts. The reaction was started by addition of an acetaldehyde solution to a final concentration of 0.125 mM and the rate of decrease of the absorbance at 340 nm was measured. For the measurements of the pH-dependency of the Adh 40 mM MES adjusted with Tris base to 8.0) and with NH3 (pH 8.5 and 9.0) was used as buffer. Protein was determined by the method of Lowry.

TABLE 2

ADH activities measured as ethanol oxidation.

|  | Wild type | with Adh II *Z. mobilis* | with Adh *Synechocystis* |
|---|---|---|---|
| 1 mM NAD+ | 0.4 | 85.2 | 1.4 |
| 1 mM NADP+ | 1.6 | 3.3 | 6.8 |
| 0.1 mM NADP+ | 2.4 | 3.4 | 8.9 |
| 1 mM NAD+ + 0.1 mM NADP+ | 2.2 | 65.7 | 8.7 |
| 1 mM NAD+ + 1 mM NADP+ | 1.3 | 25.5 | 6.4 |

Crude extracts of *Synechocystis* wild type, *Synechocystis* cells expressing Adh II of *Zymomonas mobilis*, or the AHD of *Synechocystis* were analyzed. The assays contained NAD+ and/or NADP+ in the given concentrations. Shown are specific activities in nMol $min^{-1}$ $mg^{-1}$ of total protein.

This table 2 shows that Adh II from *Zymomonas mobilis* has a higher enzymatic activity than *Synechocystis* Adh enzyme for the unwanted backreaction, the oxidation of ethanol back to acetaldehyde if $NAD^+$ or mixtures of $NAD^+$ and $NADP^+$ are used as a cosubstrates.

TABLE 3

ADH activities measured in the direction of ethanol production.

|  | Wild type | with ADH II *Z. mobilis* | with ADH *Synechocystis* |
|---|---|---|---|
| 0.3 mM NADH | 13.7 | 62.8 | 53.3 |
| 0.3 mM NADPH | 9.0 | 71.4 | 55.4 |
| 0.3 mM NADH + 1 mM NADP+ | 2.9 | 3.7 | 2.8 |

The assays contained NADH or NADPH or a combination of NADH and NADP+. Shown are the specific activities in nMol $min^{-1}$ $mg^{-1}$ of total protein.

Figure 10F:
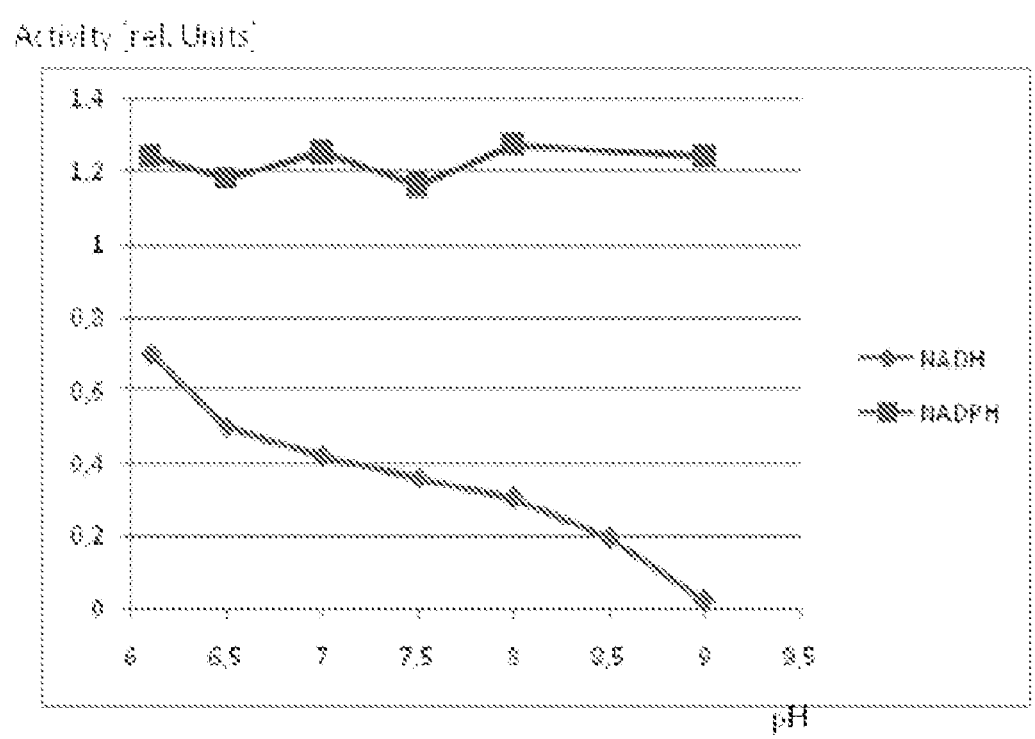
FIG. 10F is a graphic depiction of the pH-dependency of acetaldehyde reduction by crude extracts containing the Synechocystis Adh.

The pH-dependency of the acetaldehyde reduction by crude extracts containing the *Synechocystis* Adh is shown in the next FIG. 10F. Surprisingly very different results were found for NADH and NADPH. With NADH as cosubstrate a steady decrease of activity at higher pH values was measured (maximum activity at pH 6.1), whereas the NADPH dependent reduction had a broad pH optimum. This FIG. 10F shows the acetaldehyde reduction rates of a crude extract containing *Synechocystis* Adh enzyme with NADH and NADPH, respectively (0.15 nM final concentration) at different pH-values. The activities are given in dE/min.

This observation is of interest because according to literature the amount of NADPH in *Synechocystis* exceeds the amount of NADH approximately 10 times. Therefore *Synechocystis* Adh enzyme is expected to have a broad pH-optimum in transformed *Synechocystis* cells or other cyanobacterial strains.

Figure 10G:
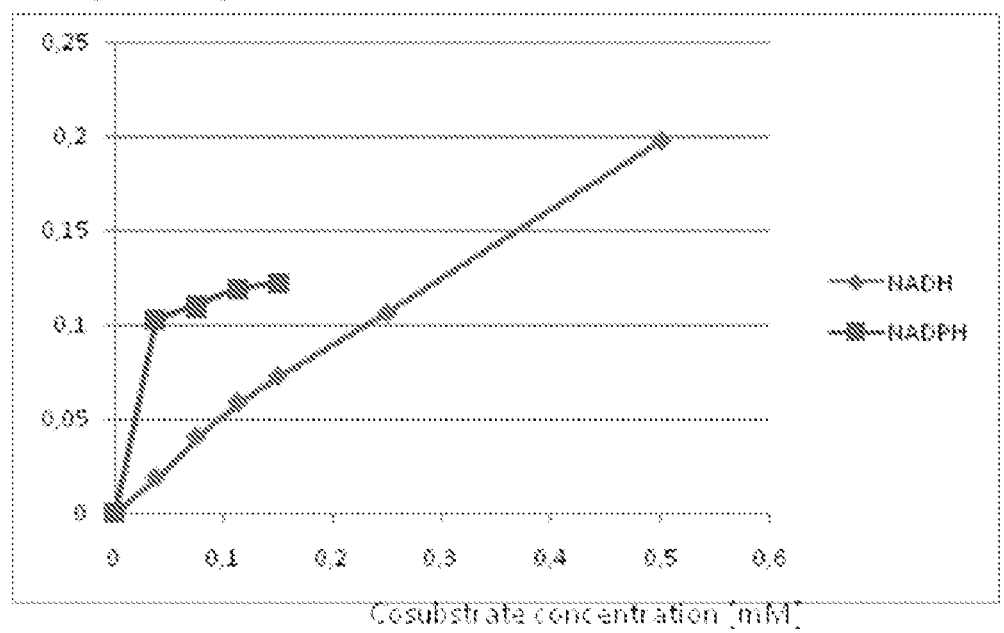
FIG. 10G is a graphic depiction summarizing the acetaldehyde reduction rates at different cosubstrate concentrations. Measurements were performed at pH 6.1
Figure 10H:
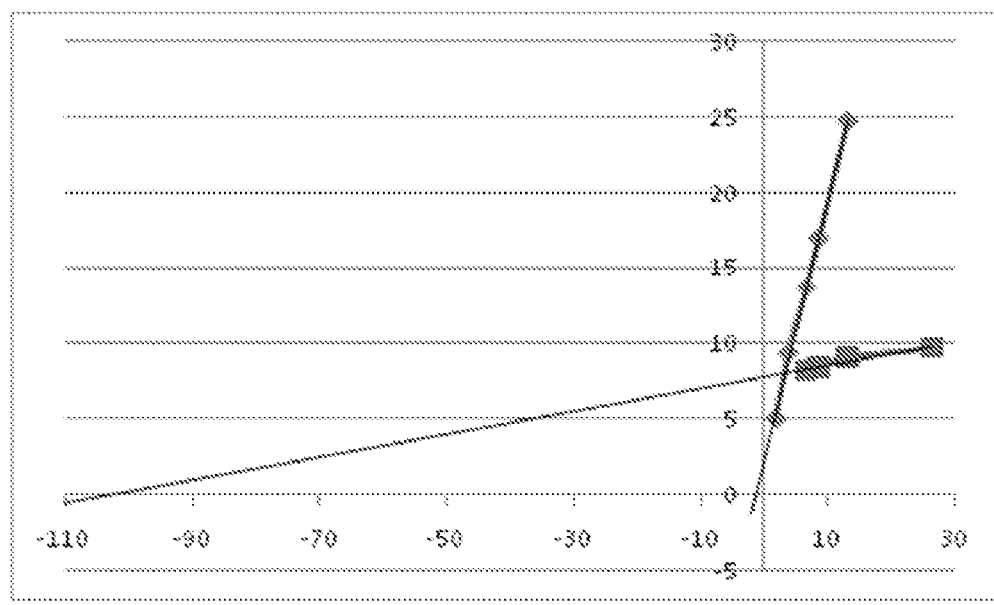
FIG. 10H is a graphic depiction of Lineweaver-Burk plots, which depict the reciprocal of the rate of acetaldehyde reduction versus the reciprocal of the concentration of NADH (squares) or NADPH (rhombi), respectively. Km and vmax values are discussed in the text.

The Adh enzyme of *Synechocystis* also has different kinetic constants for NADH and NADPH. FIG. 10G summarizes the acetaldehyde reduction rates at different cosubstrate concentrations. Measurements were performed at pH 6.1. Using Lineweaver-Burk plots, which depict the reciprocal of the rate of acetaldehyde reduction versus the reciprocal of the concentration of NADH (squares) or NADPH (rhombi), respectively (FIG. 10H) $K_m$ and $v_{max}$ for NADH were calculated with 1 mM and 1.6 µMol min$^{-1}$ ml$^{-1}$ crude extract. For NADPH $K_m$ and $v_{max}$ were 15 µM and 0.4 µMol min$^{-1}$ ml$^{-1}$ for the crude extract. The $K_m$ for the NADH-dependent reaction of the *Synechocystis* Adh enzyme was calculated to be approximately 1 mM.

Further Characterization of the Purified SynAdh Enzyme

In order to study the properties of the SynADH in more detail, a number of different measurements with the purified enzyme were performed. Experiments with cell extracts can be problematic in some circumstances, e.g. they could contain inhibiting substances or enzymes competing for the substrates.

Methods

SynADH was overexpressed as fusion protein with glutathione S-transferase (GST) in *E. coli*. The fusion protein was purified by affinity chromatography (Glutathione Sepharose™ 4, GE Healthcare). The GST part of the fusion protein was then removed by proteolytic digestion with PreScission Protease (GE Healthcare).

Heterologous Expression and Purification of the SynAdh

ORF slr1192 from *Synechocystis* was amplified by PCR using the primers:

(SEQ ID NO: 38)
5' CTCTA<u>GGATCC</u>ATGATTAAAGCCTACG 3'
and (SEQ ID NO: 39)
5' CACGGACCCA<u>GCGGCCGC</u>CTTTGCAGAG 3'.

The primers contain nucleotide exchanges, which were introduced into the primers to obtain a BamHI and a NotI restriction site (the restriction sites are underlined in the sequences). Phusion High fidelity DNA polymerase was used for the PCR, which was performed according to the protocol of the manufacturer (New England BioLabs Inc.).

The PCR resulted in an DNA fragment of 1010 bps, which was ligated into the PCR cloning vector pJET1.2 blunt (Gene-JET™ PCR Cloning Kit, Fermentas) and *E. coli* cells (a-Select Chemical Competent Cells, Bioline) were transformed with the ligation assay. Plasmidic DNA was isolated (Gene-JET™ Plasmid Miniprep Kit, Fermentas) from positive clones, the DNA was digested with BamHI and NotI and the 1010 bps fragment containing slr1192 was recovered. The fragment was ligated into pGEX-6P-1 (GE Healthcare) which had been digested with BamHI and NotI. *E. coli* was transformed and plasmidic DNA was prepared as before. The correctness of the construct was verified by digestion with different restriction enzymes and by complete sequencing of the 1010 bps insert.

For the expression of the fusion protein chemical competent BL21 *E. coli* cells were transformed with the construct. A single colony was cultured in LB-medium complemented with ampicillin (125 µg/ml) and glucose (1% w/v). The culture volume was stepwise increased to 200 ml. Cells were finally harvested by centrifugation (4500 rpm, 10 min, Rt, Rotina 420R Hettich) resuspended in 200 ml LB-medium with ampicillin (125 µg/ml) and IPTG (isopropyl thiogalactoside, 0.5 mM) and cultured under shaking at 20° C. over night. Cells were then harvested, washed with buffer A (20 mM Tris/HCl, pH 7.5, 150 mM KCl, 1 mM Dithiotreitol) and resuspended in this buffer. Cells were disrupted by sonication (UW 2070, Bandelin) under ice cooling and the lysate was cleared by centrifugation (15 min, 14,000 rpm, 4° C., Micro 200R Hettich).

4 ml column material Glutathione Sepharose™ 4 Fast Flow (GE Healthcare) was washed 5 times with buffer A and added to the cell lysate. After incubation (2 hours at Rt under shaking) the material was packed in a disposable plastic column (12 cm length, 1 cm diameter). The column material was washed with 5 column volumes (20 ml) buffer A and subsequently resuspended in 1.5 ml buffer A supplemented with 80 µl PreScission Protease (2 units/µl). After incubation at 4° C. over night, the column was eluted with buffer A. Fractions of 1.5 ml or 1 ml were collected.

SDS Polyacrylamide gel electrophoresis was performed with standard methods using 15% polyacrylamide gels. Page Ruler™ unstained protein ladder (Fermentas) was the molecular weight standard.

Alcohol dehydrogenase activity was measured in the direction of acetaldehyde reduction. The assay contained in a total volume of 1000 µl 30 mM MES/KOH, pH 6.0, 1 mM DTT, 0.3 mM NADPH and different volumes of samples. The reaction was started by addition of acetaldehyde to a final concentration of 100 mM, the rate of the decrease of the absorbance at 340 nm was measured.

Results and Discussion

Figure 10I:
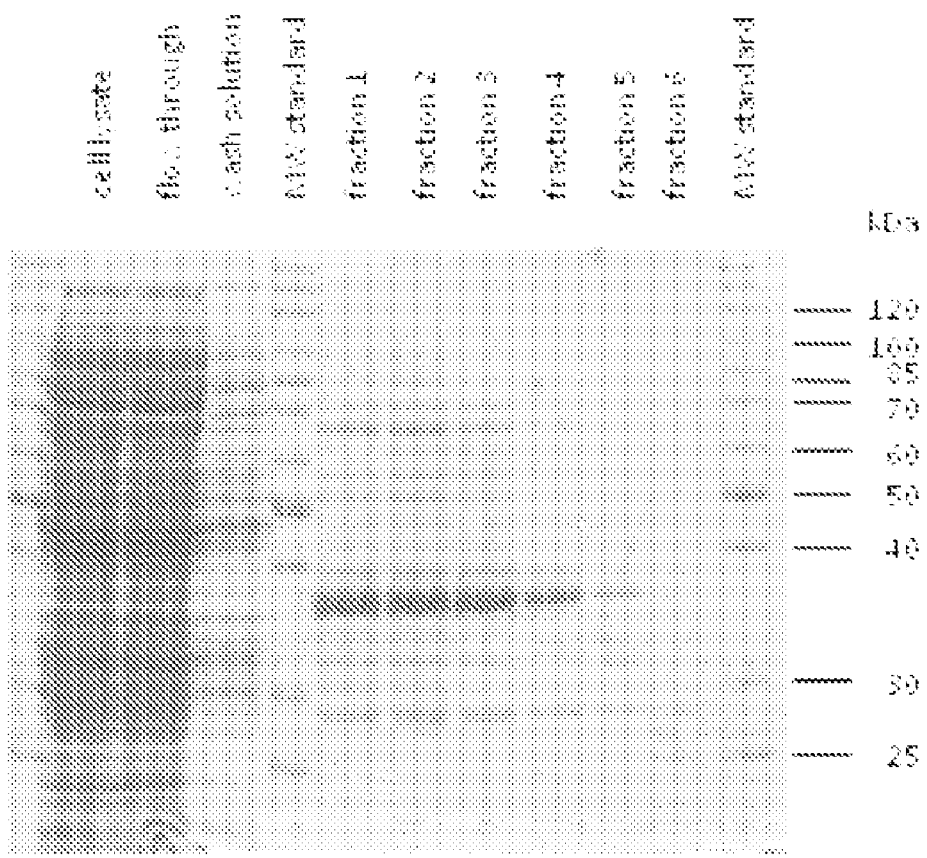
FIG. 10-I is a photographic depiction of SDS/PAGE analysis of recombinantly expressed SynADH showing that SynADH was enriched, but not purified to homogeneity.

The success of the purification was verified by SDS Polyacrylamide gel electrophoresis (SDS/PAGE) analysis and by measurement of the alcohol dehydrogenase activity. As shown in FIG. 10I the main protein in the eluate has a molecular weight of approx. 36 kDa. This corresponds to the molecular weight of the SynADH, which was calculated from the amino acid sequence with 35.9 kDa. The PreScission protease has a molecular weight of 46 kDa. The GST-tag, if expressed alone, has a molecular weight of 29 kDa. The SDS/PAGE analysis shows that SynADH was enriched, but not purified to homogeneity.

The results for the measurement of the alcohol dehydrogenase activity are given in table 1, wherein the activity of the cell lysate was defined as 100% yield. As shown therein only 50% of the SynADH in the cell lysate was bound to the column material.

| sample | volume [ml] | protein conc. [mg/ml] | activity/ vol. [μmol/min * ml] | activity/ protein [μmol/min * mg] | Purification [-fold] | total activity [μmol/min] | yield [%] |
| --- | --- | --- | --- | --- | --- | --- | --- |
| cell lysate | 15 | 14.3 | 7.86 | 0.55 | 1 | 117.9 | 100 |
| flow through | 15 | 11.7 | 3.86 | 0.33 | | 57.9 | 49 |
| wash solution | 20 | 1.5 | 0.37 | 0.25 | | 7.3 | 6 |
| fraction 1 | 1.5 | 1.25 | 10.92 | 8.7 | 15.8 | 16.4 | |
| fraction 2 | 1 | 1.25 | 10.92 | 8.7 | 15.8 | 10.9 | |
| fraction 3 | 1 | 0.91 | 9.60 | 10.5 | 19.1 | 9.6 | |
| fraction 4 | 1 | 0.35 | 3.60 | 10.3 | 18.7 | 3.6 | |
| fraction 5 | 1 | 0.11 | 1.10 | 10.0 | 18.2 | 1.1 | |
| fractions 1-5 computed value | | | 45 | | | 41.6 | 35 |

In the finally obtained fractions of the eluate the enzyme was enriched approximately 16-fold. This purification factor is not high but for a one step purification this is not unexpected. Approx. 35% of the activity was finally recovered in fractions 1 to 5 of the eluate.

Fraction 2 of the purification was used for the measurement of the kinetic parameters of the SynAdh as described in the following.

Adh enzyme activity was measured either as ethanol oxidation (back reaction) or as acetaldehyde reduction (in the direction of ethanol formation, forward reaction). The ethanol oxidation and acetaldehyde reduction were measured at room temperature as rate of change of absorbance at 340 nm.

Both ethanol oxidation and acetaldehyde reduction were analyzed at different pH values. Experiments were made at pH 7.5 in presence of high concentrations of KCl in order to mimic the intracellular conditions. In addition ethanol oxidation rates were assayed at pH 8.5 and acetaldehyde reduction rates at pH 6.0. This pH values were taken from the literature, they account for the different pH-optima of forward and backward reaction of ADH II of *Zymomonas mobilis*.

Ethanol Oxidation:

The assays for the determination of the $K_m$ values for $NAD^+$ and $NADP^+$ contained in a total volume of 1000 μl 30 mM HEPES/KOH (pH 7.5), 150 mM KCl, 1 mM DTT, 1.5 M ethanol, purified enzyme and $NAD^+$ or $NADP^+$ in different concentrations. For measurements at pH 8.5 HEPES/KOH was substituted by 30 mM Tris/HCl (pH 8.5), KCl was omitted.

The assays for the determination of the $K_m$ value for ethanol contained in a total volume of 1000 μl 30 mM HEPES/KOH (pH 7.5), 150 mM KCl, 1 mM DTT, 1 mM $NADP^+$, purified enzyme and ethanol in different concentrations. For measurements at pH 8.5 HEPES/KOH was substituted by 30 mM Tris/HCl (pH 8.5), KCl was omitted.

Acetaldehyde Reduction:

The assays for the determination of the $K_m$ values for NADH and NADPH contained in a total volume of 1000 μl 30 mM HEPES/KOH (pH 7.5), 150 mM KCl, 1 mM DTT, 2 mM acetaldehyde, purified enzyme and NADH or NADPH in different concentrations. For measurements at pH 6.0 HEPES/KOH was substituted by 30 mM MES/KOH (pH 6.0), KCl was omitted.

The assays for the determination of the $K_m$ value for acetaldehyde contained in a total volume of 1000 μl 30 mM HEPES/KOH (pH 7.5), 150 mM KCl, 1 mM DTT, 0.32 mM NADPH, purified enzyme and acetaldehyde in different concentrations. For measurements at pH 6.0 HEPES/KOH was substituted by 30 mM MES/KOH (pH 6.0), KCl was omitted.

Results

The $K_m$ and $v_{max}$ values of SynAdh for the different substrates were determined with Lineweaver-Burk plots. The $K_m$ values are summarized in table 1 and table 2.

TABLE 1

$K_m$ values of SynAdh for the different substrates of the acetaldehyde reduction.

| | pH 7.5, 150 mM KCl | pH 6.0 |
| --- | --- | --- |
| NADH | 1000 μM | — |
| NADPH | 15 μM | 20 μM |
| acetaldehyde | 180 μM | 200 μM |

Shown are the $K_m$ values for NADH, NADPH and acetaldehyde at two different conditions (see Methods);
—, not measured.

TABLE 2

$K_m$ values of SynAdh for the different substrates of the ethanol oxidation.

| | pH 7.5, 150 mM KCl | pH 8.5 |
| --- | --- | --- |
| $NAD^+$ | 10 mM | 10 mM |
| $NADP^+$ | 15 μM | 15 μM |
| ethanol | 23 mM | 59 mM |

Shown are the $K_m$ values for $NAD^+$, $NADP^+$ and ethanol at two different conditions (see Methods).

Discussion

The $K_m$ value is an inherent property of an enzyme. It is defined as the substrate concentration necessary to obtain half-maximal velocity of the enzymatic reaction. The lower the $K_m$ value, the higher the "affinity" of the enzyme to the substrate.

The $K_m$ values of SynAdh for the substrates of the acetaldehyde reduction were determined in earlier experiments with cell extracts. The results for the purified enzyme presented here are nearly identical to those results. The affinity of the enzyme for NADPH is relatively high ($K_m$ approx. 15 μM), but the affinity for NADH is very low ($K_m$ for NADH approx. 1000 μM). This means, that the reaction is much more effectively catalyzed with NADPH than with NADH, and NADPH will be the cosubstrate preferred by SynADH, all the more as in cyanobacteria, as in other photosynthetic organisms NADPH exceeds NADH by far. In *Synechocystis* PCC 6803 the pool of $NADP_{total}$ (NADP++NADPH) is approx. 10 fold higher than the pool of $NAD_{total}$ (NAD++NADH) as described in Cooley & Vermaas, J. Bacteriol. 183(14) (2001) 4251-42589. The $K_m$ value of SynAdh for acetaldehyde was determined with approx. 200 µM. As a comparison the $K_m$ value of ADH I and ADH II of *Zymomonas mobilis* given in the literature are between 8 and 21 µM for acetaldehyde and 12 to 27 µM for NADH as described in Hoppner & Doelle, Eur. J. Appl. Microbiol. Biotechnol. 17, (1983), 152-157 and Kinoshita et al., Appl. Microbiol. Biotechnol. 22, (1985), 249-254, respectively.

The affinities of SynAdh to the substrates of the acetaldehyde reduction are more or less similar to those of ADH I and ADH II of *Zymomonas mobilis*, but the properties of the back reaction are totally different. The $K_m$ value of ADH I and ADH II of *Z. mobilis* for ethanol are given in the literature with 24 µM (ADH I) and 140 µM (ADH II), the $K_m$ for $NAD^+$ with 73 µM (ADH I) and 110 µM (ADH II) [6]. The affinity of SynAdh to ethanol is by far lower, the $K_m$ value for ethanol was determined with approx. 23 mM to 59 mM. This means that ADH I and ADH II will catalyze the formation of acetaldehyde already at low ethanol concentrations, while effective acetaldehyde formation with SynAdh requires much higher ethanol concentrations. As for the forward reaction the two cosubstrates behave totally different in the back reaction. The $K_m$ for $NAD^+$ was determined with 10 mM, the $K_m$ for $NADP^+$ with 15 µM.

The finding that SynAdh has a very low affinity towards ethanol is an explanation for the ineffectiveness of the back reaction. The missing or relatively small formation of acetaldehyde may be the explanation for the increased vitality of cell strains containing the SynAdh when compared to ethanol producing strains with other ADHs, as acetaldehyde is toxic to cells.

Phylogenetic Analysis of the SynAdh Enzyme

Phylogenetic analysis shows that Adh is a member of the family of Zinc-binding GroES-like domain alcohol dehydrogenases, which is phylogenetically different from the family of short chain Rossmann fold like Adh enzymes or the family of Fe-containing Fe-Adh enzymes.

Figure 11A:
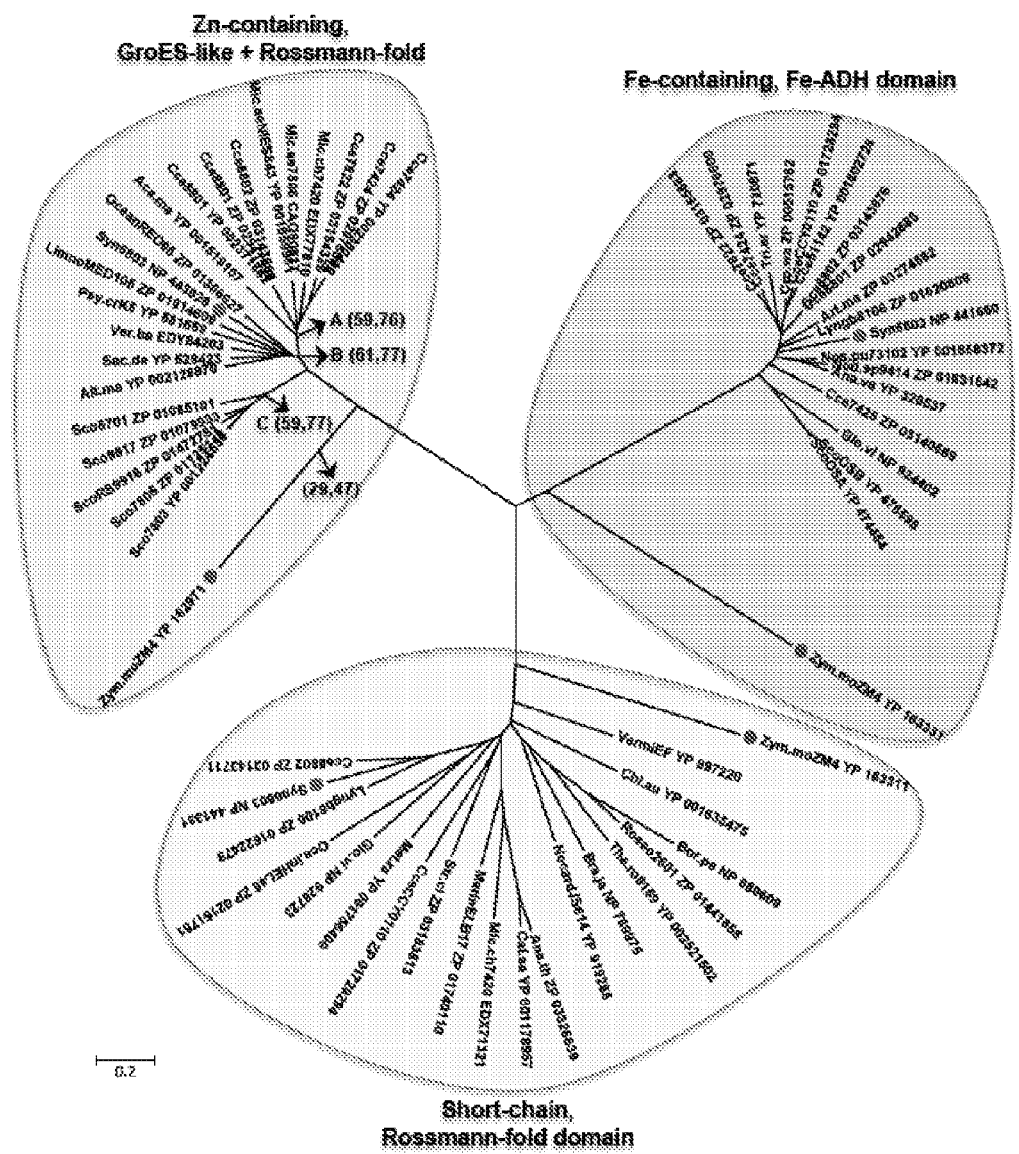
FIG. 11A presents a phylogenetic analysis examining different zinc binding ADH proteins.

The FIG. 11A shows a in-depth phylogenetic analysis of different alcohol dehydrogenase families. Within the clade of Zinc-binding GroES-like domain alcohol dehydrogenases three sub-clades denoted A to C can be found and furthermore a *Zymomonas* Adh enzyme, which is only distantly related to the other members of the Zinc-binding GroES-like domain alcohol dehydrogenases. The values in parentheses indicate the average percentage of protein sequence identity of the members of one respective sub-clade to *Synechocystis* Adh enzyme NP_443028. It can clearly be seen that for example the members of the sub-clade B including *Synechocystis* Adh enzyme share an average sequence identity with SynAdh of 61.77%. Each of the different families contain a number of representative members, which are denoted by their respective National Center for Biotechnology Information (NCBI) database entry numbers (www.ncbi.nlm.nih.gov/). In particular the phylogenetic tree was constructed with protein sequences of different Adh enzymes using Neighbor-joining method. Distinct clades includes Adh enzymes with different metal-binding domains. The locations of *Z. mobilis* and *Synechocystis* sp. 6803 were highlighted. The table of FIG. 11B shows the annotations, the organisms and the database accession codes for the protein sequences of the different sub-clades A to C in the clade of Zinc-binding GroES-like domain alcohol dehydrogenases shown in FIG. 11A.

Protocol for the Clade Analysis

Genes encoding the alcohol dehydrogenase (Adh) from *Synechocystis* sp. PCC 6803 were compared to all proteins from the NCBI non-redundant database (http://www.ncbi.nlm.nih.gov) with BLAST (1) to retrieve top bacterial sequence matches, including 40 from extant cyanobacteria. Protein sequences of these adh genes were aligned with ClustalW (2). Phylogenetic tree was constructed with MEGA version 3.1 (3) using the neighbor-joining method with Poisson correction substitution model and 100 bootstrap replicates assuming uniform heterogeneity among sites. The detailed options are as following:

Method: Neighbor-Joining
Phylogeny Test and options: Bootstrap (100 replicates; seed=64238)
Include Sites: ==============================
Gaps/Missing Data Pairwise Deletion
Substitution
Model: ==============================
Model: Amino: Poisson correction
Substitutions to Include: All
Pattern among Lineages: Same (Homogeneous)
Rates among sites: Uniform rates
No. of Sites: 315
No Of Bootstrap Reps=100

The above phylogenetic analysis revealed three clades of structurally and catalytically different types of alcohol dehydrogenases: 1) Zn-containing 'long-chain' ADH with a GroES-like (ADH-N) domain at the N' terminal end; 2) Insect-type, or 'short-chain' ADH; and 3) Fe-containing ADH (FIG. 11). The Zn-containing ADHs (4, 5) are dimeric or tetrameric enzymes that bind two atoms of zinc per subunit. Both zinc atoms are coordinated by either cysteine or histidine residues; the catalytic zinc is coordinated by two cysteines and one histidine. The Zn-containing ADH contains a GroES-like (ADH-N) domain at N' terminal and a Rossmann-fold NAD(P)+-binding (NADB_Rossmann) domain at C' terminal. A number of other Zn-dependent dehydrogenases, including the glutathione dependent formaldehyde dehydrogenase (homologous to gene adhC in *Zymomonas mobilis*) and the NADP-dependent quinone oxidoreductase (qor) are closely related to Zn-ADH (6) and are included in this family.

The short-chain ADH's belong to the short-chain dehydrogenases/reductases family (SDR) (7), most of which are proteins of about 250 to 300 amino acid residues with a Rossmann-fold NAD(P)+-binding domain. Little sequence similarity has been found in this family although there is a large degree of structural similarity.

The Fe-containing ADH's are distantly related to gene adhB from *Z. mobilis*. This group shares sequence homology with glycerol and butanol dehydrogenases.

REFERENCES

1. S. F. Altschul et al., Nucleic Acids Res. 25, 3389 (1997).
2. J. Thompson, D. Higgins, T. Gibson, Nucleic Acids Res. 22, 4673 (1994).
3. S. Kumar, K. Tamura, M. Nei, Briefings in Bioinformatics 5, 150 (2004).
4. H. Jornvall, B. Persson, J. Jeffery, Eur. J. Biochem. 167, 195 (1987).
5. H. W. Sun, B. V. Plapp, J. Mol. Evol. 34, 522 (1992).
6. B. Persson, J. Hallborn, M. Walfridsson, B. Hahn-Hagerdal, S. Keranen, M. Penttila, H. Jornvall, FEBS Lett. 324, 9 (1993).
7. H. Jornvall, B. Persson, M. Krook, S. Atrian, R. Gonzalez-Duarte, J. Jeffery, D. Ghosh, Biochemistry 34, 6003 (1995).

The FIGS. 11C to 11I show the protein sequences of the Adh enzymes of sub-clade B, which also included the Zinc-dependent *Synechocystis* Adh enzyme. In particular, FIG. 11C presents the amino acid sequence of a zinc-containing alcohol dehydrogenase family protein of *Synechocystis* sp. PCC 6803, identified by Genbank Accession No. NP_443028.1.

FIG. 11D presents the amino acid sequence of a zinc-containing alcohol dehydrogenase family protein of *Oceanobacter* sp. RED65, identified by Genbank Accession No. ZP_01306627.1.

FIG. 11E presents the amino acid sequence of an alcohol dehydrogenase, zinc-binding protein of *Limnobacter* sp. MED105, identified by Genbank Accession No. ZP_01914609.1.

FIG. 11F presents the amino acid sequence of an alcohol dehydrogenase GroES-like protein of *Psychrobacter* cryohalolentis K5, identified by Genbank Accession No. YP_581659.1.

FIG. 11G presents the amino acid sequence of an alcohol dehydrogenase GroES-like domain family of Verrucomicrobiae bacterium DG1235, identified by Genbank Accession No. EDY84203.1.

FIG. 11H presents the amino acid sequence of a zinc-containing alcohol dehydrogenase family protein of *Saccharophagus degradans* 2-40, identified by Genbank Accession No. YP_529423.1.

FIG. 11I presents the amino acid sequence of a zinc-containing alcohol dehydrogenase family protein of *Alteromonas macleodii* 'Deep ecotype', identified by Genbank Accession No. YP_002126870.1.

The FIGS. 11J to 11S represent the Adh protein sequences of sub-clade A of the above phylogenetic analysis. Sub-clade A comprises SEQ ID 23-32.

In particular FIG. 11J presents the amino acid sequence of a zinc-containing alcohol dehydrogenase family protein of *Acaryochloris marina* MBIC11017, identified by Genbank Accession No. YP 001519107.1.

FIG. 11K presents the amino acid sequence of an alcohol dehydrogenase GroES domain protein of *Cyanothece* sp. PCC 7424, identified by Genbank Accession No. YP_002380432.1.

FIG. 11L presents the amino acid sequence of an alcohol dehydrogenase GroES domain protein of *Cyanothece* sp. PCC 7424, identified by Genbank Accession No. ZP_02976085.1.

FIG. 11M presents the amino acid sequence of an alcohol dehydrogenase GroES domain protein of *Cyanothece* sp. PCC 7822, identified by Genbank Accession No. ZP_03154326.1.

FIG. 11N presents the amino acid sequence of an alcohol dehydrogenase GroES domain protein of *Cyanothece* sp. PCC 8801, identified by Genbank Accession No. YP_002371662.1.

FIG. 11O presents the amino acid sequence of an alcohol dehydrogenase GroES domain protein of *Cyanothece* sp. PCC 8801, identified by Genbank Accession No. ZP_02941996.1.

FIG. 11P presents the amino acid sequence of an alcohol dehydrogenase GroES domain protein of *Cyanothece* sp. PCC 8802, identified by Genbank Accession No. ZP_03143898.1.

FIG. 11Q presents the amino acid sequence of an alcohol dehydrogenase GroES-like domain family of Microcoleus chthonoplastes PCC 7420, identified by Genbank Accession No. EDX77810.1.

FIG. 11R presents the amino acid sequence of an uncharacterized zinc-type alcohol dehydrogenase-like protein of *Microcystis aeruginosa* NIES-843, identified by Genbank Accession No. YP_001659961.1.

FIG. 11S presents the amino acid sequence of an unnamed protein product of *Microcystis aeruginosa* PCC 7806, identified by Genbank Accession No. CAO90817.1.

The FIG. 11T to 11X show the amino acid sequences of the Adh enzymes of the sub-clade C of the above phylogenetic analysis. Sub-clade C comprises SEQ ID 33-37.

In particular FIG. 11T presents the amino acid sequence of a zinc-containing alcohol dehydrogenase superfamily protein of *Synechococcus* sp. WH 5701, identified by Genbank Accession No. ZP_01085101.1.

FIG. 11U presents the amino acid sequence of a zinc-containing alcohol dehydrogenase superfamily protein of *Synechococcus* sp. RS9917, identified by Genbank Accession No. ZP_01079933.1.

FIG. 11V presents the amino acid sequence of a zinc-containing alcohol dehydrogenase superfamily protein of *Synechococcus* sp. WH 5701, identified by Genbank Accession No. ZP_01085101.1.

FIG. 11W presents the amino acid sequence of a zn-dependent alcohol dehydrogenase of *Synechococcus* sp. WH 7803, identified by Genbank Accession No. YP_001224538.1.

FIG. 11X presents the amino acid sequence of a zinc-containing alcohol dehydrogenase superfamily protein of *Synechococcus* sp. WH 7805, identified by Genbank Accession No. ZP_01125148.1.

P.6 Ethanol Production Rates of Genetically Modified Photoautotrophic Host Cells Containing *Zymomonas Mobilis* Pdc as the Only Second Genetic Modification Almost all organisms including photoautotrophic organisms contain in their genomes genes coding for alcohol dehydrogenases (Adh). Also the cyanobacterium *Synechocystis* PCC6803 exhibit Adh activity in crude cell extracts and contains a corresponding adh gene in the genome. A point of inquiry is whether or not this endogenous Adh enzyme is active enough in order to ensure a high level ethanol production in conjunction with an overexpressed Pdc enzyme.

In order to test if this endogenous Adh enzyme is able to convert efficiently the generated acetaldehyde produced by the over-expressed Pdc enzyme, mutants were generated that express only the Pdc enzyme without additional Adh enzyme. This mutant was compared to an isogenic ethanol producing mutant of *Synechocystis* that over-express Pdc enzyme together with an additional Adh enzyme from *Zymomonas mobilis*.

Mutant Generation:

From a preexisting pVZ plasmid (pVZ321 b-PisiA-Pdc/AdhII) containing respective Pdc/Adh genes from *Zymomonas mobilis* the coding region of adhII was cut out by SacI/PstI digestion and subsequent relegation of the residual plasmid lead to pVZ321 b-PisiA-PDC (without adhII). Mutants were selected on streptomycin plates and grown in BG11 medium containing the appropriate antibiotics (kanamycin 100 mg/l; streptomycin 10 mg/l).

Growth Conditions:

Mutant and *Synechocystis* wild-type strains were grown in BG11 without iron, at 28° C., under constant light (100 µE $m^{-2}$ $s^{-1}$), aerated with $CO_2$-enriched air (0.5% $CO_2$). The initial $OD_{750}$ was 1.3 in a total culture volume of 300 ml in a 500 ml Schott-flask.

Figure 12A:
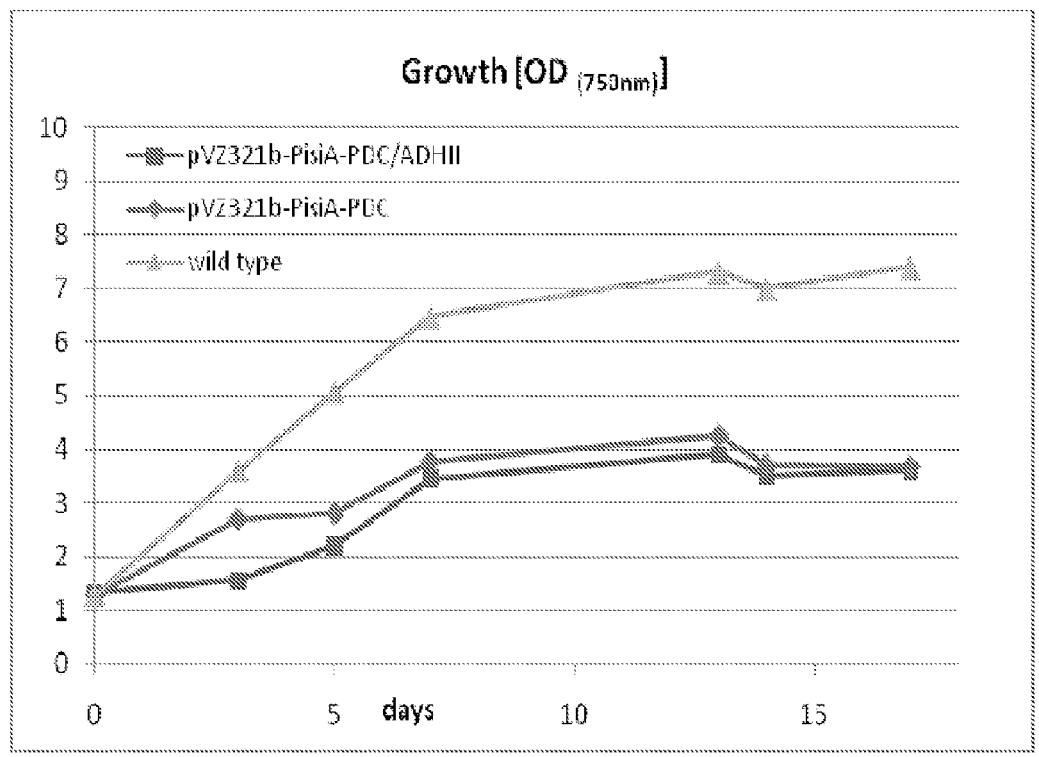
FIG. 12A is a graphic depiction of the OD750 growth properties of Synechocystis wild type and mutants that express Pdc/Adh enzyme and Pdc enzyme alone.
Figure 12B:
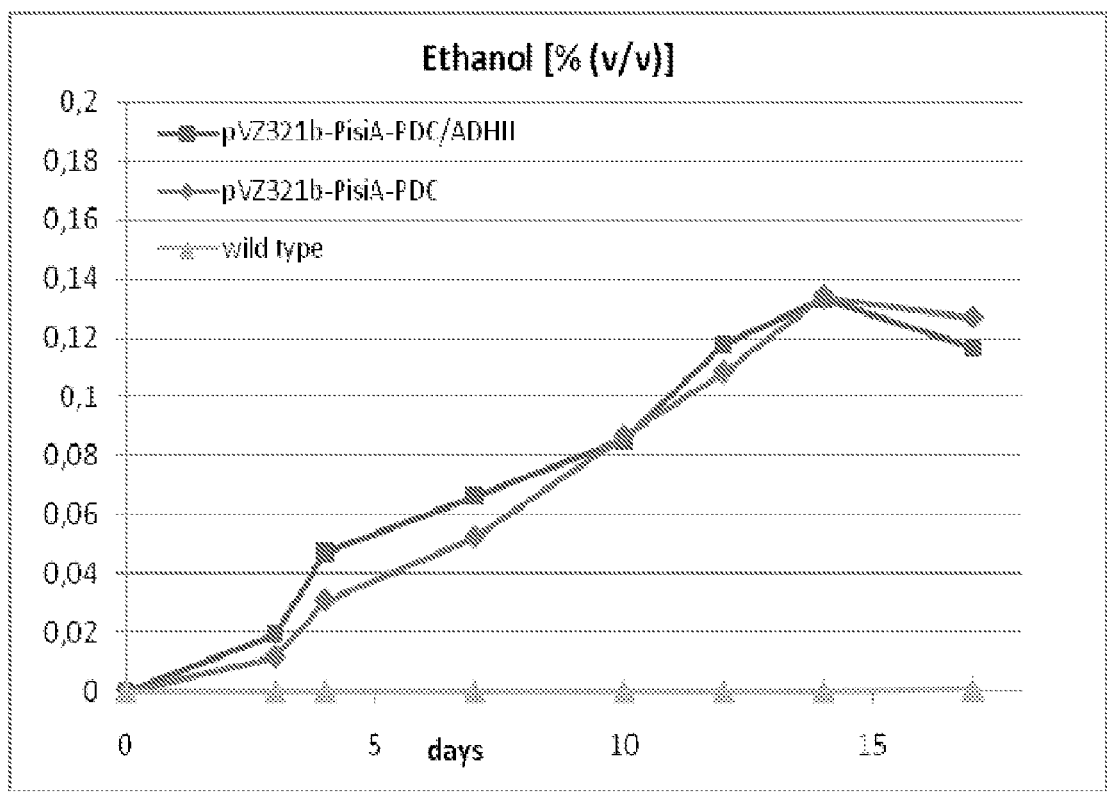
FIG. 12B is a graphic depiction of ethanol production for Synechocystis wild type and mutants that express Pdc/Adh enzyme and Pdc enzyme alone.

The FIGS. 12A and 12B show the growth as determined by measurement of the $OD_{750}$ and ethanol production of *Syn-* echocystis wild type and mutants that express Pdc/Adh enzyme and Pdc enzyme alone, respectively over the time course of 15 days.

Results and Conclusions:

Both ethanol producing mutants, the mutant overexpressing Pdc enzyme alone and the mutant overexpressing Pdc/AdhII grow very similar but show a reduced growth rate when compared to the wild type.

The mutant that expresses the Pdc enzyme alone exhibit about the same ethanol production rate compared to the mutant that co-expresses an additional Adh enzyme with the Pdc enzyme. Thus, the endogenous Adh of *Synechocystis* is able to convert efficiently the generated acetaldehyde produced by the overexpressed Pdc enzyme into ethanol. Under the conditions tested here it seems that no additional Adh enzyme is necessary to produce ethanol in *Synechocystis*. These results further show that the reaction catalyzed by the Pdc enzyme might be the rate limiting step in the ethanol production process.

P.7 Comparison of Ethanol Production Rates of Genetically Modified Photoautotrophic Host Cells Containing *Zymomonas Mobilis* Pdc as the Only Second Genetic Modification with Photoautotrophic Host Cell Harboring Pdc Enzyme in Conjunction with Various Adh Enzymes

*Synechocystis* PCC 6803 transformed with various plasmids harboring either the *Zymomonas mobilis* Pdc enzyme alone or combination with *Zymomonas mobilis* AdhII enzyme or the *Synechocystis* Adh enzyme was cultivated under conditions of $CO_2$ limitation or with sufficient $CO_2$ supply.

The condition of $CO_2$ limitation was created by shaking 50 ml cyanobacterial cultures in 100 ml Erlenmeyer flasks at 28° C. at a rate of 100 rpm. The light intensity was set to $40\,\mu E\,m^{-2}\,s^{-1}$.

The condition of sufficient $CO_2$ supply was created by cultivating cyanobacteria in cooling fingers and subjecting the cultures to a constant gas flow of 0.5% (v/v) of $CO_2$ with a rate of 10 ml/min. The temperature was at 28° C. and the light intensity was set at $100\,\mu E\,m^{-2}\,s^{-1}$.

Figure 12D:
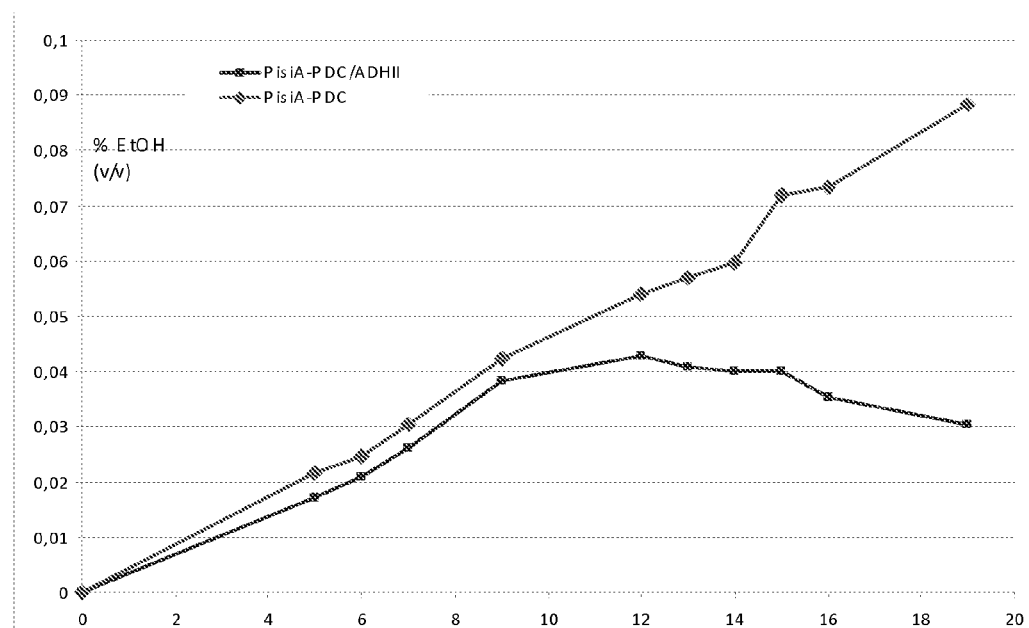
FIG. 12D is a graphical presentation of data for an ethanol concentration time course under limiting CO2 conditions; these data are presented in tabular form in FIG. 12C.
Figure 12F:
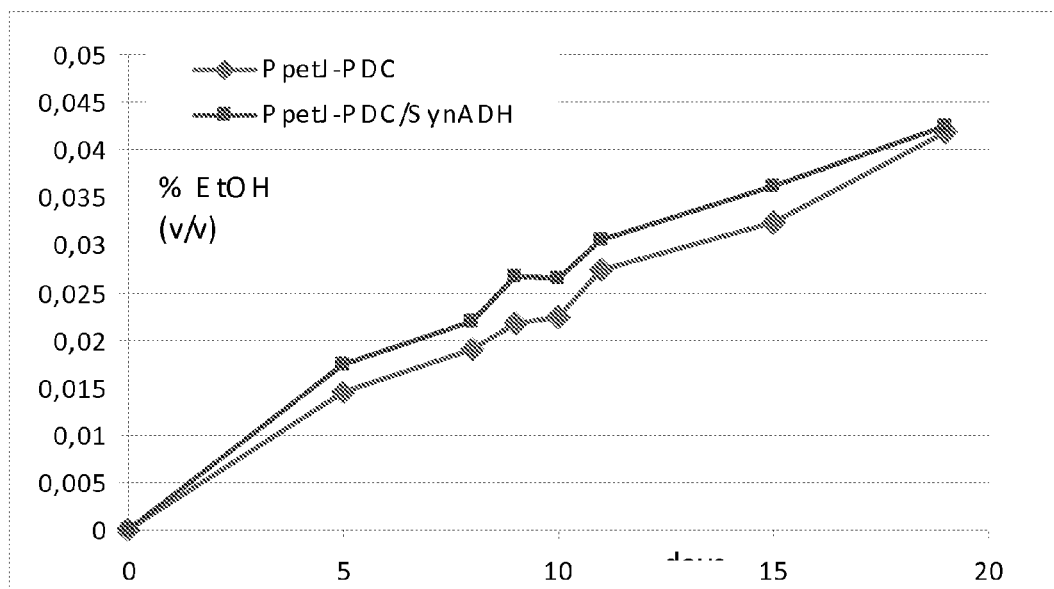
FIG. 12F is a graphical presentation of data for an ethanol concentration time course under limiting CO2 conditions; these data are presented in tabular form in FIG. 12E.

The tables presented in FIG. 12C and FIG. 12E and their respective graphical representations in the FIGS. 12D and 12F, depict the time course of the ethanol concentration in % (v/v) as determined with the enzymatic ethanol quantification methods as described above for various *Synechocystis* cultures transformed with the indicated plasmids and cultured under a condition of $CO_2$ limitation. The data in FIG. 12 reflect ethanol production vs. time. Data pairs reflect (time (in days), ethanol concentration in % (v/v)), for example, for 6803-PisiA-Zm[*Zymomonas*] PDC-ADHII (0, 0), (5, 0.0172), (6, 0.021), (7, 0.026), (8, 0.0384), (12, 0.0429), (13, 0.0407), (14, 0.0401), (15, 0.0401), (16, 0.0354), (17, 0.0304).

These data show that under conditions of $CO_2$ limitation photoautotrophic cyanobacterial host cells transformed with Pdc enzyme only exhibit about the same ethanol production rates as photoautotrophic cells transformed with Pdc in combination with *Synechocystis* Adh enzyme. In contrast to that, photoautotrophic cells transformed with Pdc enzyme in conjunction with *Zymomonas* mobilis AdhII enzyme showed lower ethanol production rates.

Figure 12H:
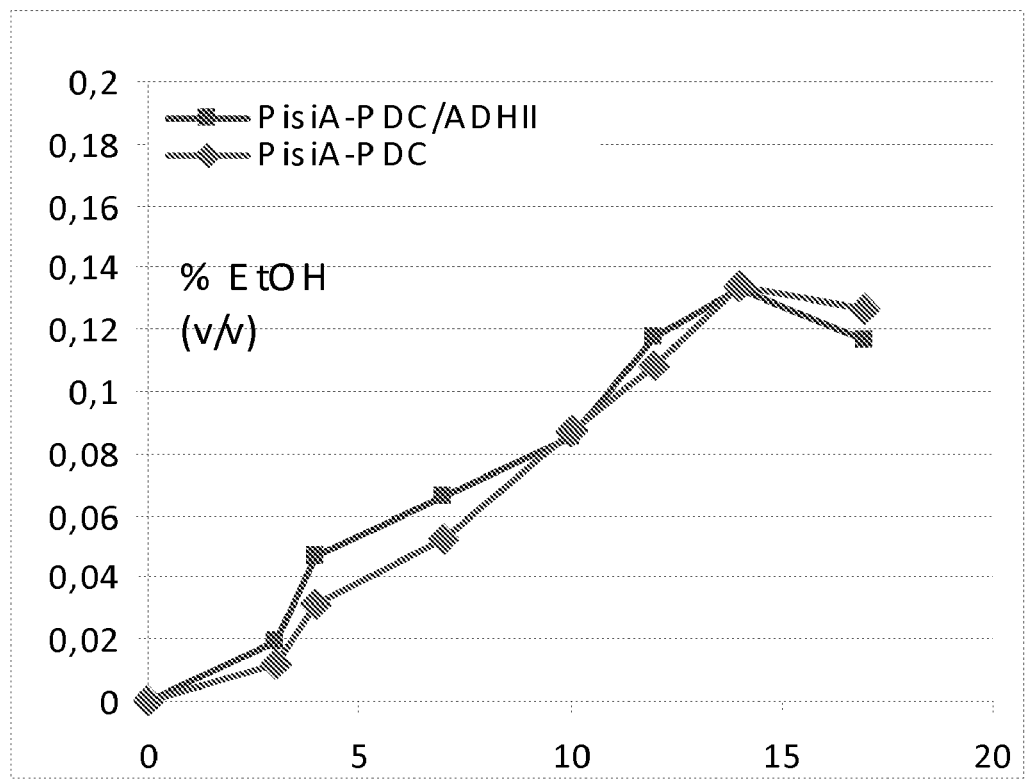
FIG. 12H is a graphical presentation of data for an ethanol concentration time course under limiting CO2 conditions; these data are presented in tabular form in FIG. 12G.
Figure 12J:
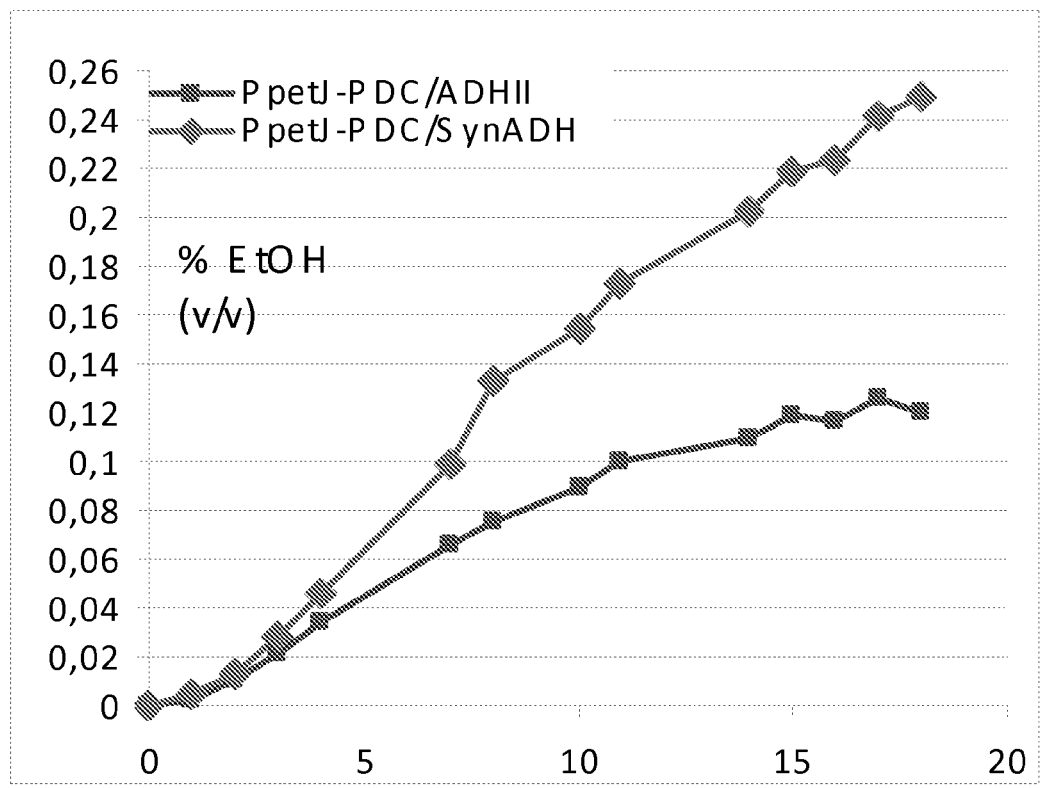
FIG. 12J is a graphical presentation of data for an ethanol concentration time course under limiting CO2 conditions; these data are presented in tabular form in FIG. 12I.
Figure 130:
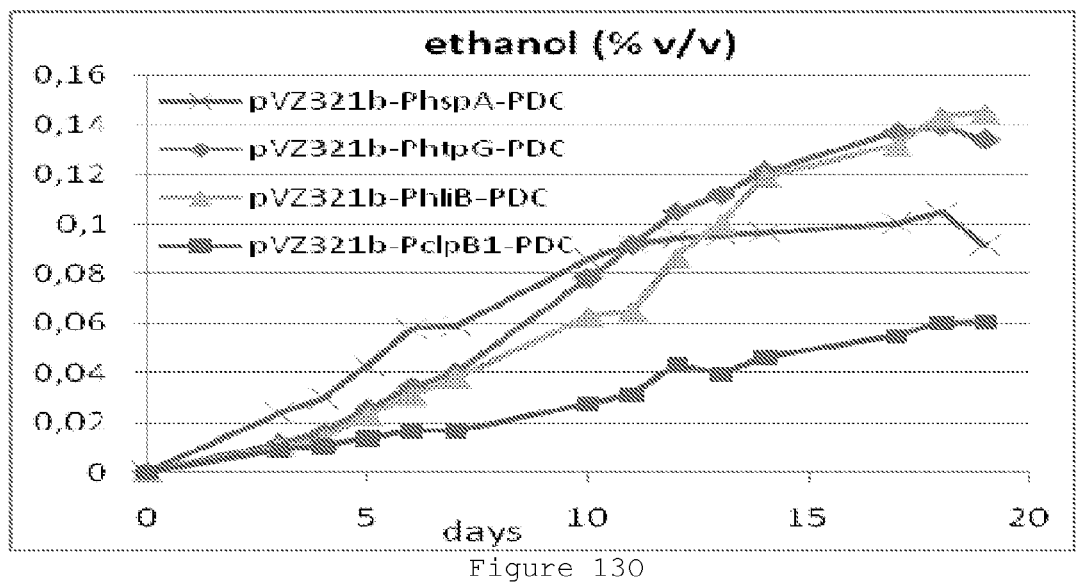

The tables shown in FIGS. 12G and 12I and their respective graphical representations in the FIGS. 12H and 12J, depict the time course of the ethanol concentration in % (v/v) as determined with the enzymatic ethanol quantification methods as described above for various *Synechocystis* cultures transformed with the indicated plasmids and cultured under a condition of sufficient $CO_2$ supply.

These data suggest that at conditions of sufficient $CO_2$ supply photoautotrophic cyanobacterial host cells harboring Pdc only or harboring a combination of Pdc enzyme and *Zymomonas mobilis* AdhII enzyme show comparable ethanol production rates, which are lower than ethanol production rates for photoautotrophic host cells with Pdc enzyme and *Synechocystis* Adh enzyme.

A shorthand representation of the results in FIG. 12 is the following:

Suboptimal conditions of $CO_2$ limitation:

PDC/ADHII<PDC only=PDC/SynADH

Optimal conditions (aerated with 0.5% CO2):

PDC/ADHII=PDC only<PDC/SynADH

P.9 Ethanol Production Rates of Genetically Modified Photoautotrophic Host Cells Containing Ethanologenic Enzymes Under Various Growth Conditions Background:

In order to get an idea about the potential of generated ethanologenic mutants, one ethanol producing mutant was cultivated over a longer time scale. Three different culture conditions were tested regarding the productivity and the duration of the ethanol formation using the cyanobacterium *Synechocystis* sp. PCC6803 that over-expresses the pyruvate decarboxylase from *Zymomonas mobilis* and the endogenous alcohol dehydrogenase.

Growth Conditions:

*Synechocystis* mutant was grown either at 28° C., in continuous light ($150\,\mu E\,m^{-2}\,s^{-1}$) and aerated with $CO_2$-enriched air (0.5% $CO_2$) or in day/night cycles (12 h/12 h) with a temperature cycle (25° C. night/35° C. day) and aerated with 5% $CO_2$. The initial $OD_{750}$ was 3-5 in a total culture volume of either 200 ml (continuous light) or 600 ml (day/night cycle) in bubbled glass vessels. For comparison of the ethanol production rates the mutant was cultivated in freshwater BG11 or in seawater BG11 (without copper). After two weeks of cultivation a nutrient-mix (100-fold BG11-concentrate) was weekly added to assure sufficient supply of nutrients for optimal growth conditions over longer periods of time.

Recipe for 11 Artificial Seawater (28 ppm):

| | |
|---|---|
| NaCl | 28.05 g |
| $MgSO_4$ | 6.90 g |
| $MgCl_2$ | 5.49 g |
| KCl | 0.67 g |
| $CaCl_2$ | 1.47 g |

Results and Conclusions:

Best ethanol production rates were observed for freshwater BG11 medium and continuous light. Cultivation of the mutant in seawater BG11 (mutant was pre-adapted in seawater) leads to a reduction of ethanol production of about 25%. This is probably due to the fact that the energy- and carbon-consuming synthesis of osmo-protectants (like glycosylglycerol), which allows the freshwater strain *Synechocystis* sp. PCC6803 to overcome higher salinities, decreases the availability of fixed carbon (carbohydrates) for the ethanol formation.

Figure 13B:
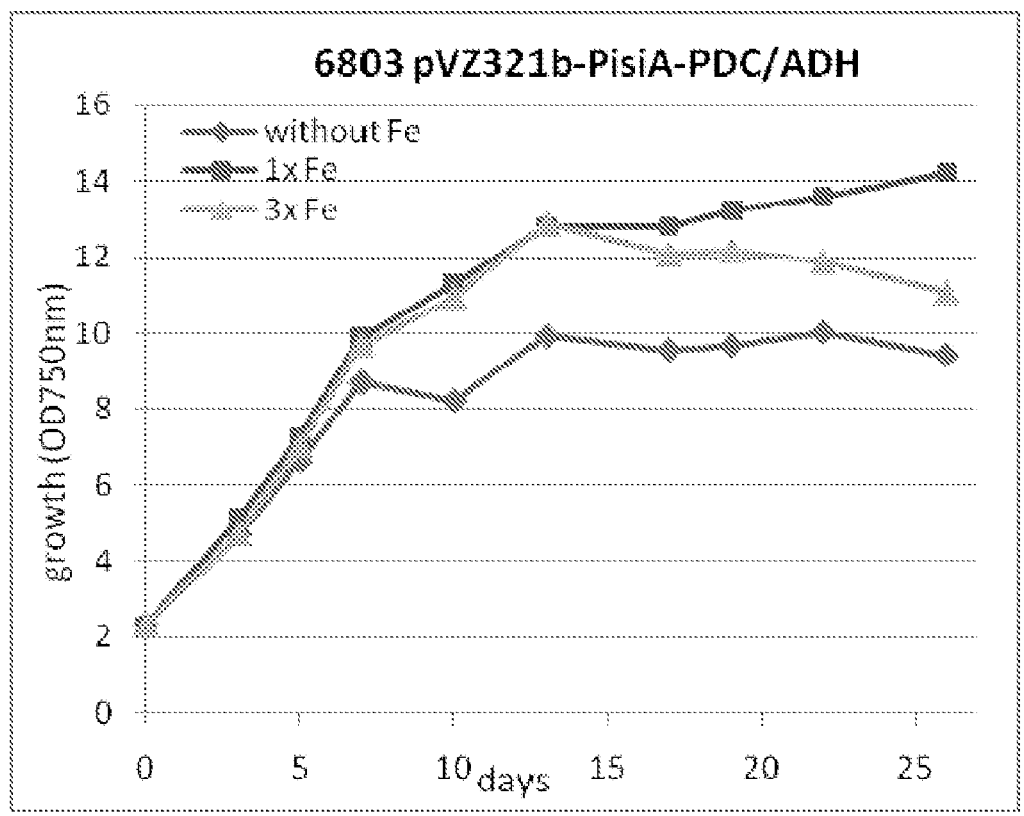
FIG. 13B is a graphic depiction of growth properties of 6803 transformed with pVZ321 b-PisiA-PDC/ADH as monitored by determining the OD750.
Figure 13C:
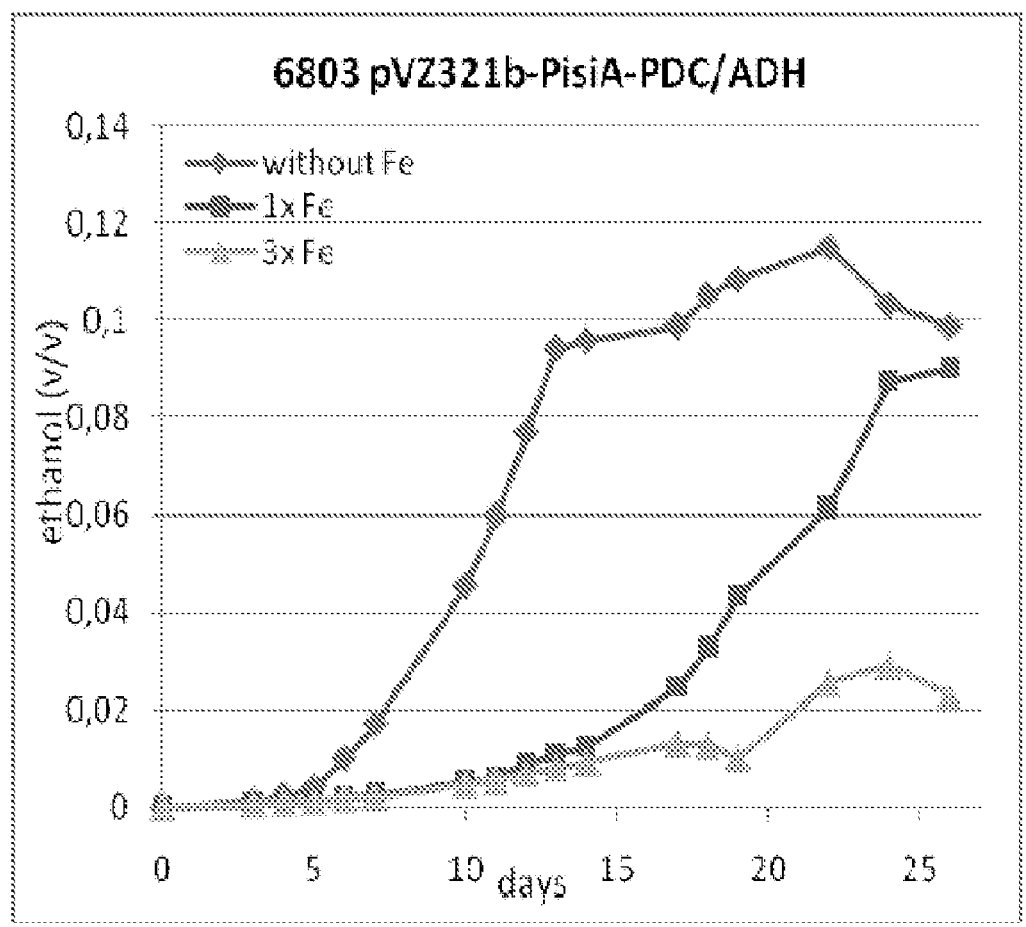
FIG. 13C is a graphic depiction of iron-induced ethanol production of 6803 transformed with pVZ321 b-PisiA-PDC/ADH.
Figure 13D:
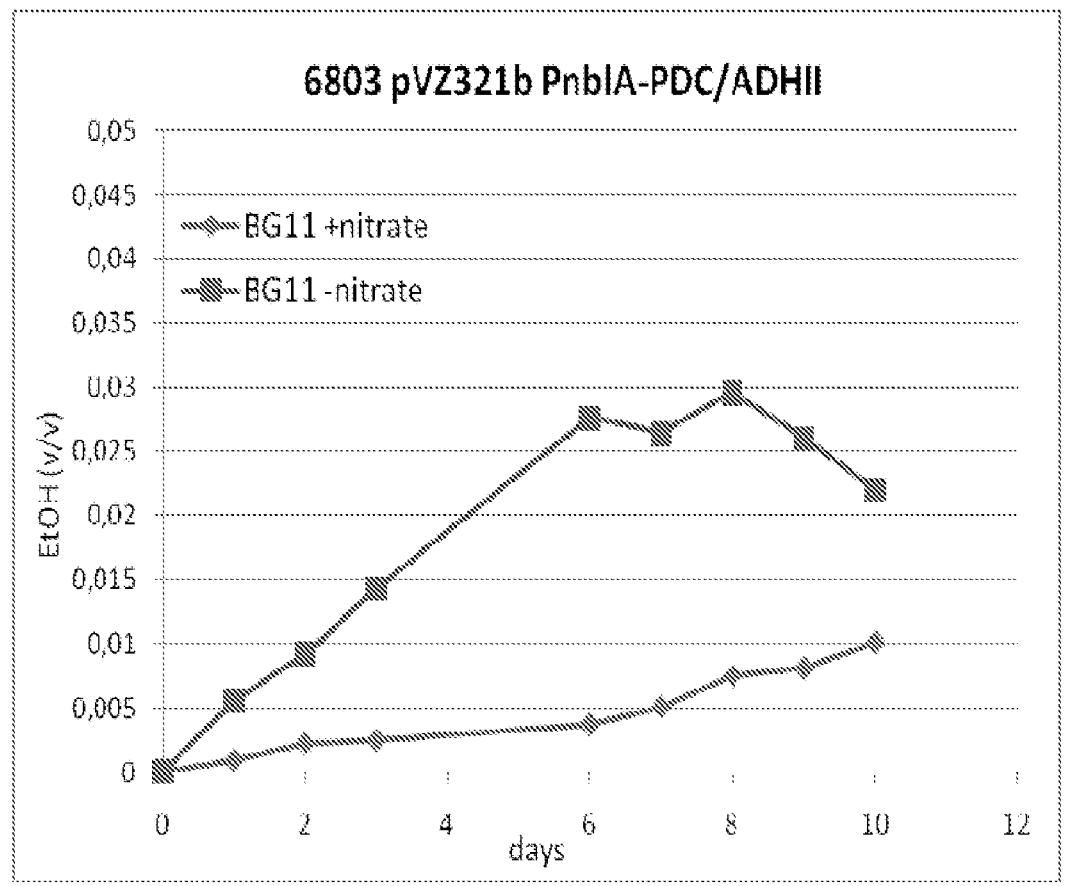
FIG. 13D is a graphic depiction of ethanol production of Synechocystis 6803 pVZ321 b-PnblA-PDC/ADH that express Pdc/Adc enzymes under the control of the nitrogen dependent nblA-promoter.
Figure 13E:
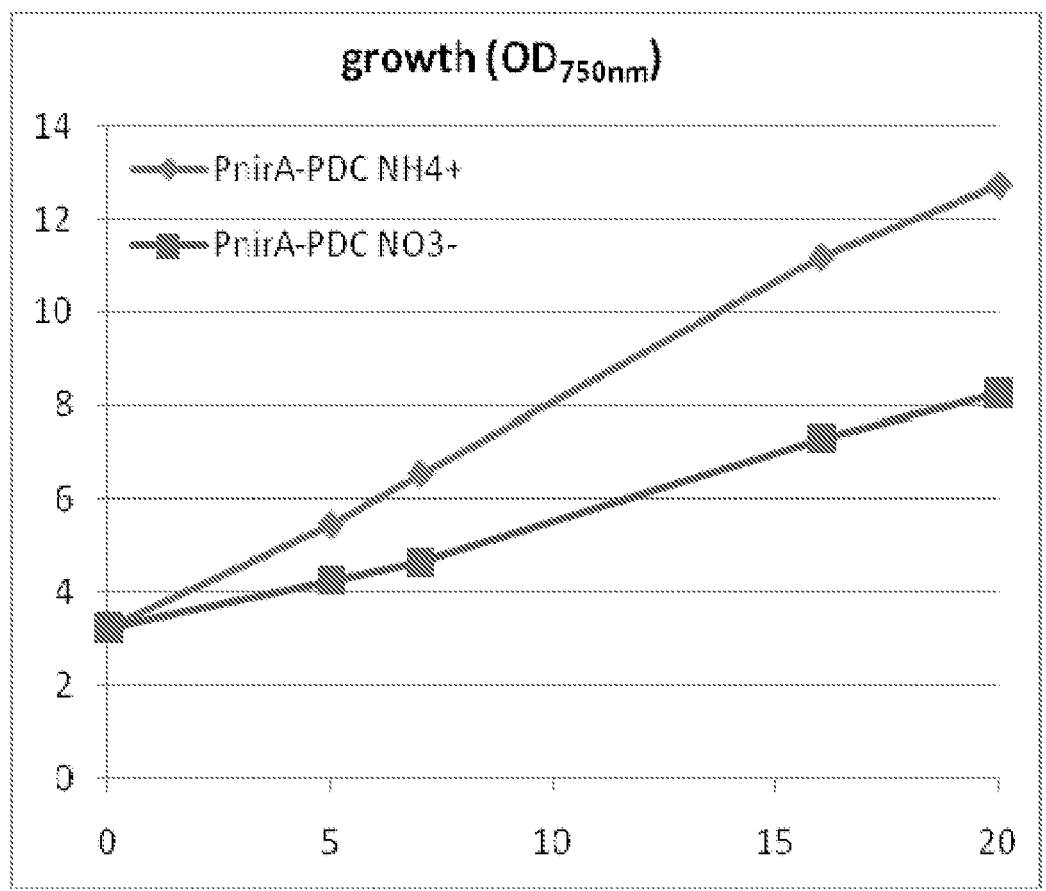
FIG. 13E is a graphic depiction of the growth properties of cells with PnirA-PDC when nitrogen is provided by ammonia or nitrate.
Figure 13F:
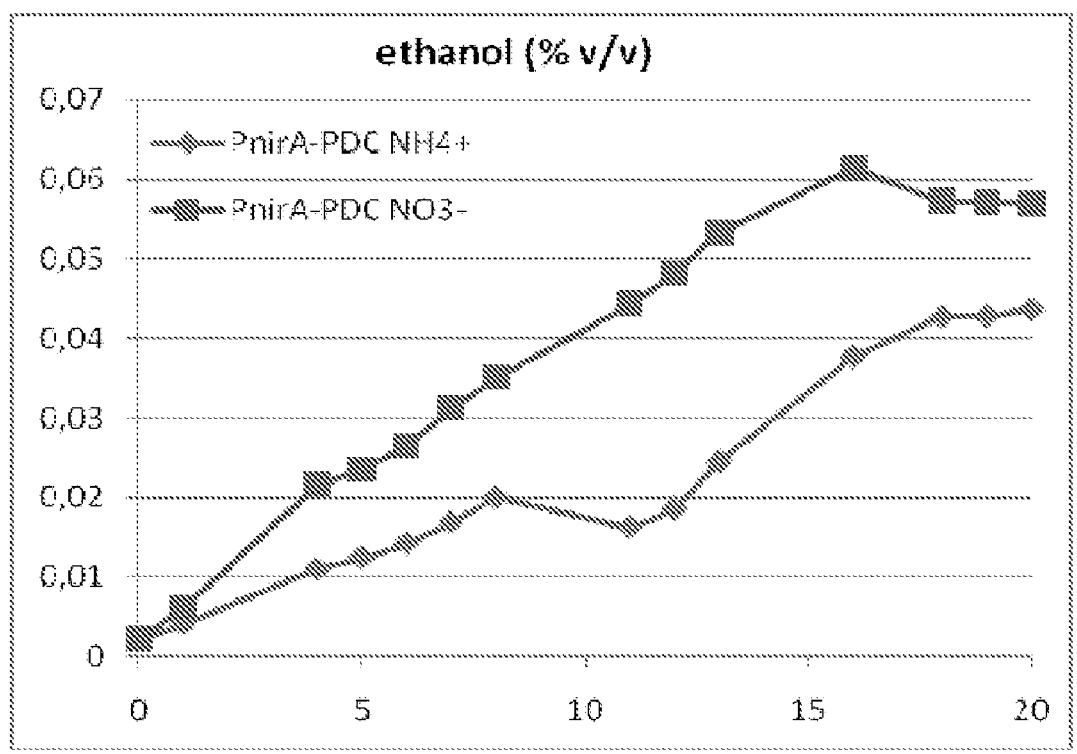
FIG. 13F is a graphic depiction of ethanol production of cells with PnirA-PDC when nitrogen is provided by ammonia or nitrate.
Figure 13G:
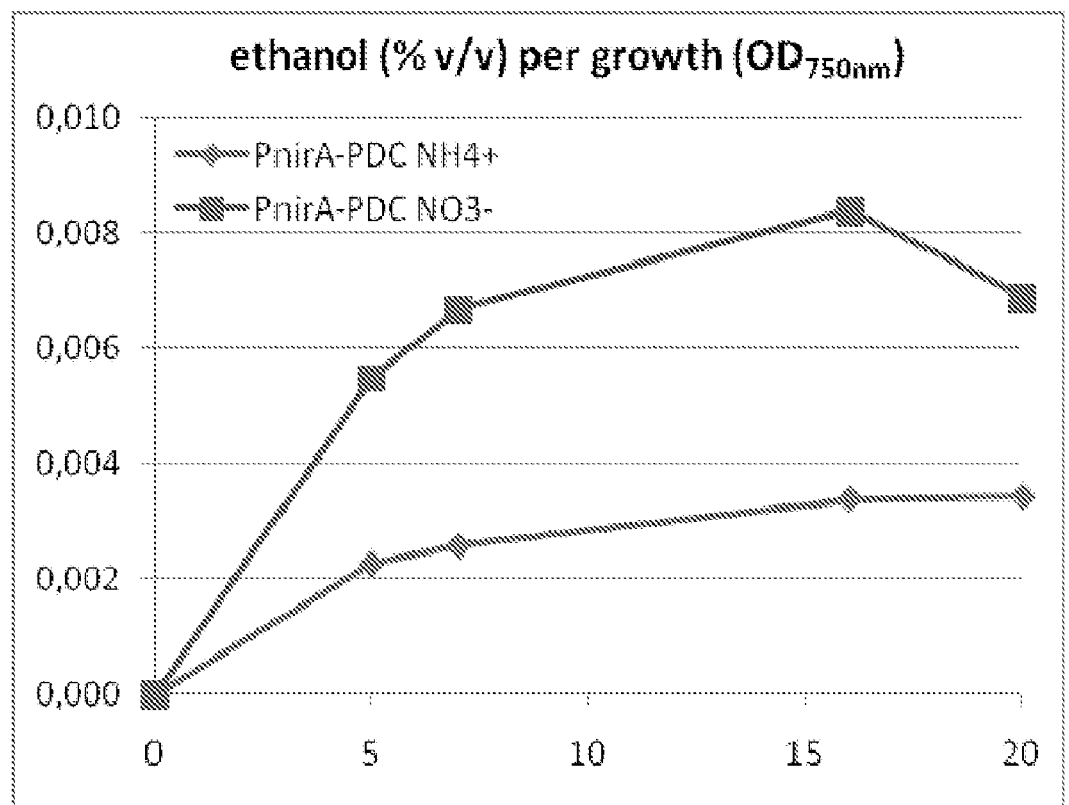
FIG. 13G is a graphic depiction of ethanol production normalized for culture optical density of cells with PnirA-PDC when nitrogen is provided by ammonia or nitrate.
Figure 13H:
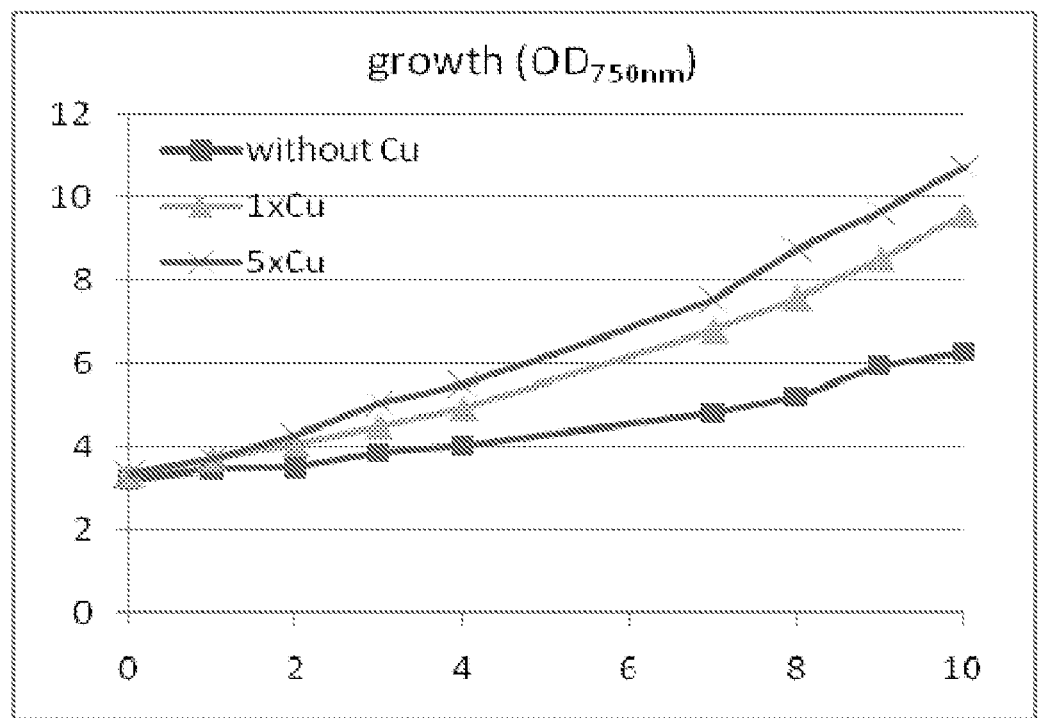
FIG. 13H is a graphic depiction of growth of Synechocystis 6803 pVZ321 b-PpetJ-PDC/ADH.
Figure 13I:
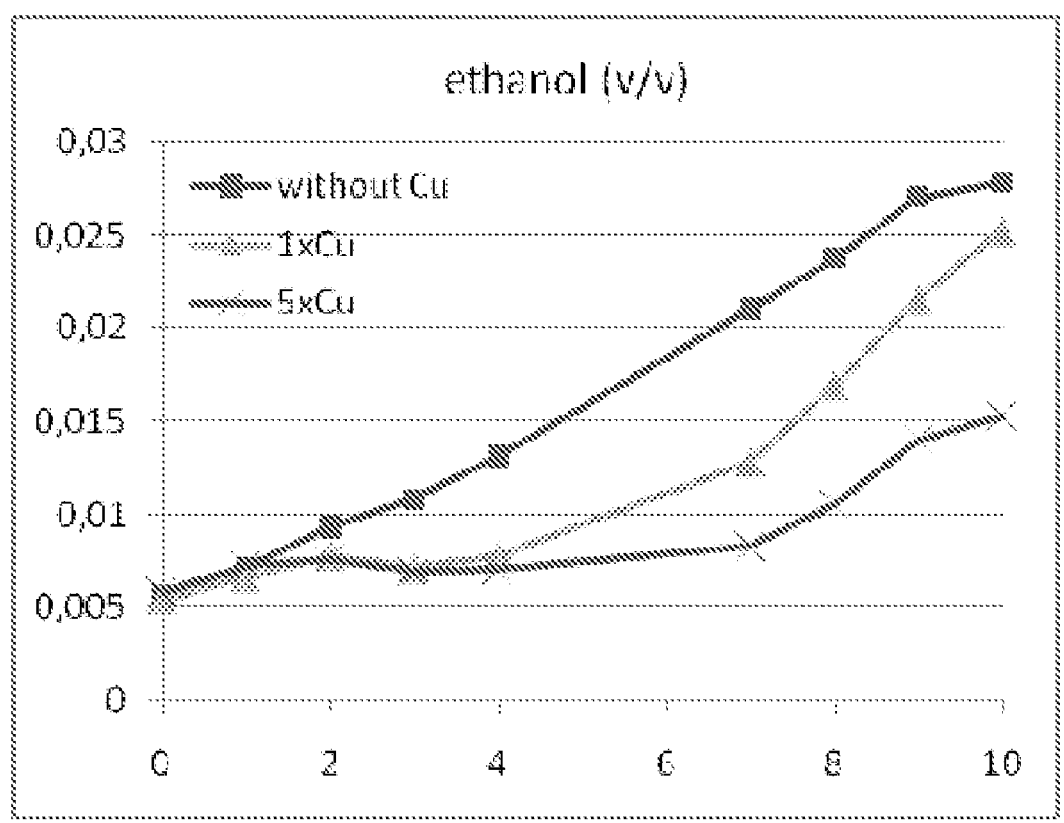
FIG. 13I is a graphic depiction of ethanol production of Synechocystis 6803 pVZ321 b-PpetJ-PDC/ADH.
Figure 13J:
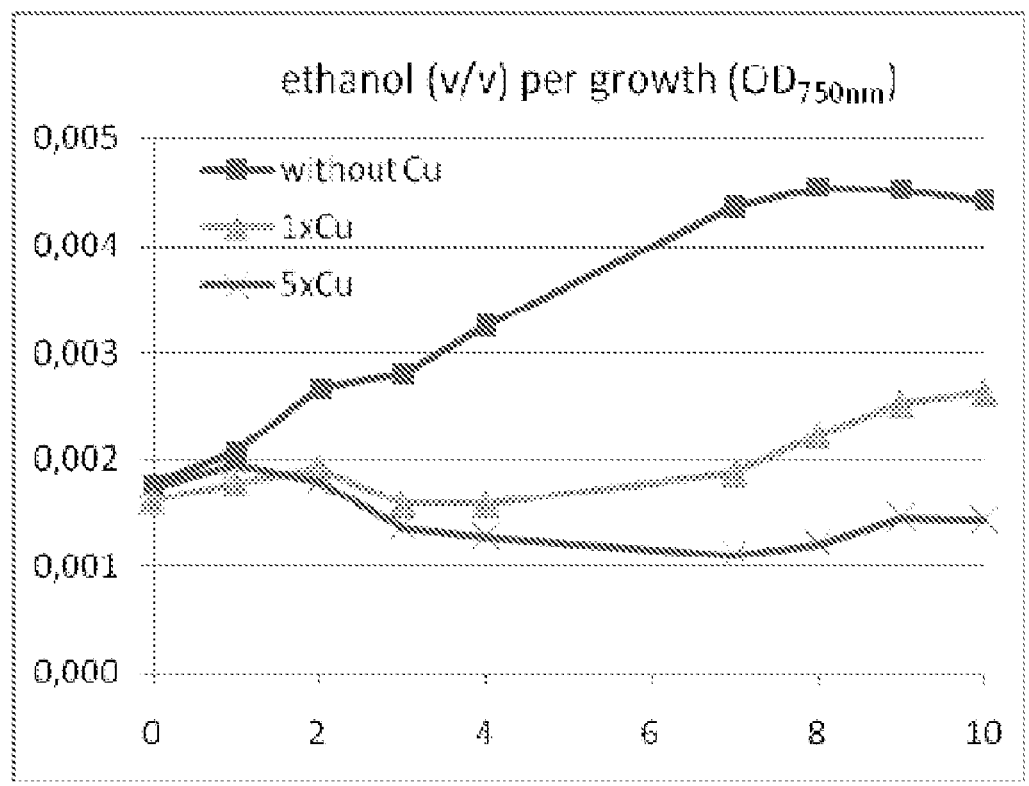
FIG. 13J is a graphic depiction ethanol productivity per growth of Synechocystis 6803 pVZ321 b-PpetJ-PDC/ADH.
Figure 13K:
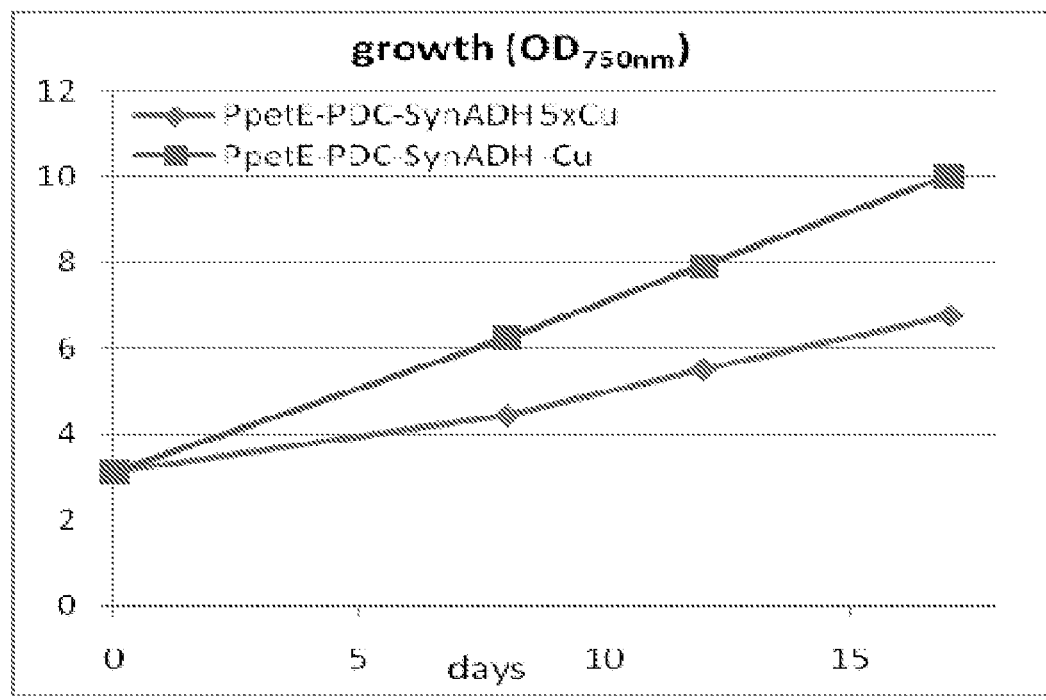
FIG. 13K is a graphic depiction of the growth of Synechocystis 6803 pVZ321 b-PpetE-PDC/ADH.
Figure 13L:
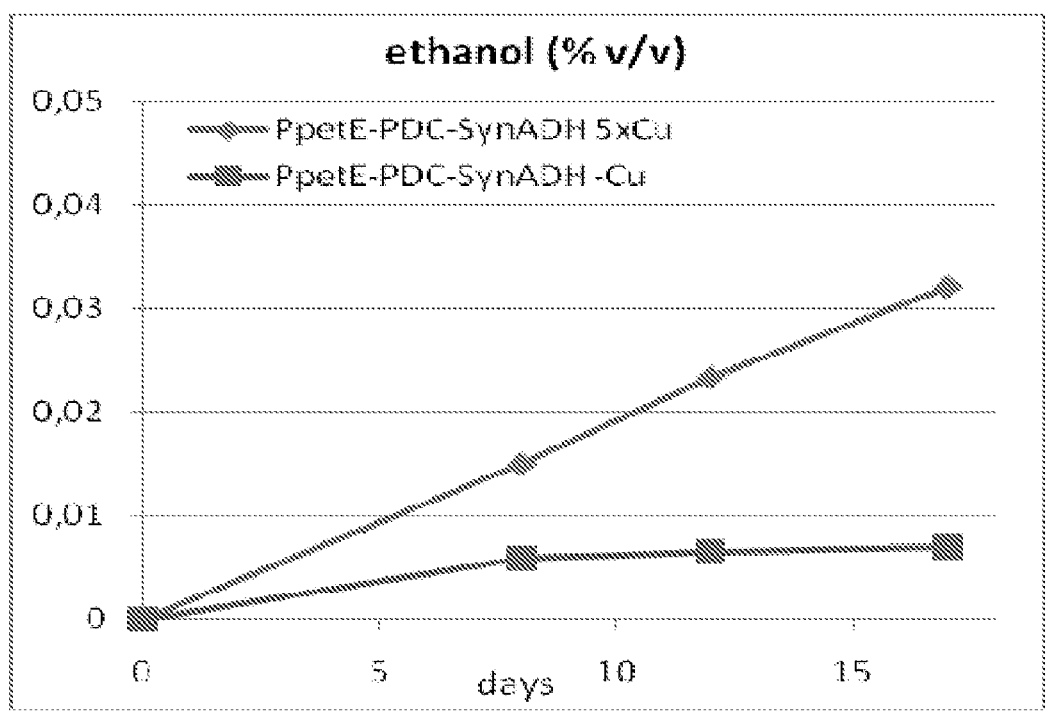
FIG. 13L is a graphic depiction ethanol production of Synechocystis 6803 pVZ321 b-PpetE-PDC/ADH.
Figure 13M:
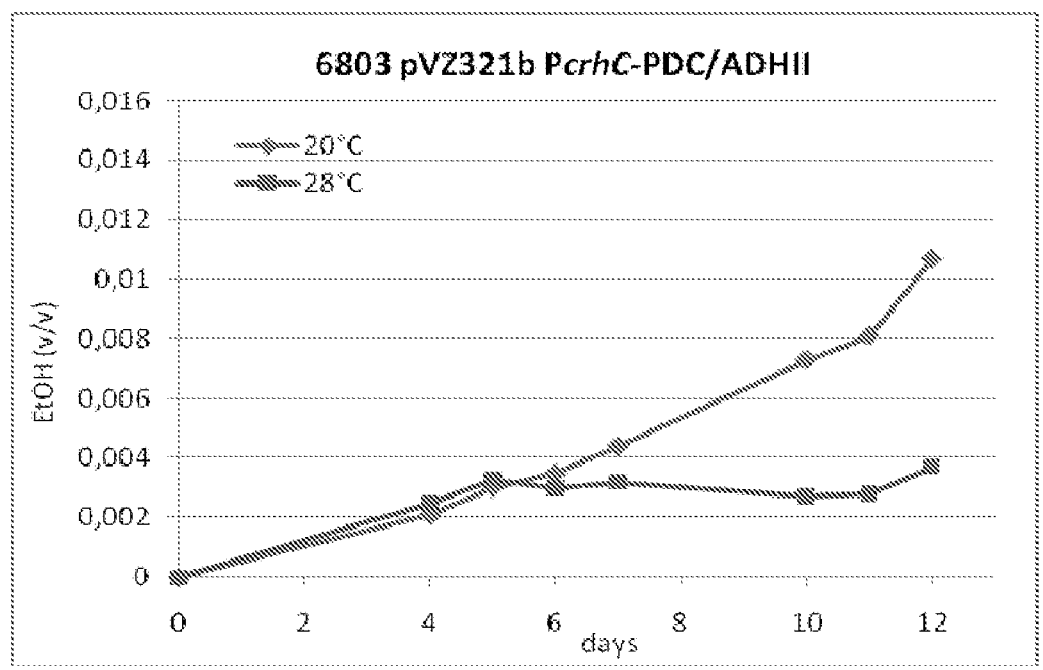
FIG. 13M is a graphic depiction of ethanol production of Synechocystis 6803 pVZ321 b-PcrhC-PDC/ADH.
Figure 13N:
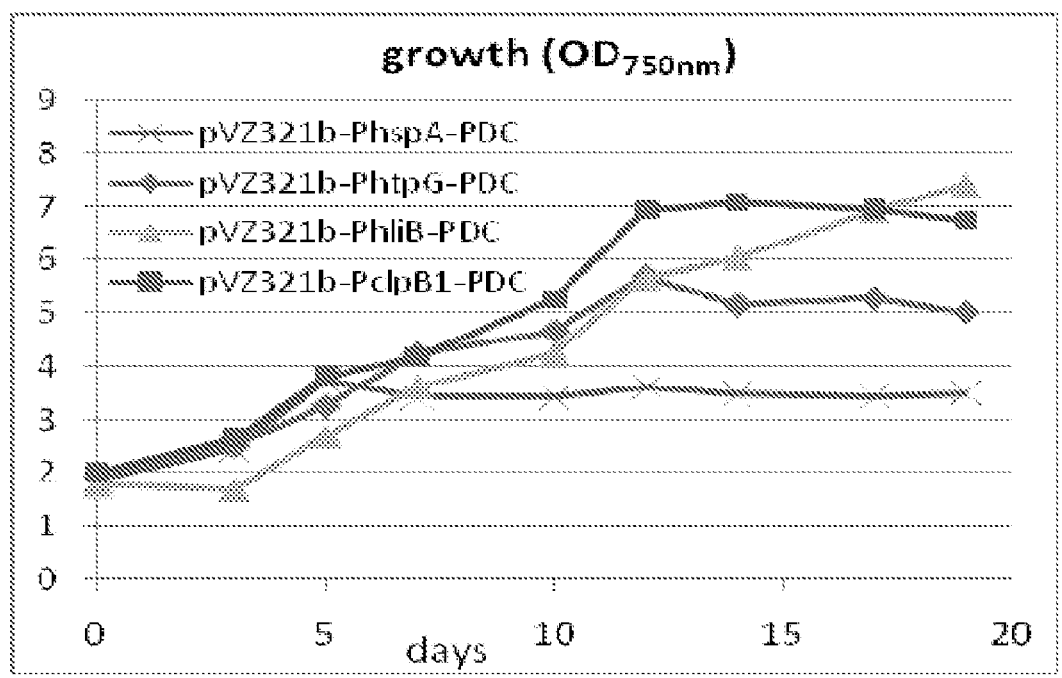
FIG. 13N is a graphic depiction of growth properties of Synechocystis 6803 pVZ321 b-PhspA-PDC, pVZ321 b-PhtpG-PDC, pVZ321 b-PhliB-PDC and pVZ321 b-PclpB1-PDC.
Figure 13P:
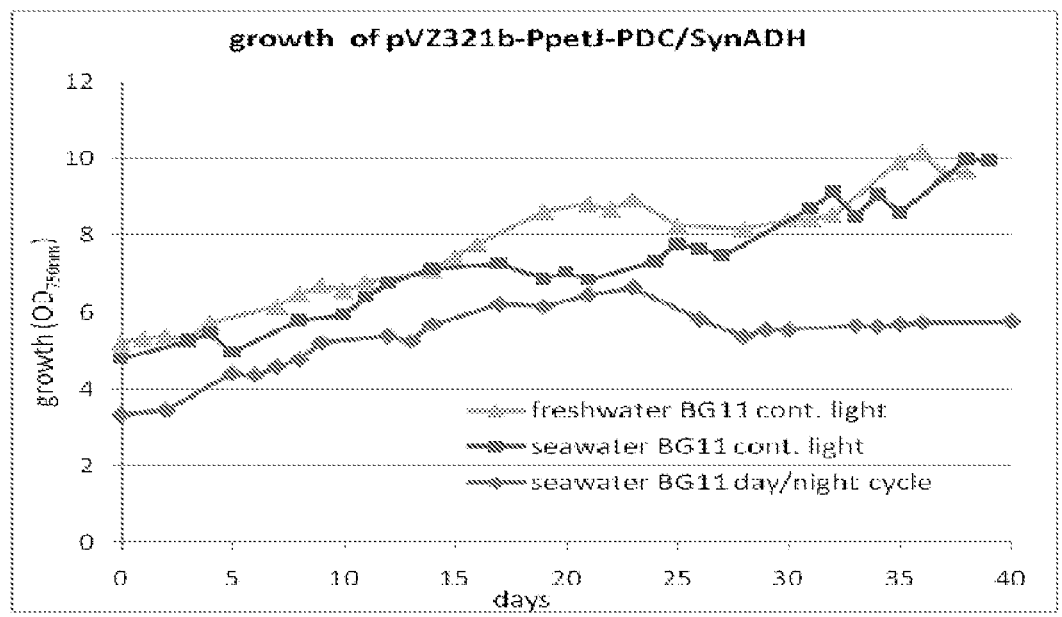
FIG. 13P is a graphic presentation of growth properties under different conditions of cells containing pVZ321 b-PpetJ-PDC/SynADH.
Figure 13Q:
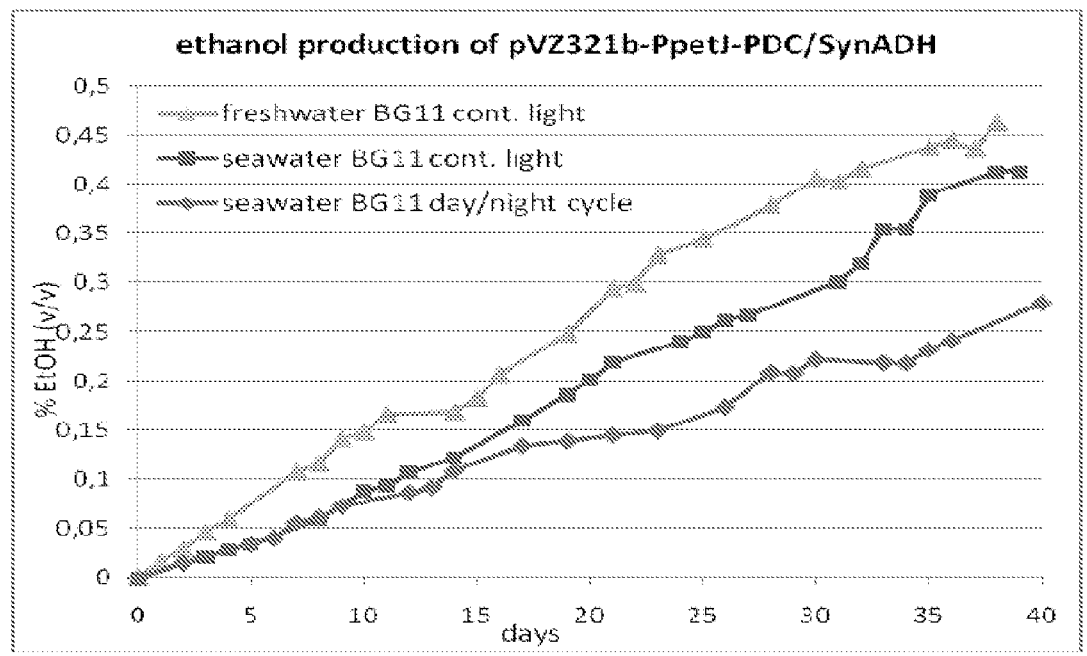
FIG. 13Q is a graphic presentation of ethanol production under different growth conditions of cells containing pVZ321b-PpetJ-PDC/SynADH.
Figure 13R:
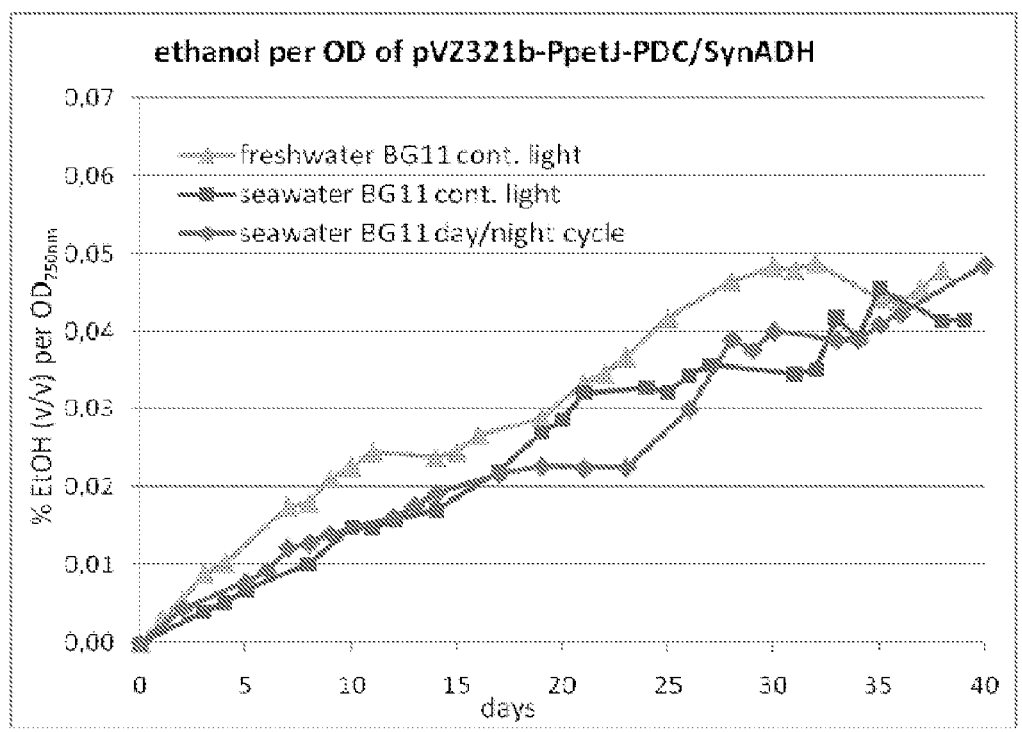
FIG. 13R is a graphic presentation of ethanol production per OD under different growth conditions of cells containing pVZ321 b-PpetJ-PDC/SynADH.

When the mutant was cultivated under day/night cycles with a temperature gradient that simulates the conditions of an outdoor production facility, the ethanol production and the growth rate was reduced compared to the continuous light conditions (FIGS. 13P, 13Q and 13R). That is not surprising because carbon fixation, that is necessary for growth and ethanol production occurs only during the light phase. Thus both, ethanol production and biomass production are reduced when cultivated in day/night cycles.

If the ethanol production is normalized to the optical density (as an indicator for growth) the productivity for each of the cultivation conditions appears relatively similar (FIG. 13R). That means the fraction of fixed carbon that flows into the ethanol branch is relatively constant despite the different growth conditions (see Tab. 1).

TABLE 1

Ethanol production rates of *Synechocystis* sp. PCC6803 pVZ321b-PpetJ-PDC/SynADH at different growth conditions.

| pVZ321b-PpetJ-PDC/SynADH after 38 days | EtOH % (v/v) | EtOH/day % (v/v) | EtOH/OD$_{750\,nm}$ % (v/v) | EtOH/OD$_{750\,nm}$*day % (v/v) |
|---|---|---|---|---|
| freshwater, contin. light | 0.46 | 0.0126 | 0.0479 | 0.00126 |
| seawater, contin. light | 0.41 | 0.0108 | 0.0413 | 0.00109 |
| seawater, day/night cycle | 0.26 | 0.0068 | 0.0450 | 0.00118 |

Detailed Description of Embodiments Related to Adding a Substrate to the Growth Medium of a Growing Culture, which is Used by the at Least One Overexpressed Enzyme for Ethanol Formation to Produce Ethanol:

Effect of Acetaldehyde on Ethanol Production by Cyanobacteria

Background: The bottle neck of the ethanol formation in the metabolism of our transgenic cyanobacteria has not been detected. Addition of pyruvate and 3-PGA to cyanobacteria expressing Pdc and Adh did not result in an increased ethanol production, but according to our experiments this metabolites of glycolysis were not absorbed by the cells. We now performed feeding experiments with acetaldehyde. The goal was to elucidate whether the ethanol production is limited solely by this immediate ethanol precursor, or by other factors, i.e. the availability of reduced co-substrates (NADH and/or NADPH).

Methods: *Synechocystis* PCC 6803 wild type and the transgenic strain "6803-pVZ-PisiA", corresponding to the above described *Synechocystis* pVZ-PisiA-Pdc-AdhII, were washed twice with BG11 (centrifugation 15 min, 4500 rpm, 4° C.; Rotina 420R, Hettich) and redissolved in BG11. Aliquots of 2 ml were spiked with acetaldehyde. The assays were incubated at room temperature under illumination. Samples of 250 µl were removed in defined time intervals (5 min or 10 min) and centrifuged (3 min, 14000 rpm, room temperature, Micro 200R, Hettich). The supernatants were stored at −70° C., subsequently the ethanol content was measured.

Ethanol was quantified with a described protocol. The method is based on oxidation of ethanol catalyzed by alcohol dehydrogenase (Sigma, Adh of *S. cerevisiae*). NADH formed in this reaction, reacts with the PMS/MTT reagent to a dye. Its absorption (measured at 580 nm) is proportionate to the ethanol content of a sample.

Principle of Ethanol Quantification:

Ethanol is oxidized by nicotinamide-adenine dinucleotide (NAD$^+$) to acetaldehyde in a reaction, which is catalyzed by the enzyme alcohol dehydrogenase (ADH) (reaction 1). The acetaldehyde, which is formed in the reaction, is quantitatively oxidized to acetic acid by the enzyme aldehyde dehydrogenase (Al-DH) (reaction 2).

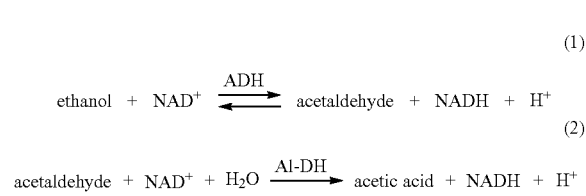

In reactions (1) and (2) reduced nicotinamide-adenine dinucleotide (NADH) is formed. The amount of NADH formed is proportionate to the amount of ethanol in the sample. NADH is easily quantified by means of its light absorbance. The absorbance is usually measured at 340 nm, Hg 365 nm or Hg 334 nm.

Procedure:

Preparation of solutions: Solution 1: 1.3 mg/ml NAD and 0.27 U aldehyde dehydrogenase in potassium diphosphate buffer, pH 9.0. Solution 2: Suspension of alcohol dehydrogenase (ADH) with approx. 4000 U/ml. Alternatively, the chemicals and solutions of the ethanol determination kit of Boehringer Mannheim/R-Biopharm (Cat. No. 10 176 290 035) can be used.

Sample and solution 1 are mixed in a ratio of 3 ml solution 1 and 0.1 ml sample (if necessary the sample is diluted with water). After approx. 3 min the absorbance is measured ($A_1$). The reaction is then started by the addition of ADH suspension (solution 2, 0.050 ml for 3 ml solution 1 and 0.1 ml sample). After completion of the reaction (approx. 5 to 10 min) the absorbance is measured again ($A_2$). The absorption measurements can be performed using a photometer or a microplate reader. For plate reader measurements all volumes are downscaled.

From the measured absorbance difference $\Delta A = (A_2 - A_1)$ the ethanol concentration in the sample is calculated with the equation:

$$c = \frac{V \times MG}{\varepsilon \times d \times v \times 2 \times 1000} \times \Delta A$$

c, ethanol concentration [g/L]; V, total volume [mL]; MG, molecular weight of ethanol (46.07 g/mol); e, extinction coefficient (6.3 L×mmol$^{-1}$×cm$^{-1}$ at 340 nm); d, light path [cm]; v, sample volume [mL]

Literature:

Protocol of the kit Ethanol, UV method for the determination of ethanol in foodstuff and other materials, Cat. No. 10176290035, R-Biopharm AG, Darmstadt, Germany.

H.-O. Beutler (1984) in: Methods in Enzymatic Analysis (Bergmeyer, H. U. ed.) 3$^{rd}$ ed. Vol. VI, pp. 598-606, Verlag Chemie, Weinheim, Germany.

Acetaldehyde was quantified by a modification of the protocol of a kit for ethanol quantification (Ethanol kit, R-Biopharm AG). Acetaldehyde is converted by aldehyde dehydrogenase under formation of NADH, which is quantified by its absorption at 340 nm. The amount is proportionate to the acetaldehyde content of the sample.

For preparation of crude extracts, cells were harvested, washed with 40 mM MES/Tris (pH 6.5), 1 mM DTT and broken (beadbeater, 2×10 min). The supernatant of a centrifugation (15 min, 14000 rpm, 4° C., Micro 200R, Hettich) was used for the determination of Adh activity in cells.

Assays for measurement of the Adh activity in the direction of ethanol formation contained in a total volume of 800 µl 40 mM MES adjusted with Tris base to pH 6.5, 1 mM DTT, different concentrations of acetaldehyde, 50 µl crude extract and 0.3 M NADH. The initial velocity was calculated from the dE/min at 340 nm.

Results: Addition of acetaldehyde to final concentrations in the range of 6.6 µM to 200 µM resulted in an increase of ethanol in the medium of cultures of the transgenic strain 6803-pVZ-PisiA. The rates of ethanol production per minute were linear at the beginning of the experiment (for at least 30 min), but finally decelerated, obviously because of the expiration of the supply of acetaldehyde (FIG. 14A).

In FIG. 14A, ethanol production is measured after addition of acetaldehyde. Different concentrations were added to a culture of strain 6803pVZPisiA and the ethanol content in the medium was measured for 60 minutes.

A plot of the initial velocity of the ethanol production versus the substrate concentration resulted in a graph similar to the substrate saturation curves of enzymes with Michaelis-Menten kinetics (FIG. 14B). $K_m$ and $V_{max}$ were calculated from a "Lineweaver-Burk" plot (1/v versus 1/[S]; FIG. 6) with $K_m$ for acetaldehyde=18 µM and $V_{max}$=3.2 µMol $L^{-1}$ $min^{-1}$. $OD_{750}$ of the culture was 0.56.

FIG. 14B presents a correlation of ethanol production rate and acetaldehyde concentration. Given are the initial ethanol rates (calculated with FIG. 4) in correlation to the initial acetaldehyde concentrations.

FIG. 14C presents a Lineweaver-Burk-Plot. Reciprocal of the initial velocity versus the reciprocal of the acetaldehyde concentration. Intact cells were used.

This experiment was repeated with a different culture of strain 6803-pVZ-PisiA of $OD_{750}$ of 1.353 and a chlorophyll concentration of 4.6 µg/ml. Similar results were obtained. The $K_m$ for acetaldehyde was calculated with 25 µM (FIG. 14D). $V_{max}$ was 4.35 µMol $L^{-1}$ $min^{-1}$, or 0.95 µMol $L^{-1}$ $mg^{-1}$ using chlorophyll as reference.

FIG. 14D presents a Lineweaver-Burk-Plot in which the reciprocal of the initial velocity versus the reciprocal of the acetaldehyde concentration. The results shown are from a repeat of the experiment with intact cells summarized in FIG. 14A to 14C.

In order to compare the dates acquired with intact cells, the kinetic constants of alcohol dehydrogenase in crude extracts of strain 6803-pVZ-PisiA were measured. The measurements were carried out in the direction of ethanol formation at pH 6.5, following a protocol in the literature. A graphical representation of the results obtained is given in form of a "Lineweaver-Burk" plot (FIG. 8). The $K_m$ for acetaldehyde was calculated with 45 µM and $V_{max}$ was 7.2 µMol $L^{-1}$ $mg^{-1}$ chlorophyll.

In a second experiment the Adh activity was measured at pH 7.5. NADH and NADPH were used as co-substrates. Activity was not significantly different for NADH and NADPH in the concentrations used (NADH 0.25 M, NADPH 0.21 M final concentration). The $V_{max}$ was calculated with 0.89 µMol $L^{-1}$ $mg^{-1}$ chlorophyll, the $K_m$ for acetaldehyde was determined in this experiment with 100 µM (FIG. 9).

FIG. 14E presents a Lineweaver-Burk-Plot In which Adh activities of a crude extract of strain 6803PVZPisiA were measured in presence of different concentration of acetaldehyde.

In contrast to the experiments with intact cells in this experiment NADH was added in excess. Shown is the reciprocal of the initial velocity versus reciprocal of the concentration of acetaldehyde.

FIG. 14F is a Lineweaver-Burk-Plot. Similar to the experiment summarized in FIG. 14E Adh activities of a crude extract of strain 6803PVZPisiA were measured in the presence of different concentrations of acetaldehyde. The assays contained an over excess either of NADH or of NADPH. Substantial differences between NADH and NADPH were not observed.

Summary: Acetaldehyde added to the medium is absorbed and converted into ethanol by intact cells. The $K_m$ for acetaldehyde of the entire process of uptake and ethanol formation was determined with approx. 20 to 25 µM. This value is similar to the $K_m$ for acetaldehyde of the purified AHDII of Z. mobilis, measured at pH 6.5. The correlation of the rate of ethanol formation and the acetaldehyde concentration clearly shows that the ethanol formation is to a larger extent limited by the availability acetaldehyde. Maximum ethanol formation rates were obtained with 200 µM acetaldehyde. When acetaldehyde was added in significant higher concentration, we tested the range of 1 mM to 10 mM, a decrease of ethanol formation was observed. It is assumed, that the acetaldehyde, which is very reactive, is in higher concentrations rapidly poisoning the cells.

Listing of Embodiments

An embodiment of the invention provides a genetically modified photoautotrophic, ethanol producing host cell comprising:
   an overexpressed pyruvate decarboxylase converting pyruvate to acetaldehyde, and
   an overexpressed zinc-dependent alcohol dehydrogenase, converting acetaldehyde to ethanol.

Pyruvate decarboxylase as well as the alcohol dehydrogenase can be heterologously or endogenously overexpressed which means that they can already be present in an unmodified wild type host cell or be introduced as a heterologous enzyme which naturally only occurs in a different host cell into the genetically modified host cell of this embodiment of the invention. Zinc-dependent alcohol dehydrogenases are much more oxygen-insensitive than iron-dependent alcohol dehydrogenases which can result in a higher activity of Zinc-dependent alcohol dehydrogenases.

Furthermore experimental data show that the Adh enzyme from Synechocystis is a member of the $Zn^{2+}$-binding GroES-like domain alcohol dehydrogenase phylogenetic family and does not catalyze the disadvantageous back-reaction, the oxidation of the formed ethanol back into acetaldehyde or only catalyzes this reaction to a very small extent. This results in a higher ethanol production rate and in addition in a higher growth rate of the genetically modified cells compared to genetically modified cells containing an Adh enzyme, which also catalyzes the oxidation of ethanol back to acetaldehyde, such as AdhI or Adh II from Zymomonas mobilis. In our phylogenetic analysis, subclade B, which includes the Adh enzyme from Synechocystis, also includes Adh not from cyanobacteria.

In a further embodiment of this invention based on phylogenetic analysis, the $Zn^{2+}$ dependent alcohol dehydrogenase enzyme is therefore selected from a group consisting of the sub-clades A, sub-clades B and sub-clades C of the Zinc-binding GroES-like domain alcohol dehydrogenases as described in the analysis below. In particular the Adh enzyme from Synechocystis is a member of the sub-clade B of the GroES-like domain alcohol dehydrogenases clade (see FIG. 11A. Sub-clade B comprises SEQ ID 16-22.). The $Zn^{2+}$ dependent alcohol dehydrogenase enzyme can furthermore be selected from a cyanobacterial $Zn^{2+}$ dependent alcohol dehydrogenase enzyme. In yet another embodiment of the invention the Zn dependent alcohol dehydrogenase enzyme has at least 60%, preferred at least 70% or 80% or most preferred 90% sequence identity to the amino acid sequence of *Synechocystis* Adh.

Genetically modified photoautotrophic, ethanol producing host cells comprising an overexpressed pyruvate decarboxylase converting pyruvate to acetaldehyde, and an overexpressed zinc-dependent alcohol dehydrogenase, converting acetaldehyde to ethanol can reach the following high ethanol production rates under continuous exposure to light for 24 hours a day (rates in % EtOH (v/v)):

Over a period of 10 days a daily production of 0.005 can be reached, more preferred 0.01% per day and most preferred 0.02% per day. One example is a photoautotrophic cyanobacterial host cell such as *Synechocystis*, which is transformed with the integrative construct pSK10-PisiA-PDC-ADHII. If normalized to $OD_{750\,nm}$ 1, a rate of 0.0032% EtOH (v/v) per OD1 and day can be reached.

Over a period of 25 days a daily production of 0.005 can be reached, more preferred 0.01% per day and most preferred 0.015% per day by using a photoautotrophic cyanobacterial host cell such as *Synechocystis* transformed with the self-replicating construct pVZ-PnirA-PDC-SynADH. If normalized to $OD_{750\,nm}$ 1, a rate of 0.0018% EtOH (v/v) per OD1 and day can be achieved.

Over a period of 40 day a daily production of 0.004 can be reached, more preferred 0.008% per day and most preferred 0.012% per day for a photoautotrophic cyanobacterial host cell transformed with the self-replicating construct pVZ-PpetJ-PDC-SynADH). If normalized to $OD_{750\,nm}$ 1, a rate of 0.0013% EtOH (v/v) per OD1 and day can be reached.

The following ethanol production rates can be reached for photoautotrophic cyanobacterial host cells under 12 hours light/12 hours dark cycle (day/night cycle) in % EtOH (v/v):

Over a period of few hours (3-4 hours) a daily production of 0.008 is reached, more preferred 0.016% per day and most preferred 0.024% per day. These ethanol production rates can be achieved by using for example a cyanobacterium such as *Synechocystis* transformed with the integrative construct pSK10-PisiA-PDC-ADHII. If normalized to $OD_{750\,nm}$ 1, a rate of 0.0048% EtOH (v/v) per OD1 and day can be measured.

Over a period of 10 days a daily production of 0.004 is reached, more preferred 0.009% per day and most preferred 0.014% per day by using the integrative construct pSK10-PisiA-PDC-ADHII in a cyanobacterial host cell such as *Synechocystis*. If normalized to $OD_{750\,nm}$ 1, a rate of 0.0035% EtOH (v/v) per OD1 and day can be reached.

Over a period of 20 days a daily production of 0.004, more preferred 0.008% per day and most preferred 0.01% per day is reached by using the self-replicating construct pVZ-PnirA-PDC-SynADH or using the self-replicating construct pVZ-PhspA-PDC-SynADH in a for example a cyanobacterial host cell. If normalized to $OD_{750\,nm}$ 1, a rate of 0.0017% EtOH (v/v) per OD1 and day can be achieved.

Over a period of 50 days a daily production of 0.003 is reached, more preferred 0.005% per day and most preferred 0.008% per day by using the self-replicating construct pVZ-PnirA-PDC-SynADH or the self-replicating construct pVZ-PhspA-PDC-SynADH. If normalized to $OD_{750\,nm}$ 1, a rate of 0.0010% EtOH (v/v) per OD1 and day can be reached.

All maximal given rates were obtained and measured only in the culture. Losses of ethanol by evaporation are not considered. A person of ordinary skill in the art can postulate a loss of 1% of present ethanol in the culture per day, resulting in a loss of 14% after 30 days and 22% after 50 days.

In general, short term experiments as well as continuous illumination result in higher rates. Different Adh enzyme types differ not significantly in their maximal rates but in the duration of ethanol synthesis and SynADH experiments result in a longer production caused by a better longevity of the cells because of the missing back reaction from ethanol to acetaldehyde.

In one further embodiment, the invention provides a genetically modified photoautotrophic, ethanol producing host cell comprising:
(a) an overexpressed pyruvate decarboxylase enzyme converting pyruvate to acetaldehyde,
(b) an overexpressed Zn2+ dependent alcohol dehydrogenase enzyme, converting acetaldehyde to ethanol; and
(c) at least one overexpressed ethanol producing enzyme having a different substrate specificity than (a) or (b).

In a further embodiment thereof, (c) comprises an overexpressed ethanol producing enzyme with a substrate specificity for acetyl-CoA or acetylphosphate. In a further embodiment thereof, (c) comprises AdhE converting acetyl-CoA into ethanol, or acetaldehyde dehydrogenase converting acetylphosphate into acetaldehyde, or a CoA-dependent acetaldehyde dehydrogenase converting acetyl-CoA into acetaldehyde.

Another embodiment of this invention also provides a construct for the transformation of a photoautotrophic host cell, the photoautotrophic host cell comprising a host genome, the construct comprising:
a coding nucleic acid sequence comprising a first gene encoding a Zinc-dependent alcohol dehydrogenase, wherein
the coding nucleic acid sequence is flanked at its 5' and 3' end by nucleic acid sequences which are able to bind at least parts of that host genome for integration of the coding nucleic acid sequence into the host genome.

Such a construct can be used, for example, in an integrative plasmid in order to introduce a gene encoding a Zinc-dependent alcohol dehydrogenase into the genome of a host cell, for example the cyanobacterium *Synechocystis* via homologous recombination.

The construct furthermore can comprise a heterologous or endogenous promoter controlling the transcription of the first gene. This embodiment of the invention also provides a construct for the transformation of a photoautotrophic host cell, comprising:
a coding nucleic acid sequence comprising a promoter and a first gene encoding a Zink-dependent alcohol dehydrogenase wherein the first gene is under the transcriptional control of the promoter.

The above-mentioned constructs can be part of a recombinant circular plasmid.

Another embodiment of the invention provides a genetically modified photoautotrophic ethanol producing host cell comprising:
an overexpressed alcohol dehydrogenase directly converting acetyl-CoA to ethanol.

Such a genetically modified photoautotrophic host cell only requires one overexpressed alcohol dehydrogenase enzyme, for example AdhE which can be a thermophilic alcohol dehydrogenase, for example obtained from the cyanobacterium *Thermosynechococcus* in order to produce ethanol from the metabolic products naturally occurring in this host cell or which can be from *E. coli*.

In addition the enzymatic activity or affinity of AdhE can be increased by introducing mutations, in particular point mutations into the protein via site directed or random mutagenesis. The AdhE is an iron-dependent, bifunctional enzyme containing a CoA-depending aldehyde dehydrogenase and an alcohol dehydrogenase activity. One characteristic of iron-dependent alcohol dehydrogenases (AdhII) is the sensitivity to oxygen. In the case of the AdhE from *E. coli* a mutant was described that shows in contrast to the wildtype also Adh activity under aerobic conditions. The site of the mutation was determined in the coding region at the codon position 568. The G to A nucleotide transition in this codon results in an amino acid exchange from glutamate to lysine (E568K). The E568K derivate of the *E. coli* AdhE is active both aerobically and anaerobically. This mutation is therefore a solution for the use of this oxygen-sensitive enzyme in an oxygen-producing photosynthetic host cell.

[Holland-Staley et al., Aerobic activity of *Escherichia coli* alcohol dehydrogenase is determined by a single amino acid, J Bacteriol. 2000 November; 182(21):6049-54].

In one embodiment, the invention provides a genetically modified photoautotrophic, ethanol producing host cell comprising:
  (a) an overexpressed alcohol dehydrogenase enzyme, directly converting acetyl-CoA to ethanol;
  (b) at least one overexpressed ethanol producing enzyme having a different substrate specificity than (a).

In one embodiment thereof, the at least one an overexpressed ethanol producing enzyme of (b) has a substrate specificity for acetaldehyde or acetylphosphate. In a further embodiment thereof, (b) comprises Adh or acetaldehyde dehydrogenase.

Another embodiment of the invention provides a construct for the transformation of a photoautotrophic host cell, the photoautotrophic host cell comprising a host genome, the construct comprising:
  a coding nucleic acid sequence comprising a gene encoding an alcohol dehydrogenase, directly converting acetyl-CoA to ethanol, wherein
  the coding nucleic acid sequence is flanked at its 5' and 3' end by nucleic acid sequences which are able to bind to at least parts of said host genome for integration of the coding nucleic acid sequence into the host genome.

Such a construct is be useful in order to introduce a nucleic acid sequence encoding for an alcohol dehydrogenase such as AdhE directly converting Acetyl-CoA to ethanol into a host genome, for example via homologous recombination.

Such a construct furthermore can comprise a heterologous or endogenous promoter controlling the transcription of the gene.

In one embodiment, the invention provides a genetically modified photoautotrophic, ethanol producing host cell comprising at least two overexpressed enzymes for ethanol production comprising at least two substrate specificities. In a further embodiment thereof, the at least two substrate specificities are selected from a group consisting of acetyl-CoA, acetaldehyde and acetylphosphate. In yet a further embodiment thereof, the at least two overexpressed enzymes for ethanol production are selected from a group consisting of Adh, AdhE, aCoA-dependent acetaldehyde dehydrogenase and an acetaldehyde dehydrogenase converting acetylphosphate into acetaldehyde.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

We claim:

1. A genetically modified cyanobacteria cell comprising:
   an overexpressed pyruvate decarboxylase enzyme converting pyruvate to acetaldehyde, and
   a Zn2+ dependent alcohol dehydrogenase enzyme Synechocystis Adh, wherein the Zn2+-dependent alcohol dehydrogenase enzyme is overexpressed.

2. The cyanobacteria cell of claim 1, wherein overexpression of the Zn2+-dependent alcohol dehydrogenase enzyme is controlled by an inducible promoter.

3. The cyanobacteria cell of claim 2, wherein overexpression of the Zn2+-dependent alcohol dehydrogenase enzyme is integrated into the genome.

4. The genetically modified cyanobacteria cell of claim 1, wherein the overexpressed dehydrogenase enzyme converts acetaldehyde into ethanol.

5. The cyanobacteria cell of claim 1, wherein the ethanol production is at a rate of at least 0.0017% EtOH (v/v) per OD1 per day.

6. The cyanobacteria cell of claim 1, wherein the cyanobacteria cell is Synechocystis sp. PCC 6803.

7. A genetically modified cyanobacteria cell comprising:
   an overexpressed pyruvate decarboxylase enzyme converting pyruvate to acetaldehyde, and
   an overexpressed Zn2+ dependent alcohol dehydrogenase enzyme derived from Synechocystis (SEQ ID 16) converting acetaldehyde to ethanol, wherein the molecular ratio of acetaldehyde to ethanol in a gas phase over a culture comprising the cyanobacteria cell is lower than 0.101.

8. The cyanobacteria cell of claim 7, wherein the ethanol production is at a rate of at least 0.0017% EtOH (v/v) per OD1 per day.

* * * * *